(12) United States Patent
Bollbuck et al.

(10) Patent No.: US 7,645,760 B2
(45) Date of Patent: Jan. 12, 2010

(54) 1-(4-BENZYL-PIPERAZIN-1-YL)-3-PHENYL-PROPENONE DERIVATIVES

(75) Inventors: Birgit Bollbuck, Weil am Rhein (DE); Jorg Eder, Rheinfelden (DE); Richard Heng, Hegenheim (FR); Laszio Revesz, Therwil (CH); Achim Schlapbach, Lorrach (DE); Rudolf Walchli, Basel (CH)

(73) Assignee: Novartis AG., Based (CH)

( * ) Notice: Subject to any disclaimer, the term of this patent is extended or adjusted under 35 U.S.C. 154(b) by 648 days.

(21) Appl. No.: 10/532,331

(22) PCT Filed: Oct. 24, 2003

(86) PCT No.: PCT/EP03/11848

§ 371 (c)(1),
(2), (4) Date: Apr. 22, 2005

(87) PCT Pub. No.: WO2004/037796

PCT Pub. Date: May 6, 2004

(65) Prior Publication Data

US 2006/0173004 A1    Aug. 3, 2006

(30) Foreign Application Priority Data

Oct. 25, 2002   (GB) .................... 0224917.5

(51) Int. Cl.
  *C07D 241/10*   (2006.01)
  *C07D 295/027*  (2006.01)
  *A61K 31/4965*  (2006.01)
(52) U.S. Cl. .................. 514/255.03; 544/358; 544/403
(58) Field of Classification Search .............. 544/358, 544/403; 514/255.03
See application file for complete search history.

(56) References Cited

U.S. PATENT DOCUMENTS 4,742,062 A * 5/1988 Ohtaka et al. .......... 514/252.12
7,098,212 B2 * 8/2006 Blumberg et al. ...... 514/252.14

FOREIGN PATENT DOCUMENTS

EP   0 209 843     1/1987
JP   2000 086603 A 3/2000

OTHER PUBLICATIONS

Paten Abstracts of Japan vol. 2000 No. 06 (2000) & JP 2000 086603 (Yoshitomi Pharm) (2000).

* cited by examiner

*Primary Examiner*—James O Wilson
*Assistant Examiner*—Ebenezer Sackey
(74) *Attorney, Agent, or Firm*—Sophie Binet Cross

(57) ABSTRACT

A compound of formula (I), or a pharmaceutically acceptable salt or ester thereof, wherein the symbols have meaning as defined, which are antagonists of CCR-1 and which find use pharmaceutically for treatment of diseases and conditions in which CCR-1 is implicated, e.g. inflammatory diseases.

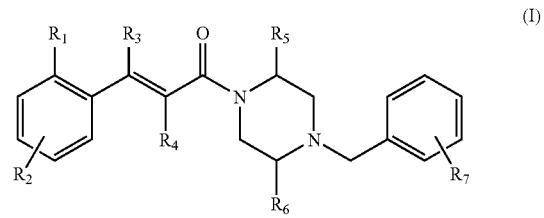

(I)

6 Claims, No Drawings

1-(4-BENZYL-PIPERAZIN-1-YL)-3-PHENYL-PROPENONE DERIVATIVES

This application relates to 1-(4Benzyl-piperazin-1-yl)-3-phenyl-propenone derivatives that are antagonists of Chemokine Receptor 1 (CCR-1) and to their use in the treatment of diseases or disorders that involve migration and activation of monocytes and T-cells, including inflammatory diseases.

Accordingly the application provides a compound of formula I, or a pharmaceutically acceptable salt or ester thereof,

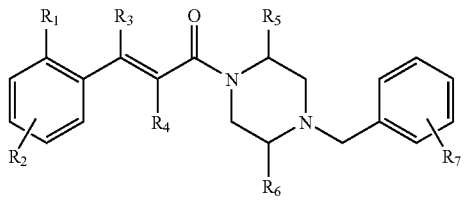

wherein
$R_1$ is —X—$R_{10}$, —X—$(R_{10})_2$ or —$NR_{11}R_{12}$
Wherein X is a linker comprising 1 atom or a chain comprising 2, 3 or 4 atoms selected from N, C, O or S, and wherein when said linker comprises 2 or more C atoms the linker may comprise 1 or more C=C or C≡C bonds;

wherein any of said atoms has up to 2 optional substituents selected from hydrogen, oxo, cyano, halo, nitro or optionally substituted oxy, lower alkyl, lower alkenyl, lower alkynyl, carbonyl, sulfur amino;

$R_{10}$ is a substituent independently selected from the group consisting of hydrogen, cyano, halo, nitro or optionally substituted oxy, lower alkyl, lower alkenyl, lower alkynyl, carbonyl, amino, cycloalkyl, heterocycloalkyl, aryl, heteroaryl;

$R_{11}$ and $R_{12}$ each represent a lower alkyl group connected together such that $R_1$ is an optionally substituted heterocycloalkyl or heteroaryl group;

$R_2$ and $R_7$ represent one or more substituents attached to the phenyl ring selected from the group consisting of hydrogen, cyano, halo, nitro or optionally substituted oxy, lower alkyl, lower alkenyl, lower alkynyl, carbonyl, amino, sulfur, cycloalkyl, heterocycloalkyl, aryl, heteroaryl or a substituent forming a bicyclic ring system of which the phenyl ring to which it is attached forms part of the bicycle for example butadiene forming napthyl, or heterobutadiene forming quinolinyl, quinoxalinyl or isoquinolinyl;

$R_3$ and $R_4$ are independently selected from the group consisting of hydrogen, cyano, halo, lower alkyl, lower alkenyl, lower alkynyl, carbonyl, cycloalkyl, heterocycloalkyl, aryl;

$R_5$ and $R_6$ are independently selected from the group consisting of hydrogen, cyano, lower alkyl, lower alkenyl, lower alkynyl, carbonyl, cycloalkyl, heterocycloalkyl, aryl;

Above and elsewhere in the present description the following terms have the following meaning The term "lower" in connection with organic radicals or compounds means a compound or radical which may be branched or unbranched with up to and including 7 carbon atoms.

A lower alkyl group is branched or unbranched and contains from 1 to 7 carbon atoms, preferably 1 to 4 carbon atoms. Lower alkyl represents for example methyl, ethyl, n-propyl, iso-propyl, n-butyl, iso-butyl, n-pentyl, t-butyl, n-heptyl. lower alkyl is optionally substituted by hydrogen, cyano, halo, nitro, amino, oxy, alkoxy.

A lower alkenyl group is branched or unbranched, contains from 2 to 7 carbon atoms, preferably 2 to 6 carbon atoms, and contains at least one double bond. Lower alkyenyl is optionally substituted by hydrogen, cyano, halo, nitro, amino. Lower alkenyl represents for example ethenyl, prop-1-enyl, but-1-enyl, pent-1-enyl, pent-1,4-dienyl.

A lower alkynyl group is branched or unbranched, contains from 2 to 7 carbon atoms, preferably 2 to 6 carbon atoms, and contains at least one tripple bond. lower alkynyl is optionally substituted by hydrogen, cyano, halo, nitro, amino. Lower alkynyl represents for example ethynyl, prop-1-ynyl, but-1-ynyl, pent-1-ynyl, pent-3-ynyl.

Amino relates to the radicals —$NH_2$ and =NH and may be optionally substituted; for instance, by lower alkyl Aryl represent carbocyclic aryl and heterocyclic aryl.

Carbocyclic aryl represents an aromatic cyclic hydrocarbon containing from 6 to 18 ring atoms. Carbocyclic aryl is mono-, bi- or tricyclic. Carbocyclic aryl represents for example phenyl, naphthyl, biphenyl. Carbocyclic aryl is optionally substituted by up to 4 substituents.

Carbonyl refers to the radical —C(O)—

Cyano or nitrile represents the radical —CN

Cycloalkyl represents a cyclic hydrocarbon containing from 3 to 12 ring atoms preferably from 3 to 7 ring atoms and may be mono-, bi- or tricyclic and includes spiro. Cycloalkyl represents for example cyclopropyl, cyclobutyl, cyclopentyl and cyclohexyl. Cycloalkyl is optionally substituted.

Halo represents chloro, fluoro or bromo but may also be iodo.

Heterocyclic aryl represents an aromatic cyclic hydrocarbon containing from 5 to 18 ring atoms of which one or more, preferably 1 to 3, are heteroatoms selected from O, N or S. It may be mono or bicyclic. Heterocyclic aryl is optionally substituted. Heterocyclic aryl represents for example pyridyl, indoyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl.

Heterocycloalkyl represents a mono-, bi- or tricyclic hydrocarbon containing from 3 to 18 ring atoms preferably from 3 to 7 ring atoms and contains one or more, preferably 1 to 3, heteroatoms selected from O, N or S. Heterocycloalkyl is optionally substituted. Heterocycloalkyl represents for example pyrrolidinyl, piperidinyl, piperazinyl, morpholinyl, indolinylmethyl, imidazolinylmethyl and 2-Aza-bicyclo[2.2.2]octanyl Nitro represents the radical —$NO_2$
Oxo represents the substituent =O
Oxy represents the radical —O—, and includes —OH
sulfur indicates the radicals —S—,

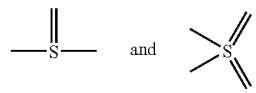

The optional substituents on carbocyclic aryl, cycloalkyl, heterocyclic aryl, heterocycloalkyl are as defined for the optional substituents on $R_{10}$ below.

The optional substituents on X are one or more, e.g. 1-3 substituents, independently selected from the group consisting of hydrogen, oxo, cyano, halo, nitro or optionally substituted oxy, lower alkyl, lower alkenyl, lower alkynyl, amino, sulfur, sulfinyl, sulfonyl;

Wherein the optionally substituted substituents are optionally substituted once or more by, e.g. 1-6 substituents, a substituent independently selected from the group consisting of hydrogen, oxo, cyano, halo, nitro, oxy, lower alkyl, lower alkyenyl, lower alkynyl, amino, sulfur, cycloalkyl, heterocyloalkyl, aryl;

The optional substituents, e.g. 1-6 substituents, on $R_{10}$ are one or more substituents independently selected from the group consisting of hydrogen, oxo, cyano, halo, nitro or optionally substituted oxy, lower alkyl, lower alkyenyl, lower alkynyl, carbonyl, amino, Sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, Sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, Sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or oxy, lower alkyl, lower alkyenyl, lower alkynyl, carbonyl, amino, sulfur, cycloalkyl, heterocycloalkyl, aryl;

The optional substituents, e.g. 1-6 substituents, on $R_2$ and $R_7$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or oxy, lower alkyl, lower alkyenyl, lower alkynyl, carbonyl, amino, sulfur, cycloalkyl, heterocycloalkyl, aryl;

The optional substituents, e.g. 1-6 substituents, on $R_3$ and $R_4$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro, oxy, lower alkyl, lower alkyenyl, lower alkynyl, carbonyl, amino, sulfur, cycloalkyl, heterocycloalkyl, aryl;

The optional substituents, e.g. 1-6 substituents, on $R_5$ and $R_6$ are one or more substituents independently selected from the group consisting of hydrogen, oxo, cyano, hydroxy, optionally substituted oxy, lower alkyl, lower alkyenyl, lower alkynyl, carbonyl, , cycloalkyl, heterocycloalkyl, aryl, imino, oxime;

Wherein the optionally substituted substituents are optionally substituted once or more by, e.g. 1-6 substituents, a substituent independently selected from the group consisting of hydrogen, oxo, hydroxy, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

Wherein the optionally substituted substituents are optionally substituted once or more by, e.g. 1-6 substituents, a substituent independently selected from the group consisting of hydrogen, oxo, cyano, halo, nitro or oxy, lower alkyl, lower alkyenyl, lower alkynyl, carbonyl, amino, sulfur, cycloalkyl, heterocycloalkyl, aryl;

In a preferred embodiment the invention also provides a compound of formula II, or a pharmaceutically acceptable salt or ester thereof, Wherein
$R'_1$ is —X'—$R'_{10}$ Wherein X' is a linker independently selected from optionally substituted —N—C—N—, —N—C—, —N—S—,

—N—S—N—, —C—N—, —S—N—, —C≡C—,
—C═C—, —N—C—S—, —C—,

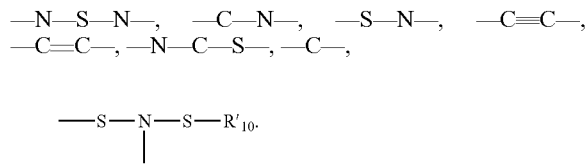

Wherein $R_2$, $R_5$, $R_6$ and $R_7$ are as defined above.

Preferably $R'_{10}$ is one or more substituents independently selected from the group consisting of hydrogen, halo, or optionally substituted carbonyl, amino, heterocycloalkyl and aryl.

when $R'_1$ is —N—C—N—$R'_{10}$ the C atom is preferably substituted by oxo, ═N—C≡N or ═C—$NO_2$.

when $R'_1$ is —N—C—N—$R'_{10}$, $R'_{10}$ is preferably Hydrogen.

when $R'_1$ is —N—C—N—$R'_{10}$, $R'_{10}$ is preferably optionally substituted by hydrogen.

Examples of $R'_1$ when X' is —N—C—N— are urea or N-cyano-guanidine.

when $R'_1$ is —N—C—$R'_{10}$ or —C—N—$R'_{10}$ the C atom is substituted by oxo.

when $R'_1$ is —N—C—$R'_{10}$ or —C—N—$R'_{10}$, $R'_{10}$ is optionally substituted methyl, piperidinyl, imidazolidinyl, pyrrolidinyl, morpholino.

when $R'_1$ is —N—C—$R'_{10}$ or —C—N—$R'_{10}$, $R'_{10}$ is substituted by hydrogen, methyl, benzyl, acetyl, oxo, dimethylamino, isopropyl, hydroxy, formic acid ethyl ester.

Examples of $R'_1$ when X' is —N—C— or —C—N— are acetamide, N-methyl-acetamide, N-(1-methyl-piperidin-4-yl)-acetamide, N-(1-benzyl-piperidin-4-yl)-acetamide, 4-Formylamino-piperidine-1-carboxylic acid ethyl ester.

when $R'_1$ is —N—S—$R'_{10}$ or

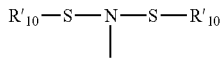

the S atom or atoms are preferably substituted twice by oxo.

when $R'_1$ is —N—S—$R'_{10}$ or

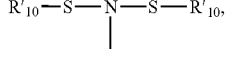

$R'_{10}$ is preferably optionally substituted methyl, imidazolyl, thiazolyl.

when $R'_1$ is —N—S—$R'_{10}$ or

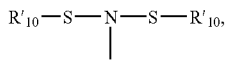

$R'_{10}$ is preferably optionally substituted by hydrogen, methyl, acetamidyl.

Examples of $R'_1$ when X' is —N—S—$R'_{10}$ or

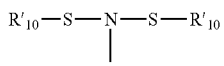

are N-Methanesulfonyl-methanesulfonamide when $R'_1$ is —N—S—N—$R'_{10}$ preferably the S atom is substituted twice by oxo and the N atom is independently optionally substituted by methyl.

when $R'_1$ is —N—S—N—$R'_{10}$, $R'_{10}$ is preferably hydrogen or optionally substituted methyl when $R'_1$ is —N—S—N—$R'_{10}$, $R'_{10}$ is preferably optionally substituted by hydrogen Examples of $R'_1$ when X' is —N—S—N— are aminosulfonic acid amide and sulfonic acid dimethylamide.

when $R'_1$ is —C≡C—$R'_{10}$, $R'_{10}$ is preferably optionally substituted methyl, isopropyl or piperindinyl when $R'_1$ is —C≡C—$R'_{10}$, $R'_{10}$ is preferably optionally substituted by hydrogen or amine Examples of $R'_1$ when X' is —C≡C— are 1-Methyl-4-ethynyl-piperidin-4-ol, 4-ethynyl-piperidin-4-ol, 3,3-Dimethyl-but-1-ynyl, 3-dimethylaminoprop-1-ynyl, 3-hydroxy-3-methylbut-1-ynyl, 4-Hydroxy-4-ethynyl-piperidine-1-carboxylic acid tert-butyl ester when $R'_1$ is —C═C—$R'_{10}$, $R'_{10}$ is preferably optionally substituted piperidinyl when $R'_1$ is —C═C—$R'_{10}$, $R'_{10}$ is preferably optionally substituted by hydroxy, methyl.

Examples of $R'_1$ when X' is —C═C— are 4-hydroxy-1-methylpiperidin-4-yl)-vinyl.

when $R'_1$ is —N—C—S—$R'_{10}$ preferably the C atom is substituted by ═N—C≡N or

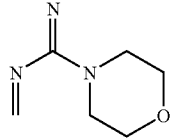

when $R'_1$ —N—C—S—$R'_{10}$, $R'_{10}$ is preferably optionally substituted methyl when $R'_1$ is —N—C—S—$R'_{10}$, $R'_{10}$ is preferably optionally substituted by hydrogen.

Examples of $R'_1$ when X' is —N—C—S— are methylthio-N'-cyano thiourea or methylthio-N'-(Morpholin-4-yl-methyleneamine)-thiourea when $R'_1$ is —C—$R'_{10}$ the C atom is optionally substituted by oxo, when $R'_1$ —C—$R'_{10}$, $R'_{10}$ is 3-oxa-1-aza-spiro[4.4]nonan-2-one, hydroxy, optionally substituted pyrrolidinyl, morpholino, piperazinyl, formic acid methyl ester, [1,2,4]triazol, imidazolidinyl, tetrazolyl, —N($CH_3$)—$OCH_3$ or methoxy.

when $R'_1$ is —C—$R'_{10}$, $R'_{10}$ is optionally substituted by hydrogen, oxo, methyl, acetyl, isopropyl, methoxy, hydroxy, formic acid methyl ester, dimethylamino or ethanone.

Examples of $R'_1$ when X' is —C— are [1,2,4]triazol-1-ylmethyl, pyrrolidin-2-one-methyl, morpholin-ylmethyl, acetic acid methyl ester, The optional substituents, e.g. 1-6 substituents, on $R'_{10}$ are one or more substituents independently selected from the group consisting of hydrogen, or optionally substituted oxy, lower alkyl, carbonyl, amino;

Wherein the optionally substituted substituents are optionally substituted once or more by, e.g. 1-6 substituents, a substituent independently selected from the group consisting of hydrogen, or optionally substituted oxy;

Wherein the optionally substituted substituents are optionally substituted once or more by, e.g. 1-6 substituents, a substituent independently selected from the group consisting of hydrogen or optionally substituted lower alkyl;
wherein said substituents are herein before defined or Preferably;
Lower alkyl is methyl, ethyl, iso-propyl, t-butyl;
Lower alkenyl is ethenyl;
Lower alkynyl is ethynyl, prop-1-ynyl, but-1-ynyl;
Heterocyclic aryl is triazolyl;
Heterocycloalkyl is pyrrolidinyl, piperidinyl, piperazinyl or morpholinyl.

In a further preferred embodiment the invention also provides a compound of formula IIa, or a pharmaceutically acceptable salt or ester thereof,

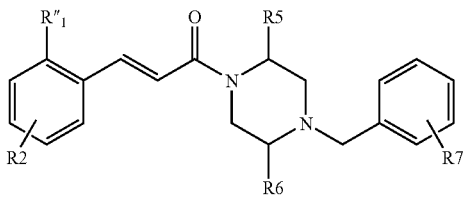

IIa

Wherein
R"$_1$ is —NR"$_{11}$R"$_{12}$
Wherein —NR"$_{11}$R"$_{12}$ collectively represents imidazolidinyl-2,4-dione, optionally substituted once or twice by a lower alkyl group.

In a further preferred embodiment the invention also provides a compound of formula III, or a pharmaceutically acceptable salt or ester thereof,

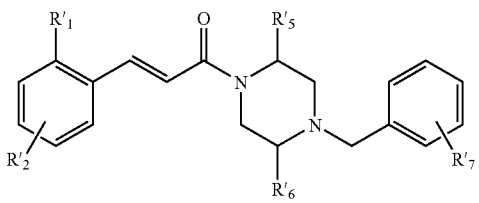

III

Wherein R'$_1$ is as defined above.
R'$_2$ and R'$_7$ are hydrogen, cyano, halo, butadienyl, methoxy, ethoxy, 2-methoxyethoxy, morpholino, trifluoromethoxy, 2-methylpropoxy, 2-propoxy.
R'$_5$ and R'$_6$ are independently selected from the group consisting of hydrogen and lower alkyl, acetyl;
wherein said substituents are herein before defined or preferably lower alkyl is methyl In particular the invention includes a compound selected from:
N-(5-Chloro-2-[(E)-3-[(R)-4-(4-fluorobenzyl)-2-methylpiperazin-1-yl]-3-oxopropenyl]phenyl)-N'-cyanoguanidine
N-(5Chloro-2-[(E)-3-[(R)-4-(4-fluorobenzyl)-2-methylpiperazin-1-yl]-3-oxopropenyl]phenyl)-acetamide
N-(5-Chloro-2-[(E)-3-[(S)-4-(4-fluorobenzyl)-2-methylpiperazin-1-yl]-3-oxopropenyl]phenyl)-acetamide
(5Chloro-2-[(E)-3-[(R)-4-(4-fluorobenzyl)-2-methylpiperazin-1-yl]-3-oxopropenyl]-phenyl)-urea
(5-Chloro-2-[(E)-3-[(S)-4-(4-fluorobenzyl)-2-methylpiperazin-1-yl]-3-oxopropenyl]-phenyl)-urea
N-(5Chloro-2-[(E)-3-[(R)-4-(4-fluorobenzyl)-2-methylpiperazin-1-yl]-3-oxopropenyl]phenyl)-N,N-dimethylsulfamide
N-(5-Chloro-2-[(E)-3-[(R)-4-(4-fluorobenzyl)-2-methylpiperazin-1-yl]-3-oxopropenyl]phenyl)-methanesulfonamide
1-Acetyl-piperidine-4-carboxylic acid (5-chloro-2-{(E)-3-[(R)-4-(4-fluoro-benzyl)-2-methyl-piperazin-1-yl]-3-oxo-propenyl}phenyl)-amide
1-Methyl-1H-imidazole-4-sulfonic acid(5-Chloro-2-[(E)-3-[(R)-4-(4-fluoro-benzyl)-2-methyl-piperazin-1-yl]-3-oxo-propenyl]-phenyl)-amide
N-[5-(5-Chloro-2-[(E)-3-[(R)-4-(4-fluoro-benzyl)-2-methyl-piperazin-1-yl]-3-oxo-propenyl-phenylsulfamoyl)-thiazol-2yl]-acetamide
2-Oxo-imidazolidine-1-carboxylic acid (5-Chloro-2-[(E)-3-[(R)-4-(4-fluoro-benzyl)-2-methyl-piperazin-1-yl]-3-oxo-propenyl]-phenyl)-amide
N-(4-Chloro-2-[(E)-3-[4-(4-fluorobenzyl)-2-methylpiperazin-1-yl]-3-oxopropenyl]-phenyl)-methylthio-N'-cyano thiourea
N-(4-Chloro-2-[(E)-3-[4-(4-fluorobenzyl)-2-methylpiperazin-1-yl]-3-oxopropenyl]-phenyl)-sulfonylurea
(5-Chloro-2-[(E)-3-[(2R,5S)-4-(4-fluorobenzyl)-2,5-dimethylpiperazin-1-yl]-3-oxopropenyl]-phenyl)-urea
(5-Chloro-2-[(E)-3-[(2R,5S)-4-(4-fluorobenzyl)-2,5-dimethylpiperazin-1-yl]-3-oxopropenyl]-phenyl)-urea
N-(5-Chloro-2-[(E)-3-[(2R,5S)-4-(4-fluorobenzyl)-2,5-dimethyl-piperazin-1-yl]-3-oxopropenyl]-phenyl)-acetamide
N-(5Chloro-2-[(E)-3-[(2S,5R)-4-(4fluorobenzyl)-2,5-dimethyl-piperazin-1-yl]-3-oxopropenyl]-phenyl)-acetamide
(5-Chloro-2-[(E)-3-[(2S,5R)-4-(4-fluorobenzyl)-2,5-dimethylpiperazin-1-yl]-3-oxopropenyl]-phenyl)-urea
N-(5-Chloro-2-[(E)-3-[-4-(4-fluorobenzyl)-piperazin-1-yl]-3-oxopropenyl]-phenyl)-acetamide
(5-Chloro-2-[(E)-3-[-4-(4-fluorobenzyl)-piperazin-1-yl]-3-oxopropenyl]-phenyl)-urea
(E)-3-[4-Chloro-2-(4-hydroxy-1-methylpiperidin-4-ylethynyl)-phenyl]-1-[(R)-4-(4-fluorobenzyl)-2-methylpiperazin-1-yl]-propenone
(E)-3-[4-Chloro-2-(4-hydroxy-1-methylpiperidin-4-ylethynyl)-phenyl]-1-[(S)-4-(4-fluorobenzyl)-2-methylpiperazin-1-yl]-propenone
(E)-3-[4-Chloro-2-[(E)-2-(4-hydroxy-1-methylpiperidin-4-yl)-vinyl]-phenyl]-1-[(R)-4-(4-fluorobenzyl)-2-methylpiperazin-1-yl]-propenone
(E)-3-[4-Chloro-2-[(E)-2-(4-hydroxy-1-methylpiperidin-4-yl)-vinyl]-phenyl]-1-[(S)-4-(4-fluorobenzyl)-2-methylpiperazin-1-yl]-propenone
4-(5-Chloro-2-[(E)-3-[(R)-4-(4-fluorobenzyl)-2-methylpiperazin-1-yl]-3-oxopropenyl]-phenylethynyl)-4-hydroxypiperidine-1-carboxylic acid tert butyl ester
(E)-3-[4-Chloro-2-(4-hydroxypiperidin-4-ylethynyl)-phenyl]-1-[(R)-4-(4-fluorobenzyl)-2-methylpiperazin-1-yl]-propenone
(E)-3-[2-(3-Amino-3-methylbut-1-ynyl-4-chlorophenyl]-1-[(R)-4-(4-fluorobenzyl)-2-methylpiperazin-1-yl]-propenone
(E)-3-[4-Chloro-2-(3-dimethylaminoprop-1-ynyl)-phenyl]-1-[4-(4-fluorobenzyl)-2-methylpiperazin-1-yl]-propenone
(E)-3-[4-Chloro-2-(3-hydroxy-3-methylbut-1-ynyl)-phenyl]-1-[4-(4-fluorobenzyl)-2-methylpiperazin-1-yl]-propenone
N-(3-[(E)-3-[(R)-4-(4-Fluorobenzyl)-2-methylpiperazin-1-yl]-3-oxopropenyl]-naphthalen-2-yl)-acetamide
(3-[(E)-3-[(R)-4-(4-Fluorobenzyl)-2-methylpiperazin-1-yl]-3-oxopropenyl]-naphthalen-2-yl)-urea N-(3-[(E)-3-[(R)-4-(4-Fluorobenzyl)-2-methylpiperazin-1-yl]-3-oxopropenyl]-naphthalen-2-yl)-N'-cyanoguanidine
N-(4-Chloro-2-[(E)-3-[4-(4-fluorobenzyl)-2-methylpiperazin-1-yl]-3-oxopropenyl]-phenyl)-N'-cyanoguanidine
N-(4-Chloro-2-[(E)-3-[4-(4-fluorobenzyl)-2-methylpiperazin-1-yl]-3-oxopropenyl]-phenyl)-acetamide
N-(6[(E)-3-[(R)-4-(4-Fluorobenzyl)-2-methylpiperazin-1-yl]-3-oxopropenyl]-quinolin-7-yl)-acetamide
(6-[(E)-3-[(R)-4-(4-Fluorobenzyl)-2-methylpiperazin-1-yl]-3-oxopropenyl]-quinolin-7-yl)-urea
N-(7-[(E)-3-[(R)-4-(4-Fluorobenzyl)-2-methylpiperazin-1-yl]-3-oxopropenyl]-quinolin-6-yl)-acetamide
2-Dimethylamino-N-(7-[(E)-3-[(R)-4-(4-fluorobenzyl)-2-methylpiperazin-1-yl]-3-oxopropenyl]-quinolin-6-yl)-acetamide
N-(7-[(E)-3-[(R)-4-(4-Fluorobenzyl)-2-methylpiperazin-1-yl]-3-oxopropenyl]-quinolin-6-yl)-methanesulfonamide
N-(5-Chloro-2-[(E)-3-[(2R,5S)-4-(4-fluorobenzyl)-2,5-dimethylpiperazin-1-yl]-3-oxopropenyl]-phenyl)-cyanoguanidine
N-(5-Chloro-2-[(E)-3-[(2R,5S)-4-(4-fluorobenzyl)-2,5-dimethylpiperazin-1-yl]-3-oxopropenyl]-phenyl)-2-dimethylacetamide
N-(5-Chloro-2-[(E)-3-[(2R,5S)-4-(4-fluorobenzyl)-2,5-dimethylpiperazin-1-yl]-3-oxopropenyl]-phenyl)-methanesulfonamide
N-(5-Chloro-2-[(E)-3-[(2R,5S)-4-(4-fluorobenzyl)-2,5-dimethylpiperazin-1-yl]-3-oxopropenyl]-4-methoxyphenyl)-acetamide
N-(5-Chloro-2-[(E)-3-[(2R,5S)-4-(4-fluorobenzyl)-2,5-dimethylpiperazin-1-yl]-3-oxopropenyl]-4-methoxyphenyl)-methanesulfonamide
N-[5-Chloro-2-[(E)-3-(R)-4-(4-fluorobenzyl)-2-methylpiperazin-1-yl]-3-oxopropenyl)-4-(2-methoxyethoxy)-phenyl]-acetamide
N-(5-Chloro-2-[(E)-3-[(R)-4-(4-fluorobenzyl)-2-methylpiperazin-1-yl]-3-oxopropenyl]-4-morpholin-4-yl-phenyl)-acetamide
N-(5-Chloro-2-{(E)-3-[(R)-2-ethyl-4-(4-fluorobenzyl)-piperazin-1-yl]-3-oxo-propenyl}-phenyl)-acetamide
(5-Chloro-2-{(E)-3-[(R)-2-ethyl-4-(4-fluoro-benzyl)-piperazin-1-yl]-3-oxo-propenyl}-phenyl)-urea.
N-(5-Chloro-4-ethoxy-2-{(E)-3-[(R)-4-(4-fluorobenzyl)-2-methyl-piperazin-1-yl]-3-oxo-propenyl}-phenyl)-acetamide
(5-Chloro-4-ethoxy-2-{(E)-3-[(R)-4-(4-fluorobenzyl)-2-methyl-piperazin-1-yl]-3-oxo-propenyl}-phenyl)-urea
N-(5-Chloro-4-ethoxy-2-{(E)-3-[(R)-4-(4-fluorobenzyl)-2-methyl-piperazin-1-yl]-3-oxo-propenyl}-phenyl)-methanesulfonamide
5-Oxo-pyrrolidine-2-carboxylic acid (5-chloro-4-ethoxy-2-{(E)-3-[®-4-(4fluorobenzyl)-2-methyl-piperazin-1yl]-3oxo-propenyl}-phenyl)-amide
N-(5-Chloro-2-{(E)-3-[(S)-4-(4-fluoro-benzyl)-2-hydroxymethyl-piperazin-1-yl]-3-oxo-propenyl}-4-methoxy-phenyl)-acetamide.
N-(5-Chloro-2-{(E)-3-[(S)-4-(4-fluoro-benzyl)-2-hydroxymethyl-piperazin-1-yl]-3-oxo-propenyl}-4-methoxy-phenyl)-methanesulfonamide
(5-Chloro-2-{(E)-3-[(S)-4-(4-fluoro-benzyl)-2-hydroxymethyl-piperazin-1-yl]-3-oxo-propenyl}-4-methoxy-phenyl)-urea
5-Oxo-pyrrolidine-2-carboxylic acid (5-chloro-2-{(E)-3-[(S)-4-(4-fluoro-benzyl)-2-hydroxymethyl-piperazin-1-yl]-3-propenyl}-4-methoxy-phenyl)-amide
N-(5-chloro-2-{(E)-3-[(S)-4-(4-fluoro-benzyl)-2-hydorxymethyl-piperazin-1-yl]-3-oxo-propenyl}phenyl)acetamide
N-(2-{(E)-3-[(R)-2-Aminomethyl-4-(4-fluoro-benzyl)-piperazin-1-yl]-3-oxo-propenyl}-5-chloro-phenyl)-acetamide
N-5-Chloro-2-{(E)-3-[(S)-4-(4-fluoro-benzyl)-2-((S)-1-hydroxy-ethyl)-piperazin-1-yl]-3-oxo-propenyl}-phenyl)-acetamide
N-(2-{(E)-3-[(S)-2-Acetyl-4-(4-fluoro-benzyl)-piperazin-1-yl]-3-oxo-propenyl}-5-chloro-phenyl)-acetamide
N-{5-Chloro-2-[(E)-3-((S)-4-(4-fluoro-benzyl)-2-{1-[hydroxyimino]-ethyl}-piperazin-1-yl]-3-oxo-propenyl}-acetamide
N-(2-{(E)-3-[(2S,5S)-2-Benzyloxymethyl-4-(4-fluoro-benzyl)-5-methyl-piperazin-1-yl]-3-oxo-propenyl}-5-chloro-phenyl)-acetamide
(S)-1-Acetyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide
(S)-1-Isopropyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide
(R)-1-Isopropyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide
(2S,4R)-1-Acetyl-4-hydroxy-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide
(E)-3-(4-Chloro-2-morpholin-4-ylmethyl-phenyl)-1-[4-(4-fluoro-benzyl)-2-methyl-piperazin-1-yl]-propenone
1-(5-Chloro-2-{(E)-3-[4-(4-fluoro-benzyl)-2-methyl-piperazin-1-yl]-3-oxo-propenyl}-benzyl)-pyrrolidin-2-one
(E)-3-(4-Chloro-2-[1,2,4]triazol-1-ylmethyl-phenyl)-1-[4-(4-fluoro-benzyl)-2-methyl-piperazin-1-yl]-propenone
(E)-3-[4-Chloro-2-(4-methyl-piperazin-1-ylmethyl)-phenyl]-1-[4-(4-fluoro-benzyl)-2-methyl-piperazin-1-yl]-propenone
(E)-3-[2-(4-Acetyl-piperazin-1-ylmethyl)-4-chloro-phenyl]-1-[4-(4-fluoro-benzyl)-2-methyl-piperazin-1-yl]-propenone
(E)-3-[4-Chloro-2-(4-isopropyl-piperazin-1-ylmethyl)-phenyl]-1-[(R)-4-(4-fluoro-benzyl)-2-methyl-piperazin-1-yl]-propenone
1-(5-Chloro-2-{(E)-3-[(R)-4-(4-fluoro-benzyl)-2-methyl-piperazin-1-yl]-3-oxo-propenyl}-benzyl)-3-oxa-1-azaspiro[4.4]nonan-2-one
3-(5-Chloro-2-{(E)-3-[(R)-4-(4-fluoro-benzyl)-2-methyl-piperazin-1-yl]-3-oxo-propenyl}-benzyl)-5,5-dimethyl-imidazolidine-2,4dione
3-(5-Chloro-2-{(E)-3-[(R)-4-(4-fluoro-benzyl)-2-methyl-piperazin-1-yl]-3-oxo-propenyl}-benzyl)-1-methyl-imidazolidine-2,4-dione
(E)-3-[4-Chloro-2-(5-methyl-tetrazol-1-ylmethyl)-phenyl]-1-[(R)-4-(4-fluoro-benzyl)-2-methyl-piperazin-1-yl]-propenone
5-Chloro-2-{(E)-3-[(R)-4-(4-fluoro-benzyl)-2-methyl-piperazin-1-yl]-3-oxo-propenyl}-N-methoxy-N-methyl-benzamide
5-Chloro-2-{(E)-3-[4-(4-fluoro-benzyl)-2-methyl-piperazin-1-yl]-3-oxo-propenyl}-benzoic acid methyl ester
(5-Chloro-2-{(E)-3-[4-(4-fluoro-benzyl)-2-methyl-piperazin-1-yl]-3-oxo-propenyl}-phenyl)-acetic acid methyl ester
5-Chloro-2-{(E)-3-[4-(4-fluoro-benzyl)-2-methyl-piperazin-1-yl]-3-oxo-propenyl}-benzoic acid 5-Chloro-2-{(E)-3-[(R)-4-(4-fluoro-benzyl)-2-methyl-piperazin-1-yl]-3-oxo-propenyl}-benzoic acid (E)-3-[4-Chloro-2-(4-methyl-piperazine-1-carbonyl)-phenyl]-1-[4-(4-fluoro-benzyl)-2-methyl-piperazin-1-yl]-propenone 5-Chloro-2-{(E)-3-[4-(4-fluoro-benzyl)-2-methyl-piperazin-1-yl]-3-oxo-propenyl}-N-isopropyl-benzamide 5-Chloro-2-{(E)-3-[4-(4fluoro-benzyl)-2-methyl-piperazin-1-yl]-3-oxo-propenyl}-N-(1-methyl-piperidin-4-yl)-benzamide N-(1-Benz-y-1)-5-chloro-2-{(E)-3-[4-(4fluoro-benzyl)-2-methyl-piperazin-1-yl-3-oxo-propenyl}-benzamide 4-(5-Chloro-2-{(E)-3-[4-(4-fluoro-benzyl)-2-methyl-piperazin-1-yl]-3-oxo-propenyl}-benzoylamino)-piperidine-1-carboxylic acid ethyl ester (2S,4R)-1-(5-Chloro-2-{(E)-3-[(R)-4-(4-fluoro-benzyl)-2-methyl-piperazin-1-yl]-3-oxo-propenyl}-benzoyl)-4-hydroxy-pyrrolidine-2-carboxylic acid methyl ester (E)-3-[4-Chloro-2-((R)-3-dimethylamino-pyrrolidine-1-carbonyl)-phenyl]-1-[(R)-4-(4-fluoro-benzyl)-2-methyl-piperazin-1-yl]-propenone (E)-3-[4-Chloro-2-((S)-3-dimethylamino-pyrrolidine-1-carbonyl)-phenyl]-1-[(R)-4-(4-fluoro-benzyl)-2-methyl-piperazin-1-yl]-propenone (E)-3-[2-(4Acetyl-piperazine-1-carbonyl)-4-chloro-phenyl]-1-[(R)-4-(4-fluoro-benzyl)-2-methyl-piperazin-1-yl]-propenone N-(5-Chloro-2-{(E)-3-[4-(4-chloro-benzyl)-2-methyl-piperazin-1-yl]-3-oxo-propenyl}-phenyl)-acetamide N-(5Chloro-2-{(E)-3-[4-(3-fluoro-benzyl)-2-methyl-piperazin-1-yl]-3-oxo-propenyl}-phenyl)-acetamide N-(5-Chloro-2-{(E)-3-[4-(2,4-difluoro-benzyl)-2-methyl-piperazin-1-yl]-3-oxo-propenyl}-phenyl)-acetamide N-(5-Chloro-2-{(E)-3-[4-(4-cyano-benzyl)-2-methyl-piperazin-1-yl]-3-oxo-propenyl}-phenyl)-acetamide N-(5-Chloro-2{(E)-3-[(R)-4-(4-fluoro-benzyl)-2-methyl-piperazin-1-yl]-3-oxo-prop-enyl}-4-methoxy-phenyl)-acetamide N-(5-Chloro-4-fluoro-2-{(E)-3-[(R)-4-(4-fluoro-benzyl)-2-methyl-piperazin-1-yl]-3-oxo-propenyl}-phenyl)-acetamide (5-Chloro-2-{(E)-3-[(R)-4-(4-fluoro-benzyl)-2-methyl-piperazin-1-yl]-3-oxo-propenyl}-4-methoxy-phenyl)-urea N-(5-Chloro-4-fluoro-2-{(E)-3-[(R)-4-(4-fluoro-benzyl)-2-methyl-piperazin-1-yl]-3-oxo-propenyl}-phenyl)-methanesulfonamide (5-Chloro-4-fluoro-2-{(E)-3-[(R)-4-(4-fluoro-benzyl)-2-methyl-piperazin-1-yl]-3-oxo-propenyl}-phenyl)-urea N-(5-Chloro-4-cyano-2-{(E)-3-[(R)-4-(4-fluoro-benzyl)-2-methyl-piperazin-1-yl]-3-oxo-propenyl}-phenyl)-acetamide N-(5-Chloro-2-{(E)-3-[(R)-4-(4-fluoro-benzyl)-2-methyl-piperazin-1-yl]-3-oxo-propenyl}-4-trifluoromethoxy-phenyl)-acetamide (5-Chloro-2-{(E)-3-[(R)-4-(4-fluoro-benzyl)-2-methyl-piperazin-1-yl]-3-oxo-propenyl}-4-trifluoromethoxy-phenyl)-urea N-(5-Chloro-2-{(E)-3-[(R)-4-(4-fluoro-benzyl)-2-methyl-piperazin-1-yl]-3-oxo-propenyl}-4-isobutoxy-phenyl)-acetamide N-(5-Chloro-2-{(E)-3-[(R)-4-(4-fluoro-benzyl)-2-methyl-piperazin-1-yl]-3-oxo-propenyl}-4-isopropoxy-phenyl)-acetamide 3-(5-Chloro-2-{(E)-3-[(R)-4-(4-fluoro-benzyl)-2-methyl-piperazin-1-yl]-3-oxo-propenyl}-4-methoxy-phenyl)-5,5-dimethyl-imidazolidine-2,4-dione 3-(5-Chloro-2-{(E)-3-[(R)-4-(4-fluoro-benzyl)-2-methyl-piperazin-1-yl]-3-oxo-propenyl}-4-methoxy-phenyl)-imidazolidine-2,4-dione 3-(5-Chloro-2-{(E)-3-[(R)-4-(4-fluoro-benzyl)-2-methyl-piperazin-1-yl]-3-oxo-propenyl}-4-methoxy-phenyl)-1,3-diaza-spiro[4.4]nonane-2,4-dione 3-(5-Chloro-4-fluoro-2{(E)-3-[(R) (4-fluoro-benzyl)-2-methyl-piperazin-1-yl]-3-oxo-propenyl}-phenyl)-1,3-diaza-spiro[4.5]decane-2,4dione 3-(5-Chloro-4-fluoro-2-{(E)-3-[(R)-4-(4-fluoro-benzyl)-2-methyl-piperazin-1-yl]-3-oxo-propenyl}-phenyl)-5,5-dimethyl-imidazolidine-2,4-dione Morpholine-4-carboxylic acid (5-chloro-2-{(E)-3-[(R)-4-(4-fluoro-benzyl)-2-methyl-piperazin-1-yl]-3-oxo-propenyl}-4-methoxy-phenyl)-amide Pyrrolidine-1-carboxylic acid (5-chloro-2-{(E)-3-[(R)-4-(4-fluoro-benzyl)-2-methyl-piperazin-1-yl]-3-oxo-propenyl}-4-methoxy-phenyl)-amide 5-Chloro-2-{(E)-3-[(R)-4-(4-fluoro-benzyl)-2-methyl-piperazin-1-yl]-3-oxo-propenyl}-4-methoxy-benzoic acid methyl ester (E)-3-[2-(4-Acetyl-piperazine-1-carbonyl)-4-chloro-5-methoxy-phenyl]-1-[(R)-4-(4-fluoro-benzyl)-2-methyl-piperazin-1-yl]-propenone Or a pharmaceutically acceptable salt, or ester thereof.

The compounds of formula I II and III and as listed above are herein after referred to as Agents of the Invention.

Pharmaceutically acceptable salts of the acidic Agents of the Invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, piperazinyl, piperidinyl constitutes part of the structure.

Agents of the Invention may also exist in the form of optical isomers; for example as hereinafter described in the Examples. Thus the invention includes both individual isomeric forms as well as mixtures, e.g. racemic and diastereoisomeric mixtures thereof unless otherwise specified. Conveniently the invention includes compounds of formula I in purified isomeric form, e.g. comprising at least 90%, or preferably at least 95%, of a single isomeric form.

Where Agents of the Invention exist in isomeric form as aforesaid, individual isomers may be obtained in conventional manner, e.g. employing optically active starting materials or by separation of initially obtained mixtures, for example using conventional chromatographic techniques.

The Agents of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may be prepared by processes as described below

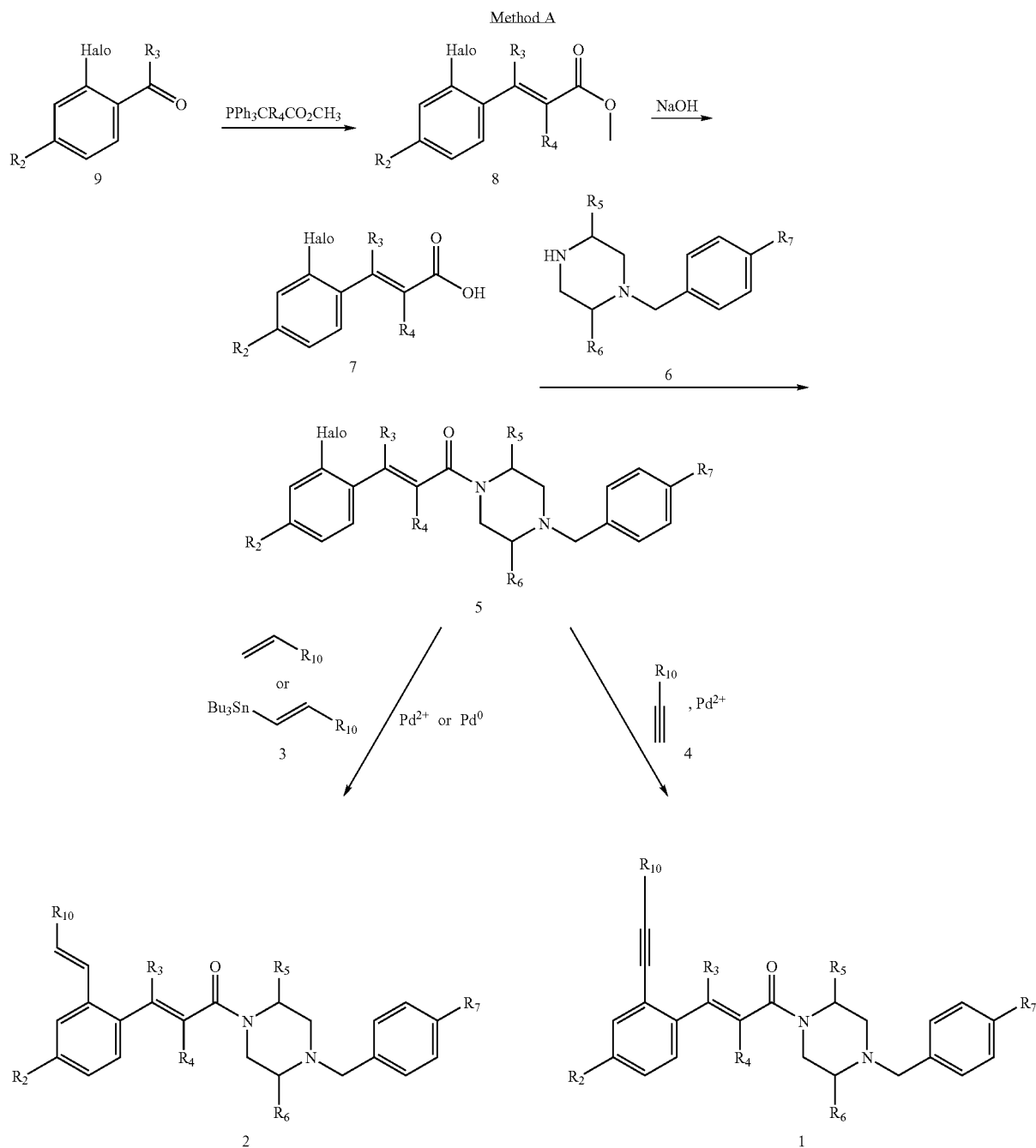
A compound of formula 1 may be prepared by coupling a compound of formula 4
4
With a compound of formula 5
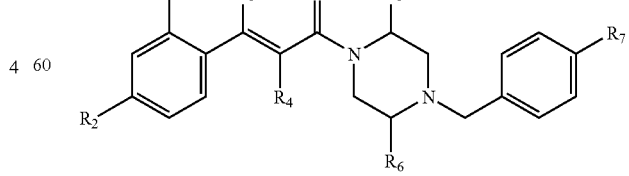
5
where in the symbols are as defined above.

For example in the presence of a suitable catalyst for example palladium acetate in an inert solvent such as diglyme and advantageously. at an elevated temperature e.g. 140° C.

A compound of formula 2 may be prepared by coupling a compound of formula 3

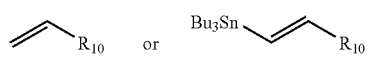

3

With a compound of formula 5.

For example in the presence of a suitable catalyst for example palladium acetate in an inert solvent such as diglyme and advantageously at an elevated temperature e.g. 140° C.

Compounds of formula 5 may be prepared by treating a compound of formula 6

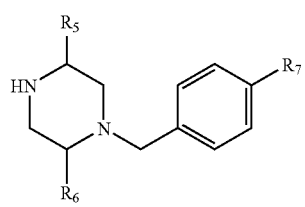

6 with a compound of formula 7

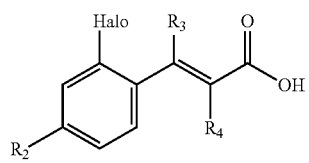

7 for example in an inert solvent such as dichloromethane.

A compound of formula 7 may be prepared by treating a compound of formula 9

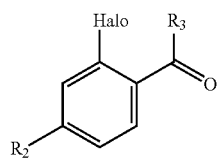

9

With a compound of formula $PPh_3CR_4CO_2CH_3$ for example in an inert solvent such as toluene and advantageously at an elevated temperature e.g. reflux, to yield a compound of formula 8

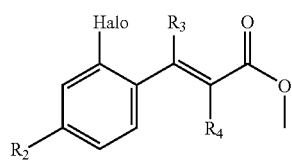

8

Which is hydrolysed to give a compound of formula 7. For example in an inert solvent such as methanol and treatment with a base e.g. sodium hydroxide.

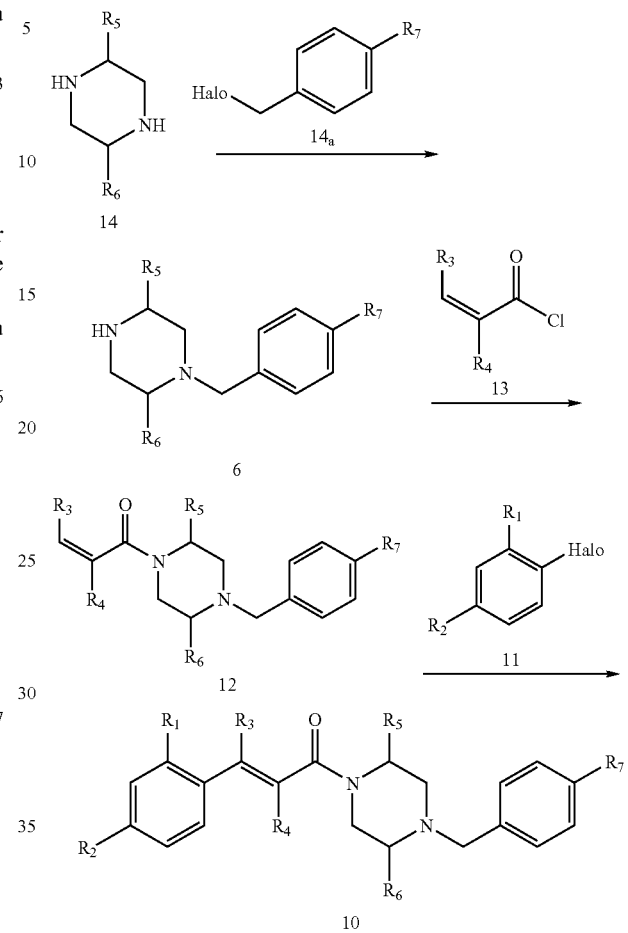

Method B

A compound of formula 10 may be prepared by coupling a compound of formula 11 with a compound of formula 12

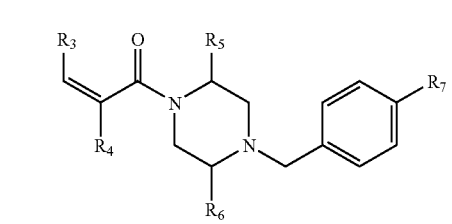

12

For example in the presence of a catalyst e.g. palladium acetate and a base such as triethylamine and preferably in an inert solvent such as DMF A compound of formula 12 may be prepared by coupling a compound of formula 13
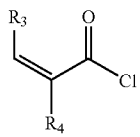
with a compound of formula 6
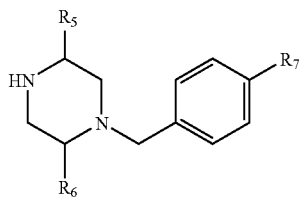
A compound of formula 6 may be prepared by coupling a compound of formula 14$_a$
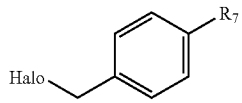
with a compound of formula 14
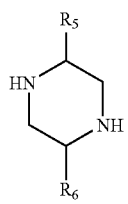
For example by the procedure set out in WO 0236581.
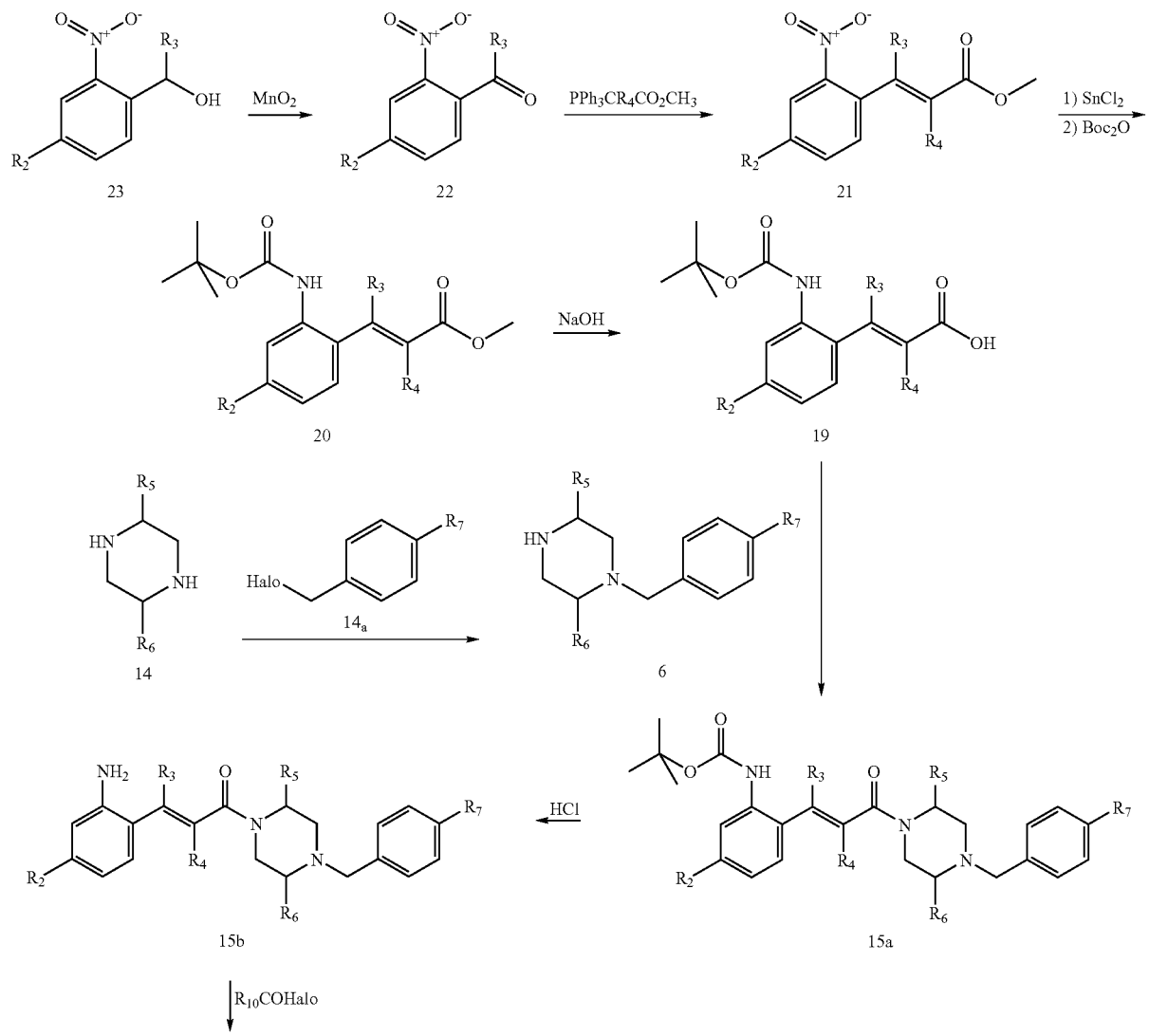

-continued

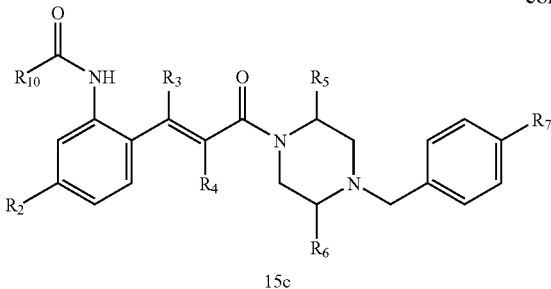

15c

A compound of formula 15c may be prepared by coupling a compound of formula 15b

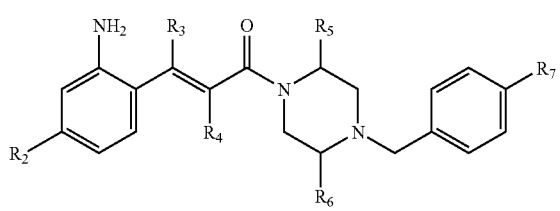

15b with a suitable compound for example a carboxylic acid or an activated carboxylic acid e.g. $R_{10}COCl$ or $R_{10}COOH$ in the presence of a suitable coupling agent e.g. $NH_2$ or EDCl.HCl advantageously in an inert solvent such as dichloromethane.

A compound of formula 15b may be prepared by deprotecting the amino group of a compound of formula 15a

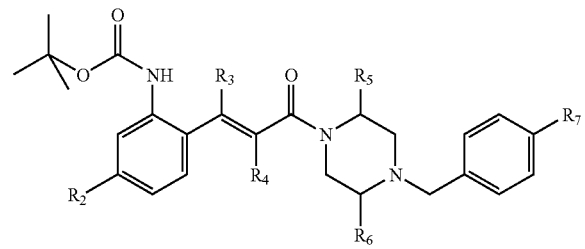

15a for example under acidic conditions e.g. with HCl

A compound of formula 15a may be prepared by coupling a compound of formula 19

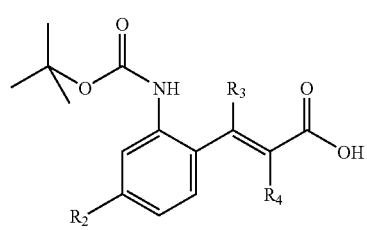

19 with a compound of formula 6

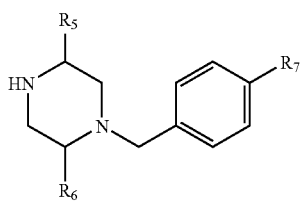

6 for example in the presence of a suitable coupling agent e.g. EDCl.HCl in an inert solvent such as dichloromethane.

A compound of formula 6 may be prepared by coupling a compound of formula $14_a$

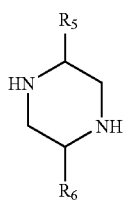

$14_a$ with a compound of formula 14

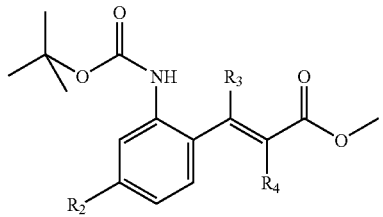

14

For example by the procedure set out in WO 0236581.

A compound of formula 19 may be prepared by hydrolysis of a compound of formula 20

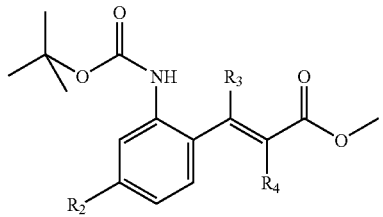

20 for example in the presence of sodium hydroxide in a suitable solvent such as methanol advantageously at an increased temperature e.g. 50° C.

A compound of formula 20 may be prepared by the reduction followed by the treatment with Boc$_2$O of a compound of formula 21

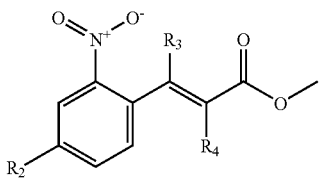
21 for example reduction with a suitable reducing agent e.g. SnCl2 in an inert solvent such as ethanol in the presence of an acid such as HCl. Then treatment with Ac$_2$O in an inert solvent such as THF and advantageously at an increased temperature e.g. reflux.

A compound of formula 21 may be prepared by treating a compound of formula 22

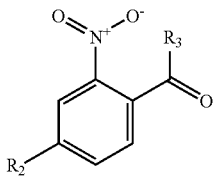
22 with PPh$_3$CR$_4$CO$_2$CH$_3$ in an inert solvent such as toluene and advantageously at an increased temperature e.g. reflux.

A compound of formula 22 may be prepared by the oxidation of a compound of formula 23

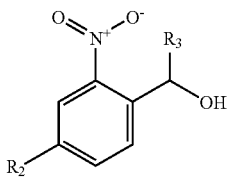
23 for example in the presence of a suitable oxidizing agent such as MnO$_2$

In a further embodiment the invention also provides a process for the preparation of a compound of formula I, II or III.

A). A process whereby a compound of formula I, II or III is prepared by coupling a compound of formula 4

4

With a compound of formula 5

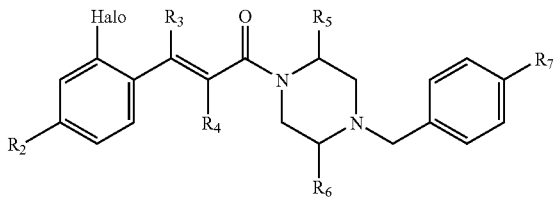
5 wherein the symbols are as defined above.

For example in the presence of a suitable catalyst for example palladium acetate in an inert solvent such as diglyme and advantageously at an elevated temperature e.g. 140° C.

B). A process where by a compound of formula I, II or III is prepared by coupling a compound of formula 3

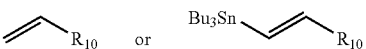
3

With a compound of formula 5.

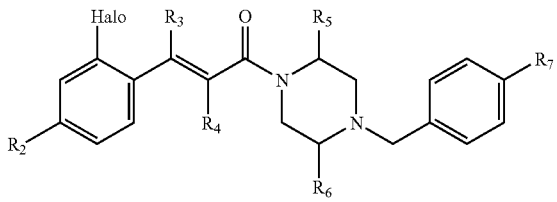
5

For example in the presence of a suitable catalyst for example palladium acetate in an inert solvent such as diglyme and advantageously at an elevated temperature e.g. 140° C.

C). A Process where by a compound of formula I, II or III may be prepared by coupling a compound of formula 11

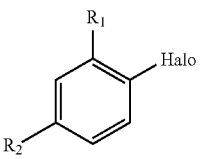
11 with a compound of formula 12

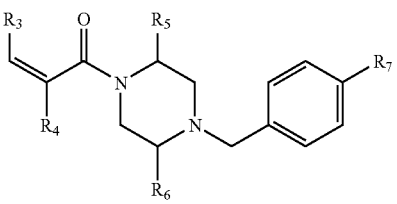
12

For example in the presence of a catalyst e.g. palladium acetate and a base such as triethylamine and preferably in an inert solvent such as DMF D). A Process whereby a compound of formula I is prepared by coupling a compound of formula 19

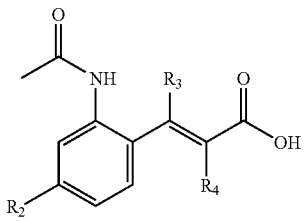

with a compound of formula 6

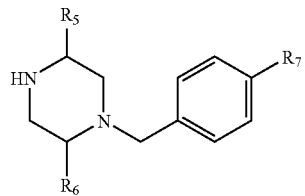

for example in the presence of a suitable coupling agent e.g. EDCl.HCl in an inert solvent such as dichloromethane.

Experimental Section

Abbreviations:

| | |
|---|---|
| Ac$_2$O: | Acetic anhydride |
| BOC: | tert.-Butyloxycarbonyl |
| DCC: | Dicyclohexyl-carbodiimide |
| DCM: | Dichloromethane |
| DMAP: | Dimethyl-pyridin-4-yl-amine |
| DME: | 1,2-Dimethoxyethane |
| DMF: | N,N-Dimethyl formamide |
| EDCl: | (3-Dimethylamino-propyl)-ethyl-carbodiimide hydrochloride |
| HCl: | Hydrochloric acid |
| HOBT: | Benzotriazol-1-ol |
| NaOH: | Sodium hydroxide |
| NEt$_3$: | Triethylamine |
| TBME | tert.-Butyl-methylether |
| TFA: | Trifluoro-acetic acid |
| THF: | Tetrahydrofuran |

EXAMPLES:

Example 1

N-(5-Chloro-2-[(E)-3-[(R)-4-(4fluorobenzyl)-2-methylpiperazin-1-yl]-3-oxopropenyl]phenyl)-N'-cyanoguanidine a) (E)-3-(2-tert-Butoxycarbonylamino-4-chlorophenyl)-acrylic acid methyl ester

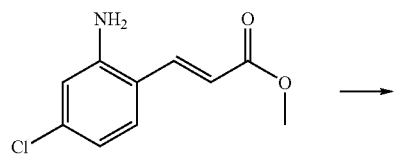

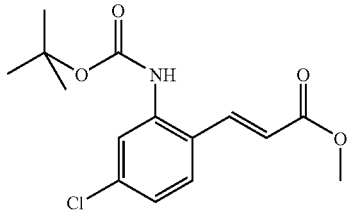

(E)-3-(2-Amino-4-chlorophenyl)-acrylic acid methyl ester (Carling, Robert W.; et al. J. Med. Chem. (1993), 36(22), 3397-408) (3.3 g, 15.6 mmol) in THF (63 ml) was combined with (BOC)$_2$O (6.8 g, 31.2 mmol) and refluxed for 4 hours. THF was evaporated and a second portion of (BOC)$_2$O added (6.8 g, 31.2 mmol). The mixture was heated to 100° C. for 18 hours. Recrystallisation from TBME/hexanes rendered the title compound as colorless crystals (4.6 g; 94%).

1H-NMR (400 MHz; DMSO-d6): 1.46 (s, 9H); 3.72 (s, 3H); 6.58 (d, 1H); 7.25 (dd, 1H); 7.47 (d, 1H); 7.72 (d, 1H); 7.82 (d, 1H); 9.33 (bs, 1H, NH).

MS (m/z) EI: 311 (M+, 20); 238 (10); 255 (20); 180 (70); 152 (65).

b) (E)-3-(2-tert-Butoxycarbonylamino-4-chlorophenyl)-acrylic acid

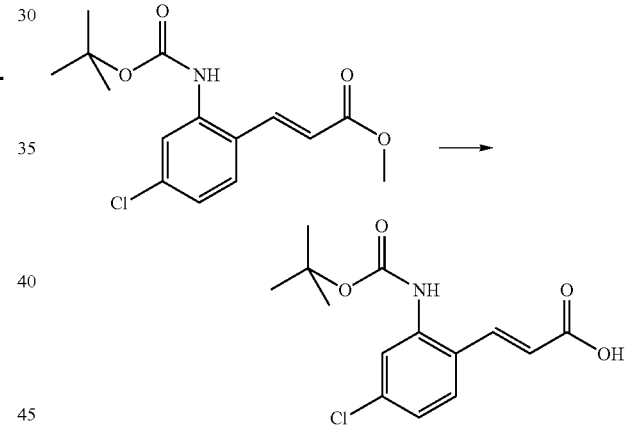

(E)-3-(2-tert-Butoxycarbonylamino-4chlorophenyl)-acrylic acid methyl ester (4.6 g, 14.7 mmol) was dissolved in MeOH (300 ml), 2N NaOH (11 ml, 22 mmol) and water (147 ml) added and stirred at 50° C. for 1 hour. The clear reaction mixture was concentrated to ~150 ml, acidified to pH 3 and extracted twice with TBME. The combined organic phases were dried over Na$_2$SO$_4$ and evaporated to dryness to yield the title acid as colorless crystals (3.8 g, 87%).

c) 5-Chloro-2-[(E)-3-[(R)-4-(4-fluorobenzyl)-2-methylpiperazin-1-yl]-3-oxopropenyl]phenyl)-carbamic acid tert-butyl ester

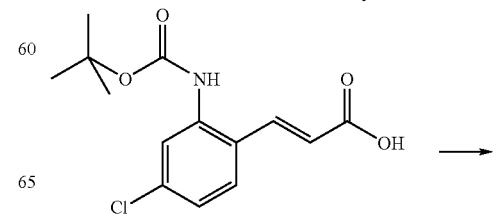

-continued

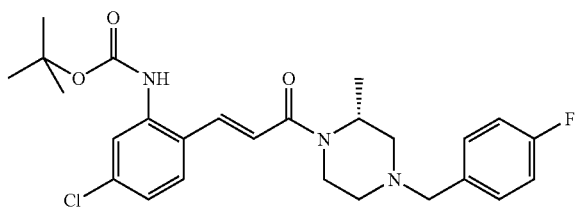

(E)-3-(2-tert-Butoxycarbonylamino-4-chlorophenyl)-acrylic acid (743 mg, 2.5 mmol) and (R)-1-(4-fluorobenzyl)-3-methylpiperazine (Hilger, Christoph-Stephan et al., WO 0236581) (520 mg, 2.5 mmol) were dissolved in CH$_2$Cl$_2$ (25 ml), combined with EDCl.HCl (480 mg, 2.5 mmol) and stirred at room temperature for 6 hours. The reaction mixture was purified via chromatography (SiO$_2$, EtOAc/hexanes 25/75 to 35/65) to yield the title compound as colorless foam (1.0 g; 81%)

1H-NMR (400 MHz; DMSO-d6): 1.26 (d, 3H); 1.45 (s, 9H); 1.98 (dt, 1H); 2.13 (dd, 1H); 2.67 (d, 1H); 2.82 (d, 1H); 3.13 (bt, 1H); 3.43 (d, 1H); 3.52 (d 1H); 4.13 (bd, 1H); 4.53 (bs, 1H); 7.02 (d, 1H); 7.12 (dd, 2H); 7.19 (dd, 1H); 7.35 (dd, 2H); 7.45 (d, 1H); 7.60 (d, 1H); 7.73 (d, 1H); 8.81 (bs, 1H).

MS (m/z) ES+: 488.2 (MH+, 100).

d) (E)-3-(2-Amino-4-chlorophenyl)-1-[(R)-4-(4-fluorobenzyl)-2-methylpiperazin-1-yl]-propenone

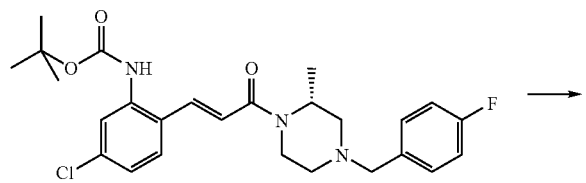

5-Chloro-2-[(E)-3-[(R)-4-(4-fluorobenzyl)-2-methylpiperazin-1-yl]-3-oxopropenyl]-phenyl)-carbamic acid tert-butyl ester (1.0 g, 2.05 mmol) was dissolved in EtOH (4 ml) and HClconc (4 ml) and stirred for 30 minutes at room temperature. The reaction mixture was treated with a saturated solution of Na$_2$CO$_3$ and extracted with EtOAc three times. The combined organic phases were dried over Na$_2$SO$_4$ and evaporated to dryness to yield the title compound as yellow crystals (630 mg, 80%).

1H-NMR (400 MHz; DMSO-d6): 1.25 (bs, 3H); 1.95 (bs, 1H); 2.10 (bs, 1H); 2.68 (d 1H); 2.83 (d, 1H); 3.10 (bs, 1H); 3.43 (d, 1H); 3.53 (d, 1H); 4.20 (bd, 1H); 4.60 (bd, 1H); 5.75 (s, 2H, NH2); 6.55 (dd, 1H); 6.73 (d, 1H); 6.97 (d, 1H); 7.18 (dd, 2H); 7.39 (dd, 2H); 7.53 (d, 1H); 7.63 (d, 1H).

MS (m/z) ES+: 388.2 (MH+, 100).

e) N-(5-Chloro-2-[(E)-3-[(R)-4-(4-fluorobenzyl)-2-methylpiperazin-1-yl]-3-oxopropenyl]phenyl)-N'-cyanoguanidine

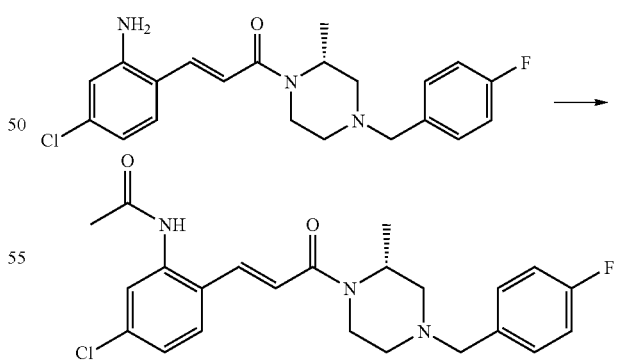

(E)-3-(2-Amino-4-chlorophenyl)-1-[(R)-4-(4-fluorobenzyl)-2-methylpiperazin-1-yl]-propenone (116 mg, 0.3 mmol) and NaN(CN)$_2$ (178 mg, 2 mmol) were heated to reflux in ethoxyethanol (3 ml). 2N HCl (1 ml) was added dropwise within 5 minutes and the reaction mixture refluxed for another 5 minutes. The reaction mixture was poured on a saturated solution of Na$_2$CO$_3$ and extracted with EtOAc twice. The combined organic phases were dried over Na$_2$SO$_4$, evaporated to dryness and purified via chromatography (SiO$_2$, EtOAc/MeOH/NH$_3$conc 95/4.5/0.5) to yield the title compound as a solid (40 mg, 30%).

1H-NMR (400 MHz; DMSO-d6): 1.28 (bs, 3H); 1.99 (bs, 1H); 2.10 (bs, 1H); 2.68 (d, 1H); 2.85 (d, 1H); 3.00 (bs, 1H); 3.43 (d, 1H); 3.55 (d, 1H); 4.20 (bd, 1H); 4.60 (bd, 1H); 5.78 (s, 1H, NH); 7.16-7.28 (m, 4H); 7.33-7.42 (m, 2H); 7.47 (d, 1H); 7.55 (d, 1H); 7.93 (d, 1H); 8.98 (s, 2H, NH2).

MS (m/z) ES+: 455.2 (MH+, 100).
[α]D=−66.2°; c=0.5 in MeOH.

Example 2

N-(5-Chloro-2-[(E)-3-[(R)-4-(4-fluorobenzyl)-2-methylpiperazin-1-yl]-3-oxopropenyl]phenyl)-acetamide (E)-3-(2-Amino-4-chlorophenyl)-1-[(R)-4-(4-fluorobenzyl)-2-methylpiperazin-1-yl]-propenone (78 mg, 0.2 mmol), NEt$_3$ (202 mg, 2 mmol) and Ac$_2$O (204 mg, 2 mmol) were refluxed in THF (4 ml) for 8 hours. The reaction mixture was evaporated to dryness and purified via chromatography (SiO$_2$, EtOAc/MeOH/NH$_3$conc 97/2.7/0.3) to yield the title compound as a white foam (60 mg. 70%).

1H-NMR (400 MHz; DMSO-d6; 100° C.): 1.28 (bs, 3H); 1.97 (bs, 1H); 2.10 (bs, 1H); 2.11 (s, 3H); 2.68 (d, 1H); 2.85 (d, 1H); 2.98 (bs, 1H); 3.43 (d, 1H); 3.55 (d, 1H); 4.20 (bd, 1H); 4.58 (bd, 1H); 7.17-7.22 (m, 3H); 7.30 (dd, 1H); 7.39 (d, 1H); 7.40 (d, 1H); 7.59 (d, 1H); 7.65 (d, 1H); 7.93 (d, 1H); 9.92 (s, 1H, NH).

MS (m/z) ES+: 430.2 (MH+, 100).

[α]D=−61.0°; c=0.5 in MeOH.

Example 3

N-(5-Chloro-2-[(E)-3-[(S)-4-(4-fluorobenzyl)-2-methylpiperazin-1-yl]-3-oxopropenyl]phenyl)-acetamide

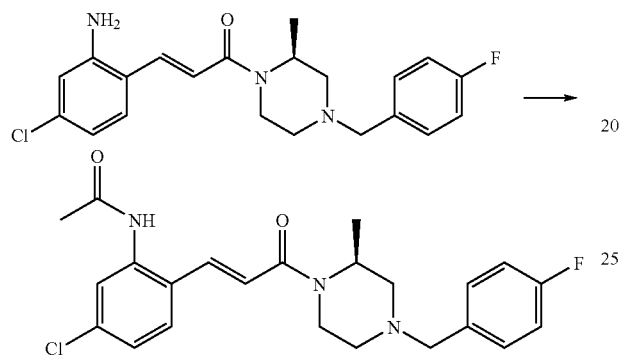

(E)-3-(2-Amino-4-chlorophenyl)-1-[(S)-4-(4-fluorobenzyl)-2-methylpiperazin-1-yl]-propenone (prepared in analogy to the R-enantiomer above) (78 mg, 0.2 mmol), NEt$_3$ (202 mg, 2 mmol) and Ac$_2$O (204 mg, 2 mmol) were refluxed in THF (4 ml) for 8 hours. The reaction mixture was evaporated to dryness and purified via chromatography (SiO$_2$, EtOAc/MeOH/NH$_3$conc 97/2.7/0.3) to yield the title compound as a white foam (50 mg. 58%).

1H-NMR (400 MHz; DMSO-d6; 120° C.): 1.30 (d, 3H); 2.06 (dt, 1H); 2.10 (s, 3H); 2.20 (dd, 1H); 2.70 (dd, 1H); 2.85 (dd, 1H); 3.20 (dt, 1H); 3.48 (d, 1H); 3.56 (d, 1H); 4.15 (bd, 1H); 4.55 (bs, 1H); 7.01 (d, 1H); 7.11 (dd, 2H); 7.23 (dd, 1H); 7.36 (dd, 2H); 7.59 (d, 1H); 7.60 (d, 1H); 7.75 (d, 1H); 9.38 (bs, 1H, NH).

MS (m/z) ES+: 430.2 (MH+, 100).

[α]D=+56.4°; c=0.5 in MeOH.

Example 4

(5-Chloro-2-[(E)-3-[(R)-4-(4-fluorobenzyl)-2-methylpiperazin-1-yl]-3-oxopropenyl]-phenyl)-urea

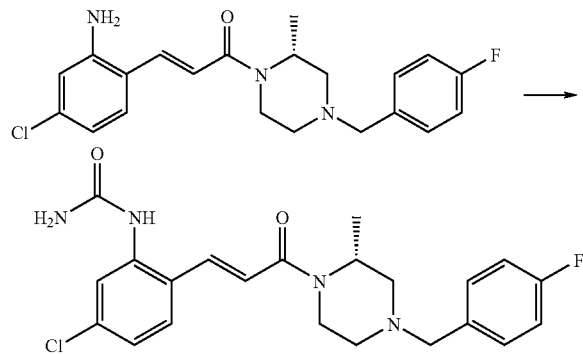

(E)-3-(2-Amino-4-chlorophenyl)-1-[(R)-4-(4-fluorobenzyl)-2-methylpiperazin-1-yl]-propenone (100 mg, 0.26 mmol) and NaOCN (34 mg, 0.504 mmol) were stirred in HOAC (5 ml) and water (10 ml) for 3 hours at room temperature. The reaction mixture was poured on 1N NaOH and extracted with EtOAc twice. The combined organic phases were dried over Na$_2$SO$_4$, evaporated to dryness and purified via chromatography (SiO$_2$, EtOAc/MeOH/NH$_3$conc 95/4.5/0.5) to yield the title compound as colorless crystals (70 mg, 63%).

1H-NMR (400 MHz; DMSO-d6): 1.29 (bd, 3H); 1.85-2.20 (bm, 2H); 2.68 (d, 1H); 2.83 (d, 1H); 3.10 bm, 1H); 3.43 (bt, 1H); 3.53 (bt, 1H); 4.20 (bd, 1H); 4.60 (bd, 1H); 6.28 (s, 2H, NH2); 7.08 (dd, 1H); 7.12-7.21 (m, 3H); 7.38 (d, 1H); 7.40 (d, 1H); 7.68 (d, 1H); 7.77 (d, 1H); 8.00 (d, 1H); 8.40 (s, 1H).

MS (m/z) ES+: 431.2 (MH+, 100).

[α]D=−64.6°; c=0.5 in MeOH.

Example 5

(5-Chloro-2-[(E)-3-[(S)-4-(4-fluorobenzyl)-2-methylpiperazin-1-yl]-3-oxopropenyl]-phenyl)-urea

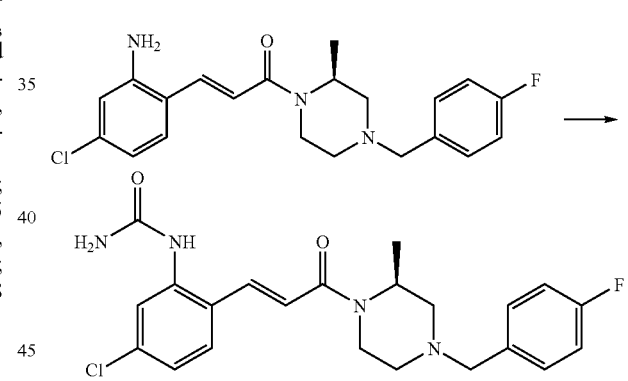

(E)-3-(2-Amino-4-chlorophenyl)-1-[(S)-4-(4-fluorobenzyl)-2-methylpiperazin-1-yl]-propenone (prepared in analogy to the R-enantiomer above) (100 mg, 0.26 mmol) and NaOCN (53 mg, 0.75 mmol) were stirred in HOAC (5 ml) and water (10 ml) for 1 hour at room temperature. The reaction mixture was poured on a saturated solution of Na$_2$CO$_3$ and extracted with EtOAc twice. The combined organic phases were dried over Na$_2$SO$_4$, evaporated to dryness and the solid purified via recrystallisation from TBME to render the title compound as colorless crystals (70 mg; 63%)

1H-NMR (400 MHz; DMSO-d6): 1.20 (bd, 3H); 1.85-2.20 (bm, 2H); 2.68 (d, 1H); 2.83 (d, 1H); 3.10 bm, 1H); 3.43 (bd, 1H); 3.53 (bd, 1H); 4.20 (bd, 1H); 4.60 (bd. 1H); 6.28 (s, 2H, NH2); 7.08 (dd, 1H); 7.12-7.21 (m, 3H); 7.38 (d, 1H); 7.40 (d, 1H); 7.65 (d, 1H); 7.75 (d, 1H); 7.98 (d, 1H); 8.38 (s, 1H).

MS (m/z) AP+: 431.2 (MH+, 90); 388.2 (50); 251.2 (100).

[α]D=+63.6°; c=0.5 in MeOH.

Example 6

N-(5-Chloro-2-[(E)-3-[(R)-4-(4-fluorobenzyl)-2-methylpiperazin-1-yl]-3-oxopropenyl]phenyl)-N,N-dimethylsulfamide

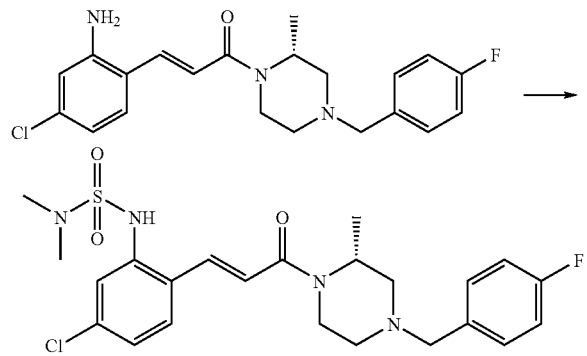

(E)-3-(2-Amino-4-chlorophenyl)-1-[(R)-4-(4-fluorobenzyl)-2-methylpiperazin-1-yl]-propenone (50 mg, 0.13 mmol) and N,N-dimethylsulfamoylchloride (83 µl, 0.77 mmol) were dissolved in pyridine (2 ml) and heated to 50° C. for 12 hours. The reaction mixture was evaporated to dryness, taken up in 2N NaOH and extracted with TBME twice. The combined organic phases were dried over $Na_2SO_4$, evaporated to dryness and purified via chromatography (acetone/hexanes 2/8 to 3/7) to yield the title compound (10 mg, 15%) as a yellow foam.

1H-NMR (400 MHz; DMSO-d6): 1.27 (bs, 3H); 1.98 (bs, 1H); 2.12 (bs, 1H); 2.67 (bd, 1H); 2.72 (s, 6H); 2.85, bd, 1H); 3.00 (bs, 1H); 3.44 (bd, 1H); 3.55 (bd, 1H); 4.22 (bs, 1H); 4.60 (bs, 1H); 7.15-7.25 (m, 3H); 7.32 (bs, 1H); 7.38-7.43 (m, 3H); 7.90 (d, 1H); 7.93 (bs, 1H); 9.80 (s, 1H, NH).

MS (m/z) ES+: 495.2 (MH+, 100).

Example 7

N-(5-Chloro-2-[(E)-3-[(R)-4-(4-fluorobenzyl)-2-methylpiperazin-1-yl]-3-oxopropenyl]phenyl)-methanesulfonamide

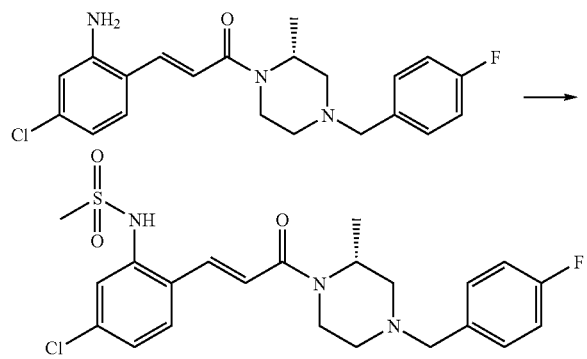

(E)-3-(2-Amino-4-chlorophenyl)-1-[(R)-4-(4-fluorobenzyl)-2-methylpiperazin-1-yl]-propenone (100 mg, 0.26 mmol) and $NEt_3$ (0.22 ml, 1.54 mmol) were dissolved in THF (4 ml) and treated with $MeSO_2Cl$ (60 µl, 0.77 mmol) under stirring for 10 minutes at room temperature. The reaction mixture was taken up in water and extracted twice with TBME. The combined organic phases were dried over $Na_2SO_4$, evaporated and purified via chromatography ($SiO_2$, TBME) to yield the disulfonamide intermediate (120 mg) as a colorless foam. The latter was dissolved in EtOH (4.5 ml) and treated with 2N NaOH (4.5 ml) for 2 minutes at room temperature. The mixture was poured on water and extracted with TBME three times. The combined organic phases were dried over $Na_2SO_4$, evaporated to dryness and purified via chromatography ($SiO_2$, TBME/MeOH 10/0 to TBME/MeOH 9/1) to yield the title compound as yellow foam (50 mg, 38%)

1H-NMR (400 MHz; DMSO-d6): 1.28 (bs, 3H); 1.98 (bs, 1H); 2.11 (bs, 1H); 2.68 (d, 1H); 2.85 (d, 1H); 3.03 (bs, 1H); 3.05 (s, 3H); 3.45 (d, 1H); 3.55 (d, 1H); 4.20 (bd, 1H); 4.60 (bd, 1H); 7.15-7.23 (m, 3H); 7.36-7.43 (m, 4H); 7.82 (d, 1H); 7.97 (d, 1H); 9.76 (bs, 1H, NH).

MS (m/z) ES+: 466.2 (MH+, 80).

$[\alpha]=-50.0°$; c=0.5 in MeOH.

Example 8

1-Acetyl-piperidine-4-carboxylic acid (5-chloro-2-{(E)-3-[(R)-4-(4-fluoro-benzyl)-2-methyl-piperazin-1-yl]-3-oxo-propenyl}-phenyl)-amide

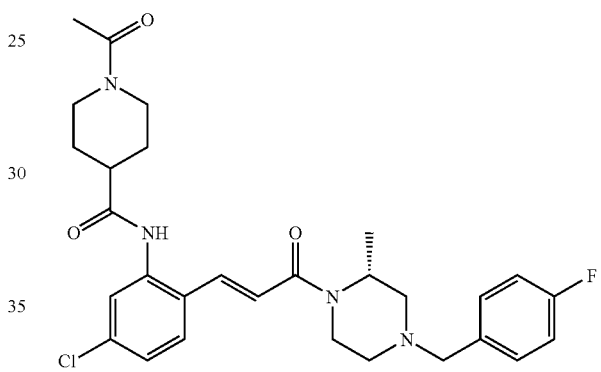

A mixture of 0.10 g (0.58 mmol) 1-Acetylpiperidine-4-carboxylic acid, 0.25 g (0.64 mmol) (E)-3(2-Amino-4-chlorophenyl)-1-[(R)-4-(4-fluorobenzyl)-2-methylpiperazin-1-yl]-propenone, 0.13 g (0.70 mmol) EDCl and 0.095 g (0.70 mmol) HOBt in 10 ml DMF was stirred at room temperature for 16 hours. The crude product obtained after addition of water and extraction into ethyl acetate was purified by RP-HPLC to yield 68 mg (22%) of the desired amide.

1H-NMR (400 MHZ, DMSO-d6): 1.24 (br s, 3H), 1.45 (qd, 1H), 1.59 (qd, 1H), 1.78-2.15 (m, 4H), 2.01 (s, 3H), 2.50-2.74 (m, 4H), 2.81 (d, 1H), 3.08 (td, 1H), 3.42 and 3.52 (AB-Sys., 2H), 3.87 (d, 1H), 4.05-4.70 (m, 3H), 7.16 (t, 2H), 7.17 (d, 1H), 7.28 (dd, 1H), 7.35 (dd, 2H), 7.50 (d, 1H), 7.58 (d, 1H), 7.89 (d, 1H), 9.84 (s, 1H).

MS (ESI+) m/z: 541 [M+H]+

Example 9

1-Methyl-1H-imidazole-4-sulfonic acid(5-Chloro-2-[(E)-3-[(R)-4-(4-fluoro-benzyl)-2-methyl-piperazin-1-yl]-3-oxo-propenyl]-phenyl)-amide

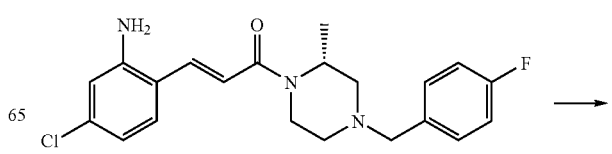

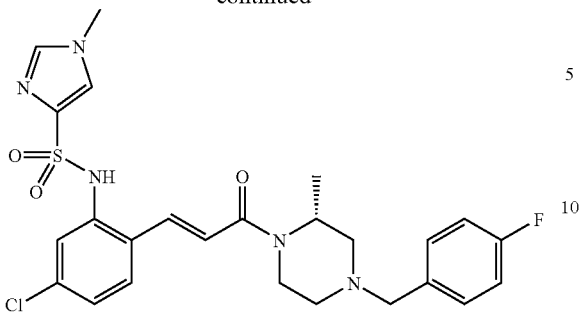

(E)-3-(2-Amino-4-chlorophenyl)-1-[(R)-4-(4-fluorobenzyl)-2-methylpiperazin-1-yl]-propenone (100 mg, 0.26 mmol) were dissolved in pyridine (6 ml) and treated under stirring at 0° C. with 1-Methylimidazol-4-sulfonylchlorid (51 mg 0.284 mmol). The reaction mixture is stirred overnight at room temperature, the solvent evaporated and the reaction mixture purified by preparative HPLC (Waters XTerra, H2O-Acetonitrile gradient 20-100%) Yield : 32 mg.

1H-NMR (400 MHz; DMSO-d6, 396 K): 1.28 (d, 3H); 2.02 (td, 2H); 2.18 (dd, 1H); 2.68 (bd, 1H); 3.16 (td, 1H); 3.48 (q, 2H); 3.66 (s, 3H); 4.1 (bd, 1H); 4.5 (bm ,1H); 6.92 (d, 1H); 7.08 (m, 2H); 7.18 (d, 1H); 7.32 (m, 3H); 7.55 (s, 1H);7.58(d, 1H); 7.64 (s, 1H); 7.66 (s, 1H); 9.8 (NH, 1H)

MS (m/z) ES+: 532.1 (MH+,100%).

Example 10

N-[5-(5-Chloro-2-[(E)-3-[(R)-4-(4-fluoro-benzyl)-2-methyl-piperazin-1-yl]-3-oxo-propenyl]-phenylsulfamoyl)-thiazol-2yl]-acetamide

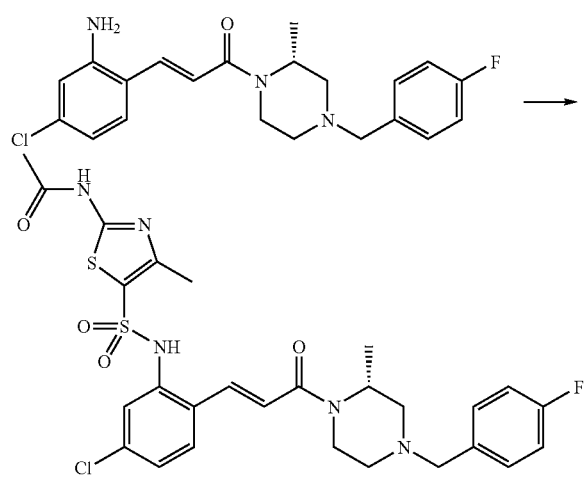

(E)-3-(2-Amino-4-chlorophenyl)-1-[(R)-4-(4-fluorobenzyl)-2-methylpiperazin-1-yl]-propenone (99.69 mg, 0.26 mmol) were dissolved in pyridine (6 ml) and treated under stirring at 0° C. with 2-Acetamido-4-methyl-5-thiazolsulfonylchloride (72 mg 0.283 mmol). The reaction mixture is stirred overnight at room temperature, the solvent evaporated and the reaction mixture purified by preparative HPLC (Waters XTerra, H2O-Acetonitrile gradient 20-100%).

Yield : 46 mg.

1H-NMR (400 MHz; DMSO-d6, 396): 1.28 (d, 3H); 2.02 (td, 2H); 2.14 (s, 3H); 2.18 (dd, 1H); 2.28 (s, 3H); 2.68 (bd, 1H); 2.82 (m, 1H, +H2O); 4.8 (q, 2H); 4.08 (bd, 1H); 4.48 (bm, 1H); 6.92 (d, 1H); 7.05 (m,2H); 7.12 (m, 1H); 7.2-7.4 (m, 3H); 7.6(d, 1H);7.77 (d, 1H)

MS (m/z) ES+: 606.02 (MH+).

Example 11

2-Oxo-imidazolidine-1-carboxylic acid (5-Chloro-2-[(E)-3-[(R)-4-(4-fluoro-benzyl)-2-methyl-piperazin-1-yl]-3-oxo-propenyl]-phenyl)-amide

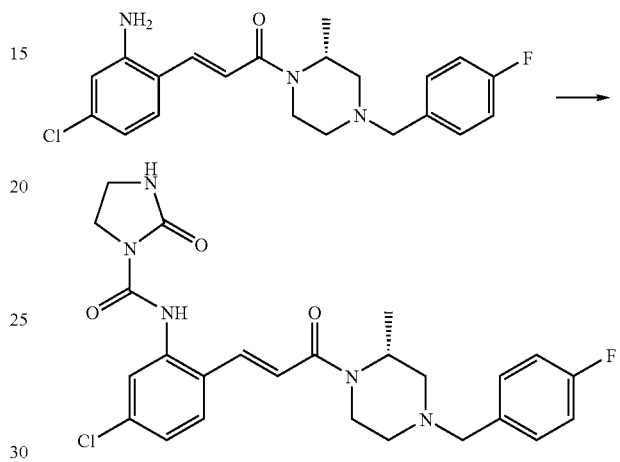

(E)-3-(2-Amino-4-chlorophenyl)-1-[(R)-4-(4-fluorobenzyl)-2-methylpiperazin-1-yl]-propenone (100.08 mg, 0.387 mmol) were dissolved in dichloromethane (5 ml) and treated under stirring with 2-Oxo-1-imidazolidinecarbonylchloride (89.8 mg, 0.580 mmol). The reaction mixture is stirred overnight at room temperature. The crystalline product formed is filtered, washed with dichloromethane and dried under in vacuo. Yield: 172 mg (88%). Melting point: 275-277° C. (uncorrected)

1H-NMR (400 MHz; DMSO-d6, 396[K]): 1.38 (d, 3H); 2.6 (bs, 1H); 2.78 (bs, 1H); 2.92 (m, 1H); 3.18 (bs, 1H); 3.41 (m, 3H); 3.8 (m, 2H); 3.98 (bd, 2H); 4.25 (d, 1H); 4,68 (bs, 1H ); 7.0 (d, 1H ); 7.12 (m, 3H); 7.46 (bs, 1H); 7.58 (m, 3H); 7,65 (d, 1H); 8,0 (d, 1H); 10.58 (bs, 1H ,NH).

MS (m/z) ES+: 500.2 (MH+, 58%); 173.1 (100%)

MS (m/z) ES−: 498.2 (M−H, 13%); 534.2 (100%, M+Cl−); 612.3 (8%, M+CF3CO2−)

Example 12

N-(4-Chloro-2-[(E)-3-[4-(4-fluorobenzyl)-2-methylpiperazin-1-yl]-3-oxopropenyl]-phenyl)-methylthio-N'-cyano thiourea

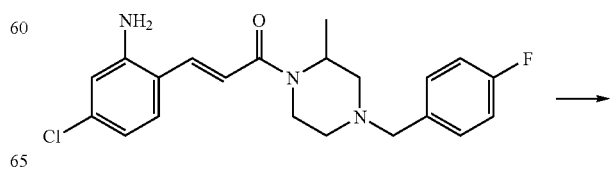

-continued

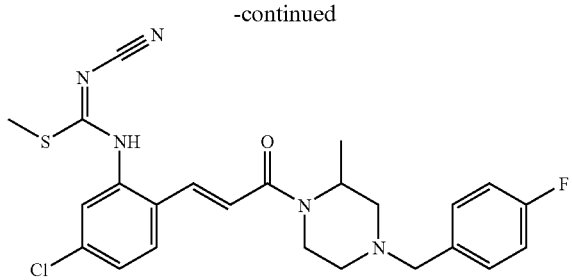

(E)-3-(2-Amino-4-chlorophenyl)-1-[4-(4-fluorobenzyl)-2-methylpiperazin-1-yl]-propenone (200 mg, 0.51 mmol)(racemic; prepared in analogy to the R-enantiomer above from racemic 1-(4-fluorobenzyl)-3-methylpiperazin (Bolos, Jordi et al. J. Med. Chem. (1996), 39(15), 2962-2970) in THF (5 ml) was treated under stirring with NaH (55% in mineral oil, 40 mg, 0.8 mmol) at room temperature followed 40 minutes later by dimethyl-N-cyanodithioiminocarbonat (113 mg, 0.77 mol). The reaction mixture was refluxed under argon for 12 hours, poured on NH4Cl-solution and extracted with TBME three times. The combined organic phases were dried over $Na_2SO_4$, evaporated to dryness and purified via chromatography ($SiO_2$, TBME/MeOH 100/0 to 98/2) to yield the title compound as a foam (150 mg, 60%).

1H-NMR (400 MHz; DMSO-d6): 1.27 (bs, 3H); 1.98 (bs, 1H); 2.12 (bs, 1H); 2.66 (bs, 3H); 2.68 (bd, 1H); 2.84 (bd, 1H); 3,00 (bs, 1H); 3.45 (d, 1H); 3.55 (bd, 1H); 4.22 (bs, 1H); 4.55 (bs, 1H); 7.18 (t, 2H); 7.28 (d, 1H); 7.36-7.53 (m, 5H); 8.03 (d, 1H); 10.42 (bs, 1H, NH).

MS (m/z) ES+: 486.3 (M+, 100).

Example 13

N-(4-Chloro-2-[(E)-3-[4-(4-fluorobenzyl)-2-methylpiperazin-1-yl]-3-oxopropenyl]-phenyl)-sulfonylurea

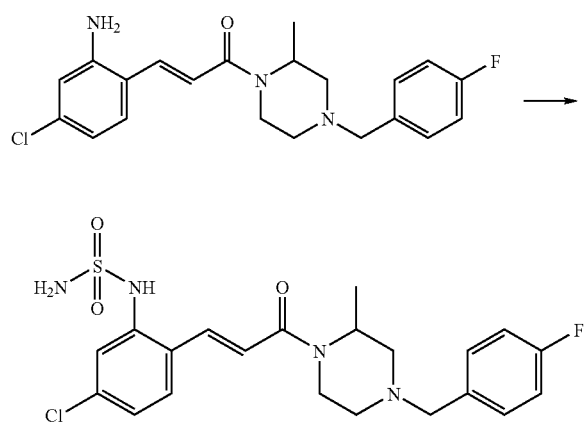

Formic acid (10 μl, 0.26 mmol; from a larger batch dried previously with B2O3 for 2 hours) in toluene (0.5 ml) was added dropwise to a solution of chlorosulfonyl-isocyanat (22 μl, 0.26 mmol) in toluene (0.25 ml) under stirring. The mixture was left for 12 hours, heated to 40° C. for 5 minutes, then cooled to 0° C. before (E)-3-(2-amino-4-chlorophenyl)-1-[4-(4-fluorobenzyl)-2-methylpiperazin-1-yl]-propenone (200 mg, 0.51 mmol)(racemic; prepared in analogy to the R-enantiomer above from racemic 1-(4-fluorobenzyl)-3-methylpiperazin (Bolos, Jordi et al. J. Med. Chem. (1996), 39(15), 2962-2970) was added in toluene (0.5 ml) followed by 1N NaOH (0.26 ml; 0.26 mmol). The reaction mixture was stirred at 0° C. for 1 hour, poured on water and extracted with TBME three times. The combined organic phases were dried over $Na_2SO_4$, evaporated and purified via chromatography (preparative HPLC, XTerra, RP18, 7 μm, acetonitrile/water followed by $SiO_2$ on EtOAc/hexanes 8/2 to 10/0) to yield a colorless glass, which was recrystallised from TBME/hexanes to deliver the title compound as colorless crystals (19 mg; 16%).

1H-NMR (400 MHz; DMSO-d6): 1.28 (bs, 3H); 1.88-2.16 (bm, 2H); 2.68 (d, 1H); 2.83 (d, 1H); 2.97 (bs, 1H); 3.43 (d, 1H); 3.55 (d, 1H); 4.20 (bd, 1H); 4.55 (bd, 1H); 7.13 (d, 1H); 7.16 (bs, 2H, NH2); 7.18 (t, 2H); 7.28 (d, 1H); 7.39 (dd, 2H); 7.53 (d, 1H); 7.81 (d, 1H); 7.90 (d, 1H); 9.30 (bs, 1H, NH).

MS (m/z) ES+: 467.2 (MH+, 100).

Example 14

(5-Chloro-2-[(E)-3-[(2R,5S)-4-(4-fluorobenzyl)-2,5-dimethylpiperazin-1-yl]-3-oxopropenyl]-phenyl)-urea a) (5-Chloro-2-[(E)-3-[(2R,5S)-4-(4-fluorobenzyl)-2,5-dimethylpiperazin-1-yl]-3-oxopropenyl]-phenyl)-carbamic acid tert-butyl ester

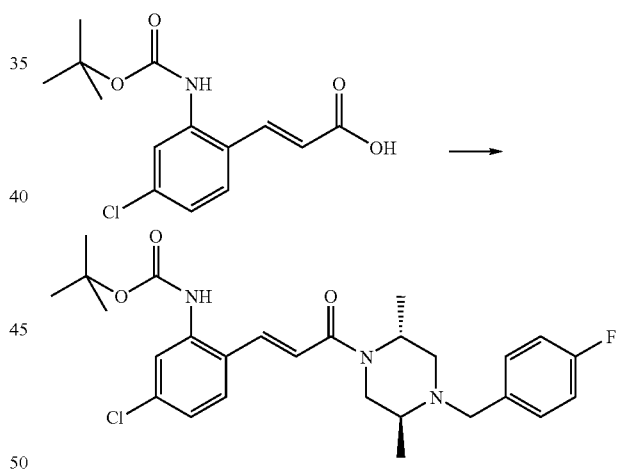

(E)-3-(2-tert-Butoxycarbonylamino-4-chlorophenyl)-acrylic acid (595 mg, 2.0 mmol) and (2S,5R)-1-(4-fluorobenzyl)-2,5-dimethylpiperazine (Mavunkel, Babu J. et al., WO 00/71535) (445 mg, 2.0 mmol) were dissolved in $CH_2Cl_2$, combined with EDCl.HCl (384 mg, 2.0 mmol) and stirred for 3 hours at room temperature. The reaction mixture was purified via chromatography ($SiO_2$, EtOAc/hexanes 2/8) to yield the title compound as colorless foam (830 mg, 81%).

1H-NMR (400 MHz; DMSO-d6): 0.95 (bs, 3H); 1.25 (bs, 3H); 1.50 (s, 9H); 2.30 (m, 1H); 2.55-2.80 (bm, 2H); 3.05 (bs, 1H); 3.45 (bd, 1H); 3.64 (bd, 1H); 4.05 (bs, 1H); 4.55 (bs, 1H); 7.09-7.20 (m, 3H); 7.15 (dd, 1H); 7.39-7.42 (m, 2H); 7.45 (bs, 1H); 7.66 (d, 1H); 7.89 (d, 1H); 9.25 (bs, 1H, NH).

MS (m/z) ES+: 502.3 (MH+, 100); 446.2 (90).

b) (E)-3-(2-Amino-4-chlorophenyl)-1-[(2R,5S)-4-(4-fluorobenzyl)-2,5-dimethylpiperazin-1-yl]-propenone

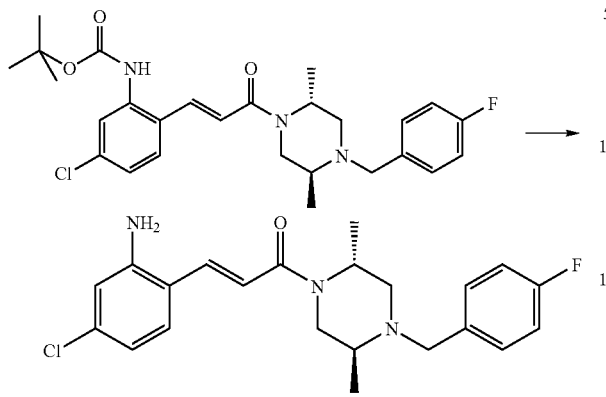

(5-Chloro-2-[(E)-3-[(2R,5S)-4-(4-fluorobenzyl)-2,5-dimethylpiperazin-1-yl]-3-oxopropenyl]-phenyl)-carbamic acid tert-butyl ester (830 mg, 1.65 mmol) was dissolved in EtOH (7 ml) and treated with HClconc (7 ml) for 30 minutes at room temperature. The reaction mixture was poured on a saturated solution of Na$_2$CO$_3$ and extracted with EtOAc twice. The combined organic phases were dried over Na$_2$SO$_4$, evaporated to dryness and purified via chromatography (SiO$_2$, EtOAc/hexanes 7/3 to 6/4) to yield the title compound as a foam (600 mg, 90%).

1H-NMR (400 MHz; DMSO-d6): 0.95 (bd, 3H); 1.23 (bd, 3H); 2.25 (d, 1H); 2.55-2.70 (m, 2H); 3.03 (bs, 1H); 3.45 (d, 1H); 3.63 (d, 1H); 4.05 bs, 1H); 4.55 (bs, 1H); 5.73 (s, 2H, NH2); 6.57 (dd, 1H); 6.75 (d, 1H); 6.97 (d, 1H); 7.18 (t, 2H); 7.41 (dd, 2H); 7.53 (d, 1H); 7.68 (d, 1H).

MS (m/z) ES+: 402.2 (MH+, 100).
[α]D=−100.2°; c=1.0 in MeOH.

Example 15

(5-Chloro-2-[(E)-3-[(2R,5S)-4-(4-fluorobenzyl)-2,5-dimethylpiperazin-1-yl]-3-oxopropenyl]-phenyl)-urea

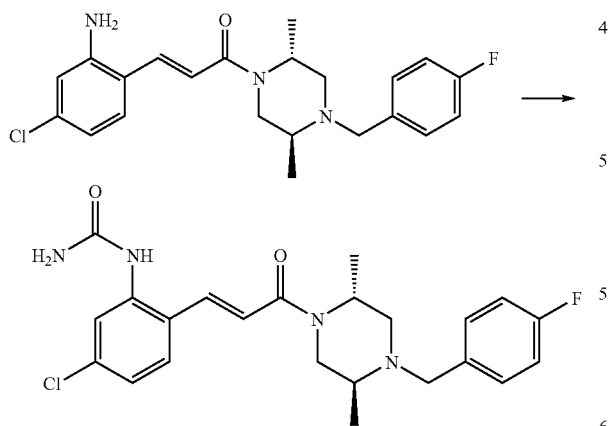

(E)-3-(2-Amino-4-chlorophenyl)-1-[(2R,5S)-4-(4-fluorobenzyl)-2,5-dimethylpipera-zin-1-yl]-propenone (101 mg, 0.25 mmol) and NaOCN (34 mg, 0.504 mmol) were stirred in HOAc (5 ml) and water (10 ml) for 3 hours at room temperature. The reaction mixture was poured on saturated Na$_2$CO$_3$ solution and extracted with EtOAc twice. The combined organic phases were dried over Na$_2$SO$_4$, evaporated to dryness and purified via chromatography (SiO$_2$, TBME/MeOH/NH$_3$conc 97/2.7/0.5) to yield the title compound as colorless crystals (60 mg, 54%).

1H-NMR (400 MHz; DMSO-d6; 120° C.): 1.01 (d, 3H); 1.30 (d, 3H); 2.33 (dd, 1H); 2.78 (dd, 1H); 3.05 (m, 1H); 3.41 (dd, 1H); 3.51 (d, 1H); 3.66 (d, 1H); 4.00 (d, 1H); 4.52 (bm, 1H); 5.86 (bs, 2H, NH2); 7.00 (d, 1H); 7.05-7.14 (m, 3H); 7.41 (dd, 2H); 7.66 (d, 1H); 7.68 (d, 1H); 7.93 (d, 1H); 8.07 (bs, 1H, NH).

MS (m/z) ESI+: 445.2 (MH+, 100).
[α]D=−85.4°; c=0.5 in MeOH.

Example 16

N-(5-Chloro-2-[(E)-3-[(2R,5S)-4-(4-fluorobenzyl)-2,5-dimethyl-piperazin-1-yl]-3-oxopropenyl]-phenyl)-acetamide

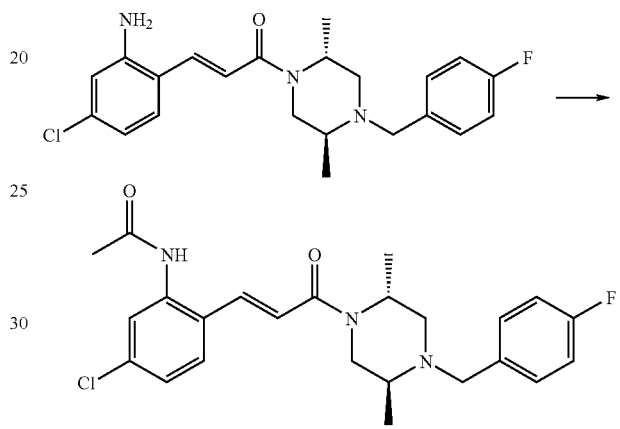

(E)-3-(2-Amino-4-chlorophenyl)-1-[(2R,5S)-4-(4-fluorobenzyl)-2,5-dimethylpipera-zin-1-yl]-propenone (101 mg, 0.25 mmol), NEt$_3$ (252 mg, 2.5 mmol) and Ac$_2$O (225 mg, 2.5 mmol) were refluxed in THF (5 ml) for 5 hours. The reaction mixture was evaporated to dryness and purified via chromatography (SiO$_2$, TBME/MeOH/NH$_3$ 97/2.7/0.3) to yield the title compound as a yellowish foam (100 mg, 90%).

1H-NMR (400 MHz; DMSO-d6): 0.95 (bs, 3H); 1.28 (bs 3H); 2.12 (s, 3H); 2.28 (d, 1H); 2.64 (bs, 1H); 3.05 (bs, 1H); 3.30 (bs, 1H); 3.50 (d, 1H); 3.65 (d, 1H); 4.05 (bs, 1H); 4.60 (bs, 1H); 7.18 (t, 3H); 7.30 (dd, 1H); 7.42 (dd, 2H); 7.60 (d, 1H); 7.68 (d, 1H); 7.94 (d, 1H); 9.92 (s, 1H, NH).

MS (m/z) ES+: 444.2 (MH+, 100).
[α]D=−87.0°; c=0.5 in MeOH.

Example 17

N-(5-Chloro-2-[(E)-3-[(2S,5R)-4-(4-fluorobenzyl)-2,5-dimethyl-piperazin-1-yl]-3-oxopropenyl]-phenyl)-acetamide a) (5-Chloro-2-[(E)-3-[(2S,5R)-4-(4-fluorobenzyl)-2,5-dimethylpiperazin-1-yl]-3-oxopropenyl]-phenyl)-carbamic acid tert-butyl ester

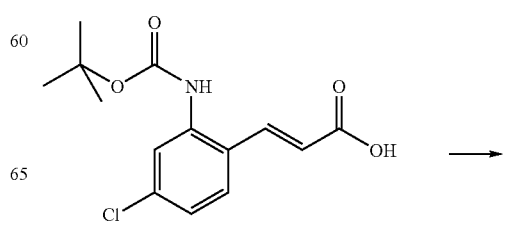

-continued

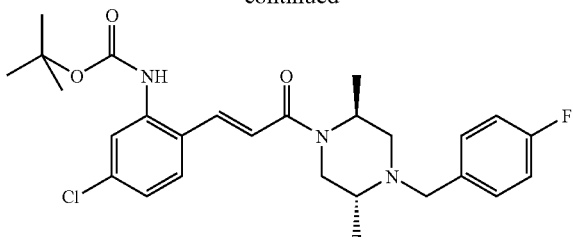

(E)-3-(2-tert-Butoxycarbonylamino-4-chlorophenyl)-acrylic acid (595 mg, 2.0 mmol) and (2R,5S)-1-(4-fluorobenzyl)-2,5-dimethylpiperazine (Mavunkel, Babu J. et al., WO 00/71535) (445 mg, 2.0 mmol) were dissolved in $CH_2Cl_2$, combined with EDCl.HCl (384 mg, 2.0 mmol) and stirred for 3 hours at room temperature. The reaction mixture was purified via chromatography ($SiO_2$, EtOAc/hexanes 2/8) to yield the title compound as colorless foam (840 mg, 81%).

1H-NMR (400 MHz; DMSO-d6): 0.95 (bs, 3H); 1.25 (bs, 3H); 1.50 (s, 9H); 2.30 (m, 1H); 2.55-2.80 (bm, 2H); 3.05 (bs, 1H); 3.45 (bd, 1H); 3.64 (bd, 1H); 4.05 (bs, 1H); 4.55 (bs, 1H); 7.09-7.20 (m, 3H); 7.15 (dd, 1H); 7.39-7.42 (m, 2H); 7.45 (bs, 1H); 7.66 (d, 1H); 7.89 (d, 1H); 9.25 (bs, 1H, NH).

MS (m/z) ES+: 502.2 (MH+, 100); 446 (80).

[α]D=+73.0°; c=1.0 in MeOH.

b) (E)-3-(2-Amino-4-chlorophenyl)-1-[(2S,5R)-4-(4-fluorobenzyl)-2,5-dimethylpiperazin-1-yl]-propenone

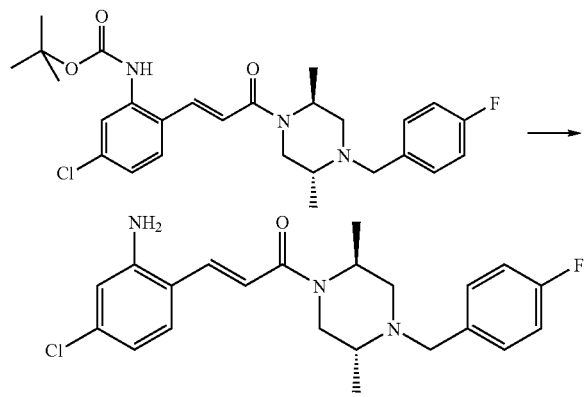

(5-Chloro-2-[(E)-3-[(2S,5R)-4-(4-fluorobenzyl)-2,5-dimethylpiperazin-1-yl]-3-oxo-propenyl]-phenyl)-carbamic acid tert-butyl ester (830 mg, 1.65 mmol) was dissolved in EtOH (7 ml) and treated with HClconc (7 ml) for 30 minutes at room temperature. The reaction mixture was poured on a saturated solution of $Na_2CO_3$ and extracted with EtOAc twice. The combined organic phases were dried over $Na_2SO_4$, evaporated to dryness and purified via chromatography ($SiO_2$, EtOAc/hexanes 7/3 to 6/4) to yield the title compound as a foam (580 mg, 87%).

1H-NMR (400 MHz; DMSO-d6): 0.95 (bd, 3H); 1.23 (bd, 3H); 2.25 (d, 1H); 2.55-2.70 (m, 2H); 3.03 (bs, 1H); 3.45 (d, 1H); 3.63 (d, 1H); 4.05 bs, 1H); 4.55 (bs, 1H); 5.73 (s, 2H, NH2); 6.57 (dd, 1H); 6.75 (d, 1H); 6.97 (d, 1H); 7.18 (t, 2H); 7.41 (dd, 2H); 7.53 (d, 1H); 7.68 (d, 1H).

MS (m/z) ES+: 402.2 (MH+, 100).

[α]D=+95.0°; c=1.0 in MeOH.

c) N-(5-Chloro-2-[(E)-3-[(2S,5R)-(4-fluorobenzyl)-2,5-dimethylpiperazin-1-yl]-3-oxopropenyl]-phenyl)-acetamide

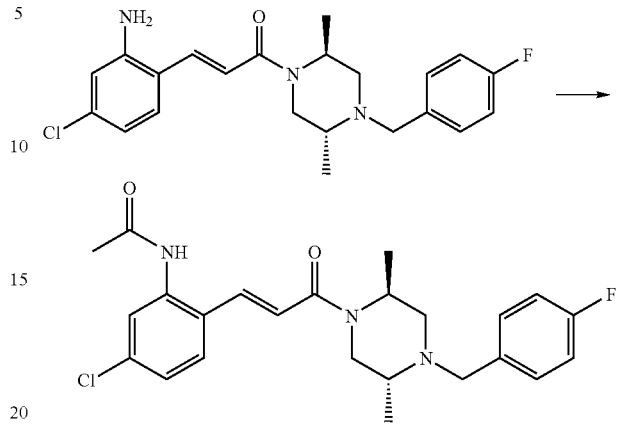

(E)-3-(2-Amino-4-chlorophenyl)-1-[(2S,5R)-4-(4-fluorobenzyl)-2,5-dimethylpipera-zin-1-yl]-propenone (101 mg, 0.25 mmol), $NEt_3$ (252 mg, 2.5 mmol) and $Ac_2O$ (255 mg, 2.5 mmol) were refluxed in THF (5 ml) for 5 hours. The reaction mixture was evaporated to dryness and purified via chromatography ($SiO_2$, TBME) to yield the title compound as a yellowish foam (100 mg. 90%).

1H-NMR (400 MHz; DMSO-d6): 0.95 (bs, 3H); 1.28 (bs 3H); 2.12 (s, 3H); 2.28 (d, 1H); 2.64 (bs, 1H); 3.05 (bs, 1H); 3.30 (bs, 1H); 3.50 (d, 1H); 3.65 (d, 1H); 4.05 (bs, 1H); 4.60 (bs, 1H); 7.18 (t, 3H); 7.30 (dd, 1H); 7.42 (dd, 2H); 7.60 (d, 1H); 7.68 (d, 1H); 7.94 (d, 1H); 9.92 (s, 1H, NH).

MS (m/z) ES+: 444.2 (MH+, 100).

[α]D=+87.0°; c=0.5 in MeOH.

Example 18

(5-Chloro-2-[(E)-3-[(2S,5R)-4-(4-fluorobenzyl)-2,5-dimethylpiperazin-1-yl]-3-oxopropenyl]-phenyl)-urea

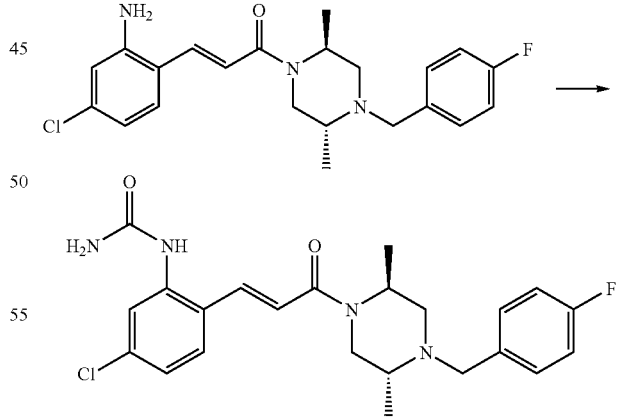

(E)-3-(2-Amino-4-chlorophenyl)-1-[(2S,5R)-4-(4-fluorobenzyl)-2,5-dimethylpipera-zin-1-yl]-propenone (101 mg, 0.25 mmol) and NaOCN (34 mg, 0.504 mmol) were stirred in HOAc (5 ml) and water (10 ml) for 3 hours at room temperature. The reaction mixture was poured on saturated $Na_2CO_3$ solution and extracted with EtOAc twice. The combined organic phases were dried over $Na_2SO_4$, evaporated to dryness and purified via chromatography (SiO$_2$, TBME/MeOH/NH$_3$conc 97/2.7/0.5) to yield the title compound as colorless crystals (80 mg, 70%).

1H-NMR (400 MHz; DMSO-d6; 120° C.): 1.01 (d, 3H); 1.30 (d, 3H); 2.33 (dd, 1H); 2.78 (dd, 1H); 3.05 (m, 1H); 3.41 (dd, 1H); 3.51 (d, 1H); 3.66 (d, 1H); 4.00 (d, 1H); 4.52 (bm, 1H); 5.86 (bs, 2H, NH2); 7.00 (d, 1H); 7.05-7.14 (m, 3H); 7.41 (dd, 2H); 7.66 (d, 1H); 7.68 (d, 1H); 7.93 (d, 1H); 8.07 (bs, 1H, NH).

MS (m/z) ES: 445.2 (MH+, 100).

[α]D=+86.2°; c=0.5 in MeOH.

Example 19

N-(5-Chloro-2-[(E)-3-[4-(4-fluorobenzyl)-piperazin-1-yl]-3-oxopropenyl]-phenyl)-acetamide a) (5-Chloro-2-[(E)-3-[-4-(4-fluorobenzyl)-piperazin-1-yl]-3-oxopropenyl]-phenyl)-carbamic acid tert butyl ester

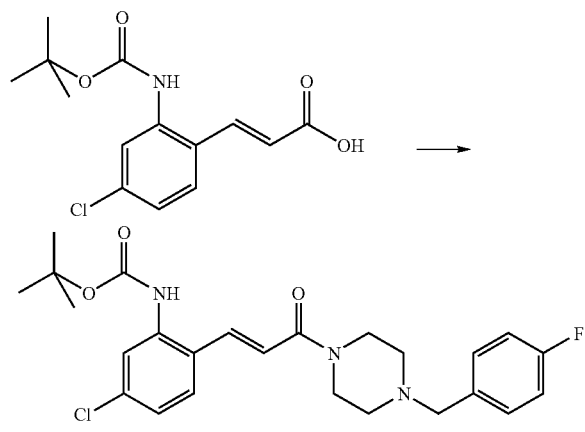

(E)-3-(2-tert-Butoxycarbonylamino-4-chlorophenyl)-acrylic acid (150 mg, 0.5 mmol), 1-(4-fluorobenzyl)-piperazine (98 mg, 0.5 mmol) and EDCl.HCl (96 mg, 0.5 mmol) were dissolved in CH$_2$Cl$_2$ and stirred at room temperature for 18 hours. The reaction mixture was purified via chromatography (SiO$_2$, EtOAc) to yield the title compound as a white foam (150 mg, 63%).

1H-NMR (400 MHz; DMSO-d6): 1.48 (s, 9H); 2.38 (bd, 4H); 3.51 (s, 2H); 3.60 (bs, 2H); 3.71 (bs, 2H); 7.13-7.21 (m, 3H); 7.26 (dd, 1H); 7.37 (d, 1H); 7.39 (d 1H); 7.48 (bs, 1H); 7.64 (d, 1H); 7.80 (d, 1H); 9.23 (s, 1H, NH)

MS (m/z) ES–: 472.2 (M–H, 100).

b) (E)-3-(2-Amino-4-chlorophenyl)-1-[4-(4-fluorobenzyl)-piperazin-1-yl]-propenone

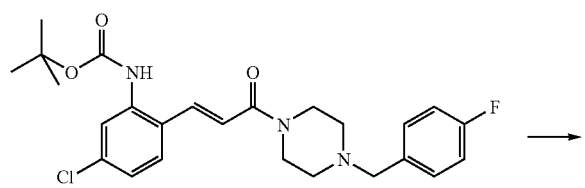

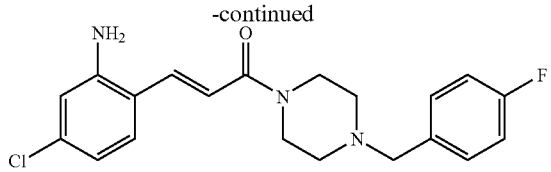

(5-Chloro-2-[(E)-3-[4-(4-fluorobenzyl)-piperazin-1-yl]-3-oxopropenyl]-phenyl)-carbamic acid tert butyl ester (330 mg, 0.7 mmol) was dissolved in EtOH (7 ml) and treated with HClconc (7 ml) for 30 minutes at room temperature. The reaction mixture was poured on a saturated solution of Na$_2$CO$_3$ and extracted with EtOAc twice. The combined organic phases were dried over Na$_2$SO$_4$, evaporated to dryness to yield the title compound as a yellow foam (240 mg 91%).

1H-NMR (400 MHz; DMSO-d6): 2.38 (bs, 4H); 3.51 (s, 2H); 3.59 (bs, 2H); 3.68 (bs, 2H); 5.75 (s, 2H, NH2); 6.55 (dd, 1H); 6.73 (d, 1H); 7.00 (d, 1H); 7.18 (t, 2H); 7.38 (dd, 2H); 7.53 (d, 1H); 7.64 (d, 1H);

MS (m/z) ES–: 372.2 (M–H, 100).

c) N-(5-Chloro-2-[(E)-3-[-4-(4-fluorobenzyl)-piperazin-1-yl]-3-oxopropenyl]-phenyl)-acetamide

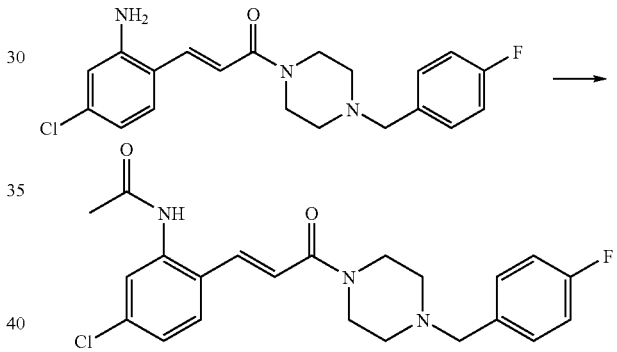

(E)-3-(2-Amino-4-chlorophenyl)-1-[4-(4-fluorobenzyl)-piperazin-1-yl]-propenone (75 mg, 0.2 mmol), NEt$_3$ (202 mg, 2.0 mmol) and Ac$_2$O (204 mg, 2.0 mmol) were refluxed in THF (4 ml) for 6 hours. The reaction mixture was evaporated to dryness and purified via chromatography (SiO$_2$, EtOAc/MeOH/NH$_3$conc 95/4.5/0.5) to yield the title compound as colorless crystals (40 mg. 48%)

1H-NMR (400 MHz; DMSO-d6): 2.11 (s, 3H); 2.40 (bs, 4H); 3.53 (s, 2H); 3.60 (bs, 2H); 3.70 (bs, 2H); 7.15-7.25 (m, 3H); 7.30 (dd, 1H); 7.38 (dd, 2H); 7.58 (d, 1H); 7.62 (d, 1H); 7.92 (d, 1H); 9.89 (s, 1H, NH).

MS (m/z) ES+: 416.2 (MH+, 100).

Example 20

(5-Chloro-2-[(E)-3-[-4-(4-fluorobenzyl)-piperazin-1-yl]-3-oxopropenyl]-phenyl)-urea

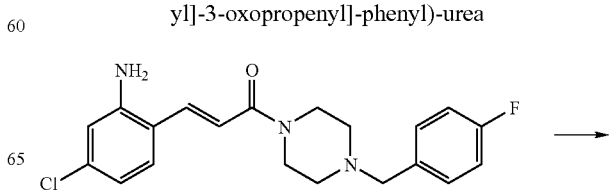

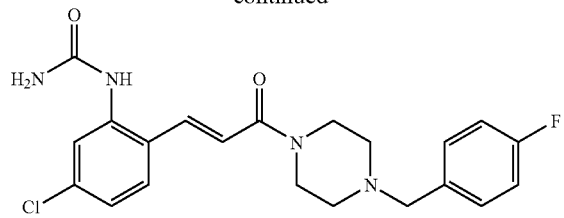

(E)-3-(2-Amino-4-chlorophenyl)-1-[4-(4-fluorobenzyl)-piperazin-1-yl-propenone (80 mg, 0.215 mmol) and NaOCN (29 mg, 0.43 mmol) were stirred in HOAc (5 ml) and water (10 ml) for 2 hours at room temperature. The reaction mixture was poured on 2N NaOH and extracted with EtOAc twice. The combined organic phases were dried over Na$_2$SO$_4$, evaporated to dryness and purified via chromatography (SiO$_2$, EtOAc/MeOH/NH$_3$conc 95/4.5/0.5) to yield the title compound as colorless crystals (40 mg, 50%).

1H-NMR (400 MHz; DMSO-d6): 2.40 (m, 4H); 3.52 (s, 2H); 3.60 (s, 2H); 3.70 (s, 2H); 6.26 (s, 2H, NH2); 7.08 (dd, 1H); 7.13-7.20 (m, 3H); 7.36 (dd, 2H); 7.68 (d, 1H); 7.78 (d, 1H); 7.97 (d, 1H); 8.41 (s, 1H, NH).

MS (m/z) ES+: 417.2 (MH+, 100).

Example 21

(E)-3-[4-Chloro-2-(4-hydroxy-1-methylpiperidin-4-ylethynyl)-phenyl]-1-[(R)-4-(4-fluorobenzyl)-2-methylpiperazin-1-yl]-propenone a) (E)-3-(2-Bromo-4chlorophenyl)-acrylic acid methyl ester

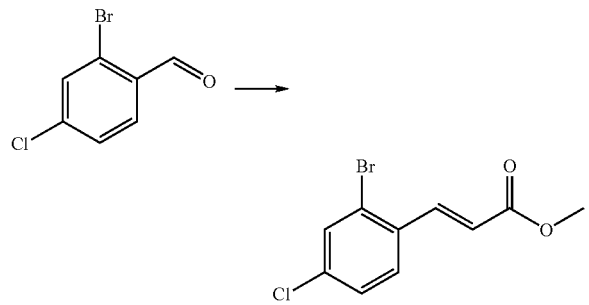

2-Bromo-4-chlorobenzaldehyde (Boegesoe, Klaus P. et al., J. Med. Chem. (1983), 26(7), 93547) (6.3g, 28.7 mmol) and methoxycarbonylmethylenetriphenylphosphor-ane (10.5 g, 31.6 mmol) were refluxed in toluene (143 ml) for 1 hour. The reaction mixture was cooled and purified via chromatography (SiO$_2$, acetone/hexanes 5/95) to yield the title compound as colorless crystals (4.8 g, 61%).

1H-NMR (400 MHz; DMSO-d6): 3.50 (s, 3H); 6.48 (d, 1H); 7.30 (d, 1H); 7.60 (d, 1H); 7.65 (d, 1H); 7.72 (d, 1H).

MS (m/z) EI: 276 (M+, 20); 245 (20); 195 (100); 136 (55), 99 (50), 74 (80).

b) (E)-3-(2-Bromo-4-chlorophenyl)-acrylic acid

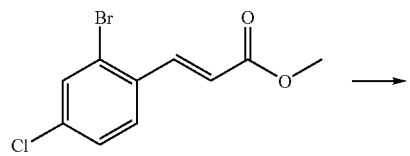

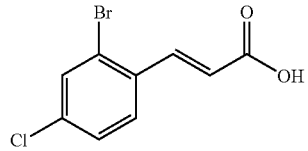

(E)-3-(2-Bromo-4-chlorophenyl)-acrylic acid methyl ester (6.8 g, 17.4 mmol) was dissolved in MeOH (175 ml) and treated with 2N NaOH (13 ml; 26 mmol) and water (87 ml) for 1 hour at 50° C. The mixture was acidified with 2N HCl (15 ml) and extracted with TBME twice. The combined organic phases were dried over Na$_2$SO$_4$ and evporated to dryness to yield the title compound as a solid, which was recrystallised from TBME/hexanes to yield the title compound as colorless crystals (4.4 g, 90%).

1H-NMR (400 MHz; DMSO-d6): 6.62 (d, 1H); 7.55 (dd, 1H); 7.80 (d, 1H); 7.90 (d, 1H); 7.95 (d, 1H); 12.8 (bs, 1H).

MS (m/z) ES-: 261 (M-H, 100).

c) (E)-3-(2-Bromo-4-chlorophenyl)-1-[(R))-4-(4-fluorobenzyl)-2-methylpiperazin-1-yl]propenone

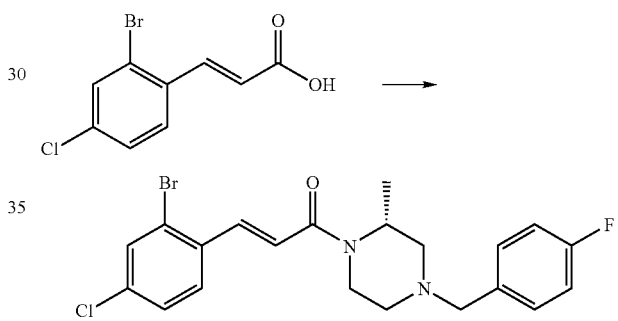

(E)-3-(2-Bromo-4-chlorophenyl)-acrylic acid (3.9 g, 15 mmol) and EDCl.HCl (2.87 g, 15 mmol) and (R)-1-(4-fluorobenzyl)-3-methylpiperazine (Hilger, Christoph-Stephan et al., WO 0236581) (3.12 g, 15 mmol) were dissolved in CH$_2$Cl$_2$ (150 ml) and stirred at room temperature for 18 hours. The reaction mixture was purified via chromatography (SiO2, EtOAc/hexanes 3/7) to yield the title compound as yellowish crystals (5.3 g, 78%).

1H-NMR (400 MHz; DMSO-d6): 1.26 (bs, 3H); 1.86-2.20 (bd, 2H); 2.65 (d, 1H); 2.82 (d, 1H); 2.98 (d, 1H); 3.42 (d, 1H); 3.53 (d, 1H); 4.08-4.20 (bd, 1H); 4.43-4.68 (bd, 1H); 7.17 (t, 2H); 7.28 (d, 1H); 7.37 (dd, 2H); 7.53 (dd, 1H); 7.70 (d, 1H); 7.83 (d, 1H); 8.03 (d, 1H);

MS (m/z) AP+: 453.1 (100); 451.1 (MH+, 80).

d) (E)-3-[4-Chloro-2-(4-hydroxy-1-methylpiperidin-4-ylethynyl)-phenyl]-1-[(R)-4-(4-fluorobenzyl)-2-methylpiperazin-1-yl]-propenone

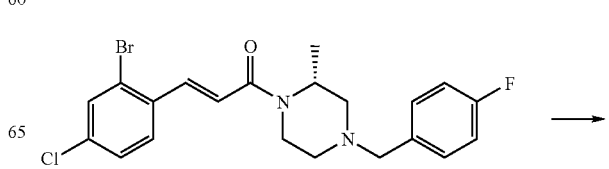

-continued

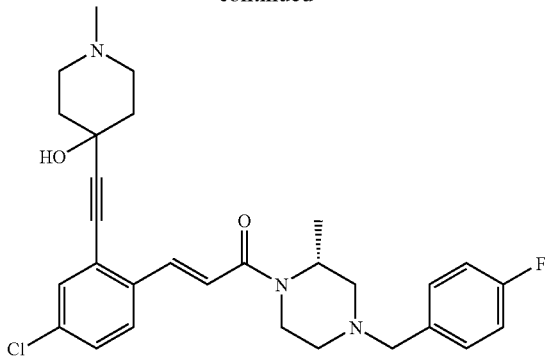

(E)-3-(2-Bromo-4-chlorophenyl)-1-[(R))-4-(4-fluorobenzyl)-2-methylpiperazin-1-yl]propenone (200 mg; 0.44 mmol) was dissolved in diglyme (1.5 ml), PdCl2(PPh3)2 (62 mg; 0.088 mmol) and DIPEA (2 ml) added, followed by 4-ethynyl-1-methylpiperidin-4-ol (Exploratory Library; 124 mg; 0.88 mmol), CuI (68 mg; 0.35 mmol) and $CS_2CO_3$ (290 mg; 0.88 mmol) and heated to 130° C. for 25 minutes. The reaction mixture was evaporated, taken up in TBME, filtered and purified via chromatography ($SiO_2$; TBME/MeOH/$NH_3$conc 95/5/0.5) to yield 230 mg of a yellow foam, which was further purified via preparative HPLC (XTerra, RP18, 7 μm, acetonitrile/water) to deliver the title compound (175 mg; 78%) as a slightly yellow foam.

1H-NMR (400 MHz; DMSO-d6; 120° C.): 1.32 (d, 3H); 1.84 (bt, 2H); 1.94 (bd, 2H); 2.08 (bt, 1H); 2.22 (bd, 1H); 2.24 (s, 3H); 2.38 (bt 2H); 2.60 (bs, 2H); 2.70 (bd, 1H); 2.85 (bd, 1H); 3.20 (bt, 1H); 3.47 (d, 1H); 3.56 (d, 1H); 4.13 (bd, 1H); 4.54 (bs, 1H); 5.06 (bs, 1H, OH); 7.12 (t, 2H); 7.20 (d, 1H); 7.38 (bt, 2H); 7.43 (bs, 1H); 7.47 (d, 1H); 7.79 (d, 1H); 7.81 (bs, 1H).

MS (m/z) ES+: 510.3 (MH+, 100).
[α]D=−50.1°; c=0.5 in MeOH.

Example 22

(E)-3-[4Chloro-2-(4-hydroxy-1-methylpiperidin-4-ylethynyl)-phenyl]-1-[(S)-4-(4-fluorobenzyl)-2-methylpiperazin-1-yl]-propenone

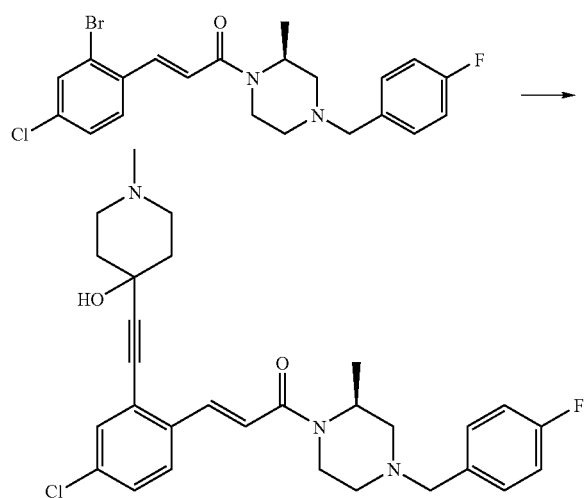

Was prepared in analogy to the R-enantiomer above and yielded the title compound as a yellow foam (88 mg, 78%).

1H-NMR (400 MHz; DMSO-d6; 120° C.): 1.32 (d, 3H); 1.84 (bt, 2H); 1.94 (bd, 2H); 2.08 (bt, 1H); 2.22 (bd, 1H); 2.24 (s, 3H); 2.38 (bt 2H); 2.60 (bs, 2H); 2.70 (bd, 1H); 2.85 (bd, 1H); 3.20 (bt, 1H); 3.47 (d, 1H); 3.56 (d, 1H); 4.13 (bd, 1H); 4.54 (bs, 1H); 5.06 (bs, 1H, OH); 7.12 (t, 2H); 7.20 (d, 1H); 7.38 (bt, 2H); 7.43 (bs, 1H); 7.47 (d, 1H); 7.79 (d, 1H); 7.81 (bs, 1H).

MS (m/z) ES+: 510.3 (MH+, 100).
[α]D=+53.3°; c=0.5 in MeOH.

Example 23

(E)-3-[4-Chloro-2-[(E)-2-(4-hydroxy-1-methylpiperidin-4-yl)-vinyl]-phenyl]-1-[(R)-4-(4-fluorobenzyl)-2-methylpiperazin-1-yl]-propenone a) 1-Methyl-4-((E)-2-tributylstannanyl-vinyl)-piperidin-4-ol

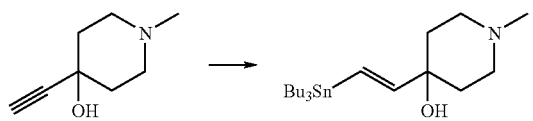

4-Ethynyl-1-methylpiperidin-4-ol (Exploratory Library; 3.34 g; 24 mmol) and $PdCl_2(PPh_3)_2$ (337 mg; 0.48 mmol) were dissolved and stirred in THF (100 ml), cooled in a water bath to 180C, while Bu3SnH (7.6 ml; 28.8 mmol) was added dropwise within 3 minutes. The reaction mixture was stirred at room temperature for 4 hours, poured directly on a column of $SiO_2$ and chromatographed (EtOAc/MeOH/$NH_3$ 95/5/0.5) to deliver the title compound as a greenish oil (3.45 g; 33%).

1H-NMR (400 MHz; DMSO-d6): 0.88 (m, 15H); 1.30 (m, 6H); 1.40 (m, 2H); 1.50 (m, 6H); 1.60 (m, 2H); 2.15 (s, 3H); 2.27 (bt, 2H); 2.40 (m, 2H); 4.33 (s, 1H, OH); 6.03 (d, 1H); 6.11 (d, 1H).

MS (m/z) ES+: 432 (MH+, 100).

b) (E)-3-[4-Chloro-2-[(E)-2-(4-hydroxy-1-methylpiperidin-4-yl)-vinyl]-phenyl]-1-[(R)-4-(4-fluorobenzyl)-2-methylpiperazin-1-yl]-propenone

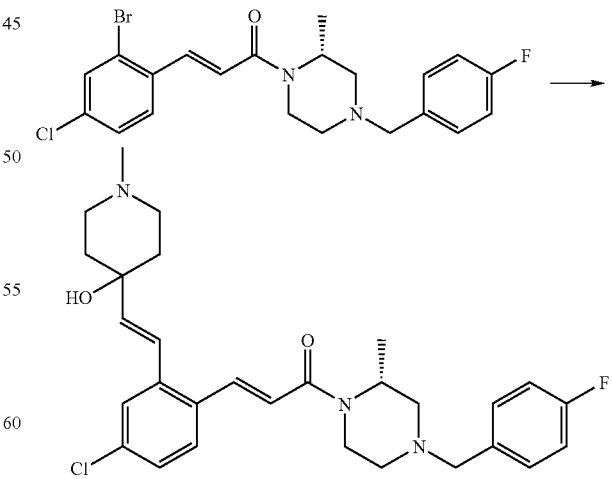

(E)-3-(2-Bromo-4-chlorophenyl)-1-[(R)-4-(4-fluorobenzyl)-2-methylpiperazin-1-yl]propenone (200 mg; 0.44 mmol) and 1-methyl-4-((E)-2-tributylstannanyl-vinyl)-piperidin-4-ol (370 mg, 0.88 mmol) were dissolved in diglyme (5 ml) and added heated to 140° C. Pd(OAc)$_2$ (400 mg; 1.77 mmol) was dissolved in diglyme (26 ml) and added dropwise under stirring within 15 minutes. The reaction mixture was heated at 140° C. for 5 minutes, filtered, evaporated and purified via chromatography (SiO$_2$; TBME/MeOH/NH$_3$conc 90/10/1 to 80/20/2) to yield 230 mg of a brown foam, which was further purified via preparative HPLC (XTerra, RP18, 7 μm, acetonitrile/water) to deliver the title compound (43 mg; 19%) as a slightly yellow foam.

1H-NMR (400 MHz; DMSO-d6; 120° C.): 1.32 (d, 3H); 1.62 (bd, 2H); 1.78 (bt, 2H); 2.08 (bt, 1H); 2.21 (bd, 1H); 2.22 (s, 3H); 2.40-2.51 (m, 4H); 2.70 (bd, 1H); 2.86 (bd, 1H); 3.21 (bt, 1H); 3.48 (d, 1H); 3.57 (d, 1H); 4.14 (bd, 1H); 4.16 (bs, 1H, OH); 4.53 (bs, 1H); 6.29 (d, 1H); 6.87 (d, 1H); 6.94 (d, 1H); 7.12 (t, 2H); 7.28 (dd, 1H); 7.39 (dd, 2H); 7.48 (d, 1H); 7.66 (d, 1H); 7.71 (d, 1H).

MS (m/z) ES+: 512.3 (MH+, 100).

[α]D=−48.0°; c=0.5 in MeOH.

Example 24

(E)-3-[4-Chloro-2-[(E)-2-(4-hydroxy-1-methylpiperidin-4-yl)-vinyl]-phenyl]-1-[(S)-4-(4-fluorobenzyl)-2-methylpiperazin-1-yl]-propenone

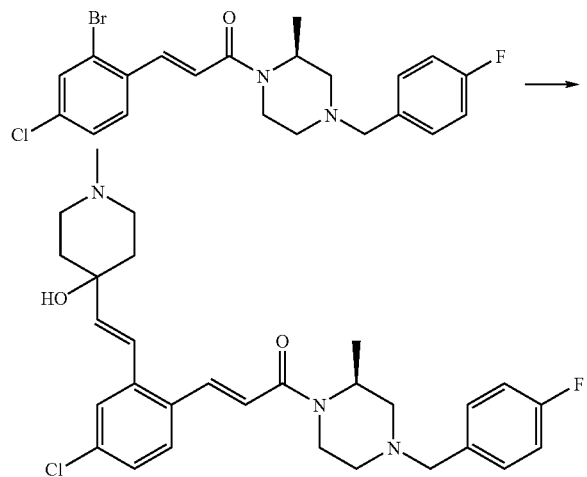

Was prepared and purified in analogy to the R-enantiomer above and yielded the title compound as a yellow foam (49 mg, 29%).

1H-NMR (400 MHz; DMSO-d6; 120° C.): 1.32 (d, 3H); 1.62 (bd, 2H); 1.78 (bt, 2H); 2.08 (bt, 1H); 2.21 (bd, 1H); 2.22 (s, 3H); 2.40-2.51 (m, 4H); 2.70 (bd, 1H); 2.86 (bd, 1H); 3.21 (bt, 1H); 3.48 (d, 1H); 3.57 (d, 1H); 4.14 (bd, 1H); 4.16 (bs, 1H, OH); 4.53 (bs, 1H); 6.29 (d, 1H); 6.87 (d, 1H); 6.94 (d, 1H); 7.12 (t, 2H); 7.28 (dd, 1H); 7.39 (dd, 2H); 7.48 (d, 1H); 7.66 (d, 1H); 7.71 (d, 1H).

MS (m/z) ES+: 512.3 (MH+, 100).

[α]D=+47.4°; c=0.5 in MeOH.

Example 25

4-(5-Chloro-2-(E)-3-[(R)-4-(4-fluorobenzyl)-2-methylpiperazin-1-yl]-3-oxopropenyl]-phenylethynyl)-4-hydroxypiperidine-1-carboxylic acid tert butyl ester

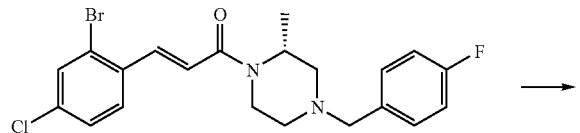

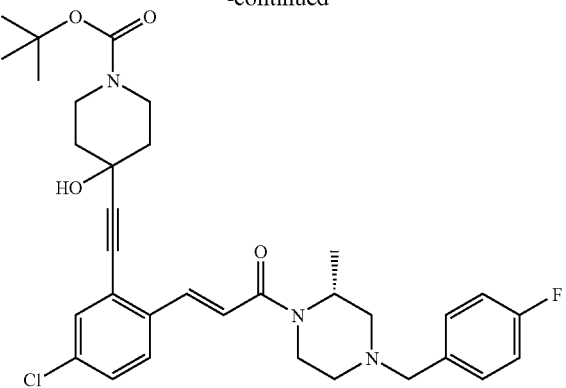

(E)-3-(2-Bromo-4-chlorophenyl)-1-[(R))-4-(4-fluorobenzyl)-2-methylpiperazin-1-yl]propenone (200 mg; 0.44 mmol) was dissolved in diglyme (1.5 ml), PdCl$_2$(PPh$_3$)$_2$ (62 mg; 0.088 mmol) and DIPEA (2 ml) added, followed by 4-ethynyl-1-tert butoxycarbonylpiperidin-4-ol (Kath, John Charles et al., WO 0044728) (150 mg, 0.66 mmol), CuI (68 mg; 0.35 mmol) and Cs$_2$CO$_3$ (290 mg; 0.88 mmol) and heated to 130° C. for 25 minutes. The reaction mixture was evaporated, taken up in TBME, filtered and purified via chromatography (SiO$_2$; acetone/hexanes 2/8 to 3/7) to yield 174 mg of a yellow-brown foam, which was further purified via preparative HPLC (XTerra, RP18, 7 μm, acetonitrile/water) to deliver the title compound (106 mg; 39%) as a slightly yellow foam.

1H-NMR (400 MHz; DMSO-d6; 120° C.): 1.30 (d, 3H); 1.44 (s, 9H); 1.71-1.78 (m, 2H); 1.90-1.97 (m, 2H); 2.07 (bt, 1H); 2.22 (dd, 1H); 2.70 (bd, 1H); 2.82 (bd, 1H); 3.21 (bt, 1H); 2.28-3.37 (m, 2H); 3.48 (d, 1H); 3.56 (d, 1H); 3.63-3.71 (m, 2H); 4.14 (bd, 1H); 4.55 (bs, 1H); 5.34 (s, 1H, OH); 7.12 (dd, 2H); 7.21 (d, 1H); 7.35-7.45 (m, 3H); 7.51 (d, 1H); 7.79 (d, 1H); 7.80 (s, 1H);

MS (m/z) ES+: 596.2 (MH+, 100).

[α]D=−42.6°; c=0.5 in MeOH.

Example 26

(E)-3-[4-Chloro-2-(4-hydroxypiperidin-4-ylethynyl)-phenyl]-1-[(R)-4-(4-fluorobenzyl)-2-methylpiperazin-1-yl]-propenone

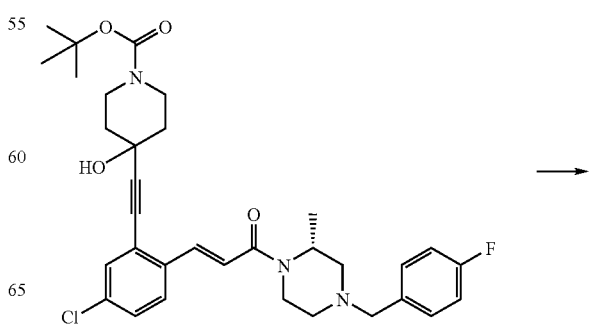

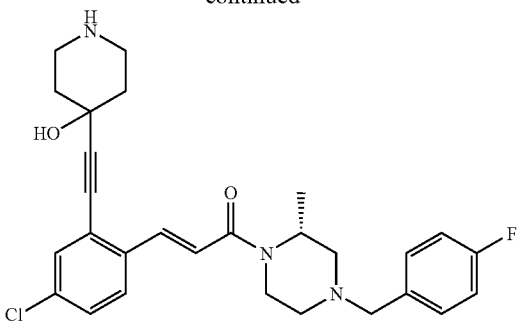

4-(5-Chloro-2-[(E)-3-[(R)-4-(4-fluorobenzyl)-2-methylpiperazin-1-yl]-3-oxoprop-enyl]-phenylethynyl)-4-hydroxypiperidine-1-carboxylic acid tert butyl ester (80 mg, 0.13 mmol) was disolved in CH$_2$Cl$_2$/TFA (4 ml; 1/1) and stirred at 0° C. for 30 minutes. The reaction mixture was evaporated, taken up in TBME and washed with 2N NaOH. The organic phase was dried over Na$_2$SO$_4$, filtered, evaporated and yielded the title compound as yellow foam (63 mg, 95%).

1H-NMR (400 MHz; DMSO-d6): 1.25 (bs, 3H); 1.58 (bt, 2H); 1.85 (bd, 2H); 1.95 (bs, 1H); 2.07 (bs, 1H); 2.61-2.72 (m, 3H); 2.79-2.90 (m, 3H); 3.31 (bs, 1H); 3.41 (d, 1H); 3.52 (d, 1H); 4.18 (bs, 1H); 4.56 (bs, 1H); 5.61 (s, 1H, OH); 7.16 (t, 2H); 7.33 (d, 1H); 7.38 (d, 1H); 7.46-7.50 (m, 2H); 7.98 (d, 1H); 8.00 (d, 1H).

MS (m/z) ES+: 496.2 (MH+, 100).

[α]D=−47.7°; c=0.5 in MeOH.

Example 27

(E)-3-[2-(3-Amino-3-methylbut-1-ynyl-4-chlorophenyl]-1-[(R)-4-(4-fluorobenzyl)-2-methylpiperazin-1-yl]-propenone

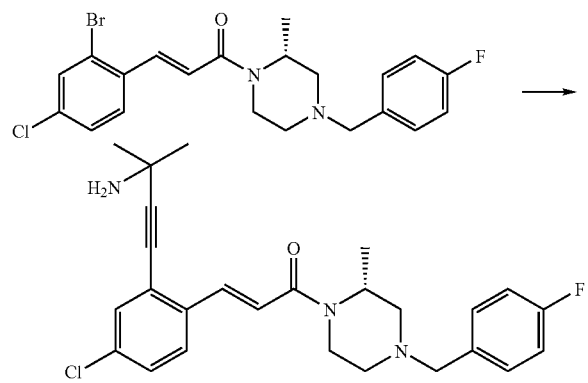

(E)-3-(2-Bromo-4-chlorophenyl)-1-[(R))-4-(4-fluorobenzyl)-2-methylpiperazin-1-yl]propenone (200 mg; 0.44 mmol) was dissolved in diglyme (1.5 ml), PdCl$_2$(PPh$_3$)$_2$ (62 mg; 0.088 mmol) and DIPEA (2 ml) added, followed by 1,1-dimethylpropargyl-amine (0.5 ml, 4.4 mmol), CuI (68 mg; 0.35 mmol) and Cs$_2$CO$_3$ (290 mg; 0.88 mmol) and heated to 130° C. for 25 minutes. The reaction mixture was evaporated, taken up in TBME, filtered and purified via chromatography (SiO$_2$; TBME/MeOH/NH$_3$conc 95/5/5) to yield a yellow-brown foam, which was further purified via preparative HPLC (XTerra, RP18, 7 μm, acetonitrile/water) to deliver the title compound (156 mg; 78%) as a slightly yellow foam.

1H-NMR (400 MHz; DMSO-d6): 1.23 (bs, 3H); 1.41 (s, 6H); 1.96 (bs, 1H); 2.07 (bs, 1H); 2.14 (bs, 2H, NH2); 2.65 (bd, 1H); 2.82 (bd, 1H); 3.10 (m, 1H); 3.42 (d, 1H); 3.52 (d, 1H); 4.20 (bs, 1H); 4.60 (bs, 1H); 7.17 (t, 2H); 7.31 (d, 1H); 7.38 (dd, 2H); 7.45 (m, 2H); 7.86 (d, 1H); 7.98 (d, 1H).

MS (m/z) ES+: 454.3 (MH+, 100).

[α]D=−59.9°; c=0.5 in MeOH.

Example 28

(E)-3-[4-Chloro-2-(3-dimethylaminoprop-1-ynyl)-phenyl]-1-[4-(4-fluorobenzyl)-2-methylpiperazin-1-yl]-propenone

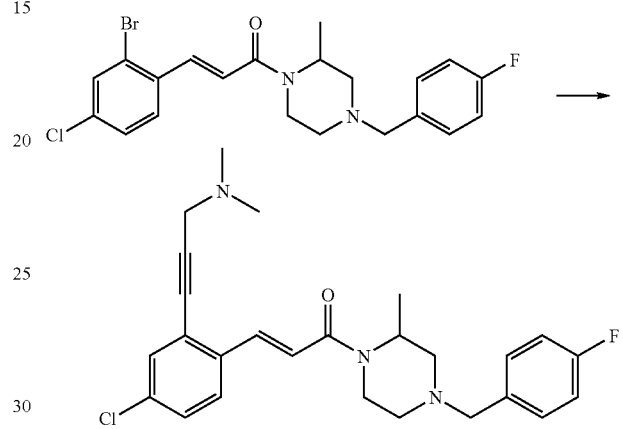

(E)-3-(2-Bromo-4-chlorophenyl)-1-[4-(4-fluorobenzyl)-2-methylpiperazin-1-yl]-propenone (prepared in analogy to the R-enantiomer described above using racemic 1-(4-fluorobenzyl)-3-methylpiperazine (Bolos, Jordi et al. J. Med. Chem. (1996), 39(15), 2962-2970) (100 mg, 2.2 mmol) was dissolved in diglyme (2.0 ml), PdCl$_2$(PPh$_3$)$_2$ (31 mg; 0.044 mmol) and DIPEA (3 ml) added, followed by 1-dimethylamino-2-propyne (0.26 ml, 2.2 mmol), CuI (34 mg; 0.17 mmol) added, Cs$_2$CO$_3$ (145 mg; 0.44 mmol) and heated to 130° C. for 30 minutes. The reaction mixture was evaporated, taken up in TBME, filtered and purified via chromatography (SiO$_2$; TBME/MeOH/NH$_3$conc 97/3/0.3) to yield a yellow-brown foam, which was further purified via preparative HPLC (XTerra, RP18, 7 μm, acetonitrile/water) to deliver the title compound (42 mg; 42%) as colorless foam.

1H-NMR (400 MHz; DMSO-d6, 120° C.): 1.30 (d, 3H); 2.07 (dt, 1H); 2.20 (dd, 1H); 2.32 (s, 6H); 2.70 (d, 1H); 2.85 (bd, 1H); 3.20 (dt, 1H); 3.48 (d, 1H); 3.55 (s, 2H); 3.57 (d, 1H); 4.13 (bd, 1H); 4.53 (bs, 1H); 7.12 (t, 2H); 7.19 (d, 1H); 7.35-7.45 (m, 3H); 7.50 (d, 1H); 7.80 (d, 1H); 7.83 (s, 1H);

MS (m/z) ES+: 454.3 (MH+, 100).

Example 29

(E)-3-[4-Chloro-2-(3-hydroxy-3-methylbut-1-ynyl)-phenyl]-1-[4-(4-fluorobenzyl)-2-methylpiperazin-1-yl]-propenone

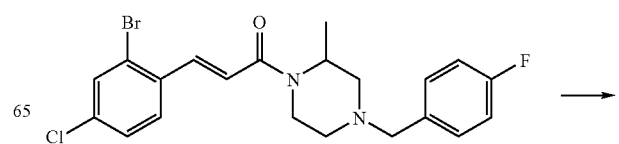

-continued

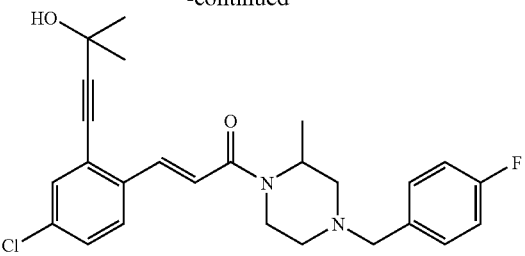

(E)-3-(2-Bromo-4-chlorophenyl)-1-[4-(4-fluorobenzyl)-2-methylpiperazin-1-yl]propenone (prepared in analogy to the R-enantiomer described above using racemic 1-(4-fluorobenzyl)-3-methylpiperazine (Bolos, Jordi et al. J. Med. Chem. (1996), 39(15), 2962-2970) (100 mg, 2.2 mmol) was dissolved in diglyme (2.0 ml), PdCl$_2$(PPh$_3$)$_2$ (31 mg; 0.044 mmol) and DIPEA (3 ml) added, followed by 2-methyl-3-butyn-2-ol (0.22 ml, 2.6 mmol), CuI (34 mg; 0.17 mmol) and Cs$_2$CO$_3$ (145 mg; 0.44 mmol) and heated to 130° C. for 15 minutes. The reaction mixture was taken up in TBME, filtered and purified via chromatography (SiO$_2$; TBME/hexanes 1/1 to 1/0; followed by a second column with acetone/hexanes 3/7) to yield the title compound as colorless foam (60 mg, 60%).

1H-NMR (400 MHz; DMSO-d6): 1.27 (bs, 3H); 1.52 (s, 6H); 1.97 (bs, 1H); 2.12 (bs, 1H); 2.68 (d, 1H); 2.83 (d, 1H); 3.00 (bs, 1H); 3.45 (d, 1H); 3.54 (d, 1H); 4.20 (bs, 1H); 4.59 (bs, 1H); 5.59 (d, 1H, OH); 7.18 (t, 2H); 7.33-7.41 (m, 3H); 7.48-7.51 (m, 2H); 7.87 (d, 1H); 8.00 (d, 1H).

MS (m/z) ES+: 455.3 (MH+, 50); 437.3 (100).

Example 30

N-(3-[(E)-3-[(R)-4-(4-Fluorobenzyl)-2-methylpiperazin-1-yl]-3-oxopropenyl]-naphthalen-2-yl)-acetamide a) (E)-3-(Nitronaphthalen-2-yl)-acrylic acid methyl ester

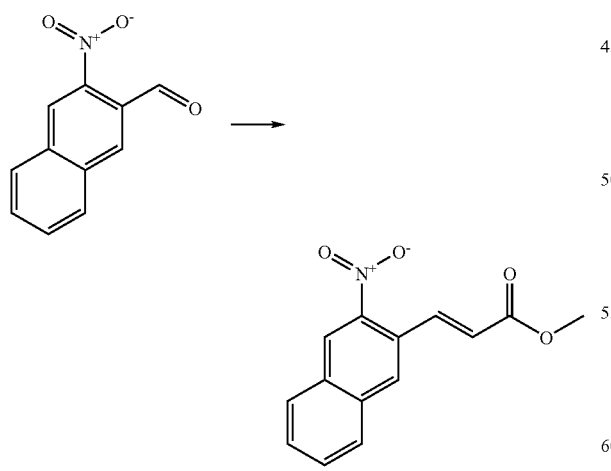

3-Nitronaphthalene-2-carbaldehyde (Kienzle, Frank. Helv. Chim. Acta (1980), 63(8), 2364-9.) (1.3 g; 6.46 mmol) and methoxycarbonylmethylenetriphenylphosphorane (2.37 g. 7.1 mmol) were refluxed in toluene (32 ml) for 1 hour. The reaction mixture was purified via chromatography (SiO$_2$, acetone/hexanes 10/90) to yield the title compound as colorless crystals, which were recrystallised from TBME/hexanes to yield the title compound (1.3 g, 78%).

MS (m/z) EI: 257 (M+, 15); 211 (100; 180 (20); 139 (25); 115 (40).

b) (E)-3-(Nitronaphthalen-2-yl)-acrylic acid

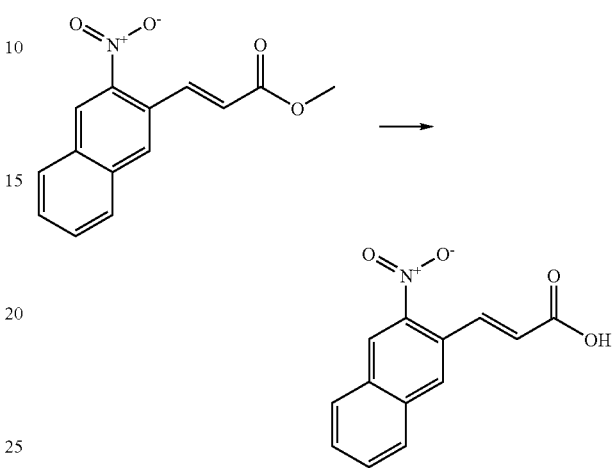

(E)-3-(Nitronaphthalen-2-yl)-acrylic acid methyl ester (1.3 g, 5.05 mmol) was dissolved in MeOH (50 ml) and treated with 2N NaOH (3.8 ml; 7.6 mmol) and water (25 ml) for 1 hour at 50° C. The mixture was acidified with 2N HCl (4.2 ml; 8.33 mmol), water (100 ml) added and filtered to render the desired acid as yellow crystals (1.05 g; 80%).

1H-NMR (400 MHz; DMSO-d6): 6.61 (d, 1H); 7.72-7.82 (m, 2H); 7.98 (d, 1H); 8.13 (d, 1H); 8.22 (d, 1H); 8.53 (s, 1H); 8.85 (s, 1H); 12.80 (s, 1H).

MS (m/z) EI: 243 (M+, 20); 197 (100); 170 (10); 152 (20); 115 (40).

c) (E)-1-[(R)-4-(4-Fluorobenzyl)-2-methylpiperazin-1-yl]-3-(3-nitronaphthalen-2-yl)-propenone

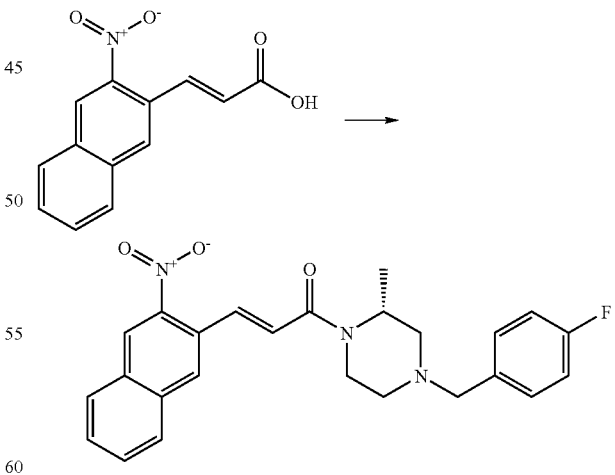

(E)-3-(Nitronaphthalen-2-yl)-acrylic acid (900 mg, 3.7 mmol) and EDCl.HCl (710 mg, 3.7 mmol) and (R)-1-(4-fluorobenzyl)-3-methylpiperazine (Hilger, Christoph-Stephan et al., WO 0236581) (770 mg, 3.7 mmol) were dissolved in DMF (18 ml) and stirred at room temperature for 3 hours. The reaction mixture was poured on water and extracted with EtOAc three times. The combined organic phases were dried over Na₂SO₄, filtered and evaporated to dryness and purified via chromatography (SiO₂, TBME) to yield the title compound as yellow foam (1.1 g, 69%).

1H-NMR (400 MHz; DMSO-d6): 1.20-1.38 (bs, 3H); 1.88-2.22 (bs, 2H); 2.67 (d, 1H); 2.85 (d, 1H); 3.00 (bs, 1H); 3.42 (d, 1H); 3.53 (d, 1H); 4.23 (bs, 1H); 4.61 (bs, 1H); 7.17 (t, 2H); 7.30 (d, 1H); 7.38 (dd, 2H); 7.73 (t, 1H); 7.77 (d, 1H); 7.83 (d, 1H); 8.10 (d, 1H); 8.20 (d, 1H); 8.55 (s, 1H); 8.80 (s, 1H).

MS (m/z) ES+: 434 (MH+, 100), 257 (20).

d) (E)-3-(3-Aminonaphthalen-2-yl)-1-[(R)-4-(4-fluorobenzyl)-2-methylpiperazin-1-yl]propenone

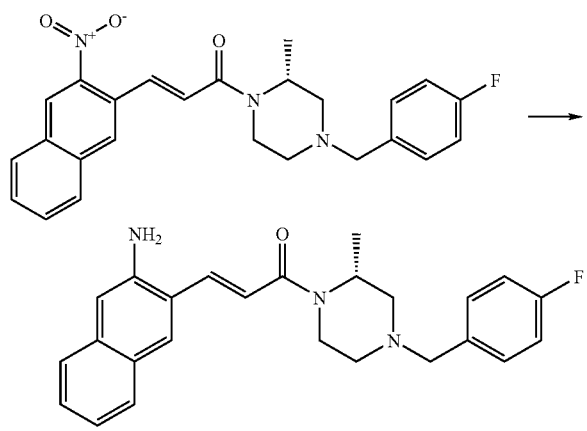

(E)-1-[(R)-4-(4-Fluorobenzyl)-2-methylpiperazin-1-yl]-3-(3-nitronaphthalen-2-yl)-propenone (1.1 g 2.55 mmol) dissolved in EtOH (26 ml) and HClconc (2.6 ml) was treated with SnCl2 (2.42 g, 12.75 mmol) for 5 minutes at 50° C. The reaction mixture was poured on 2N Na₂CO₃ and extracted with TBME three times. The combined organic phases were dried over Na₂SO₄, filtered and evaporated to dryness and purified via chromatography (SiO₂, TBME/MeOH/NH₃conc 95/4.5/0.5) to yield the title compound as yellow foam (850 mg, 82%).

1H-NMR (400 MHz; DMSO-d6): 1.20-1.38 (bs, 3H); 1.88-2.22 (bs, 2H); 2.67 (d, 1H); 2.85 (d, 1H); 3.00 (bs, 1H); 3.42 (d, 1H); 3.53 (d, 1H); 4.23 (bs, 1H); 4.61 (bs, 1H); 7.17 (t, 2H); 7.30 (d, 1H); 7.38 (dd, 2H); 7.73 (t, 1H); 7.77 (d, 1H); 7.83 (d, 1H); 8.10 (d, 1H); 8.20 (d, 1H); 8.55 (s, 1H); 8.80 (s, 1H).

MS (m/z) ES+: 404.2 (MH+, 100).

e) N-(3[(E)-3-[(R)-4-(4-Fluorobenzyl)-2-methylpiperazin-1-yl]-3-oxopropenyl]-naphthalen-2-yl)-acetamide

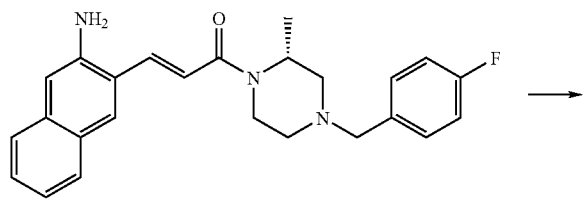

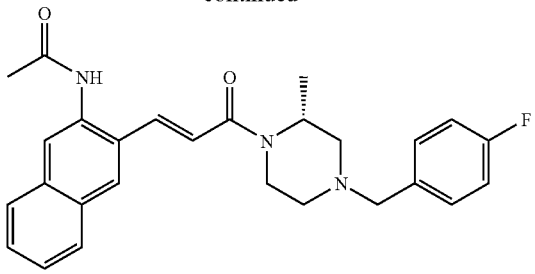

(E)-3-(3-Aminonaphthalen-2-yl)-1-[(R)-4-(4-fluorobenzyl)-2-methylpiperazin-1-yl]-propenone (101 mg, 0.25 mmol), NEt₃ (252 mg, 2.5 mmol) and Ac₂O (255 mg, 2.5 mmol) were refluxed in THF (5 ml) for 18 hours. The reaction mixture was evaporated to dryness and purified via chromatography (SiO₂, TBME/MeOH/NH₃conc 95/4.5/0.5) to yield the title compound as colorless foam (30 mg, 27%).

1H-NMR (400 MHZ; DMSO-d6): 1.30 (bs, 3H); 1.95 (bs, 1H); 2.10 (bs, 1H); 2.15 (s, 3H); 2.68 (bd, 1H); 2.84 (bd, 1H); 3.25 (m, 1H); 3.42 (bd, 1H); 3.55 (bd, 1H); 4.25 (bs, 1H); 4.63 (bs, 1H); 7.15 (t, 2H); 7.29 (d, 1H); 7.48 (dd, 2H); 7.50 (m, 2H); 7.77 (d, 1H); 7.83 (bd, 1H); 7.92 (m, 2H); 8.44 (s, 1H); 9.87 (s, 1H, NH).

MS (m/z) ES+: 446.2 (MH+, 100).

[α]D=−52.3°; c=0.5 in MeOH.

Example 31

(3-[(E)-3-[(R)-4-(4-Fluorobenzyl)-2-methylpiperazin-1-yl]-3-oxopropenyl]-naphthalen-2-yl)-urea

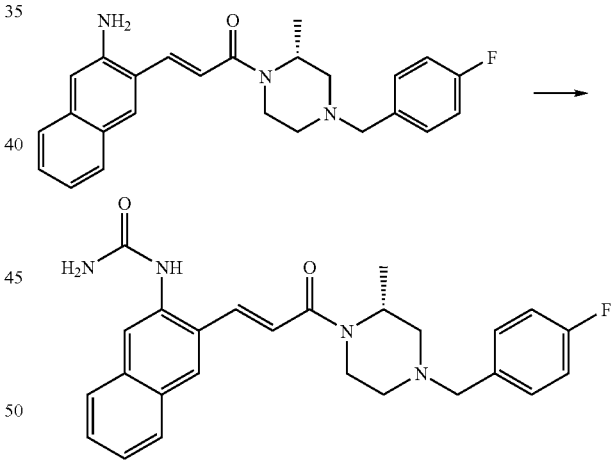

(E)-3-(3-Aminonaphthalen-2-yl)-1-[(R)-4-(4-fluorobenzyl)-2-methylpiperazin-1-yl]-propenone (101 mg, 0.25 mmol) and NaOCN (34 mg, 0.5 mmol) were stirred in HOAc (5 ml) and water (10 ml) for 15 minutes at room temperature. The reaction mixture was poured on 2N NaOH and extracted with EtOAc twice. The combined organic phases were dried over Na₂SO₄, evaporated to dryness and purified via chromatography (SiO₂, TBME/MeOH/NH₃conc 95/4.5/0.5) to yield the title compound as colorless foam (70 mg, 62%).

1H-NMR (400 MHz; DMSO-d6): 1.20-1.38 (m, 3H); 1.88-2.21 (m, 2H); 2.68 (d, 1H); 2.86 (d, 1H); 3.35 (bs, 1H); 3.45 (d, 1H); 3.53 (d, 1H); 4.25 (bd, 1H); 4.60 (bd, 1H); 6.13 (s, 2H, NH2); 7.16 (t, 2H); 7.27 (d, 1H); 7.34-7.47 (m, 4H); 7.73-7.86 (m, 3H); 8.20 (s, 1H); 8.26 (s, 1H); 8.30 (s, 1H).

MS (m/z) ES+: 447.2 (MH+, 100).
[α]D=−57.2°; c=0.5 in MeOH.

Example 32

N-(3-[(E)-3-[(R)-4-(4-Fluorobenzyl)-2-methylpiperazin-1-yl]-3-oxopropenyl]-naphthalen-2-yl)-N'-cyanoguanidine

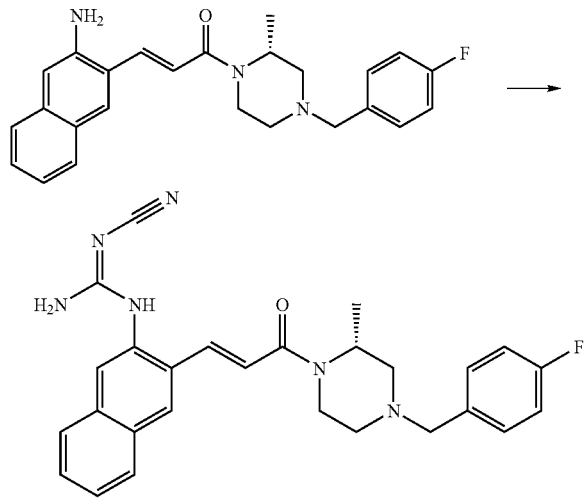

(E)-3-(3-Aminonaphthalen-2-yl)-1-[(R)-4-(4-fluorobenzyl)-2-methylpiperazin-1-yl]-propenone (120 mg, 0.30 mmol) and NaN(CN)$_2$ (178 mg, 2 mmol) were heated to reflux in ethoxyethanol (3 ml). 2N HCl (1 ml) was added dropwise within 5 minutes and the reaction mixture refluxed for another 5 minutes. The reaction mixture was poured on a saturated solution of Na$_2$CO$_3$ and extracted with EtOAc twice. The combined organic phases were dried over Na$_2$SO$_4$, evaporated to dryness and purified via chromatography (SiO$_2$, TBME/MeOH/NH$_3$conc 95/4.5/0.5) to yield the title compound as yellow crystals (30 mg, 22%).

1H-NMR (400 MHz; DMSO-d6): 1.30 (bs, 3H); 2.00 (bs, 1H); 2.12 (bs, 1H); 2.68 (bd, 1H); 2.86 (bd, 1H); 2.98 (bs, 1H); 3.43 (bd, 1H); 3.55 (bd, 1H); 4.23 (bs, 1H); 4.60 (bs, 1H); 7.05 (s, 2H, NH2); 7.17 (t, 2H); 7.32 (d, 1H); 7.38 (dd, 2H); 7.53 (m, 2H); 7.70 (d, 1H); 7.82 (s, 1H); 7.92 (m, 2H); 8.46 (s, 1H); 9.02 (s, 1H, NH).

MS (m/z) ES+: 471.2 (MH+, 100).
[α]D=−53.0°; c=0.5 in MeOH.

Example 33

N-(4-Chloro-2-[(E)-3-[4-(4-fluorobenzyl)-2-methylpiperazin-1-yl]-3-oxopropenyl]-phenyl)-N'-cyanoguanidine a) (E)-3-(2-tert-Butyloxycarbonylamino-5chlorophenyl)-acrylic acid methyl ester

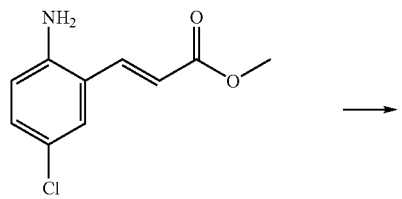

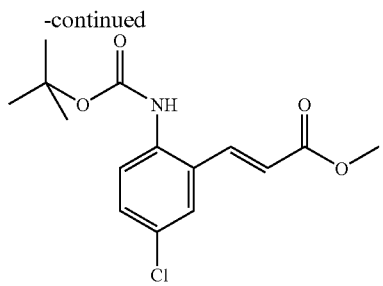

(E)-3-(2-Amino-5-chlorophenyl)-acrylic acid methyl ester (Gonzalez-Zamora, Eduardo et al Chem. Comm. (2001), (17), 1684-1685.) (1.7 g, 8.0 mmol) in THF (6.5 ml) was combined with (BOC)$_2$O (6.98 g9 32.0 mmol) and refluxed for 4 hours. THF was evaporated and the residue purified via chromatography (SiO$_2$, acetone/hexanes 5/95) followed by recrystallisation from hexanes to yield the title compound as yellow crystals (1.8 g; 72%).

1H-NMR (400 MHz; DMSO-d6): 1.47 (s, 9H); 3.75 (s, 3H); 6.68 (d, 1H); 7.38 (d, 1H); 7.46 (dd, 1H); 7.73 (d, 1H); 7.90 (d, 1H); 9.22 (bs, 1H, NH).

MS (m/z) ES−: 310.2 (M−H; 100).

b) (E)-3-(2-tert-Butyloxycarbonylamino-5-chlorophenyl)-acrylic acid

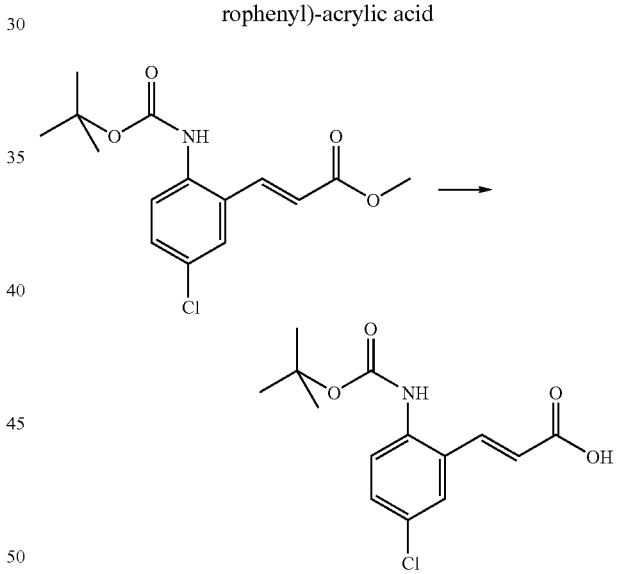

(E)-3-(2-tert-Butyloxycarbonylamino-5-chlorophenyl)-acrylic acid methyl ester (1.8 g, 5.77 mmol) was dissolved in MeOH (115 ml), 2N NaOH (4.3 ml, 8.6 mmol) added and stirred at 60°C. for 2 hours. The reaction mixture was evaporated to dryness, acidified to pH 3.5 by adding water (200 ml) and 2N HCl (4.35 ml) and extracted twice with TBME. The combined organic phases were dried over Na$_2$SO$_4$ and evaporated to dryness to yield the title acid as a solid, which was recrystallised from TBME/hexanes to render the title compound as colorless crystals (1.0 g, 59%).

1H-NMR (400 MHz; DMSO-d6): 1.47 (s, 9H); 6.55 (d, 1H); 7.38 (d, 1H); 7.42 (dd, 1H); 7.68 (d, 1H); 7.83 (s, 1H); 9.28 (s, 1H, NH); 12.50 (s, 1H, COOH).

MS (m/z) ES−: 296 (M−H; 20); 222.0 (90); 178.0 (100).- c) (4-Chloro-2-[(E)-3-[4-(4-fluorobenzyl)-2-methylpiperazin-1-yl]-3-oxopropenyl]-phenyl)-carbamic acid tert butyl ester

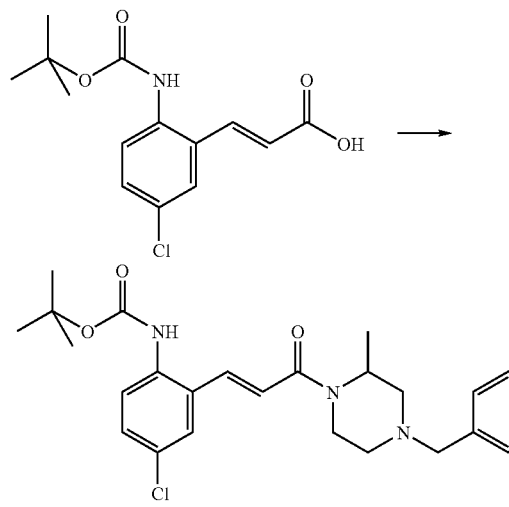

(E)-3-(2-tert-Butyloxycarbonylamino-5chlorophenyl)-acrylic acid (1.0 g, 3.36 mmol) and EDCl.HCl (645 mg, 3.36 mmol) and racemic 1-(4-fluorobenzyl)-3-methyl-piperazine (Bolos, Jordi et al. J. Med. Chem. (1996), 39(15), 2962-2970) (770 mg, 3.7 mmol) were dissolved in CH$_2$Cl$_2$ (34 ml) and stirred at room temperature for 4 hours. The reaction mixture was purified via chromatography (SiO$_2$, EtOAc/hexanes 1/1) to yield the title compound as colorless foam (1.2 g, 74%).

1H-NMR (400 MHz; DMSO-d6): 1.18-1.35 (m, 3H); 1.47 (s, 9H); 1.83-2.20 (bs, 2H); 2.68 (d, 1H); 2.85 (d, 1H); 3.00 (bs, 1H); 3.43 (bd, 1H); 3.53 (bd, 1H); 4.22 (bs, 1H); 4.63 (bs, 1H); 7.18 (t, 2H); 7.23 (d, 1H); 7.40 (m, 4H); 7.62 (d, 1H); 7.97 (s, 1H); 9.10 (bs, 1H, NH).

MS (m/z) ES−: 486.3 (M−H, 100).

d) E)-3-(2-Amino-5-chlorophenyl)-1-[4-(4-fluorobenzyl)-2-methylpiperazin-1-yl]propenone

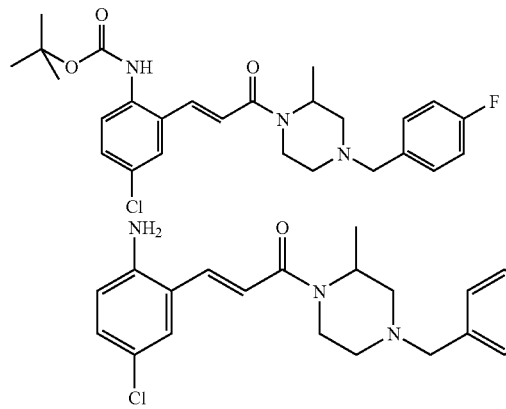

(4-Chloro-2-[(E)-3-[4-(4-fluorobenzyl)-2-methylpiperazin-1-yl]-3-oxopropenyl]-phenyl)-carbamic acid tert butyl (1.2 g, 2.45 mmol) was dissolved in EtOH (10 ml) and treated with HClconc (10 ml) for 15 minutes at 50° C. The reaction mixture was poured on a saturated solution of Na$_2$CO$_3$ and extracted with EtOAc twice. The combined organic phases were dried over Na$_2$SO$_4$, evaporated to dryness to yield the title compound as a yellow foam (900 mq. 91%).

1H-NMR (400 MHz; DMSO-d6): 1.25 (bs, 3H); 1.95 (bs, 1H); 2.08 (bs, 1H); 2.66 (d, 1H); 2.83 (d, 1H); 2.95 (bs, 1H); 3.43 (d, 1H); 3.54 (d, 1H); 4.20 (bs, 1H); 4.60 (bs, 1H); 5.60 (s, 2H, NH2); 6.70 (d, 1H); 7.03-7.08 (m, 2H); 7.17 (t, 2H); 7.39 (dd, 2H); 7.57-7.66 (m, 2H).

MS (m/z) ES+: 388.2 (MH+, 100); 209.2 (30).

e) N-(4-Chloro-2-[(E)-3-[4-(4-fluorobenzyl)-2-methylpiperazin-1-yl]-3-oxopropenyl]-phenyl)-N'-cyanoguanidine

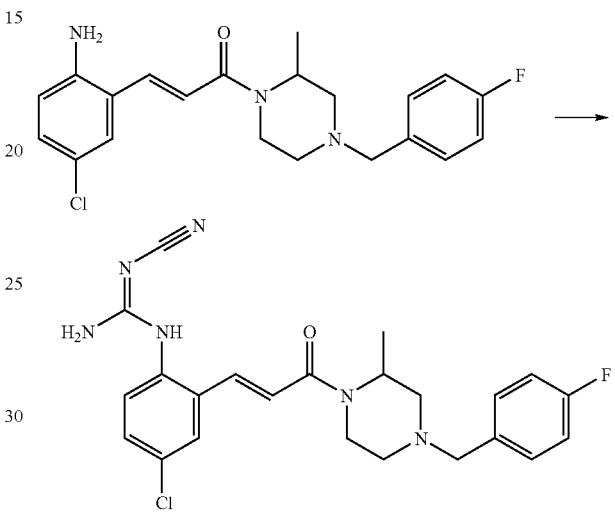

(E)-3-(2-Amino-5-chlorophenyl)-1-[4-(4-fluorobenzyl)-2-methylpiperazin-1-yl]-propenone (116 mg, 0.3 mmol) and NaN(CN)$_2$ (106 mg, 1.2 mmol) were heated to reflux in ethoxyethanol (3 ml). 2N HCl (0.6 ml) was added dropwise within 5 minutes and the reaction mixture refluxed for another 15 minutes. The reaction mixture was poured on a saturated solution of Na$_2$CO$_3$ and extracted with EtOAc twice. The combined organic phases were dried over Na$_2$SO$_4$, evaporated to dryness and purified via chromatography (SiO$_2$, TBME/MeOH/NH$_3$conc 90/9/1) to yield the title compound as a yellow solid (40 mg, 30%).

1H-NMR (400 MHz; DMSO-d6): 1.16 (bs, 3H); 1.86-2.21 (m, 2H); 2.68 (bd, 1H); 2.83 (bd, 1H); 3.00 (bs, 1H); 3.46 (bs, 1H); 3.54 (bs, 1H); 4.26 (bs, 1H); 4.60 (bs, 1H); 7.11 (s, 2H, NH2); 7.19 (t, 2H); 7.30-7.45 (m, 5H); 7.52 (d, 1H); 8.06 (s, 1H); 8.90 (s, 1H).

MS (m/z) ES+: 453.3 (M−H, 100).

Example 34

N-(4-Chloro-2-[(E)-3-[4-(4-fluorobenzyl)-2-methylpiperazin-1-yl]-3-oxopropenyl]-phenyl)-acetamide

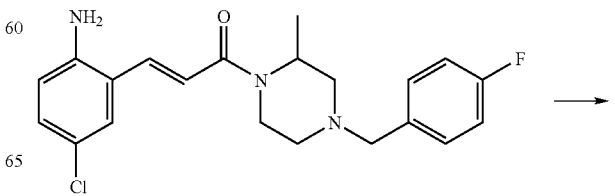

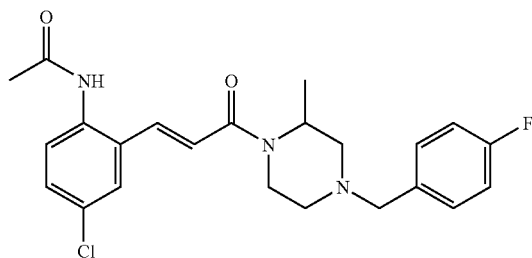

(E)-3-(2-Amino-5-chlorophenyl)-1-[4-(4-fluorobenzyl)-2-methylpiperazin-1-yl]prop-enone (116 mg, 0.3 mmol) NEt$_3$ (303 mg, 3.0 mmol) and Ac$_2$O (306 mg, 3.0 mmol) were refluxed in THF (6 ml) for 4 hours. The reaction mixture was evaporated to dryness and purified via chromatography (SiO$_2$, TBME/MeOH/NH$_3$conc 98/1.8/0.2) to yield the title compound as a yellowish foam (100 mg. 90%).

1H-NMR (400 MHz; DMSO-d6): 1.25 (bs, 3H); 1.86-2.20 (m, 2H); 2.68 (d, 1H); 2.83 (d, 1H); 3.00 (bs, 1H); 3.45 (d, 1H); 3.55 (d, 1H); 4.25 (bs, 1H); 4.62 (bs, 1H); 7.19 (t, 2H); 7.28 (d, 1H); 7.36-7.42 (m, 3H); 7.47 (d, 1H); 7.61 (d, 1H); 8.02 (d, 1H); 9.83 (s, 1H, NH).

MS (m/z) ES+: 430.2 (MH+, 100).

Example 35

N-(6-[(E)-3-[(R)-4-(4-Fluorobenzyl)-2-methylpiperazin-1-yl]-3-oxopropenyl]-quinolin-7-yl)-acetamide a) 7-Nitroquinolin-6-carbaldehyde

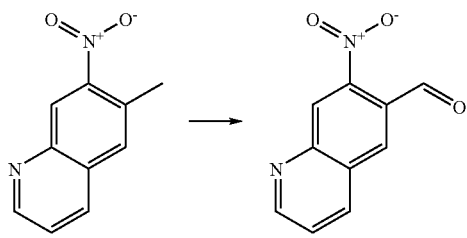

6-Methyl-7-nitroquinoline (Achylediani,R. et al. Izvestiya Akademii Nauk Gruzii, Seriya Khimicheskaya (1996), 22(1-4), 43-47) (14 g; 74 mmol) was dissolved in DMF (200 ml) and treated with tert.butoxy-bis(dimethylamino)methan (64.5 ml; 313 mmol) at 160° C. for 30 min. The reaction mixture was evaporated and purified by dissolving in THF (30 ml), adding TBME (1.5 l) and filtering from the brown precipitate. The filtrate was evaporated to dryness and dissolved in THF (300 ml). NaIO4 (95.6 g; 446 mmol) dissolved in water (5 l) was added under stirring within 45 min. The reaction mixture was extracted with EtOAc three times, the combined organic phases were dried over Na2SO4, evaporated to dryness and purified via chromatography (SiO2, toluene/TBME 96/10) to yield the title compound as yellowish crystals (9.5 g; 63%), which were used in the following step.

b) (E)-3-(7-Nitroquinolin-6-yl)-acrylic acid methyl ester

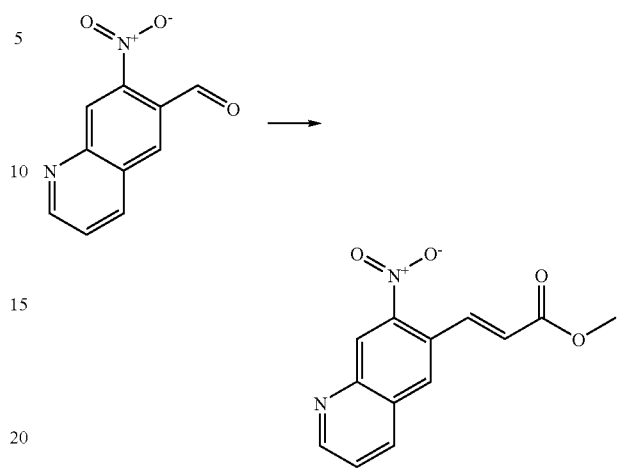

7-Nitroquinoline-6-carbaldehyde (370 mg; 1.83 mmol) in toluene (10 ml) was treated with (methoxycarbonylmethylen)triphenylphosphoran (672 mg; 2.0 mmol) for 1 h at reflux temperature. The pure title compound crystallised after cooling the reaction mixture and adding TBME (470 mg; 78%).

1H-NMR (400 MHz; DMSO-d6): 3.80 (s, 3H); 6.75 (d, 1H); 7.82 (dd, 1H); 8.03 (d, 1H); 8.55 (d, 1H); 8.65 (s, 1H); 8.73 (s, 1H); 9.13 (d, 1H).

MS (m/z) ES+: 259.1 (MH+, 100).

c) (E)-3-(7-Nitroquinolin-6-yl)-acrylic acid

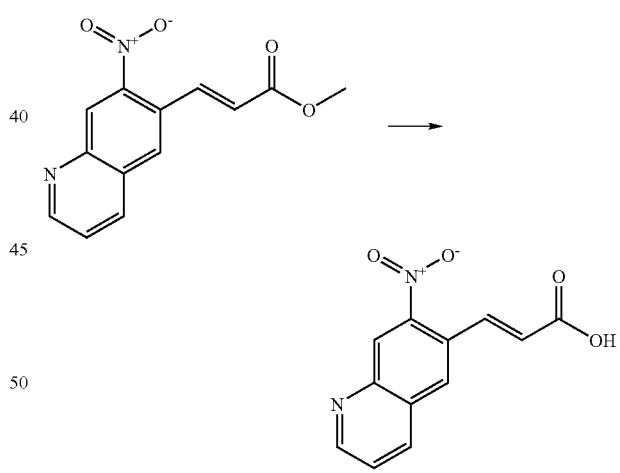

(E)-3-(7-Nitroquinolin-6-yl)-acrylic acid methyl ester (470 mg, 1.82 mmol) in EtOH (9 ml) was treated with 2N NaOH (1.38 ml; 2.76 mmol) for 30 min. at 50° C. The reaction mixture was acidified with 2N HCl to pH 3.5 and extracted with EtOAc/EtOH (10/1) three times. The combined organic phases were washed with water, dried over Na2SO4 and evaporated to dryness to yield the title compound as colorless crystals (430 mg; 90%).

1H-NMR (400 MHz; DMSO-d6): 6.62 (d, 1H); 7.81 (dd, 1H); 7.96 (dd, 1H); 8.57 (d 1H); 8.65 (s, 1H); 8.72 (s, 1H); 9.13 (d, 1H).

MS (m/z) ES+: 245.2 (MH+, 100).

d) (E)-1-[(R)-4-(4-Fluorobenzyl)-2-methylpiperazin-1-yl]-3-(7-nitroquinolin-6-yl)-propenone

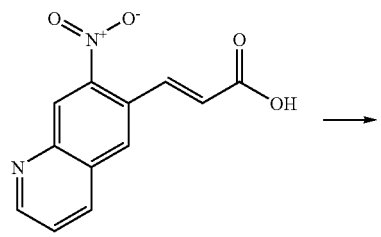

(E)-3-(7-Nitroquinolin-6-yl)-acrylic acid (540 mg; 2.2 mmol), (R)-1-(4-fluorobenzyl)-3-methylpiperazine (Hilger, Christoph-Stephan et al., WO 0236581) (462 mg; 2.2 mmol) and EDCl.HCl (424 mg; 2.2 mmol) were dissolved in DMF (11 ml) and stirred for 18 h at room temperature. The reaction mixture was poured on water and extracted with EtOAc three times. The combined organic phases were dried over Na2SO4, evaporated and purified via chromatography (SiO2; EtOAc/MeOH/NH3conc 100/0/0 to 98/1.8/0.2) to yield the title compound as colorless foam (500 mg; 57%).

1H-NMR (400 MHz; DMSO-d6): 1.22-1.42 (m, 3H); 1.91-2.28 (m, 2H); 2.70 (bd, 1H); 2.87 (bd, 1H); 3.05 (m, 1H); 3.45 (bd, 1H); 3.56 (bd, 1H); 4.12-4.38 (m, 1H); 4.53-4.73 (m, 1H); 7.19 (dd, 2H); 7.35 (d, 1H); 7.40 (m, 2H); 7.80 (d, 1H); 7.82 (dd, 1H); 8.52 (d, 1H); 8.65 (s, 1H); 8.68 (s, 1H); 9.10 (dd, 1H).

MS (m/z) ES+: 435.2 (MH+, 100).

e) (E)-3-(7-Aminoquinolin-6-yl)-1-[(R)-4-(4-fluorobenzyl)-2-methylpiperazin-1-yl]-propenone

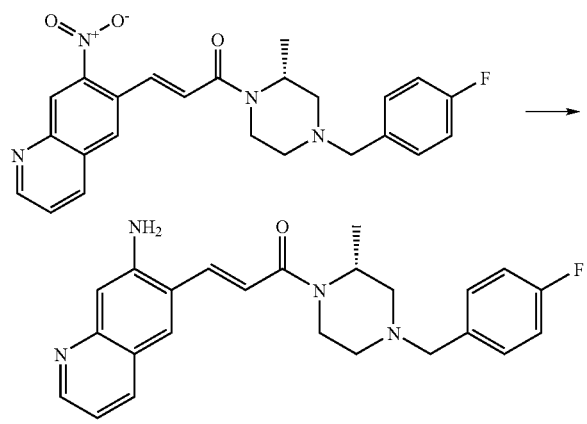

(E)-1-((R)-4-(4-Fluorobenzyl)-2-methylpiperazin-1-yl]-3-(7-nitroquinolin-6-yl)-propenone (500 mg; 1.15 mmol) was dissolved in EtOH/HClconc (20 ml; 1:1). SnCl2 (1.3 g; 6.9 mmol) was added in one portion and stirred for 5 min. A second portion of SnCl2 (654 mg; 3.95 mmol) was added and stirring continued for 5 min. The reaction mixture was poured on Na2CO3 satd and extracted with TBME three times. The combined organic phases were washed with 2N Na2CO3, dried over Na2SO4, evaporated to dryness and purified via chromatography (SiO2; TBME/MeOH/NH3conc 100/0/0 > 90/9/1) to yield the title compound as yellow foam (420 mg; 90%).

1H-NMR (400 MHz; DMSO-d6): 1.18-1.39 (m, 3H); 1.87-2.22 (m, 2H); 2.70 (bd, 1H); 2.85 (bd, 1H); 2.97 (bs, 1H); 3.46 (bd, 1H); 3.55 (bd, 1H); 4.10-4.40 (bd, 1H); 4.46-4.75 (bd, 1H); 5.83 (s, 2H, NH2); 7.10-7.23 (m, 5H); 7.40 (m, 2H); 7.80 (m, 1H); 8.04 (d, 1H); 8.11 (s, 1H); 8.62 (dd, 1H).

MS (m/z) ES+: 405.2 (MH+, 100).

f) N-(6-[(E)-3-[(R)-4-(4-Fluorobenzyl)-2-methylpiperazin-1-yl]-3-oxopropenyl]quinolin-7-yl)-acetamide

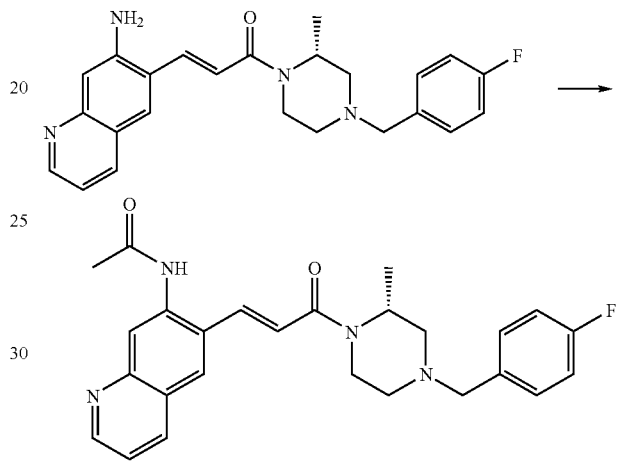

(E)-3-(7-Aminoquinolin-6-yl)-1-[(R)-4-(4-fluorobenzyl)-2-methylpiperazin-1-yl]-propenone (61 mg; 0.15 mmol) and NEt3 (0.065 ml; 0.5 ml) were dissolved in THF (2 ml) and treated with acetylchloride (0.036 ml; 0.5 mmol) for 30 min. at room temperature. The reaction mixture was poured on water and extracted with EtOAc three times. The combined organic phases were washed with water and 2N Na2CO3, dried over Na2SO4, evaporated and purified via chromatography (SiO2; TBME/MeOH/NH3conc 95/4.5/0.5) to yield the title compound as yellow foam (35 mg; 47%).

1H-NMR (400 MHz; DMSO-d6): 1.23-1.40 (m, 3H); 1.90-2.12 (m, 2H); 2.15 (s, 3H); 2.70 (bd, 1H); 2.88 (bd, 1H); 3.05 (bs, 1H); 3.45 (bd, 1H); 3.55 (bd, 1H); 4.13-4.47 (m, 1H); 4.50-4.75 (m, 1H); 7.20 (dd, 2H); 7.33 (d, 1H); 7.39 (dd, 2H); 7.52 (dd, 1H); 7.82 (d, 1H); 8.12 (s, 1H); 8.33 (d, 1H); 8.50 (s, 1H); 8.90 (dd; 1H); 9.97 (s, 1H).

MS (m/z) ES+: 447.2 (MH+; 100).

Example 36

(6-[(E)-3-[(R)-4-(4-Fluorobenzyl)-2-methylpiperazin-1-yl]-3-oxopropenyl]-quinolin-7-yl)-urea

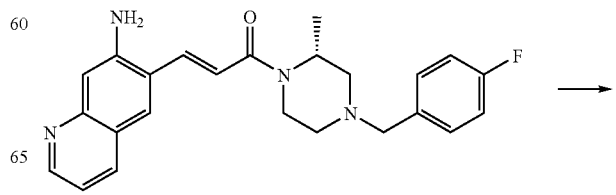

-continued

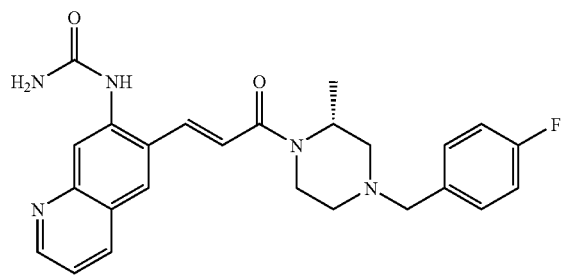

(E)-3-(7-Aminoquinolin-6-yl)-1-[(R)-4-(4-fluorobenzyl)-2-methylpiperazin-1-yl]-propenone (61 mg; 0.15 mmol) was dissolved in HOAc (3 ml) and water (6 ml) and warmed to 70° C. NaOCN (315 mg; 4.5 mmol) was added in 4 portions within 20 min. The reaction mixture was poured on Na2CO3 3N and extracted with EtOAc three times. The combined organic phases were purified via chromatography (TBME/MeOH/NH3conc 90/9/1 to 80/18/2 to yield the title compound (18 mg; 27%).

1H-NMR (400 MHz; DMSO-d6): 1.20-1.40 (bs, 3H); 1.85-2.25 (m, 2H); 2.70 (bd, 1H); 2.85 (bd, 1H); 3.00 (bs, 1H); 3.33-3.62 (m, 2H); 4.10-4.40 (m, 1H); 4.50-4.80 (m, 1H); 6.30 (bs, 1H); 6.78 (bs, 2H); 7.18 (dd, 2H); 7.30 (d, 1H); 7.40 (m, 2H); 7.86 (d, 1H); 8.30 (s, 1H); 8.40 (s, 1H); 8.47 (d, 2H); 8.81 (d, 1H).

MS (m/z) ES+: 448.2 (MH+, 100).

Example 37

N-(7-[(E)-3-[(R)-4-(4-Fluorobenzyl)-2-methylpiperazin-1-yl]-3-oxopropenyl]-quinolin-6-yl)-acetamide a) 7-Methyl-6-nitroquinoline

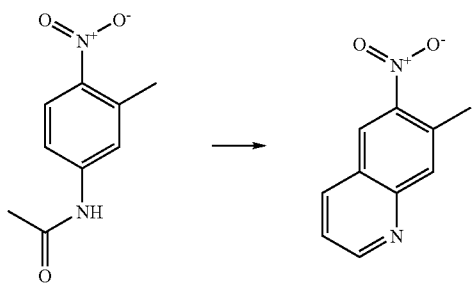

4-Acetamido-2-methylnitrobenzene (4.5 g; 23.2 mmol) glycerol (9 g; 100 mmol), H2SO4 conc (6.75 g) and As2O5.5H2O (3.6 g; 46.4 mmol) were heated at 130° C. for 20 h. The reaction mixture was poured on water, adjusted to pH 7-8 by adding NH3conc. and extracted with EtOAc three times. The combined organic phases were dried over Na2SO4, evaporated and purified via chromatography (SiO2; TBME/hexanes 70/30) to yield the title compound (1.5 g; 34%). The isomeric 5-methyl-6-nitroquinoline was eluted from the column after the title compound (850 mg; 19%).

1H-NMR (400 MHz; DMSO-d6): 2.64 (s, 3H); 7.65 (dd, 1H); 8.10 (s, 1H); 8.58 (d, 1H); 8.79 (s, 1H); 9.05 (bd, 1H).

The assignment of regioisomers was in agreement with ROESY-spectra.

MS (m/z) EI: 188 (M+; 40); 171 (100); 141 (40); 116 (60).

b) 6-Nitroquinolin-7-carbaldehyde

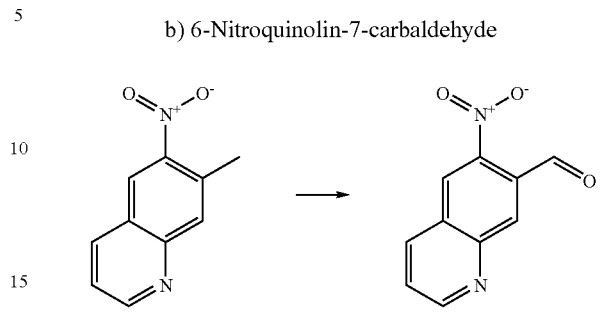

7-Methyl-6-nitroquinolin (1.22 g; 6.5 mmol) and tert.butoxy-bis(dimethylamino)methan (5.2 ml; 27.3 mmol) in DMF (13 ml) were heated for 15 min. in an oil bath, which was preheated to 160° C. The reaction mixture was evaporated to dryness, taken up in THF (26 ml). NaIO4 (8.3 g; 39 mmol) in water (520 ml) was added at room. temperature within 1.5 h and after stirring for another 1 h the reaction mixture was extracted with EtOAc twice. The combined organic phases were dried over Na2SO4, evaporated and purified via chromatography (SiO2; TBME) to yield the title compound as a yellow foam (920 mg; 70%).

1H-NMR (400 MHz; DMSO-d6): 7.87 (dd, 1H); 8.51 (s, 1H); 8.73 (d, 1H); 8.97 (s, 1H); 9.22 (dd, 1H); 10.36 (s, 1H).

MS (m/z) EI: 202 (M+, 20); 172 (40); 144 (25); 127 (70); 116 (100); 89 (60).

c) (E)-3-(6-Nitroquinolin-7-yl)-acrylic acid methyl ester

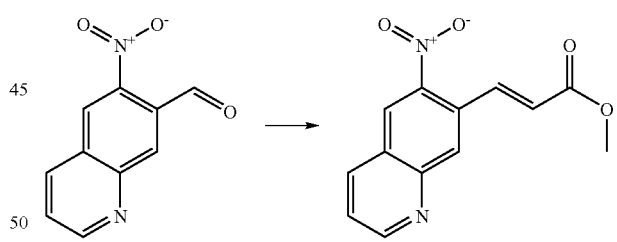

6-Nitroquinolin-7-carbaldehyde (920 mg; 4.55 mmol) in toluene (46 ml) and (methoxycarbonylmethylen)triphenylphosphoran (1.67 g; 5.0 mmol) were refluxed for 1 h. The title compound crystallised upon cooling and was filtered off. Recrystallisation from hot EtOAc (250 ml) gave pure title compound (700 mg). The mother liquor was purified via chromatography (SiO2; acetone/hexanes 30/70) to yield a further batch of pure title compound (300 mg). Total yield: 1 g; 85%.

1H-NMR (400 MHz; DMSO-d6): 3.80 (s, 3H); 6.79 (d, 1H); 7.75 (dd, 1H); 8.07 (d, 1H); 8.50 (s, 1H); 8.66 (d, 1H); 8.95 (s, 1H); 9.16 (dd, 1H).

MS (m/z) EI: 258 (M+, 20); 212 (100); 181 (25); 143 (50); 116 (40).

d) (E)-3-(6-Nitroquinolin-7-yl)-acrylic acid

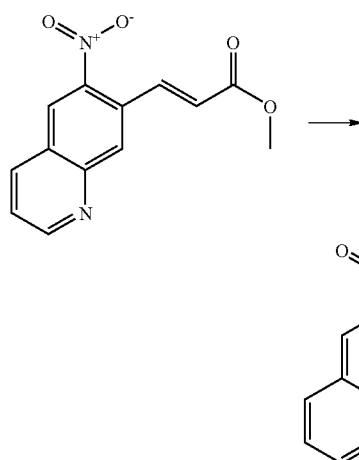

(E)-3-(6-Nitroquinolin-7-yl)-acrylic acid methyl ester (1 g; 3.9 mmol) was suspended in 2N NaOH (2.9 ml; 5.8 mmol) and MeOH (39 ml) and stirred at 55° C. for 1 h. The clear solution was cooled, treated with 2N HCl (3.2 ml; 6.4 mmol), diluted with water (70 ml) and the precipitated title compound filtered and dried (900 mg; 94%).

1H-NMR (400 MHz; DMSO-d6): 6.68 (d, 1H); 7.75 (dd, 1H); 7.97 (d, 1H); 8.45 (s, 1H); 8.65 (d, 1H); 8.93 (s, 1H); 9.15 (dd, 1H); 13.30 (s, 1H).

MS (m/z) EI: 244 (M+, 10); 198 (100); 171 (20); 143 (50); 116 (60).

e) (E)-1-[(R)-4-(4-Fluorobenzyl)-2-methylpiperazin-1-yl]-3-(6-nitroquinolin-7-yl)-propenone

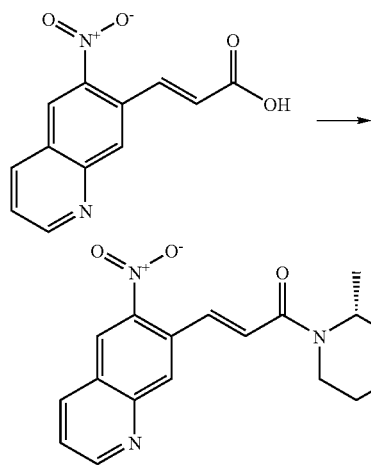

(E)-3-(6-Nitroquinolin-7-yl)-acrylic acid (122 mg; 0.5 mmol) and (R)-1-(4-fluorobenzyl)-3-methylpiperazine (Hilger, Christoph-Stephan et al., WO 0236581) (104 mg; 0.5 mmol) and EDCl.HCl (96 mg; 0.5 mmol) were dissolved in DMF (5 ml) and stirred for 18 h at room temperature. The reaction mixture was poured on water and extracted with EtOAc three times. The combined organic phases were dried over Na2SO4, evaporated and purified via chromatography (SiO2; acetone/hexanes 40/60) to yield the title compound as colorless oil (150 mg; 69%).

1H-NMR (400 MHz; DMSO-d6): 1.21-1.48 (m, 3H); 1.90-2.23 (m, 2H); 2.66 (bd, 1H); 2.83 (bd, 1H); 3.00 (m, 1H); 3.44 (bd, 1H); 3.53 (bd, 1H); 4.28 (bs, 1H); 4.63 (bs, 1H); 7.17 (dd, 2H); 7.38 (dd, 2H); 7.44 (d, 1H); 7.72 (dd, 1H); 7.83 (d, 1H); 8.62 (dd, 2H); 8.88 (s, 1H); 9.13 (dd, 1H).

MS (m/z) ES+: 435.2 (MH+).

f) (E)-3-(6-Aminoquinolin-7-yl)-1-[(R)-4-(4-fluorobenzyl)-2-methylpiperazin-1-yl]-propenone

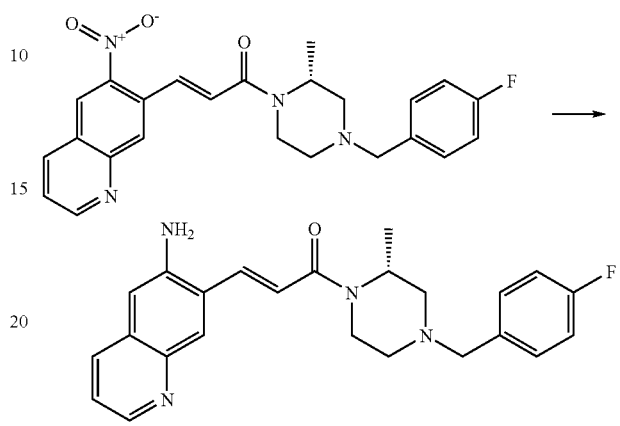

(E)-1-[(R)-4-(4-Fluorobenzyl)-2-methylpiperazin-1-yl]-3-(6-nitroquinolin-7-yl)-propenone (150 mg; 0.36 mmol) 1.15 mmol) was dissolved in EtOH/HClconc (6 ml; 1:1). SnCl2 (387 mg; 2.04 mmol) was added in one portion and stirred for 5 min. The reaction mixture was poured on saturated Na2CO3 solution and extracted with TBME three times. The combined organic phases were washed with 2N Na2CO3, dried over Na2SO4, evaporated to dryness and purified via chromatography (SiO2; acetone/hexanes 40/60) to yield the title compound as yellow foam (110 mg; 82%).

1H-NMR (400 MHz; DMSO-d6): 1.18-1.38 (m, 3H); 1.90-2.23 (m, 2H); 2.67 (bd, 1H); 2.83 (bd, 1H); 2.98 (bs, 1H)3.42 (bd, 1H); 3.53 (bd, 1H); 4.12-4.38 (bd, 1H); 4.50-4.75 (bd, 1H); 5.66 (bs, 2H), NH2); 6.94 (s, 1H); 7.18 (dd, 2H); 7.28 (m, 2H); 7.38 (m, 2H); 7.80 (d, 1H); 7.91 (d, 1H); 8.17 (s, 1H); 8.52 (dd, 1H).

MS (m/z) ES+: 405.2 (MH+, 100).

g) N-(7-[(E)-3-[(R)-4-(4-Fluorobenzyl)-2-methylpiperazin-1-yl]-3-oxopropenyl]-quinolin-6-yl)-acetamide

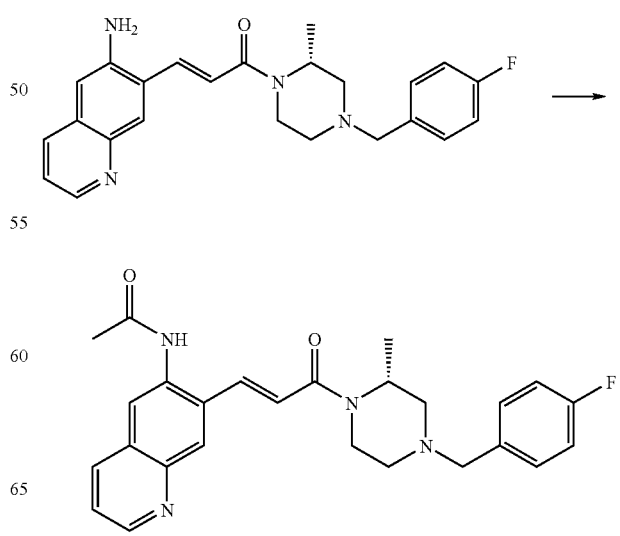

(E)-3-(6-Aminoquinolin-7-yl)-1-[(R)-4-(4-fluorobenzyl)-2-methylpiperazin-1-yl]-propenone (81 mg; 0.2 mmol) and NEt3 (0.2 ml; 1.6 mmol) were dissolved in THF (5 ml) and treated with acetylchloride (0.087 ml; 1.2 mmol) for 2 h at 55° C. The reaction mixture was poured on water and extracted with EtOAc three times. The combined organic phases were washed with water and 2N Na2CO3, dried over Na2SO4, evaporated and purified via chromatography (SiO2; acetone/hexanes 50/50) to yield the title compound as yellow solid (60 mg; 66%).

1H-NMR (400 MHz; DMSO-d6): 1.20-1.48 (m, 3H); 1.88-2.23 (m, 2H); 2.15 (1,3H); 2.68 (bd, 1H); 2.83 (bd, 1H); 3.00 (bs, 1H); 3.45 (d, 1H); 3.53 (bd, 1H); 4.28 (bs, 1H); 4.66 (bs, 1H); 7.18 (dd, 2H); 7.37 (dd, 2H); 7.41 (d, 1H); 7.50 (dd, 1H); 7.80 (d, 1H); 8.04 (s, 1H); 8.30 (d, 1H); 8.53 (s, 1H); 8.88 (dd, 1H); 9.95 (s, 1H).

MS (m/z) ES−: 445.3 (M−H−)

Example 38

2-Dimethylamino-N-(7-[(E)-3-[(R)-4-(4-fluorobenzyl)-2-methylpiperazin-1-yl]-3-oxopropenyl]-quinolin-6-yl)-acetamide

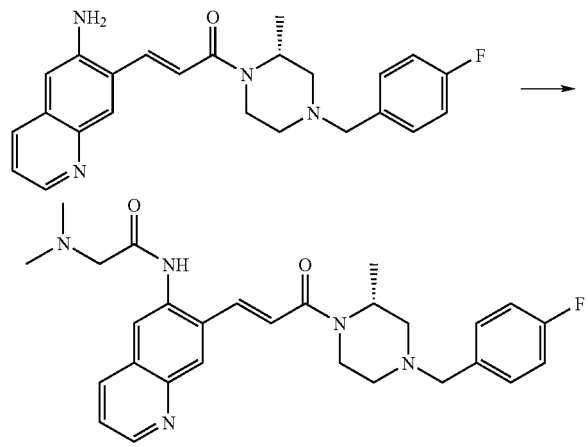

(E)-3-(6Aminoquinolin-7-yl)-1-[(R)-4-(4-fluorobenzyl)-2-methylpiperazin-1-yl]-propenone (121 mg; 0.3 mmol) and chloroacetylchloride (45 mg; 0.4 mmol) in CH2Cl2 (6 ml) were stirred for 1 h at room temperature, poured on 2N Na2CO3 and extracted with EtOAc three times. The combined organic phases were washed with water, dried over Na2SO4 and evaporated to dryness to yield the chloroacetamide intermediate (110 mg; 77%) as a yellowish foam. The chloroacetamide intermediate (48 mg; 0.1 mmol) was dissolved in THF (6 ml) and treated with 6 drops of dimethylamine, stirred for 2 h at room temperature, poured on 2N Na2CO3 and extracted with EtOAC three times. The combined organic phases were washed with water, dried over Na2SO4, evaporated to dryness and purified via chromatography (SiO2; TBME/MeOH|NH3conc 95/4.5/0.5) to yield the title compound as slightly colored foam (20 mg; 45%).

1H-NMR (400 MHz; DMSO-d6): 1.20-1.38 (m, 3H); 1.88-2.23 (m, 2H); 2.35 (s, 6H); 2.68 (bd, 1H); 2.83 (bd, 1H); 3.00 (bs, 1H); 3.15 (s, 2H); 3.43 (bd, 1H); 3.53 (bd, 1H); 4.28 (bs, 1H); 4.63 (bs, 1H); 7.18 (dd, 2H); 7.38 (dd, 2H); 7.41 (d, 1H); 7.51 (dd, 1H); 7.78 (d, 1H); 8.13 (s,1H); 8.32 (d, 1H); 8.52 (d, 1H); 8.88 (d, 1H); 9.90 (s, 1H).

MS (m/z) ES+: 490.2 (MH+, 100).

Example 39

N-(7-[(E)-3-[(R)-4-(4-Fluorobenzyl)-2-methylpiperazin-1-yl]-3-oxopropenyl]-quinolin-6-yl)-methanesulfonamide a) N,N-(7-[(E)-3-[(R)-4-(4-Fluorobenzyl)-2-methylpiperazin-1-yl]-3-oxopropenyl]-quinolin-6-yl)-bis-methanesulfonamide

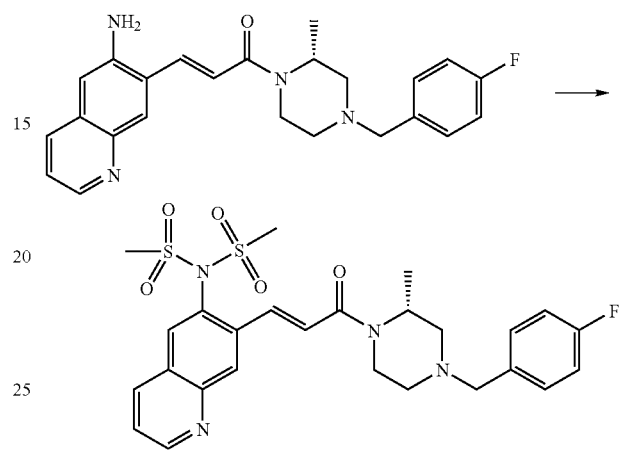

(E)-3-(6-Aminoquinolin-7-yl)-1-[(R)-4-(4-fluorobenzyl)-2-methylpiperazin-1-yl]-propenone (81 mg; 0.2 mmol) in THF (4 ml) and NEt3 (0.17 ml; 1.2 mmol) was treated with methanesulfonyl chloride (0.047 ml; 0.6 mmol) for 1 h at room temperature. The reaction mixture was poured on water and extracted with EtOAc three times. The combined organic phases were washed with water, dried over Na2SO4, evaporated to dryness and purified via chromatography (SiO2; acetone/hexanes 30/70) to yield the title compound as yellow foam (100 mg; 89%).

b) N-(7-[(E)-3-[(R)-4-(4-Fluorobenzyl)-2-methylpiperazin-1-yl]-3-oxopropenyl]-quinolin-6-yl)-methanesulfonamide

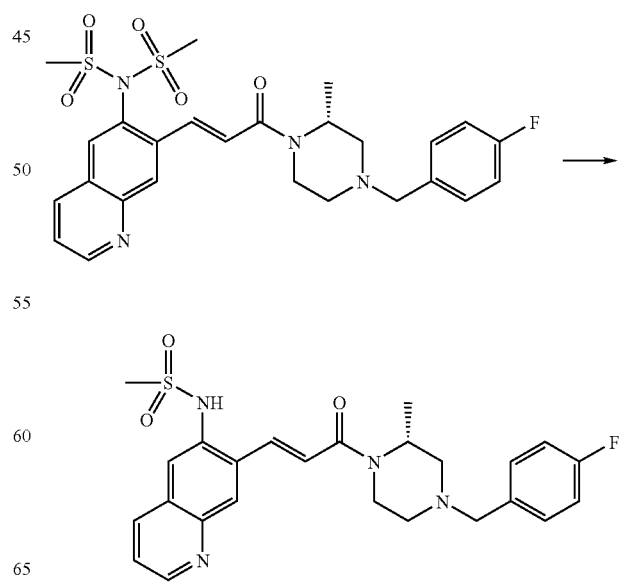

N,N-(7-[(E)-3-[(R)-4-(4-Fluorobenzyl)-2-methylpiperazin-1-yl]-3-oxopropenyl]-quinolin-6-yl)-bis-methanosulfonamide (100 mg; 0.17 mmol) was dissolved in EtOH (3.4 ml) and treated with 2N NaOH (3.4 ml) for 30 min at room temperature. The reaction mixture was poured on water and extracted with EtOAc three times. The combined organic phases were washed with water, dried over Na2SO4, evaporated to dryness and purified via chromatography (SiO2; TBME/MeOH/NH3conc 90/10/1) to yield the title compound as yellow foam (55 mg; 54%).

1H-NMR (400 MHz; DMSO-d6): 1.20-1.37 (m, 3H); 1.90-2.22 (m, 2H); 2.67 (bd, 1H); 2.83 (bd, 1H); 2,97 (s, 3H); 3.00 (bs, 1H); 3.42 (bd, 1H); 3.53 (bd, 1H); 4.27 (bs, 1H); 4.62 (bs, 1H); 7.15 (dd, 2H); 7.35 (dd, 2H); 7.39 (dd, 1H); 7.42 (dd, 1H); 7.78 (s, 1H); 8.02 (d, 1H); 8.22 (d, 1H); 8.43 (s, 1H); 8.78 (dd, 1H).

MS (m/z) ES+: 483.1 (M+, 100).

Example 40

N-(5-Chloro-2-[(E)-3-[(2R,5S)-4-(4-fluorobenzyl)-2,5-dimethylpiperazin-1-yl]-3-oxopropenyl]-phenyl)-cyanoguanidine

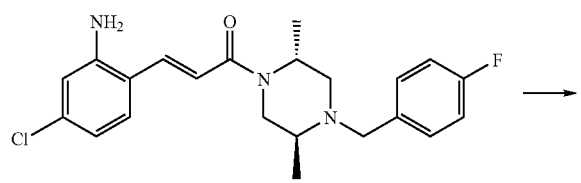

(E)-3-(2-Amino-4-chlorophenyl)-1-[(2R,5S)-4-(4-fluorobenzyl)-2,5-dimethylpiperazin-1-yl]-propenone (60 mg; 0.15 mmol), ethoxyethanol (2.6 ml), water (2.6 ml) 2N HCl (1.5 ml) and NaN(CN)2 (534 mg; 6.0 mmol) were kept. in an oil bath for 2 min, which was preheated to 150° C. The reaction mixture was poured on 2N Na2CO3 and extracted with CH2Cl2 /EtOH (10/1) three times. The combined organic phases were evaporated and purified by HPLC (XTerra RP16 acetonitril/water) to yield the title product (8 mg; 10%) as colorless foam.

1H-NMR (400 MHz; DMSO-d6): 0.95 (bd, 3H); 1.25 (bs, 3H); 2.25 (bd, 1H); 2.65 (bs, 1H); 3.00 (bs, 1H); 3.43 (m, 2H); 3.60 (bd, 1H); 4.03 (bs, 1H); 4.50 (bs, 1H); 7.08-7.22 (m, 4H); 7.28 (d, 1H); 7.38 (m, 2H); 7.53 (d, 1H); 7.88 (d, 1H); 9.2 (bs, 1H, NH).

MS (m/z) ES+: 469 (MH+, 100).

Example 41

N-(5-Chloro-2-[(E)-3-[(2R,5S)-4-(4-fluorobenzyl)-2,5-dimethylpiperazin-1-yl]-3-oxopropenyl]-phenyl)-2-dimethylacetamide

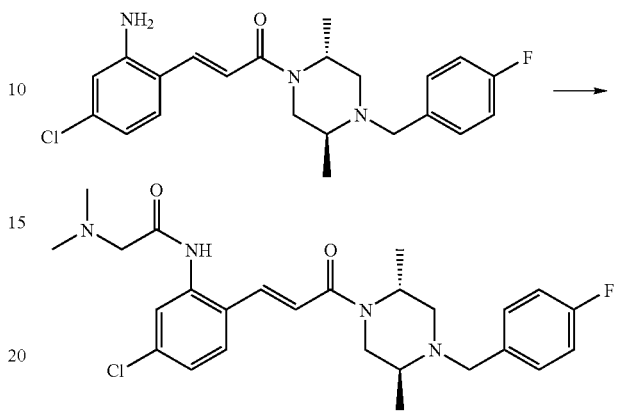

(E)-3(2-Amino-4-chlorophenyl)-1-[(2R,5S)-4-(4-fluorobenzyl)-2,5-dimethylpiperazin-1-yl]-propenone (50 mg; 0.125 mmol) was treated with chloroacetylchloride followed by dimethylamine as described above for APF697 to yield the title compound as colorless foam (45 mg; 75%).

1H-NMR (400 MHz, DMSO-d6): 0.93 (bd, 3H); 1.24 (bd, 3H); 2.25 (bd, 1H); 2.33 (s, 6H); 2.65 (bs, 1H); 3.03 (m, 2H); 3.12 (s, 2H); 3.46 (d 1H); 3.62 (d, 1H); 4.04 (bs, 1H); 4.55 (bs, 1H); 7.13 (m, 3H); 7.28 (dd, 1H); 7.38 (dd, 2H); 7.59 (d, 1H); 7.63 (d, 1H); 7.90 (d, 1H); 9.80 (s, 1H).

MS (m/z) ES+: 487.2 (MH+, 100).

Example 42

N-(5-Chloro-2-[(E)-3-[(2R,5S)-4-(4-fluorobenzyl)-2,5-dimethylpiperazin-1-yl]-3-oxopropenyl]-phenyl)-methanesulfonamide

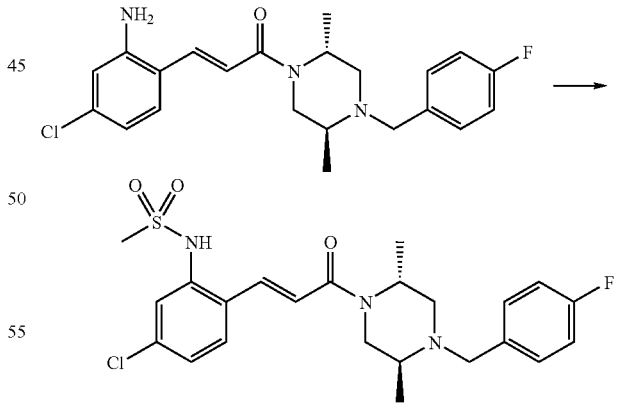

(E)-3-(2-Amino-4-chlorophenyl)-1-[(2R,5S)-4-(4-fluorobenzyl)-2,5-dimethylpiperazin-1-yl]-propenone (61 mg; 0.15 mmol) in pyridine (1.5 ml) was treated with methanesulfonyl chloride (0.035 ml; 0.45 mmol) at room temperature for 30 min. The reaction mixture was poured on 2N Na2CO3 and extracted with EtOAc three times. The combined organic phases were washed with water, dried over Na2SO4, evaporated to dryness and purified via chromatography (SiO2;

TBME/MeOH/NH3conc 90/10/1 to EtOAc/EtOH 90/10) to yield the title compound as yellow foam (50 mg; 69%).

1H-NMR (400 MHz; DMSO-d6: 0.92 (bd, 3H); 1.24 (m, 3H); 2.23 (bd, 1H); 2.64 (bs, 1H); 2.99 (s, 3H); 3.03 (d, 2H); 3.43 (d, 1H); 3.60 (d, 1H); 4.03 (bs, 1H); 4.50 (bs, 1H); 7.08-7.19 (m, 4H); 7.25-7.35 (m, 1H); 7.49 (m, 2H); 7.80 (d, 1H); 7.90 (bd, 1H); 9.80 (bs, 1H, NH).

MS (m/z) ES+: 480 (MH+, 100).

Example 43

N-(5-Chloro-2-[(E)-3-[(2R,5S)-4-(4-fluorobenzyl)-2,5-dimethylpiperazin-1-yl]-3-oxopropenyl]-4-methoxyphenyl)-acetamide

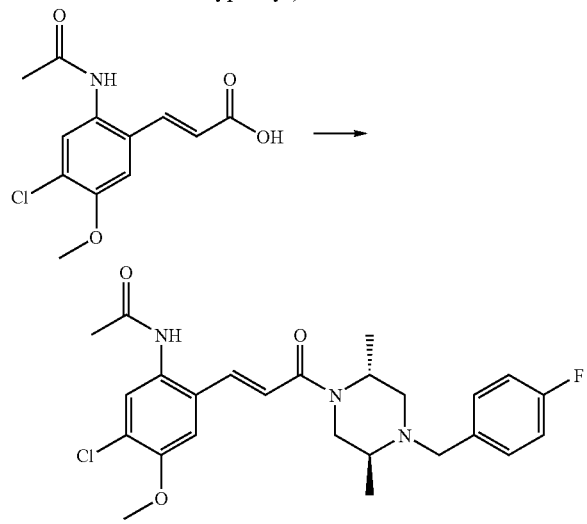

(E)-3-(2-Acetylamino-4-chloro-5-methoxyphenyl)-acrylic acid (100 mg; 0.37 mmol), (2R,5S)-1-(4-fluorobenzyl)-2,5-dimethylpiperazine (Mavunkel, Babu J. et al., WO 00/71535) (83 mg; 0.37 mmol) and EDCl.HCl (85 mg, 0.44 mmol) were dissolved in DMF (3 ml) and stirred over night. The reaction mixture was evaporated, taken up in 2N Na2CO3 and extracted with EtOAc three times. The combined organic phases were evaporated and purified via chromatography (SiO2 acetone/hexanes 3/7 to 4/6) to yield the title compound as colorless crystals (97 mg; 55%).

1H-NMR (400 MHz; DMSO-d6: 0.93 (bd, 3H); 1.25 (bs, 3H); 2.08 (s, 3H); 2.16 (bd, 1H); 2.50 (bs, 1H); 2.68 (bs, 1H); 3.02 (bs, 1H); 3.45 (d, 1H); 3.61 (bd, 1H); 3.93 (s, 3H); 4.05 (bs, 1H); 4.56 (bs, 1H); 7.11-7.27 (m, 3H); 7.36-7.50 (m, 4H); 7.58 (d, 1H); 9.68 (s, 1H, NH).

MS (m/z) ES+: 474 (MH+, 100).

Example 44

N-(5-Chloro-2-[(E)-3-[(2R,5S)-4-(4-fluorobenzyl)-2,5-dimethylpiperazin-1-yl]-3-oxopropenyl]-4-methoxyphenyl)-methanesulfonamide a) (E)-3-(2-Amino-4-chloro-5-methoxyphenyl)-acrylic acid ethyl ester

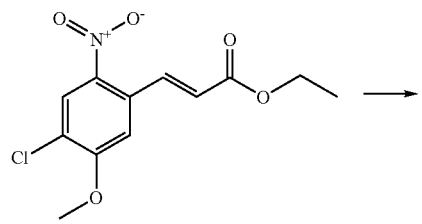

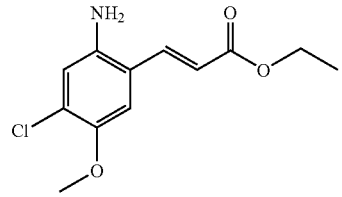

(E)-3-(2-Nitro-4-chloro-5-methoxyphenyl)-acrylic acid ethyl ester (2 g; 7 mmol) and SnCl2 (7 g; 36 mmol) were dissolved in THF/water (60 ml; 5/1), heated to reflux for 2 min. and then left at room temperature for 20 min. The reaction mixture was poured on 2N Na2CO3 and extracted with TBME/EtOH three times. The combined organic phases were dried over Na2SO4 and evaporated to dryness to yield a semi-crystalline raw material, which was triturated with TBME/hexanes 1/1 to render the title compound as yellow crystals (1 g; 56%).

1H-NMR (400 MHz; DMSO-d6: 1.35 (t, 3H); 3.85 (s, 3H); 4.28 (q, 2H); 6.33 (d, 1H); 6.78 (s, 1H); 6.93 (s, 1H); 7.73 (d, 1H).

MS (m/z) EI: 255 (M+; 50); 210 (100); 194 (40); 182 (30); 166 (30).

b) (E)-3-(4-Chloro-2-methanesulfonylamino-5-methoxyphenyl)-acrylic acid ethyl ester

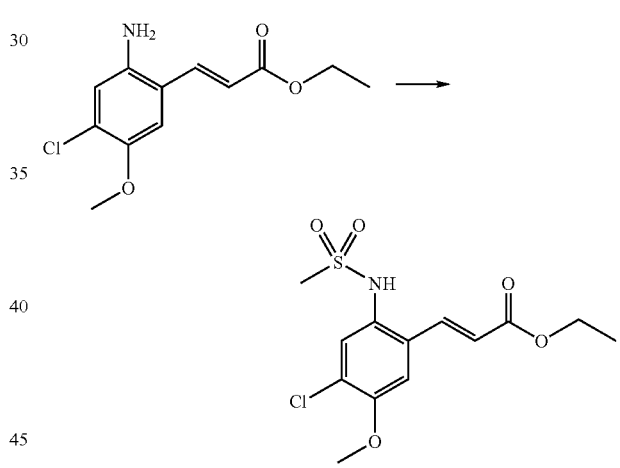

(E)-3-(2-Amino-4-chloro-5-methoxyphenyl)-acrylic acid ethyl ester (250 mg; 0.98 mmol) in pyridine (2 ml) was treated with methanesulfonyl chloride (0.15 ml; 2 mmol) for 15 min. at room temperature. The reaction mixture was poured on water and extracted with TBME three times. The combined organic phases were evaporated to dryness and purified via chromatography (SiO2; acetone/hexanes 2/8) to yield the title compound as slightly yellow crystals (216 mg; 66%)

c) (E)-3-(4-Chloro-2-methanesulfonylamino-5-methoxyphenyl)-acrylic acid

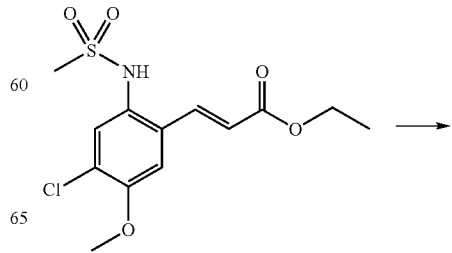

-continued

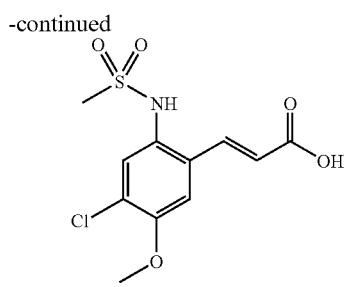

(E)-3-(4Chloro-2-methanesulfonylamino-5-methoxyphenyl)-acrylic acid ethyl ester (320 mg; 0.96 mmol) was refluxed in 2N NaOH/EtOH 1/10 for 10 min. The resulting suspension was cooled to 0° C., filtered, taken up in water and acidified with 2N HCl and extracted with TBME three times. The combined organic phases were dried over Na2SO4 and evaporated to dryness to yield the title compound as yellowish crystals (114 mg; 39%).

1H-NMR (400 MHz; DMSO-d6: 2.97 (s, 3H); 3.93 (s, 3H); 6.68 (d, 1H); 7.40 (s, 1H); 7.51 (s, 1H); 7.90 (s, 1H).

MS (m/z) ES−: 304 (M−; 100).

d) N-(5-Chloro-2-[(E)-3-[(2R,5S)-4-(4-fluorobenzyl)-2,5-dimethylpiperazin-1-yl]-3-oxopropenyl]-4-methoxyphenyl)-methanesulfonamide

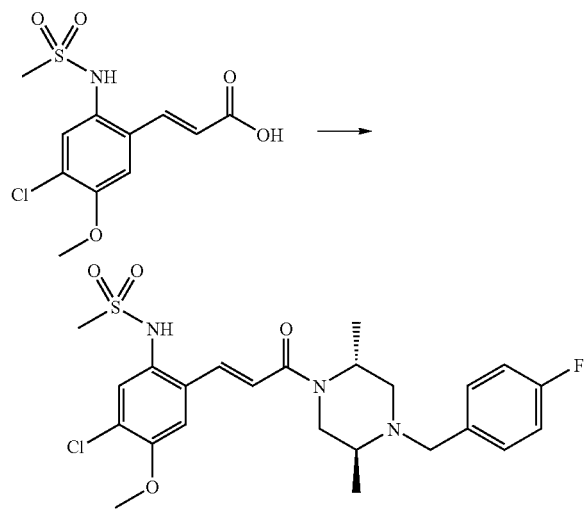

(E)-3-(4-Chloro-2-methanesulfonylamino-5-methoxyphenyl)-acrylic acid (100 mg; 0.32 mmol), (2R,5S)-1-(4-fluorobenzyl)-2,5-dimethylpiperazine (Mavunkel, Babu J. et al., WO 00171535) (73 mg; 0.32 mmol) and EDCl.HCl (75 mg, 0.39 mmol), HOBt (5 mg; 0.03 mmol) were dissolved in DMF (2 ml) and stirred over night. The reaction mixture was evaporated, taken up in 2N Na2CO3 and extracted with EtOAc three times. The combined organic phases were evaporated and purified via chromatography (SiO2 acetone/hexanes 3/7) to yield the title compound as yellow foam (135 mg; 81%)

1H-NMR (400 MHz; DMSO-d 6: 0.93 (bd, 3H); 1.23 (bs, 3H); 2.23 (bd, 1H); 2.67 (bs, 2H); 2.94 (s, 3H); 3.00 (bs, 1H); 3.45 (bd, 1H); 3.61 (bd, 1H); 3.95 (s, 3H); 4.05 (bs, 1H); 4.55 (bs, 1H); 7.13 (dd, 2H); 7.20 (bd, 1H); 7.36 (s, 1H); 7.38 (dd, 2H); 7.50 (s, 1H); 7.78 (d, 1H); 9.40 (s, 1H).

MS (m/z) ES+: 510 (MH+, 100).

Example 45

N-[5-Chloro-2-[(E)-3-(R)-4-(4-fluorobenzyl)-2-methylpiperazin-1-yl]-3-oxopropenyl]-4-(2-methoxyethoxy)-phenyl]-acetamide a) 1-Chloro-2-(2-methoxyethoxy)-4-methyl-5-nitrobenzene

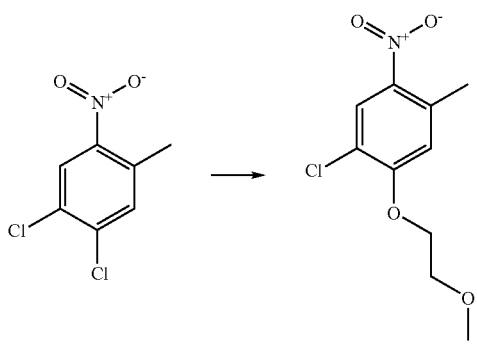

1,2-Dichloro-4-methyl-5-nitrobenzene (R.J. De Lang, et al. Tetrahedron (1998), 54(12), 2953-2966.) (860 mg; 4.17 mmol) was added to solution of sodium (115 mg; 5.01 mmol) dissolved in 2-methoxyethanol (15 ml). The brown reaction mixture was stirred at 100° C. for 1 h, poured on brine (50 ml) and extracted with TBME three times. The combined organic phases were evaporated and purified via chromatography (SiO2 acetone/hexanes 1/9) to yield the title compound as orange crystals (640 mg; 63%)

1H-NMR (400 MHz, CDCl3): 2.55 (s, 3H); 3.41 (s, 3H); 3.77 (t, 2H); 4.18 (t, 2H); 6.75 (s, 1H); 8.10 (s, 1H).

b) (E)-3-[4-Chloro-5-(2-methoxyethoxy)-2-nitrophenyl]-acrylic acid methyl ester

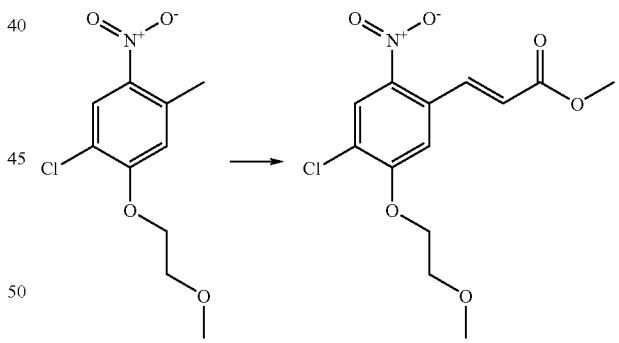

1-Chloro-2-(2-methoxyethoxy)-4-methyl-5-nitrobenzene (300 mg; 1.22 mmol) in DMF (3 ml) was treated with tert-.butoxy-bis(dimethylamino)methan (1.06 ml; 5.1 mmol) in DMF (13 ml) at 160° C. for 20 min. The reaction mixture was evaporated to dryness and taken up in THF (6 ml). NaIO4 (1.6 g; 7.3 mmol) in water (25 ml) was added at room temperature within 0.5 h and after stirring for another 1 h, the reaction mixture was extracted with EtOAc twice. The combined organic phases were dried over Na2SO4 and evaporated to dryness to yield the intermediate 4-chloro-5-(2-methoxyethoxy)-2-nitrobenzaldehyde as brown solid (360 mg; quant.). 4-chloro-5-(2-methoxyethoxy)-2-nitrobenzaldehyde (360 mg; 1.22 mmol) and (methoxycarbonylmethylen) triphenylphosphoran (449 mg; 1.34 mmol) were refluxed for 1 h in toluene (20 ml). After cooling the reaction mixture, toluene (100 ml) was added and the resulting crystals filtered off and purified via chromatography (SiO2, TBME/hexanes 1/1) to yield the title compound as a cis-trans mixture (290 mg). Recrystallisation from hot TBME rendered the pure trans isomer (180 mg; 47%) as slightly yellow crystals.

1H-NMR (400 MHz, CDCl3): 3.70 (s, 3H); 4.08 (m, 5H); 4.55 (dd, 2H); 6.53 (d, 1H); 7.31 (s, 1H); 8.41 (d, 1H); 8.43 (s, 1H).

c) (E)-3-[2-Acetylamino-4-chloro-5-(2-methoxy-ethoxy)-phenyl]acrylic acid

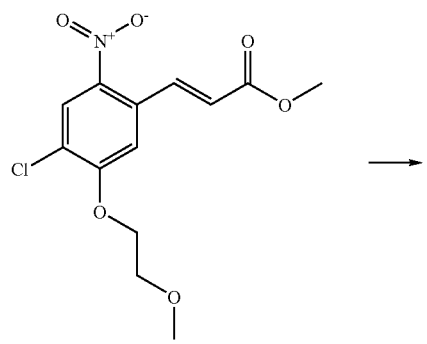

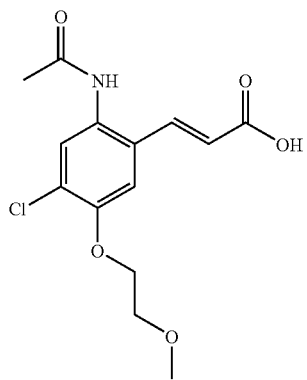

(E)-3-[4Chloro-5-(2-methoxyethoxy)-2-nitrophenyl]-acrylic acid methyl ester (910 mg; 2.88 mmol) was dissolved in MeOH (160 ml)/HClconc (50 ml). SnCl2 (7.4 g; 39 mmol) was added and the reaction mixture stirred for 1 h at room temperature, poured on saturated Na2CO3 and extracted with TBME three times. The combined organic phases were dried over Na2SO4 and evaporated to dryness to yield the intermediate (E)-3-[2-amino-4-chloro-5-(2-methoxyethoxy)-phenyl]acrylic acid methyl ester (740 mg; 90%).

(E)-3-[2-aminochloro-5-(2-methoxyethoxy)-phenyl] acrylic acid methyl ester (740 mg, 2.6 mmol) was dissolved in pyridine (20 ml) and treated with acetylchloride (1 ml; 13 mmol), which was added at room temperature in 5 portions. After stirring for 10 min, the reaction mixture was poured on water and extracted with EtOAc three times. The combined organic phases were dried over Na2SO4 and evaporated to dryness to yield the intermediate (E/Z)-3-[2-acetylamino-4-chloro-5-(2-methoxyethoxy)-phenyllacrylic acid methyl ester (730 mg; 87%) as yellow crystals.

(E/Z)-3-[2-acetylamino-4-chloro-5-(2-methoxyethoxy)-phenyllacrylic acid methyl ester (730 mg; 2.23 mmol) was dissolved in MeOH (30 ml) and treated with 2N NaOH (1.7 ml; 3.34 mmol) at 60° C. for 1 h. 2N HCl (10 ml) and water (20 ml) were added and extracted with EtOAc three times. The combined organic phases were dried over Na2SO4 and evaporated to dryness to yield the title compound (E)-3-[2-acetylamino-4-chloro-5-(2-methoxyethoxy)-phenyl]acrylic acid as yellow crystals (570 mg; 82%).

1H-NMR (400 MHz; DMSO-d 6: 2.07 (s, 3H); 3.31 (s, 3H); 3.70 (dd, 2H); 4.27 (dd, 2H); 6.62 (d, 1H); 7.43 (s, 1H); 7.47 (s, 1H); 7.62 (d, 1H); 9.72 (s, 1H, NH). 12.2 (bs, 1H, COOH).

MS (m/z) El: 313 (M+, 70); 271 (35); 213 (50); 168 (30).

d) N-[5-Chloro-2-[(E)-3-(R)-4-(4-fluoroberzyl)-2-methylpiperazin-1-yl]-3-oxopropenyl)-(2-methoxy-ethoxy)-phenyl]-acetamide (ATQ503)

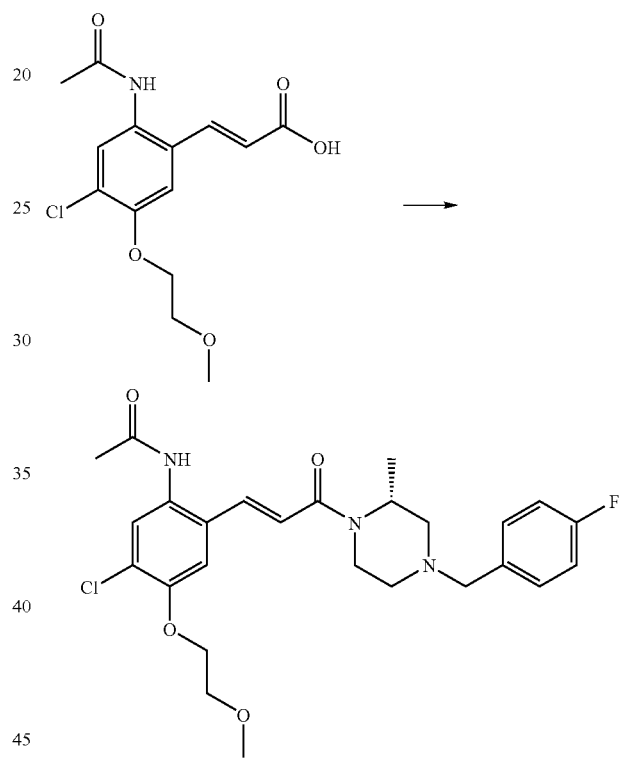

(E)-3-[2-Acetylamino-4-chloro-5-(2-methoxyethoxy)-phenyl]acrylic acid (100 mg; 0.32 mmol), (R)-1-(4-fluorobenzyl)-3-methylpiperazine (Hilger, Christoph-Stephan et al., WO 0236581) (66 mg; 0.32 mmol) EDCl.HCl (73 mg; 0.38 mmol) and HOBt (58 mg; 0.38 mol) were dissolved in DMF (4 ml) and stirred for 18 h at room temperature. The reaction mixture was poured on water and extracted with TBME three times. The combined organic phases were dried over Na2SO4, evaporated and purified via chromatography (SiO2; acetone/hexanes 2/8 to 1/1) to yield the title compound as slightly yellow crystals (65 mg; 38%).

1H-NMR (400 MHz; DMSO-d6): 1.08-1.31 (m, 3H); 1.85-2.22 (m, 2H); 2.03 (s, 3H); 2.68 (bd, 1H); 2.83 (bd, 1H); 3.00 (bs, 1H); 3.31 (s, 3H); 2.93 (bd, 1H); 3.53 (bd, 1H); 3.71 (dd, 2H); 4.17 (bs, 1H); 4.28 (dd, 2H); 4.60 (bs, 1H); 7.15 (dd, 2H); 7.20 (d, 1H); 7.35 (dd, 2H); 7.43 (s, 1H); 7.48 (s, 1H); 7.55 (d, 1H); 9.68 (s, 1H, NH).

MS (m/z) E+: 504.2 (MH+, 100).

Example 46

N-(5-Chloro-2-[(E)-3-[(R)-4(4-fluorobenzyl)-2-methylpiperazin-1-yl]-3-oxopropenyl]-4-morpholin-4-yl-phenyl)-acetamide a) 4-(2-Chloro-5-methyl-4-nitrophenyl)-morpholine

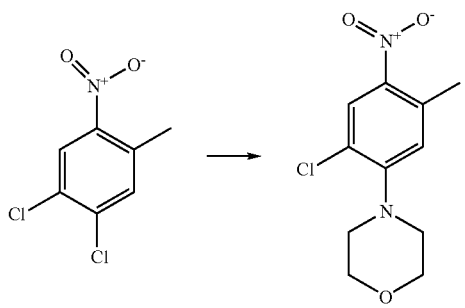

1,2-Dichloro-4-methyl-5-nitrobenzene (R.J. De Lang, et al. Tetrahedron (1998), 54(12), 2953-2966.) (1 g; 4.8 mmol), morpholine (1 ml) and 1,2-diethoxyethane (1 ml) were heated in a microwave oven at 160° C. for 2 h. The reaction mixture was poured on water/2N HCl 10/1 (50 ml) and extracted with TBME three times. The combined organic phases were dried over Na2SO4, evaporated and recrystallised from hot TBME to yield the title compound as yellow crystals (670 mg; 54%).

1H-NMR (400 MHz, CDCl3: 2.52 (s, 3H); 3.11 (t, 4H); 3.82 (t, 4H); 6.78 (s, 1H); 8.08 (s, 1H).

MS (m/z) EI: 256 (M+, 100); 198 (80); 181 (90).

b) N-(5-Chloro-2-[(E)-3-[(R)-4-(4-fluorobenzyl)-2-methylpiperazin-1-yl]-3-oxopropenyl]-4 morpholin-4-yl-phenyl)-acetamide

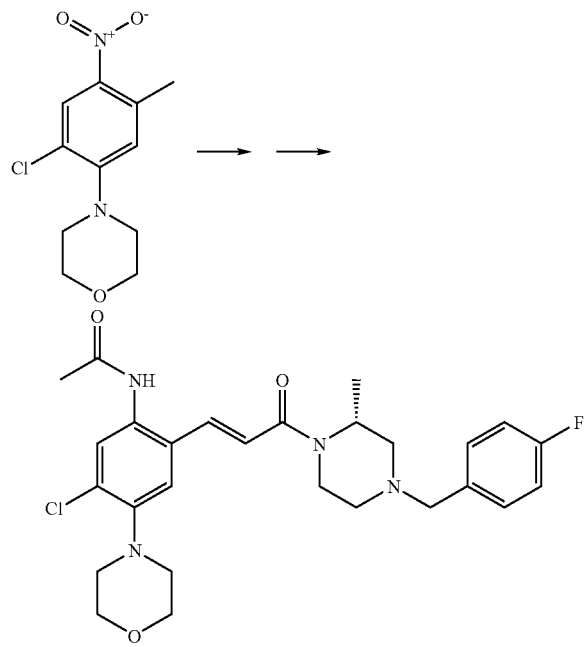

In analogy to the synthesis described above for N-[5-Chloro-2-[(E)-3-(R)-4-(4-fluorobenzyl)-2-methylpiperazin-1-yl]-3-oxopropenyl)-4-(2-methoxyethoxy)-phenyl]-acetamide, 4-(2-chloro-5-methyl-4-nitrophenyl)-morpholine was converted into N-(5-chloro-2-[(E)-3-[(R)-4-(4-fluorobenzyl)-2-methylpiperazin-1-yl]-3-oxopropenyl]-4-morpholin-4-yl-phenyl)-acetamide.

1H-NMR (400 MHz; DMSOd6): 1.18-1.33 (m, 3H); 1.85-2.20 (m, 2H); 2.05 (s, 3H); 2.68 (bd, 1H); 2.83 (bd, 1H); 3.03 (bt, 5H); 3.42 (bd, 1H); 3.53 (bd, 1H); 3.75 (bt, 4H); 4.18 (bs, 1H); 4.58 (bs, 1H); 7.12-7.20 (m, 3H); 7.35 (dd, 2H); 7.47 (s, 1H); 7.49 (s, 1H); 7.56 (d, 1H); 9.72 (1H, NH).

MS (m/z) E+: 515.3 (M+, 100).

Example 47

N-(5-Chloro-2-(E)-3-[(R)-2-ethyl-4-(4-fluorobenzyl)-piperazin-1-yl]-3-oxo-propenyl)-phenyl)-acetamide a) (4-Fluorobenzylamino)-acetic acid ethyl ester 4-Fluorobenzylamine (13.86 g, 110 mmol) was dissolved in 25 ml THF and the solution was cooled to 0° C. Bromoacetic acid ethyl ester (8.35 g, 50 mmol) dissolved in 25 ml THF was added dropwise at 0° C. After stirring for 2 hours at room temperature the solid was filtered off and the fitrate was evaporated. The title compound was purified by chromatography (SiO2, c-hexane/ethyl acetate, 2/1) and was isolated as yellow oil (10.35 g, 98%).

1H-NMR (400 MHz; DMSO-d6): 1.20 (t, 3H); 3.30 (s, 2H); 3.70 (s, 2H); 4.10 (qa, 2H); 7.15 (dd, 2H); 7.35 (dd, 2H).

MS (m/z) ES+: 212.1 (MH+, 100).

b) [((R)-2-tert-Butoxycarbonylamino-butyryl)-(4-fluorobenzyl)-amino]-acetic acid ethyl ester

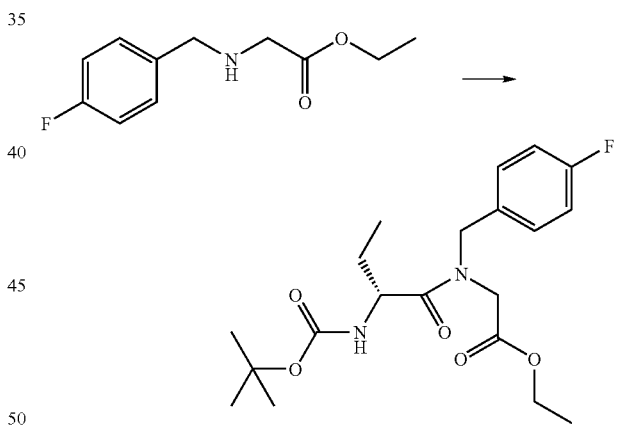

Boc-D-Abu-OH (4.06 g, 20 mmol), EDCl (4.20 g, 22 mmol) and HOBT (2.97 g, 22 mmol) were dissolved in 100 ml THF. At room temperature the amine (4.20 g, 20 mmol) the title compound of step a) was added and the mixture was stirred for 4 hours at room temperature. After evaporation the residue was dissolved in DCM and washed three times with water and once with saturated sodium chloride solution. The title compound was purified by chromatography (SiO2, c-hexane/ethyl acetate, 2/1) and was isolated as yellow oil (6.41 g, 80%).

1H-NMR (400 MHz; DMSO-d6, 120° C.): 0.90 (t, 3H); 1.20 (t, 3H); 1.40 (s, 9H); 1.55-1.80 (m, 2H); 4.05-4.15 (m, 4H); 4.35 (bs, 1H); 4.65 (bs, 2H); 6.20 (bs, 1H); 7.10 (bt, 2H); 7.35 (bt, 2H).

MS (m/z) ES+: 419.2 (MNa+, 100).

c) (R)-3-Ethyl-1-(4-fluoro-benzyl)-piperazine-2,5-dione

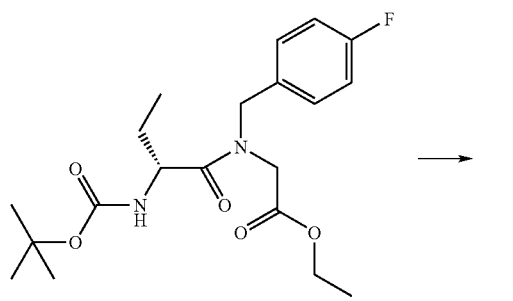

Title compound of step b) (6.0 g15.1 mmol) was dissolved in 20 ml of 4N HCl in dioxane and stirred for 2 hours at room temperature. After evaporation the residue was dissolved in 200 ml water and 1N NaOH was added to reach pH~10. This solution was extracted with ethyl acetate, dried with sodium sulfate and evaporated. The residue was dissolved in 20 ml ethyl acetate and allowed to stand over night. The title compound was purified by chromatography (SiO$_2$, ethyl acetate/MeOH/NH$_3$conc, 95/5/0.5) and was isolated as yellow solid (2.98 g, 79%)

1H-NMR (400 MHz; DMSO-d6): 0.85 (t, 3H); 1.65-1.85 (m, 2H); 3.82 (dd, 2H); 3.90-3.95 (m, 1H); 4.45 (d, 1H); 4.60 (d, 1H); 7.20 (dd, 2H); 7.35 (dd, 2H); 8.35 (bs, 1 NH).

MS (m/z) ES+: 251.1 (MH+, 100).

d) (R)-3-Ethyl-1-(4-fluorobenzyl)-piperazine

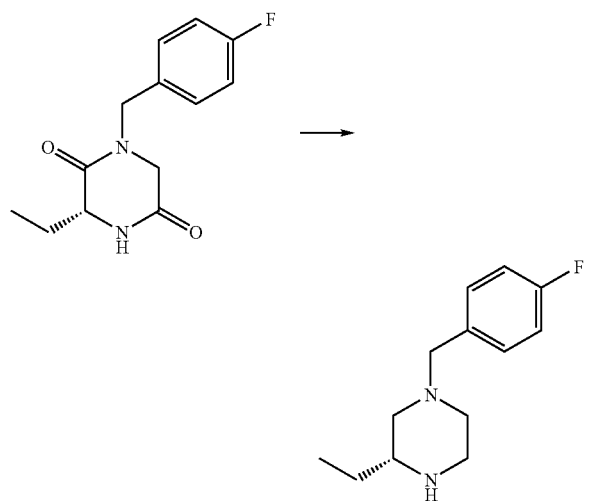

Title compound of step c) (1.0 g, 4 mmol) was dissolved in 50 ml THF. At 0° C. 15 ml (34.5 mmol) lithium aluminium hydride as a 2.3 M solution in THF was added dropwise. After stirring at 60° C. for 5 hours, saturated sodium sulfate (100 ml) was added dropwise at 0° C. The title compound was isolated by extraction with ethyl acetate, was further purified by chromatography (SiO$_2$, ethyl acetate/MeOH/NH$_3$conc, 7/3/0.3) and was isolated as a yellow oil (0.77 g, 86%)

1H-NMR (400 MHz; DMSO-d6): 0.82 (t, 3H); 1.35 (m, 1H); 1.55 (t, 1H); 1.85 (m, 1H); 2.40-2.50 (m, 1H); 2.55-2.70 (m, 4H); 2.77-2.85 (m, 1H); 3.35-3.45 (m, 3H); 7.15 (dd, 2H); 7.35 (dd, 2H).

MS (m/z) ES+: 223.2 (MH+, 100).

e) N-(5-Chloro-2-{(E)-3-[(R)-2-ethyl-4-(4-fluorobenzyl)-piperazin-1-yl]-3-oxo-propenyl}-phenyl)-acetamide.

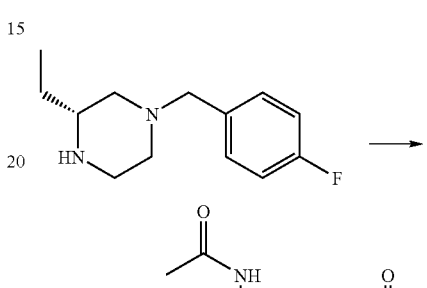

(R)-3-Ethyl-1-(4-fluorobenzyl)-piperazine (44.4 mg, 0.2 mmol), EDC1 (76 mg, 0.4 mmol), HOBT (55 mg, 0.4 mmol) and (E)-3-(2-Acetylamino-4-chloro-phenyl)-acrylic acid (47.8 mg, 0.2 mmol) were dissolved in 5 ml DCM and this mixture was stirred at room temperature overnight. The mixture was diluted with 50 ml DCM and extracted 3 times with water and once with saturated sodium chloride solution. The title compound, purified by chromatography (SiO$_2$, ethyl acetate/MeOHINH3conc, 98/2/0.2) and was isolated as pale solid (81 mg, 91%)

1H-NMR (400 MHz; DMSO-d6): 0.75 (t, 3H); 1.60-1.75 (m, 2H); 1.80-2.00 (m, 2H); 2.07 (s, 3H); 2.70-2.95 (m, 2H); 3.25-3.30 (m, 1H); 3.35-3.60 (m, 2H); 4.05-4.45 (bdxbdd, 2H); 7.10-7.20 (m, 3H); 7.25 (bd, 1H); 7.30-7.38 (m, 2H); 7.55 (bs, 1H); 7.55-7.65 (m, 2H); 7.90 (bd, 1H); 9.85 (bs, I NH).

MS (m/z) ES+: 466.2 (MNa+, 100).

Example 48

(5-Chloro-2-{(E)-3-[(R)-2-ethyl-4-(4-fluoro-benzyl)-piperazin-1-yl]-3-oxo-propenyl}-phenyl)-urea.

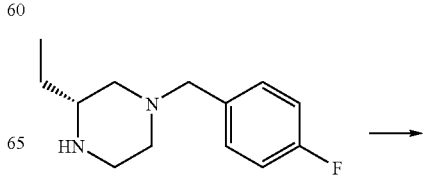

-continued

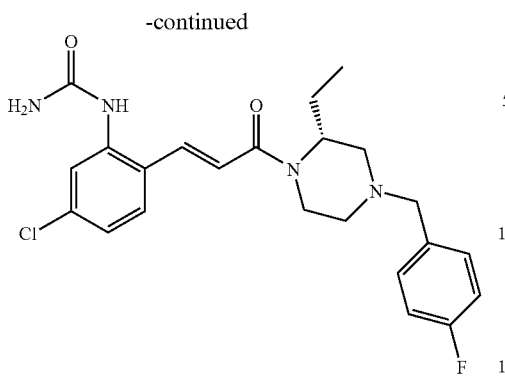

(R)-3-Ethyl-1-(4-fluorobenzyl)-piperazine (88.8 mg, 0.4 mmol), EDCI (152 mg, 0.8 mmol), HOBT (110 mg, 0.8 mmol) and (E)-3-(4-Chloro-2-ureido-phenyl-acrylic acid (96 mg, 0.4 mmol) were dissolved in 5 ml DCM and this mixture was stirred at room temperature over night. The mixture was diluted with 50 ml DCM and extracted 3 times with water and once with saturated sodium chloride solution. The title compound was purified by chromatography (SiO$_2$, ethyl acetate/ MeOH/NH$_3$conc, 98/2/0.2) and was isolated as pale solid (60 mg, 34%)

1H-NMR (400 MHz; DMSO-d6): 0.75 (t, 3H); 1.60-1.75 (m, 2H); 1.80-2.00 (m, 2H); 2.75-2.95 (m,2H); 3.23-3.30 (m, 1H); 3.35-3.45 (m, 1H); 3.45-3.55 (m, 1H); 4.05-4.45 (bdx-bdd, 2H); 6.25 (bs, 2NH); 7.05 (bd, 1H); 7.10-7.18 (m, 3H); 7.30-7.38 (m, 2H); 7.55-7.65 (m, 2H); 7.95 (bs, 1H); 8.45 (bs, 1NH).

MS (m/z) ES+: 445.2 (MH+, 100).

Example 49

N-(5-Chloro-4-ethoxy-2-{(E)-3-[(R)-4-(4-fluorobenzyl)-2-methyl-piperazin-1-yl]-3-oxo-propenyl}phenyl)-acetamide a) 4-Chloro-3-ethoxy-phenol

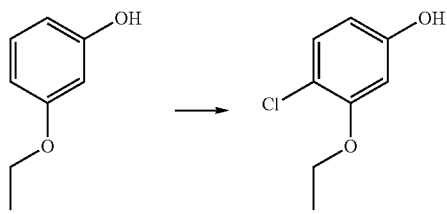

3-Methoxyphenol (14.9 g, 120.0 mmol) was dissolved in 60 ml chloroform. At 0° C. 17.12 g (126.0 mmol) sulfurylchloride were added dropwise over 1 hour. After 2 hours stirring at 0° C. 100 ml water and 50 ml DCM were added. The organic layer was separated and washed with water and saturated sodium chloride solution. The title compound was purified by chromatography (SiO$_2$, ethyl acetate/c-hexane 2/8) and was isolated as a yellow liquid (7.50 g, 39%)

1H-NMR (400 MHz; DMSO-d6): 1.37 (t, 3H); 4.02 (qa, 2H); 6.30 (dd, 1H); 6.48 (d, 1H); 7.15 (d, 1H); 9.70 (bs, 10H)

MS (m/z) EI: 172 (M+, 100).

b) 4-Chloro-5-ethoxy-2-nitro-phenol

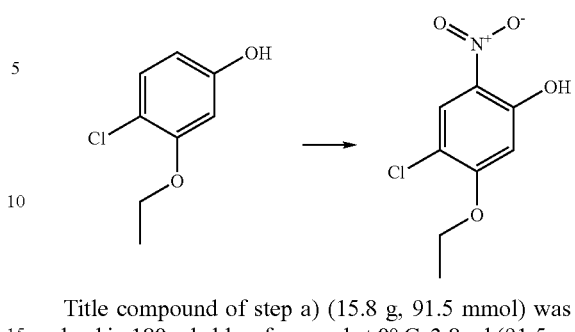

Title compound of step a) (15.8 g, 91.5 mmol) was dissolved in 180 ml chloroform and at 0° C. 3.8 ml (91.5 mmol) nitric acid fuming 100% was added dropwise. Stirring was continued for 20 Min. at 0° C., then 100 ml DCM were added. The organic layer was washed twice with water and once with saturated sodium chloride solution. The title compound was purified by chromatography (SiO$_2$, ethyl acetate/c-hexane 2/8) and was isolated as a yellow solid (10.17 g, 51%)

1H-NMR (400 MHz; DMSO-d6): 1.36 (t, 3H); 4.17 (qa, 2H); 6.75 (s, 1H); 8.03 (s, 1H); 11.05 (bs, 10H)

MS (m/z) EI: 217 (M+, 100).

c) Trifluoro-methanesulfonic acid 4-chloro-5-ethoxy-2-nitro-phenyl ester

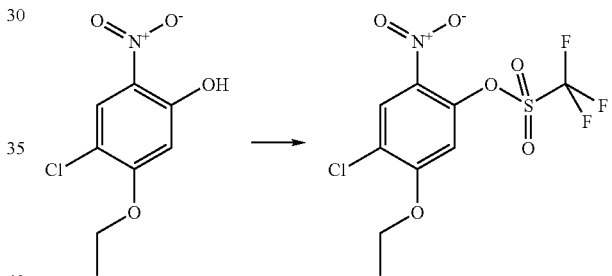

Title compound of step b) (10.2 g46.8 mmol) was dissolved in 250 ml DCM and 7.71 ml (56.2 mmol) NEt$_3$ were added. At 0° C. 5.44 ml (51.5 mmol) Trifluoro methanesulfonic acid chloride was added dropwise. After stirring at 0° C. for 90 min. the solution was washed twice with water and once with saturated sodium chloride solution. The title compound was purified by chromatography (SiO$_2$, ethyl acetate/ c-hexane 2/8) and was isolated as a yellow oil (15.98 g, 97%)

1H-NMR (400 MHz; DMSO-d6): 1.40 (t, 3H); 4.35 (qa, 2H); 7.48 (s, 1H); 8.50 (s, 1H)

MS (m/z) EI: 349 (M+, 100).

d) (E)-3-(4-Chloro-5-ethoxy-2-nitro-phenyl)-acrylic acid ethyl ester

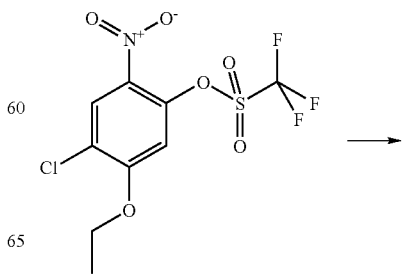

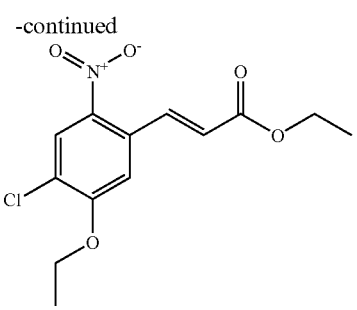

Title compound of step c) (3.0 g, 8.58 mmol) and 4.0 g (10.3 mmol) (E)-3-tributylsyannanyl-acrylic acid ethyl ester were dissolved in 75 ml DMF and 120 mg Bis(triphenylphosphine)palladium(II)dichloride were added. This mixture was stirred at 140° C. for 20 min. After evaporation the title compound was purified by chromatography (SiO$_2$, ethyl acetate/c-hexane 2/8) and was isolated as a pale solid (1.53 g, 59%)

1H-NMR (400 MHz; DMSO-d6): 1.27 (t, 3H); 1.38 (t, 3H); 4.20 (qa, 2H); 4.35 (qa, 2H); 6.75 (d, 1H); 7.45 (s, 1H); 7.95 (d, 1H); 8.22 (s, 1H)

MS (m/z) ES+: 322.1 (MNa+, 100).

e) (E)-3-(4-Chloro-5-ethoxy-2-nitro-phenyl)-acrylic acid

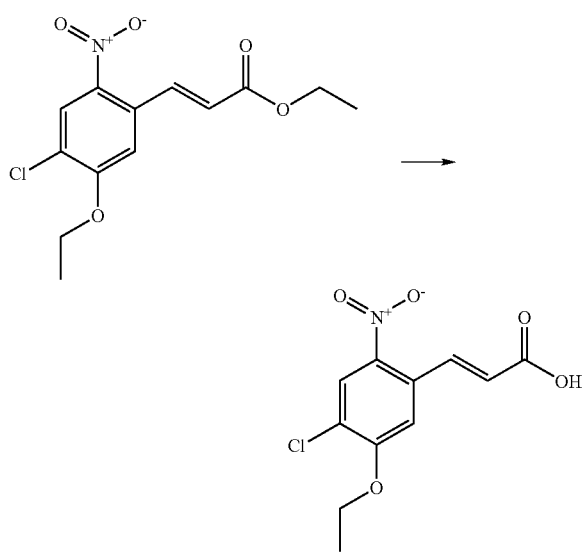

Title compound of step d) (1.40 g, 4.77 mmol) was dissolved in 50 ml EtOH and 2.1 ml 2N NaOH was added, this mixture was heated to 95° C. for 20 min. The solution was cooled to room temperature and 2N HCl was added to reach pH~1. The precipitated solide was washed with EtOH, water and diethylether and dried for 8 hours at 60° C. to yield title compound as pale solid (1.1 g, 84%)

1H-NMR (400 MHz; DMSO-d6): 1.40 (t, 3H); 4.35 (qa, 2H); 6.62 (d, 1H); 7.45 (s, 1H); 7.87 (d, 1H); 8.20 (s, 1H); 12.80 (bs, 1OH)

MS (m/z) ES−: 270 (M−H−, 45), 197 (75), 169 (100)

f) N-(5-Chloro-4-ethoxy-2-{(E)-3-[(R)-4-(4-fluorobenzyl)-2-methyl-piperazin-1-yl]-3-oxo-propenyl}-phenyl)-acetamide

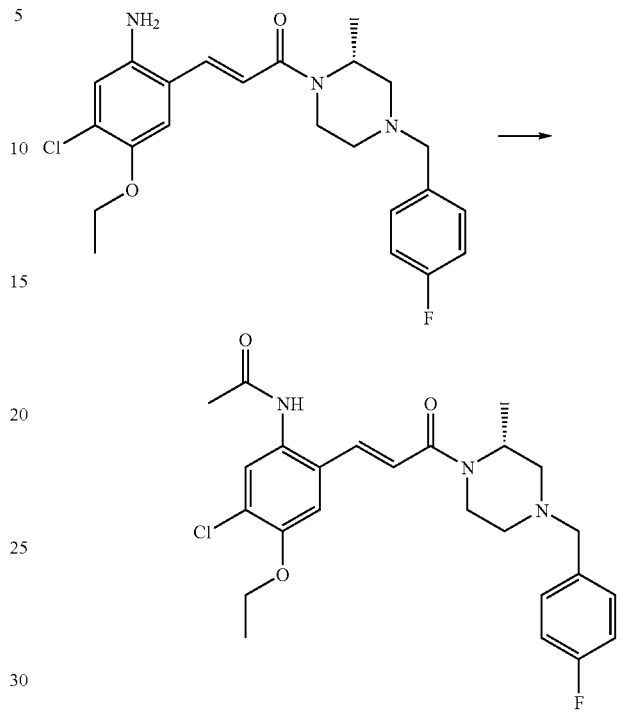

(E)-3-(2-Amino-4-chloro-5-ethoxyphenyl)-1-[(R)-4-(4-fluorobenzyl)-2-meyhyl-piperazin-1-yl]-propenone (prepared by amide coupling and SnCl2 reduction as described in example 30) (0.1 g, 0.23 mmol) was dissolved in 10 ml THF and 38.7 µl (0.28 mmol) NEt$_3$ and 16.5 µl (0.23 mmol) acetyl chloride were added. This mixture was stirred for 20 min. at room temperature. Then the mixture was diluted with 10 ml saturated sodium carbonate solution and extracted with ethyl acetate. The title compound was purified by chromatography (SiO$_2$, ethyl acetate/MeOH/NH$_3$conc. 95/5/0.5) and was isolated as a pale solid (89 mg, 81%)

1H-NMR (400 MHz; DMSO-d6) 1.25 (m, 3H); 1.35 (t. 3H); 1.90-2.15 (m, 5H); 2.65-2.70 (m, 1H); 2.82 (bd, 1H); 2.90-3.15 (m, 1H); 3.40-3.50 (m, 2H); 4.10-4.25 (m, 3H); 4.50-4.65 (m, 1H); 7.10-7.20- (m, 3H); 7.35-7.40 (m, 2H); 7.43 (d, 2H);, 7.55 (d, 1H); 9.65 (s, 1NH)

MS (m/z) ES+: 474.2 (MH+, 100%).

Example 50

(5-Chloro-4-ethoxy-2-{(E)-3-[(R)A(4-fluorobenzyl)-2-methyl-piperazin-1-yl]-3-oxo-propenyl}phenyl)-urea

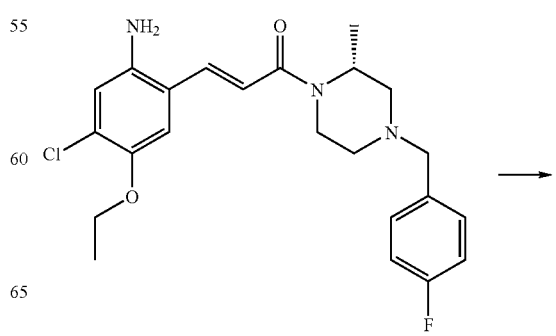

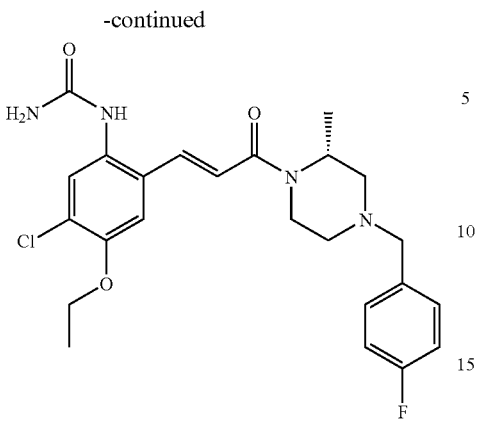

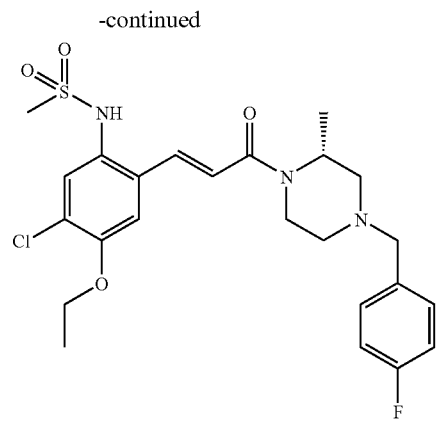

(E)-3-(2-Amino-4-chloro-5-ethoxyphenyl)-1-[(R)-4-(4-fluorobenzyl)-2-meyhyl-piperazin-1-yl]-propenone (0.1 g, 0.23 mmol) was dissolved in 1 ml acetic acid and 1 ml water and 30 mg (0.46 mmol) sodium isocyanate were added. This mixture was stirred at room temperature for 30 min., then the mixture was diluted with 10 ml saturated sodium carbonate solution and extracted with ethyl acetate. The title compound was purified by chromatography (SiO$_2$, ethyl acetate/MeOH/NH$_3$conc. 95/5/0.5) and was isolated as a pale solid (55 mg, 50%)

1H-NMR (400 MHz; DMSO-d6) 1.20-1.30 (m, 3H); 1.35 (t, 3H); 1.85-2.15 (m, 2H); 2.60-2.70 (m, 1H); 2.83 (bd, 1H); 2.90-3.05 (m, 1H); 3.40-3.60 (m, 2H); 4.13 (qa, 2H); 4.15-4.30 (m, 1H); 4.45-4.65 (m, 1H); 6.00 (bs, 2NH); 7.10-7.17 (m, 3H); 7.30-7.38 (m, 3H); 7.60 (d, 1H); 7.70 (s,1H); 8.15 (bs, 1NH)

MS (m/z) ES+: 475.2 (MH+, 100%).

(E)-3-(2-Amino-4-chloro-5-ethoxyphenyl)-1-[(R)-4-(4-fluorobenzyl)-2-meyhyl-piperazin-1-yl]-propenone (0.1 g, 0.23 mmol) was dissolved in 15 ml THF, then 38.7 μl (0.03 mmol) NEt$_3$ and 17.7 μl (0.23 mmol) methanesulfonyl chloride were added at −78° C. Stirring was continued for 4 hours at −78° C., then the mixture was allowed to warm up to room temperature and was evaporated. The title compound was purified by chromatography (SiO$_2$, ethyl acetate/MeOH/NH$_3$conc. 95/5/0.5) and was isolated as a pale solid (60 mg, 51%)

1H-NMR (400 MHz; DMSO-d6) 1.20-1.30 (m, 3H); 1.37 (t, 3H); 1.90-2.15 (m, 2H); 2.65-2.70 (m, 1H); 2.80 (bd, 1H); 2.94 (s, 3H); 3.00-3.25 (m, 1H); 3.40-3.60 (m, 2H); 4.10-4.30 (m, 3H); 4.50-4.65 (m, 1H); 7.15 (dd, 2H); 7.18 (d, 1H); 7.30-7.35 (m, 3H); 7.50 (s, 1H); 7.75 (d, 1H); 9.38 (bs, 1NH)

MS (m/z) ES+: 510.1 (MH+, 100%).

Example 51

N-(5-Chloro-4-ethoxy-2-{(E)-3-[(R)-4-(4-fluorobenzyl)-2-methyl-piperazin-1-yl]-3-oxo-propenyl}-phenyl)-methanesulfonamide

Example 52

5-Oxo-pyrrolidine-2-carboxylic acid (5-chloro-4-ethoxy-2-{(E)-3-[®-4-(4-fluorobenzyl)-2-methyl-piperazin-1yl]-3oxo-propenyl}-phenyl)-amide

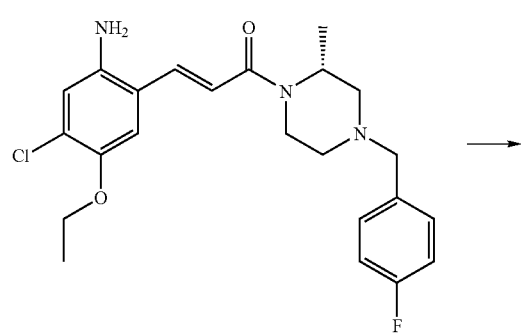

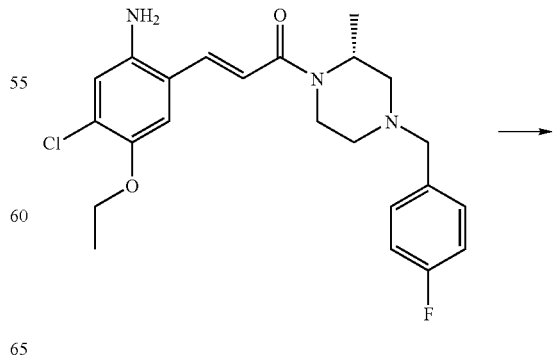

-continued

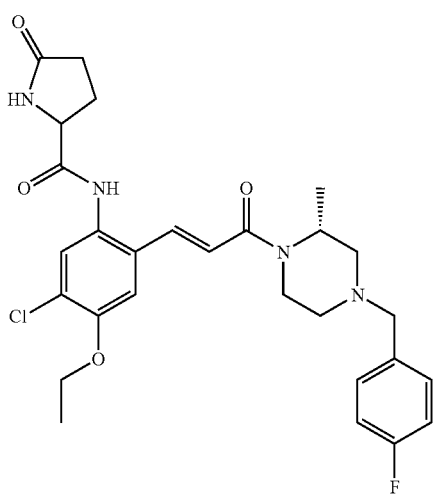

(E)-3-(2-Amino-4-chloro-5ethoxyphenyl)-1-[(R)-4-(4-fluorobenzyl)-2-methyl-piperazin-1-yl]-propenone (0.1 g, 0.23 mmol), EDCI (97 mg, 0.28 mmol), HOBT (34.4 mg, 0.28 mmol) and 30 mg (0.23 mmol) pyroglutamic acid were dissolved in 20 ml THF. This mixture was stirred at room temperature over night and evaporated. The title compound was purified by chromatography (SiO$_2$, ethyl acetate/MeOH/ NH$_3$conc. 95/5/0.5) and was isolated as a pale solid (25 mg, 20%)

1H-NMR (400 MHz; DMSO-d6) 1.20-1.30 (m, 3H); 1.37 (t, 3H); 1.90-2.25 (m, 5H); 2.30-2.40 (m, 1H); 2.60-2.70 (m, 1H); 2.83 (bd, 1H); 2.90-3.10 (m, 1H); 3.40-3.60 (m, 2H); 4.10-4.30 (m, 4H); 4.45-4.65 (m, 1H); 7.12 (dd, 2H); 7.18 (d, 1H); 7.30-7.38 (m, 2H); 7.40 (s, 1H); 7.45 (s, 1H); 7.52 (d, 1H); 7.83 (bs, 1NH); 9.80 (bs, 1H)

MS (m/z) ES+: 543.2 (MH+, 100).

Example 53

N-(5-Chloro-2-{(E)-3-[(S)-4-(4-fluoro-benzyl)-2-hydroxymethyl-piperazin-1-yl]-3-oxo-propenyl}-4-methoxy-phenyl)-acetamide a) (E)-3-(4-Chloro-5-methoxy-2-nitro-phenyl)-1-[(S)-4-(4-fluoro-benzyl)-2-hydroxymethyl piperazin-1-yl]-propenone

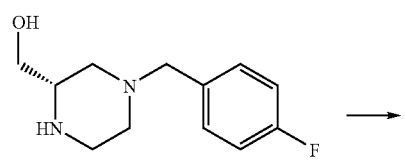

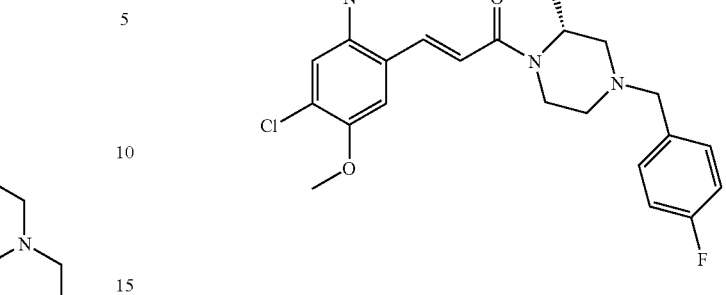

(E)-3-(4-Chloro-5-methoxy-2-nitro-phenyl)-acrylic acid (prepared analogous to example 49) (2.0 g, 7.76 mmol), EDCI (1.6 g, 8.54 mmol); HOBT (1.2 g, 8.54 mmol) and 1.7 g (7.76 mmol) [(S)-4-(4-Fluorobenzyl)-piperazin-2-yl]-methanol (prepared as outlined in example 47) were dissolved in 60 ml THF and stirred for 2 hours at room temperature. After evaporation the title compound was purified by chromatography (SiO$_2$, ethyl acetate/MeOH/NH$_3$conc. 90/10/1) and was isolated as a pale solid (0.86 g, 24%)

1H-NMR (400 MHz; DMSO-d6, 120° C.): 2.05 (td, 1H); 2.15 (dd, 1H); 2.95 (bd, 1H); 3.10 (bt, 1H); 3.48 (s, 2H); 3.65-3.75 (m, 2H); 4.05 (s, 3H); 4.18 (bd, 1H); 4.27-4.35 (m, 2H); 7.05-7.10 (m, 3H); 7.32 (bt, 2H); 7.40 (s, 1H); 7.72 (d, 1H); 8.10 (s, 1H)

MS (m/z) ES+: 464.0 (MH+, 100%).

b) Acetic acid (S)-1-[(E)-3-(4-chloro-5-methoxy-2-nitro-phenyl) acryloyl]-4-(4-fluoro-benzyl)-piperazin-2-yl methyl ester

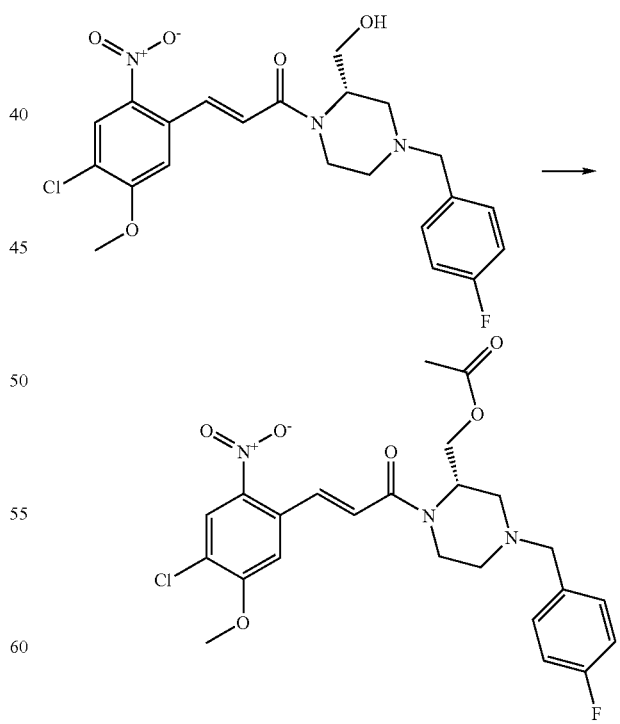

Title compound of step a) (0.5 g, 1.08 mmol) was dissolved in 10 ml THF and 1.5 ml NEt$_3$ was added. Acetyl chloride (0.85 g, 10.8 mmol) was added at room temperature. After 20 min. the solution was diluted with 100 ml saturated sodium carbonate solution and extracted with ethyl acetate. The title compound was purified by chromatography (SiO$_2$, ethyl acetate/MeOH/NH$_3$conc. 90/10/1) and was isolated as a pale solid (0.50 g, 91%)

1H-NMR (400 MHz; DMSO-d6, 120° C.): 1.92 (s, 3H); 2.05-2.15 (m, 2H); 2.20-2.25 (m, 1H); 2.90-2.95 (m, 1H); 3.15 (bt, 1H); 3.50 (dd, 2H); 4.06 (s, 3H); 4.15-4.25 (m, 2H); 4.45 (bt, 1H); 4.60 (bs, 1H); 7.00-7.10 (m, 3H); 7.30 (dd, 2H); 7.40 (s, 1H); 7.75 (d, 1H); 8.10 (s, 1H)

MS (m/z) ES+: 506.0 (MH+, 100%).

c) Acetic acid (S)-1-[(E)-3-(2-amino-4-chloro-5-methoxy-phenyl)-acryloyl]-4-(4-fluoro-benzyl)-piperazin-2-yl methyl ester

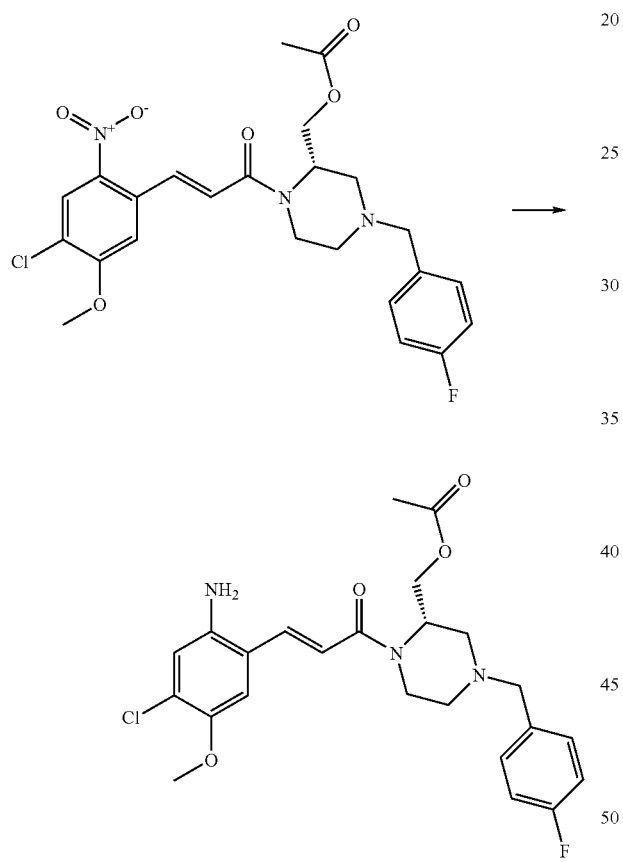

Title compound of step b) (0.5 g, 0.99 mmol) was dissolved in 12.5 ml THF and 2.5 ml water and 1.5 g (7.0 mmol) stannous chloride anhydrous were added. This mixture was stirred at 80° C. for 20 min., then the mixture was diluted with 100 ml saturated sodium carbonate solution and extracted with ethyl acetate. The title compound was purified by chromatography (SiO$_2$, ethyl acetate/MeOH/NH$_3$conc. 95/5/0.5) and was isolated as a pale solid (0.35 g, 74%)

1H-NMR (400 MHz; DMSO-d6): 1.85-2.05 (m, 6H); 2.90-2.75 (m, 3H); 3.45 (bs, 2H); 3.77 (s, 3H); 4.10-4.30 (m, 2H); 4.45-4.55 (m, 1H); 5.25 (bs, 2NH); 6.75 (s, 1H); 6.95 (bd, 1H); 7.05-7.15 (m, 3H); 7.25-7.35 (m, 2H); 7.60 (bd, 1H)

MS (m/z) ES+: 476.2 (MH+, 100%).

d) Acetic acid (S)-1-[(E)-3-(2-acetylamino-4-chloro-5-methoxy-phenyl)-acryloyl]-4-(4-fluoro-benzyl)-piperazin-2-yl methyl ester

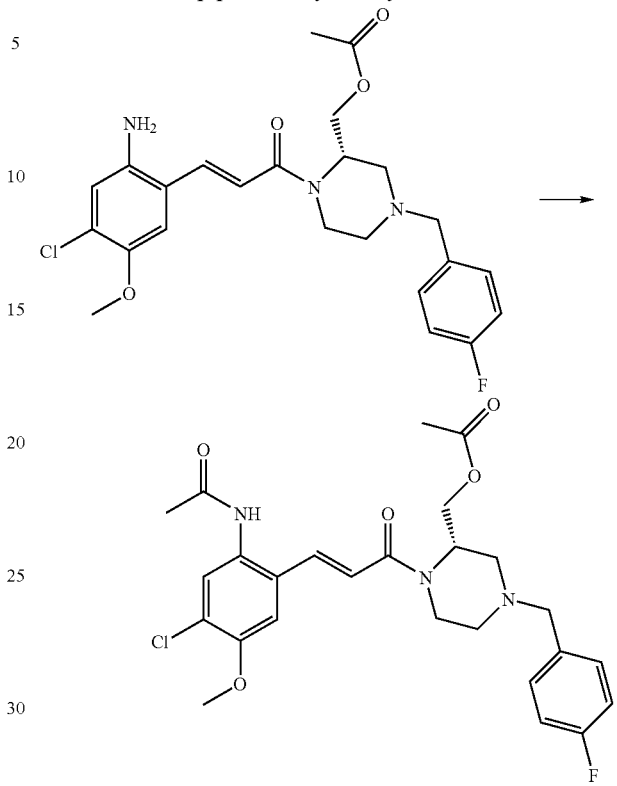

Title compound of step c) (0.2 g, 0.42 mmoq) was dissolved in 20 ml THF and 0.58 ml (4.2 mmol) NEt$_3$ and 0.3 ml (4.2 mmol) acetyl chloride were added. This mixture was stirred for 20 min. at room temperature. Then the mixture was diluted with 100 ml saturated sodium carbonate solution and extracted with ethyl acetate. The title compound was purified by chromatography (SiO$_2$, ethyl acetate/MeOH/NH$_3$conc. 98/2/0.2) and was isolated as a pale solid (40 mg, 19%)

1H-NMR (400 MHz; DMSO-d6): 1.85-1.95 (m, 5H); 2.02 (s, 3H); 2.75-2.95 (m, 2H); 3.35-3.55 (m, 4H); 3.90 (s, 3H); 4.10-4.25 (m, 2H); 4.45-4.55 (m, 1H); 7.05-7.15 (m, 3H); 7.25-7.35 (m, 2H); 7.40 (s, 1H); 7.45-7.60 (m, 2H); 9.65 (s, 1NH)

MS (m/z) ES+: 540.2 (MNa+, 100%).

e) N-(5-Chloro-2-{(E)-3-[(S)-4-(4-fluoro-benzyl)-2-hydroxymethyl-piperazin-1-yl]-3-oxo-propenyl}-4-methoxy-phenyl)-acetamide

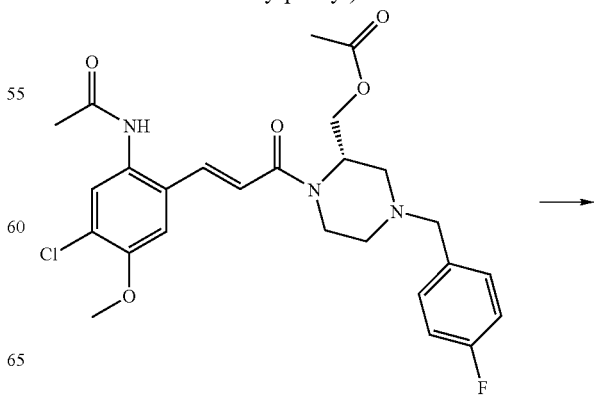

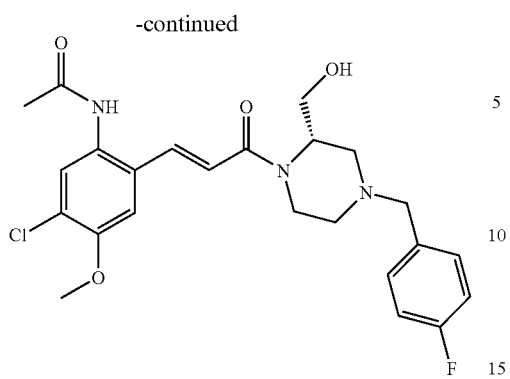

Title compound of step d) (110 mg, 0.21 mmol) was dissolved in 10 ml MeOH and 1 ml 1N NaOH was added. This solution was stirred at room temperature for 4 hours. Then the mixture was diluted with 100 ml water and extracted with ethyl acetate. The title compound was purified by chromatography (SiO$_2$, ethyl acetate/MeOH/NH$_3$conc. 95/5/0.5) and was isolated as a pale solid (44 mg, 40%)

1H-NMR (400 MHz; DMSO-d6, 120° C.): 1.95-2.15 (m, 6H); 2.95 (bd, 1H); 3.05 (bt, 1H); 3.45 (bs, 2H); 3.65 (bs, 2H); 3.90 (s, 3H); 4.15-4.35 (m, 3H); 6.95-7.05 (m, 3H); 7.25-7.30 (m, 3H); 7.40 (s, 1H); 7.45 (d 1H); 9.10 (s, 1NH)

MS (m/z) ES+: 476.2 (MH+, 100%).

Example 54

N-(5-Chloro-2-{(E)-3-[(S)-4-(4-fluoro-benzyl)-2-hydroxymethyl-piperazin-1-yl]-3-oxo-propenyl}-4-methoxy-phenyl)-methanesulfonamide

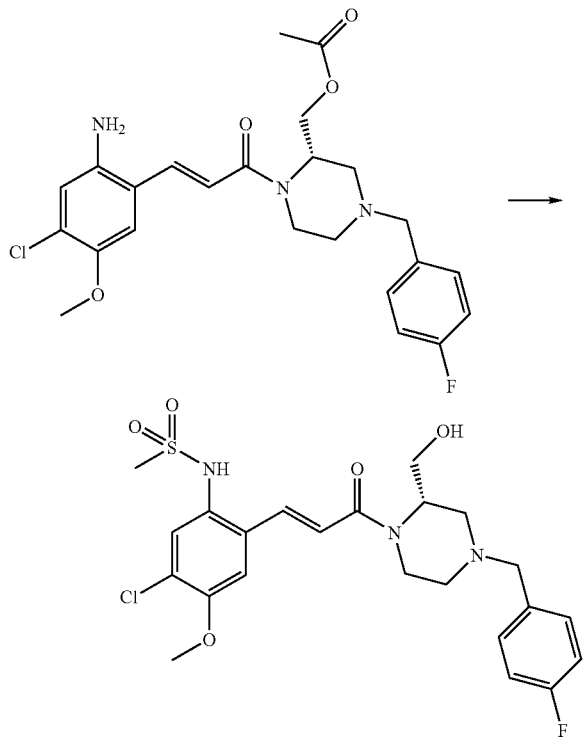

Title compound of step c) of example 53 (200 mg, 0.42 mmol) was dissolved in 30 ml THF, then 0.07 ml (0.5 mmol) NEt$_3$ and 0.03 ml (0.42 mmol) methanesulfonyl chloride were added at −78° C. Stirring was continued for 4 hours at −78° C., then the mixture was allowed to warm up to room temperature and was evaporated The crude product was then treated as outlined in step e) of example 53. The title compound was purified by chromatography (SiO$_2$, ethyl acetate/MeOH/NH$_3$conc. 95/5/0.5) and was isolated as a pale solid (58 mg, 27%)

1H-NMR (400 MHz; DMSO-d6, 120° C.): 2.05 (bt, 1H); 2.15 (bd, 1H); 2.90-2.95 (m, 4H); 3.05-3.15 (bt, 1H); 3.45 (bs, 2H); 3.70 (bd, 2H); 3.95 (s, 3H); 4.15-4.35 (m, 3H); 7.05-7.10 (m, 3H); 7.30-7.40 (m, 4H); 7.70 (d, 1H); 8.95 (bs, 1NH)

MS (m/z) ES+: 512.2 (MH+, 100%).

Example 55

(5-Chloro-2-{(E)-3-[(S)-4-(4-fluoro-benzyl)-2-hydroxymethyl-piperazin-1-yl]-3-oxo-propenyl}-4-methoxy-phenyl)-urea

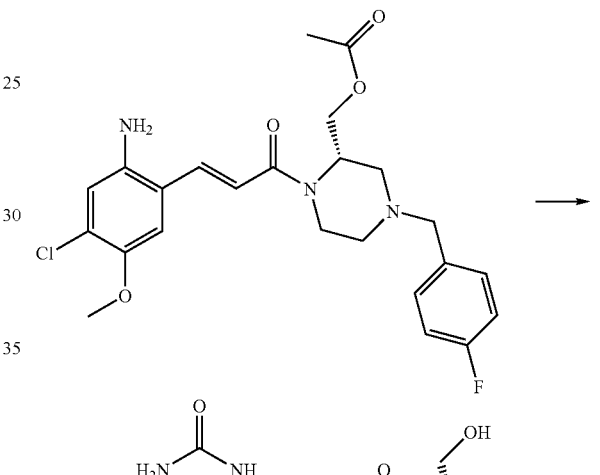

Title compound of step c) of example 53 (160 mg, 0.34 mmol) was dissolved in 1.5 ml acetic acid and 1.5 ml water and 44 mg (0.68 mmol) sodium isocyanate were added. This mixture was stirred at room temperature for 30 min., then the mixture was diluted with 10 ml saturated sodium carbonate solution and extracted with ethyl acetate. The crude product was then treated as outlined in step e) of example 53. The title compound was purified by chromatography (SiO$_2$, ethyl acetate/MeOH/NH$_3$conc. 95/5/0.5) and was isolated as a pale solid (30 mg, 18%)

1H-NMR (400 MHz; DMSO-d6): 1.85-2.15 (m, 2H); 2.75-3.05 (m, 3H); 3.45 (bs, 2H); 3.55-3.70 (m, 2H); 3.85 (s, 3H); 4.30-4.80 (m, 2H); 6.00 (bs, 2NH); 7.05-7.15 (m, 3H); 7.30-7.35 (m, 3H); 7.60 (d, 1H); 7.70 (bs, 1H); 8.13 (bs, 1NH)

MS (m/z) ES+: 477.0 (MH+, 100%).

Example 56

5-Oxo-pyrrolidine-2-carboxylic acid (5-chloro-2-{(E)-3-[(S)-4-(4-fluoro-benzyl)-2-hydroxymethyl-piperazin-1-yl]-3-propenyl}-4-methoxy-phenyl)-amide

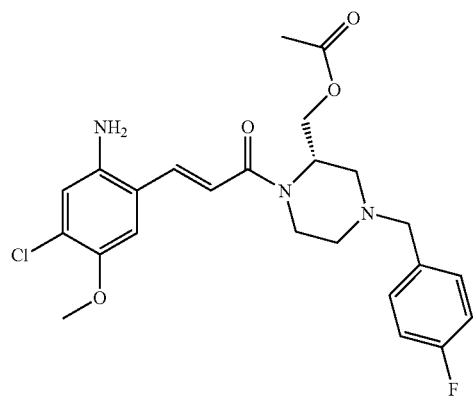

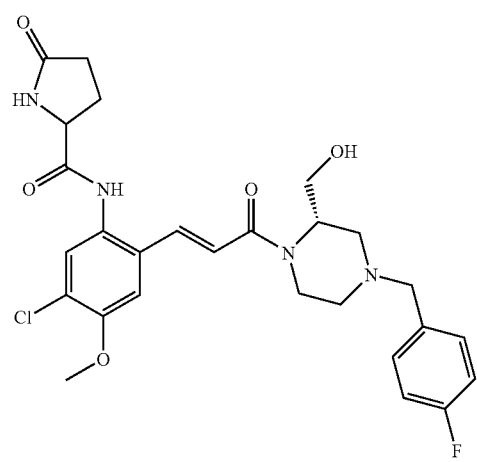

Title compound of step c) of example 53 (220 mg, 0.46 mmol), EDCI (97 mg, 0.5 mmol), HOBT (69 mg, 0.5 mmol) and 60 mg (0.46 mmol) pyroglutamic acid were dissolved in 20 ml DMF. This mixture was stirred at room temperature overnight and evaporated. The crude product was then treated as outlined in step e) of example 53. The title compound was purified by chromatography (SiO$_2$, ethyl acetate/MeOH/NH$_3$conc. 90/10/1) and was isolated as a pale solid (56 mg, 22%)

1H-NMR (400 MHz; DMSO-d6): 1.85-2.25 (m, 5H); 2.30-2.40 (m, 1H); 2.77 (bd, 1H); 2.85-3.05 (m, 2H); 3.45 (bs, 2H); 3.55-3.75 (m, 2H); 3.92 (s, 3H); 4.22 (dd, 1H); 4.30-4.80 (m, 2H); 7.12 (bt, 2H); 7.20 (bd, 1H); 7.30-7.35 (m, 2H); 7.40 (s, 1H); 7.41-7.50 (m, 1H); 7.53 (d, 1H); 7.80 (bs, 1H); 9.80 (bs, 1NH)

MS (m/z) ES+: 545.0 (MH+, 100%).

Example 57

N-(5-chloro-2-{(E)-3-[(S)-4-(4-fluoro-benzyl)-2-hydroxymethyl-piperazin-1-yl]-3-oxo-propenyl}-phenyl)acetamide

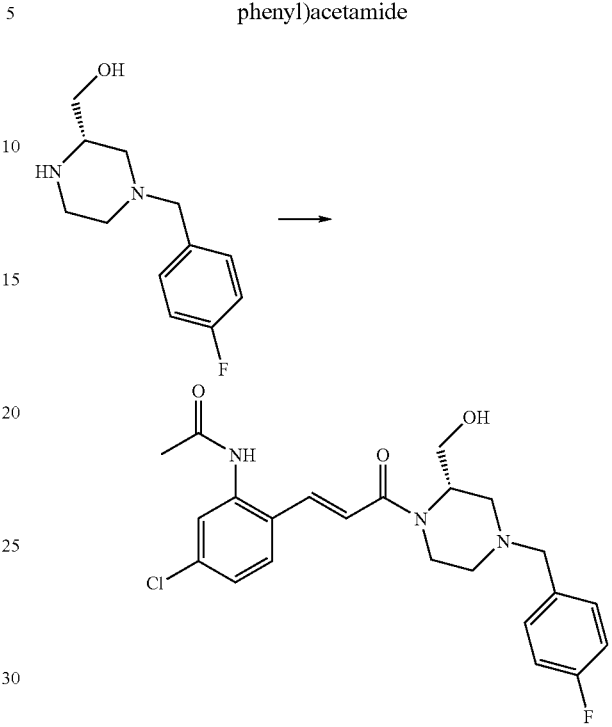

(E)-3-(2-Acetylamino-4-chloro-phenyl)-acrylic acid (2.2 g, 9.36 mmol), EDCI (3.6 g, 18.7 mmol); HOBT (2.5 g, 18.7 mmol) and 2.1 g (9.36 mmol) [(S)-4-(4-Fluorobenzyl)-piperazin-2-yl]-methanol were dissolved in 200 ml THF and stirred for 20 hours at room temperature. This mixture was then extracted 3 times with water and once with saturated sodium chloride solution. The title compound was purified by chromatography (SiO$_2$, ethyl acetate/MeOH/NH$_3$conc. 90/10/1) and was isolated as a pale solid (1.6 g, 39%)

1H-NMR (400 MHz; DMSO-d6, 120° C.): 1.95-2.15 (m, 5H); 2.70-2.85 (m, 3H); 2.95 (bd, 1H); 3.10 (bt, 1H); 3.70-3.80 (m, 2H); 4.30-4.50 (m, 2H); 7.00 (d, 1H); 7.05-7.15 (m, 2H); 7.25 (bd, 1H); 7.35-7.45 (m, 2H); 7.55-7.65 (m, 2H); 7.70 (d, 1H); 9.30 (bs, 1NH)

MS (m/z) ES+: 468.1 (MNa+, 100%).

Example 58

N-(2-{(E)-3-[(R)-2-Aminomethyl-4-(4-fluoro-benzyl)-piperazin-1-yl]-3-oxo-propenyl}-5-chloro-phenyl)-acetamide

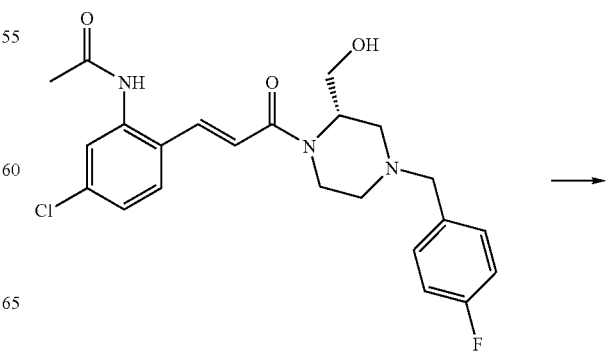

-continued

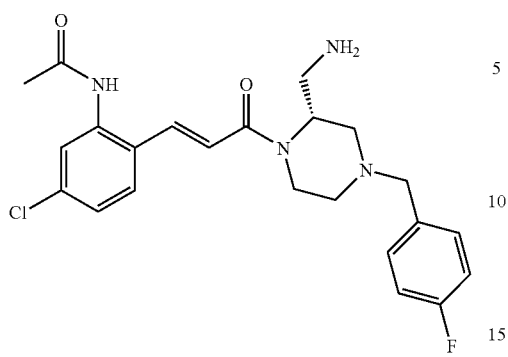

Title compound of example 9 (0.5 g, 1.1 mmol) was dissolved in 5 ml DCM and was then slowly added at −70° C. to a mixture of 0.29 ml (2.8 mmol) oxalyl chloride, 0.39 ml (5.6 mmol) dimethyl sulfoxide and in 13 ml DCM. Stirring was continued at −70° C. for 3 hours, then the mixture was allowed to warm up to −50° C. and 1.5 ml (11.0 mmol) NEt₃ and 20 ml water were added and the mixture was extracted with DCM. The organic layer was evaporated and immediately used for next step. The crude aldehyde was dissolved in 8 ml MeOH and 1.0 g (13.5 mmol) ammonium acetate and 62.8 mg (0.95 mmol) sodium cyanoborohydride were added. This mixture was stirred at room temperature over night, then 2 ml 1N HCl were added and stirring continued for 30 min. 2N NaOH was added to reach basic pH, and the mixture was extracted with DCM. The title compound was purified by chromatography (SiO₂, ethyl acetate/MeOH/NH₃conc. 90/10/1) and was isolated as a pale solid (25 mg, 5%)

1H-NMR (400 MHz; DMSO-d6, 120° C.): 1.95-2.15 (m, 5H); 2.85 (m, 1H); 2.95 (bd, 1H); 3.08 (bt, 1H); 3.45 (bs, 2H); 3.72 (d, 2H); 4.20-4.35 (m, 2H); 6.95 (d, 1H); 7.05-7.15 (m, 2H); 7.18-7.22 (m, 1H); 7.30-7.40 (m, 2H); 7.55-7.60 (m, 2H); 7.70 (d, 1H); 9.30 (bs, 1NH)

MS (m/z) ES+: 446.0 (MH+, 100%).

Example 59

N-(5-Chloro-2-{(E)-3-[(S)-4-(4-fluoro-benzyl)-2-((S)-1-hydroxy-ethyl)-piperazin-1-yl]-3-oxo-propenyl}-phenyl)-acetamide

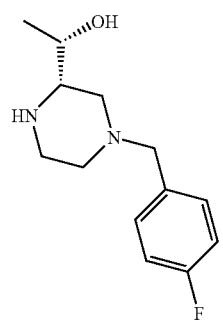

-continued

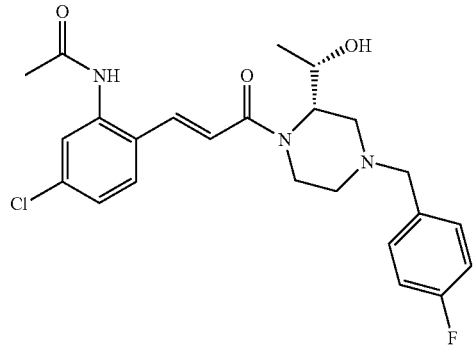

(E)-3-(2-Acetylamino-4-chloro-phenyl)-acrylic acid (2.1 g, 8.8 mmol), EDCI (3.4 g, 17.6 mmol); HOBT (2.4 g, 17.6 mmol) and 2.1 g (8.8 mmol) (S)-1-[(S)-4-(4-Fluorobenzyl)-piperazin-2-yl]-ethanol were dissolved in 180 ml THF and stirred for 20 hours at room temperature. This mixture was then extracted 3 times with water and once with saturated sodium chloride solution. The title compound was purified by chromatography (SiO₂, ethyl acetate/MeOH/NH₃conc. 90/10/1) and was isolated as a pale solid (2.5 g, 62%)

1H-NMR (400 MHz; DMSO-d6): 0.95 (bd, 3H); 1.85-2.10 (m, 5H); 2.65-2.90 (m, 2H); 2.95 (bt, 1H); 3.45 (m, 2H); 3.85 (bd, 1H); 4.05-4.15 (m, 1H); 4.35 (bd, 1H); 4.75 (bd, 1OH); 7.05-7.15 (m, 3H); 7.25-7.35 (m, 3H); 7.50-7.60 (m, 2H); 7.73 (bd, 1H); 9.80 (bs, 1NH)

MS (m/z) ES+: 460.1 (MH+, 100%).

Example 60

N-(2-{(E)-3-[(S)-2-Acetyl-4-(4-fluoro-benzyl)-piperazin-1-yl]-3-oxo-propenyl}-5-chloro-phenyl)-acetamide

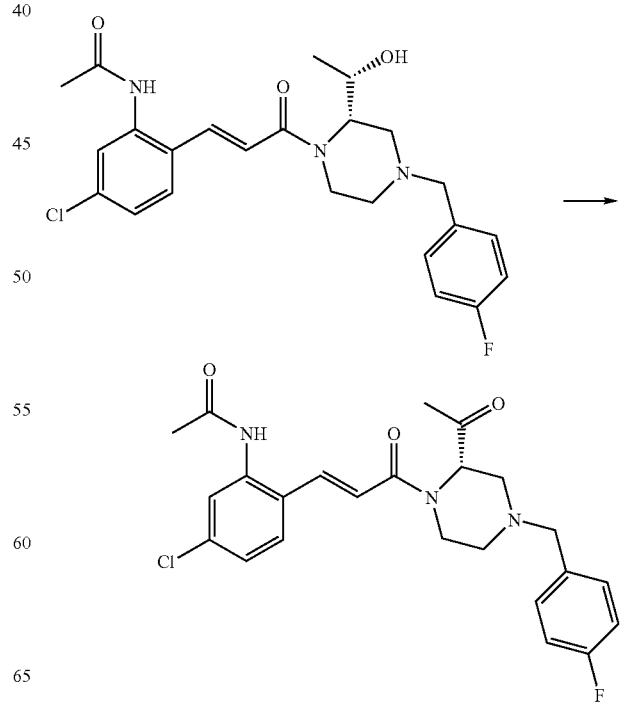

Title compound of example 11 (1.5 g, 3.2 mmol) was dissolved in 15 ml DCM and was then slowly added at −70° C. to a mixture of 0.7 ml (8.0 mmol) oxalyl chloride and 1.2 ml (16.0 mmol) dimethyl sulfoxide in 45 ml DCM. Stirring was continued at −70° C. for 3 hours, then the mixture was allowed to warm up to −50° C. and 4.5 ml (32.0 mmol) NEt3 and 60 ml water were added and the mixture was extracted with DCM. The title compound was purified by chromatography (SiO$_2$, ethyl acetate/MeOH/NH$_3$conc. 95/5/0.5) and was isolated as a pale solid (1.02 g, 69%)

1H-NMR (400 MHz; DMSO-d6): 1.90-2.30 (m, 5H); 3.25 (bd, 1H); 3.20-3.60 (m, 4H); 4.20 (bdd, 1H); 5.05 (bd, 1H); 6.95-7.35 (m, 6H); 7.55 (dd, 1H); 7.60 (dd, 1H); 7.90 (dd, 1H); 9.85 (m, 1NH)

MS (m/z) ES+: 480.2 (MNa+, 100%).

Example 61

N-{5-Chloro-2-[(E)-3-((S)-4-(4-fluoro-benzyl)-2-{1-[hydroxyimino]-ethyl}-piperazin-1-yl)-3-oxo-propenyl}-acetamide

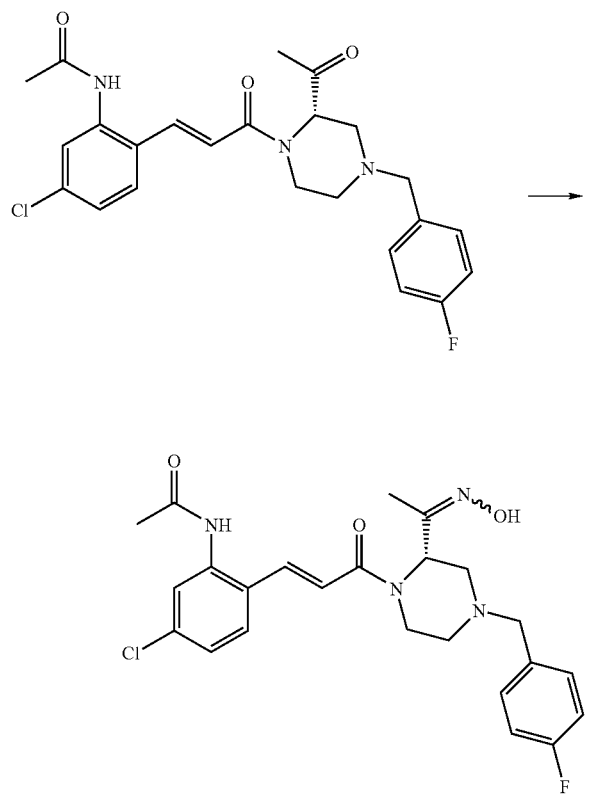

N-(2-{(E)-3-[(S)-2-Acetyl-4-(4-fluoro-benzyl)-piperazin-1-yl]-3-oxo-propenyl}-5-chloro-phenyl)-acetamide (250 mg, 0.55 mmol) was dissolved in 8 ml MeOH and 83.5 mg (1.2 mmol) hydroxylamine hydrochloride were added. This mixture was stirred under reflux for 16 hours and then evaporated. The title compound was purified by chromatography (SiO$_2$, ethyl acetate/MeOH/NH$_3$conc. 95/5/0.5) and was isolated as a pale solid (30 mg, 12%)

1H-NMR (400 MHz; DMSO-d6): 1.55-1.65 (2bs, 3H); 1.95-2.20 (m, 5H); 2.80 (bd, 1H); 2.95-3.15 (m, 2H); 3.35-3.60 (m, 2H); 4.15 (bdd, 1H); 5.00 (bd, 1H); 6.95-7.35 (m, 6H); 7.50 (bs, 1H); 7.65 (bd, 1H); 7.85 (bdd, 1H); 9.85 (m, 1NH); 10.50-10.65 (2bs, 1OH)

MS (m/z) ES+: 473.0 (MH+, 100%).

Example 62

N-(2-{(E)-3-[(2S,5S)-2-Benzyloxymethyl-4-(4-fluoro-benzyl)-5-methyl-piperazin-1-yl]-3-oxo-propenyl}-5-chloro-phenyl)-acetamide

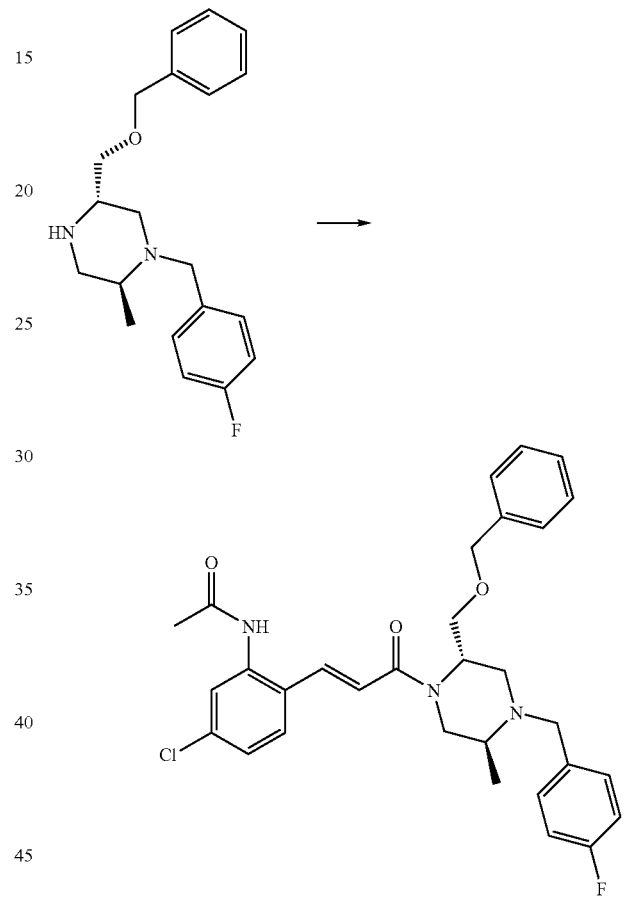

(E)-3-(2-Acetylamino-4-chloro-phenyl)-acrylic acid (168 mg, 0.7 mmol), EDCI (269 mg, 1.4 mmol); HOBT (190 mg, 1.4 mmol) and 230 mg (0.7 mmol) (2S,5S)-5-Benzyloxymethyl-1-(4-fluorobenzyl)-2-methyl-piperazine (prepared as outlined in example 47) were dissolved in 10 ml THF and stirred for 28 hours at room temperature. This mixture was then extracted 3 times with water and once with saturated sodium chloride solution. The title compound was purified by chromatography (SiO$_2$, ethyl acetate/MeOH/NH$_3$conc. 90/10/1) and was isolated as a pale solid (180 mg, 47%)

1H-NMR (400 MHz; DMSO-d6, 120° C.): 0.95 (d, 3H); 2.10 (s, 3H); 2.55 (dd, 1H); 2.75 (dd, 1H); 2.95-3.05 (m, 1H); 3.25-3.35 (m, 1H); 3.45 (d, 1H); 3.60 (d, 1H); 3.70-3.80 (m, 2H); 4.00-4.05 (m, 1H); 4.45 (s, 2H); 4.45-4.55 (m, 1H); 6.95-7.05 (m, 3H); 7.20-7.30 (m, 5H); 7.30-7.35 (m, 3H); 7.60-7.70 (m, 3H); 9.85 (bs, 1H)

MS (m/z) ES+: 550.1 (MH+, 100%).

Example 63

(S)-1-Acetyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide

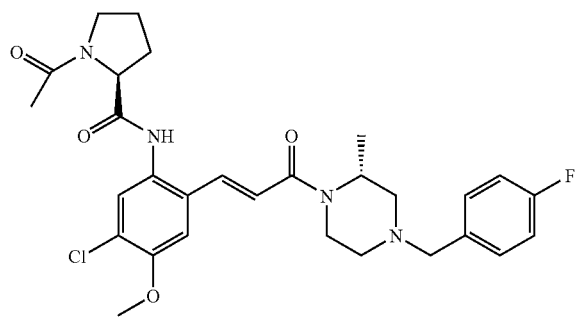

a) (E)-3-(4-Chloro-5methoxy-2-nitro-phenyl)-1-[(R)-4-(4-fluoro-benzyl)-2-methyl-piperazin-1-yl]-propenone A mixture of 1.70 g (8.2 mmol) (R)-1-(4-Fluoro-benzyl)-3-methyl-piperazine and 2.00 g (7.8 mmol) (E)-3-(4-Chloro-5-methoxy-2-nitro-phenyl)-acrylic acid was coupled as described in example 8 to yield 3.00 g (6.7 mmol, 86%) of the title compound.

1H-NMR (400 MHZ, DMSO-d6): 1.25 (br s, 3H), 1.87-2.24 (m, 2H), 2.67 (d, 1H), 2.84 (d, 1H), 2.90-3.40 (m, 1H), 3.44 and 3.53 (AB-Sys., 2H), 4.07 (s, 3H), 4.08-4.70 (m, 2H), 7.15 (t, 2H), 7.24 (d, 1H), 7.35 (dd, 2H), 7.46 (s, 1H), 7.78 (d, 1H), 8.21 (s, 1H).

MS (ESI+) m/z: 448 [M+H]+ b) (E)-3-(2-Amino-4-chloro-5-methoxy-phenyl)-1-[(R)-4-(4-fluoro-benzyl)-2-methyl-piperazin-1-yl]-propenone Reduction of 2.50 g (5.60 mmol) of the nitro compound using SnCl2 as described in example 30 yielded 2.30 g (98%) of the corresponding aniline.

1H-NMR (400 MHZ, DMSO-d6): 1.24 (br s, 3H), 1.86-2.18 (m, 2H), 2.66 (d, 1H), 2.82 (d, 1H), 3.42 and 3.51 (AB-Sys., 2H), 3.77 (s, 3H), 4.03-4.65 (m, 2H), 5.22 (s, 2H), 6.79 (s, 1H), 7.98 (d, 1H), 7.15 (t, 2H), 7.19 (s, 1H), 7.34 (dd, 2H), 7.59 (d, 1H).

MS (ESI+) m/z: 418 [M+H]+ c) (S)-1-Acetyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide 0.15 g (0.36 mmol) (E)-3-(2-Amino-4-chloro-5-methoxy-phenyl)-1-[(R)-4-(4-fluoro-benzyl)-2-methyl-piperazin-1-yl]-propenone, 0.062 g (0.40 mmol) N-acetyl-L-proline, 0.083 g (0.43 mmol) EDCI and 0.058 g (0.43 mmol) HOBt were stirred in 5 ml DMF at room temperature for 16 hours. Aqueous workup and RP-HPLC yielded 0.090 g (0.16 mmol, 45%) of the title compound.

1H-NMR (400 MHZ, DMSO-d6): 1.25 (br s, 3H), 1.78-2.20 (m, 6H), 2.00 (s, 3H), 2.66 (br d, 1H), 2.83 (d, 1H), 3.30-3.65 (m, 5H), 3.92 (s, 3H), 4.08-4.27 (m, 1H), 4.40 (dd, 1H), 4.50-4.66 (m, 1H), 7.15 (t, 2H), 7.18 (d, 1H), 7.32 (s, 1H), 7.35 (dd, 2H), 7.46 (s, 1H), 7.51 (d, 1H), 9.62 (s, 1H).

MS (ESI+) m/z: 557 [M+H]+

Similarly the following compounds were synthesized:

Example 64

(S)-1-Isopropyl-pyrrolidine-2-carboxylic acid (5-chloro-2-{(E)-3-[(R)-4-(4-fluoro-benzyl)-2-methyl-piperazin-1-yl]-3-oxo-propenyl}-4methoxy-phenyl)-amide

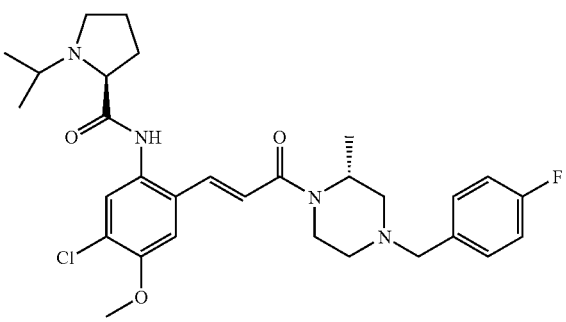

1H-NMR (400 MHZ, DMSO-d6): 1.04 (d, 3H), 1.06 (d, 3H), 1.24 (br s, 3H), 1.42-1.51 (m, 3H), 1.68-2.16 (m, 4H), 2.60-2.71 (m, 1H), 2.74-2.88 (m, 2H), 3.08-3.13 (m, 1H), 3.20-3.30 (m, 1H), 3.37-3.60 (m, 3H), 3.92 (s, 3H), 4.08-4.25 (m, 1H), 4.50-4.68 (m, 1H), 7.15 (t, 2H), 7.20 (d, 1H), 7.35 (dd, 2H), 7.45 (s, 1H), 7.54 (d, 1H), 7.68 (s, 1H), 9.83 (s, 1H).

MS (ESI+) m/z: 556 [M+H]+

Example 65

(R)-1-Isopropyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide

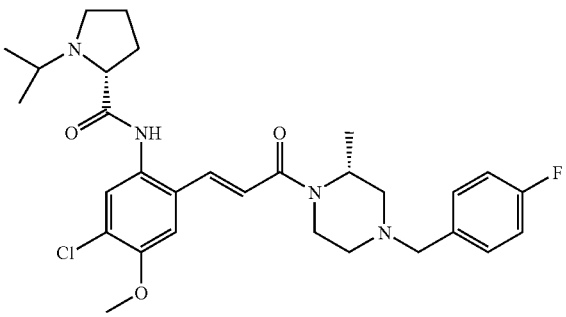

1H-NMR (400 MHZ, DMSO-d6): 1.04 (d, 3H), 1.06 (d, 3H), 1.24 (br s, 3H), 1.42-1.51 (m, 3H), 1.68-2.16 (m, 4H), 2.60-2.71 (m, 1H), 2.74-2.88 (m, 2H), 3.08-3.13 (m, 1H), 3.27 (t, 1H), 3.37-3.60 (m, 3H), 3.91 (s, 3H), 4.08-4.25 (m, 1H), 4.50-4.68 (m, 1H), 7.14 (t, 2H), 7.20 (d, 1H), 7.35 (dd, 2H), 7.44 (s, 1H), 7.54 (d, 1H), 7.66 (s, 1H), 9.83 (s, 1H).

MS (ESI+) m/z: 556 [M+H]+

Example 66

(2S,4R)-1-Acetyl-4-hydroxy-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide

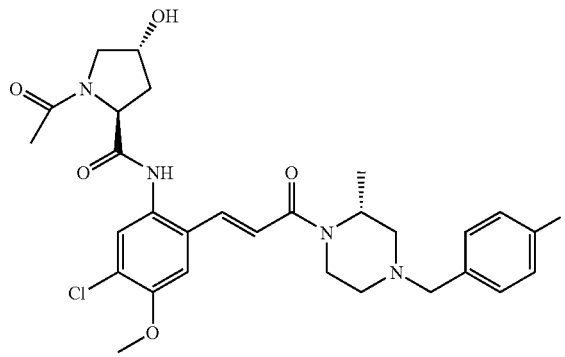

1H-NMR (400 MHZ, DMSO-d6, 120° C.): 1.28 (d, 3H), 1.93, (s, 3H), 1.98-2.21 (m, 3H), 2.68 (dt, 1H), 2.78-2.87 (m, 2H), 3.19 (td, 1H), 3.38-3.75 (m, 4H), 3.92 (s, 3H), 4.12 (br d, 1H), 4.34-4.42 (m, 1H), 4.50-4.70 (m, 3H), 7.01 (d, 1H), 7.08 (t, 2H), 7.34 (dd, 2H), 7.38 (s, 1H), 7.40 (s, 1H), 7.46 (d, 1H), 9.27 (br s, 1H).

MS (ESI+) m/z: 573 [M+H]+

Example 67

(E)-3-(4-Chloro-2-morpholin-4-ylmethyl-phenyl)-1-[4-(4-fluoro-benzyl)-2-methyl-piperazin-1-yl]-propenone a) 1-[4-(4-Fluoro-benzyl)-2-methyl-piperazin-1-yl]-propenone

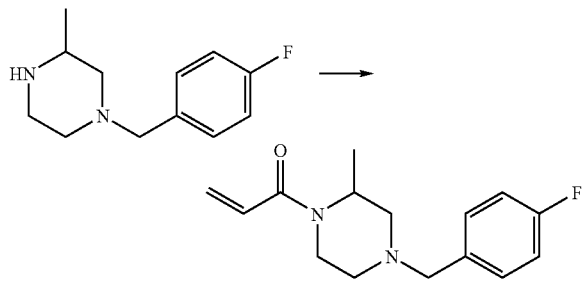

3.00 g (14.4 mmol) 1-(4-Fluoro-benzyl)-3-methyl-piperazine and 2.0 ml (14.4 mmol) triethylamine were dissolved in 50 ml dichloromethane. The solution was cooled to 0° C. and 1.19 ml (14.4 mmol) acryloyl chloride was added dropwise. Stirring was continued for another 4 hours. The solvent was evaporated and the residue was partitioned between sodium bicarbonate solution and ethyl acetate. Further extraction with ethyl acetate and washing of the organic phase with water and brine yielded 3.60 g (13.6 mmol, 95%) of the acroyl amide.

1H-NMR (400 MHz, DMSO-d6): 1.20 (bs, 3H), 1.84-2.14 (m, 2H), 2.62 (d, 1H), 2.79 (d, 1H), 3.41 and 3.50 AB-Sys., 2H), 3.72-4.68 (m, 3H), 5.66 (dd, 1H), 6.09 (dd, 1H), 6.76 (dd, 1H), 7.15 (t, 2H), 7.35 (dd, 2H).

MS (ESI+) m/z: 263 [M+H]+

Analogously the corresponding 1-[(R)-4-(4-Fluoro-benzyl)-2-methyl-piperazin-1-yl]-propenone was prepared in 71% yield starting from the enantiopure 4-Fluorobenzyl-piperazine.

b) 4-(2-Bromo-5-chloro-benzyl)-morpholine

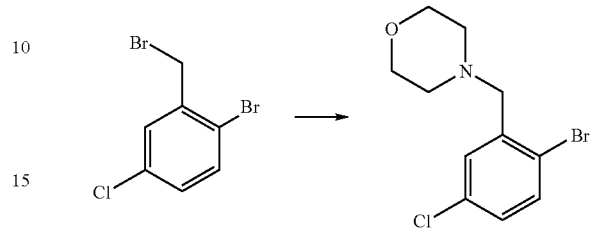

A mixture of 0.50 g (1.76 mmol) 1-Bromo-2-bromomethyl-4-chloro-benzene, 0.17 g (1.94 mmol) morpholine and 0.29 ml (210 mmol) triethylamine in 20 ml DMF was stirred overnight at room temperature. 200 ml of ethylacetate was added and the solution was extracted with sodium bicarbonate, water and brine. 0.47 g (1.62 mmol, 92%) of the title compound were obtained as a viscous oil.

1H-NMR (400 MHz, DMSO-d6): 2.43 (t, 4H), 3.54 (s, 2H), 3.60 (t, 4H), 7.29 (dd, 1H), 7.52 (d, 1H), 7.64 (d, 1H).

MS (ESI+) m/z: 290 [M+H]+ c) (E)-3-(4-Chloro-2-morpholin-4-ylmethyl-phenyl)-1-[4-(4-fluoro-benzyl)-2-methyl-piperazin-1-yl]-propenone

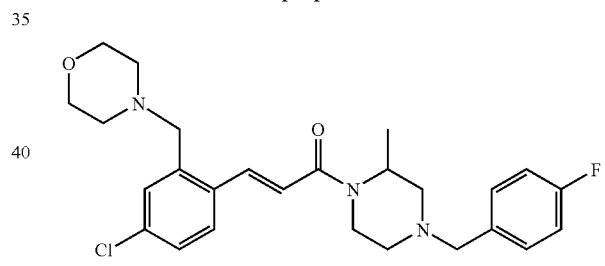

0.20 g (0.69 mmol) 4-(2-Bromo-5-chloro-benzyl)-morpholine, 0.20 g (0.76 mmol) 1-[4-(4-Fluoro-benzyl)-2-methyl-piperazin-1-yl]-propenone and 0.29 ml (2.07 mmol) triethylamine were dissolved in 7 ml DMF. 21 mg tri(o-tolyl) phosphine and 16 mg palladium(II)-acetate were added and the reaction mixture was heated to 100° C. for 16 hours. 100 ml ethylacetate was added, the organic phase was washed with sodium bicarbonate solution, water and brine. The crude product which was obtained after evaporation was further purified by prep. HPLC (acetonitrile/water) to obtain 0.13 g (0.27 mmol, 39%) of the desired title compound.

1H-NMR (400 MHZ, DMSO-d6): 1.26 (d, 3H), 1.88-2.00 (m, 1H), 2.04-2.13 (m, 1H), 2.34-2.40 (m, 4H), 2.66 (d, 1H), 2.82 (d, 1H), 3.42 and 3.52 (AB-Sys., 2H), 3.54 (br s, 4H), 4.08-4.29 (m, 1H), 4.45-4.64 (m, 1H), 7.10 (d, 1H), 7.16 (t, 2H), 7.34-7.40 (m, 3H), 7.42 (d, 1H), 7.82 (d, 1H), 7.83 (d, 1H).

MS (ESI+) m/z: 472 [M+H]+

In similar manner the following compounds were synthesised:

Example 68

1-(5-Chloro-2-{(E)-3-[4-(4-fluoro-benzyl)-2-methyl-piperazin- -yl]-3-oxo-propenyl}-benzyl)-pyrrolidin-2-one a) 1-(2-Bromo-5-chloro-benzyl)-pyrrolidin-2-one

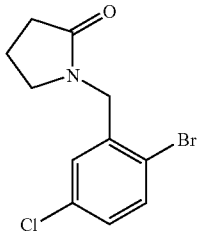

1H-NMR (400 MHz, DMSO-d6): 1.97 (quint, 2H), 2.32 (t, 2H), 3.30 (t, 2H), 4.41 (s, 2H), 7.25 (d, 1H), 7.33 (dd, 1H), 7.67 (d, 1H).
MS (ESI+): 310 [M+Na]+ b) 1-(5-Chloro-2-{(E)-3-[4-(4-fluoro-benzyl)-2-methyl-piperazin-1-yl]-3-oxo-propenyl}-benzyl)-pyrrolidin-2-one

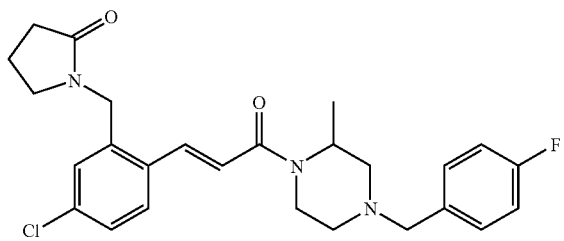

1H-NMR (400 MHz, DMSO-d6): 1.24 (d, 3H), 1.87-2.13 (m, 4H), 2.28 (t, 2H), 2.64 (d, 1H), 2.83 (d, 1H), 2.90-3.05 (m, 1H), 3.19 (t, 2H), 3.42 and 3.53 (AB-Sys., 2H), 4.00-4.67 (m, 2H), 4.48 (s, 2H), 7.09 (d, 1H), 7.16 (t, 2H), 7.26 (s, 1H), 7.32-7.43 (m, 3H), 7.64 (d, 1H), 7.33 (d, 1H).
MS (ESI+): 471 [M+H]+

Example 69

(E)-3-(4-Chloro-2-[1,2,4]triazol-1-ylmethyl-phenyl)-1-[4-(4-fluoro-benzyl)-2-methyl-piperazin-1-yl]-propenone a) 1-(2-Bromo-5chloro-benzyl)-1H-[1,2,4]triazole

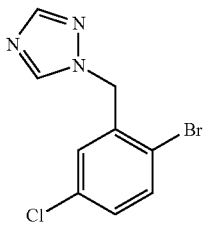

1H-NMR (400 MHz, DMSO-d6): 5.50 (s, 2H), 7.21 (d, 1H), 7.39 (dd, 1H), 7.70 (d, 1H), 8.04 (s,1H), 8.68 (s, 1H).
MS (ESI+): 272 [M+H]+ b) (E)-3-(4-Chloro-2-[1,2,4]triazol-1-ylmethyl-phenyl)-1-[4-(4-fluoro-benzyl)-2-methyl-piperazin-1-yl]-propenone

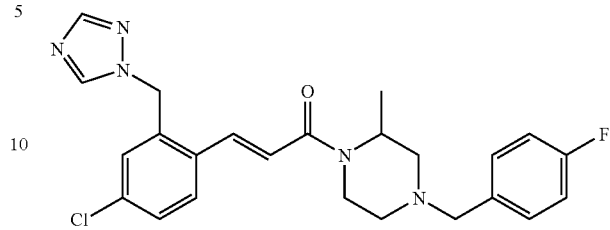

1H-NMR (400 MHz, DMSO-d6): 1.24 (d, 3H), 1.87-2.16 (m, 2H), 2.66 (d, 1H), 2.82 (d, 1H), 2.88-3.05 (m, 1H), 3.42 and 3.53 (AB-Sys., 2H), 4.02-4.68 (m, 2H), 5.59 (s, 2H), 7.12 (d, 1H), 7.17 (t, 2H), 7.28 (d, 1H), 7.36 (dd, 2H), 7.45 (dd, 1H), 7.70 (d, 1H), 7.87 (d, 1H), 7.98 (s, 1H), 8.59 (s,1H).
MS (ESI+): 454 [M+H]+

Example 70

(E)-3-[4-Chloro-2-(4-methyl-piperazin-1-ylmethyl)-phenyl]-1-[4-(4-fluoro-benzyl)-2-methyl-piperazin-1-yl]-propenone a) 1-(2-Bromo-5-chloro-benzyl)-4-methyl-piperazine

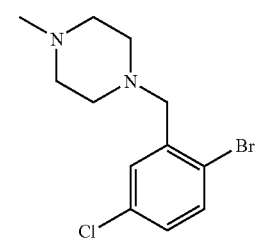

1H-NMR (400 MHz, DMSO-d6): 2.17 (s, 3H), 2.22-2.50 (m, 8H), 3.50 (s, 2H), 7.28 (d, 1H), 7.48 (s,1H), 7.62 (d, 1H).
MS (ESI+): 303 [M+H]+ b) (E)-3-[4-Chloro-2-(4-methyl-piperazin-1-ylmethyl)-phenyl]-1-[4-(4-fluoro-benzyl)-2-methyl-piperazin-1-yl]-propenone

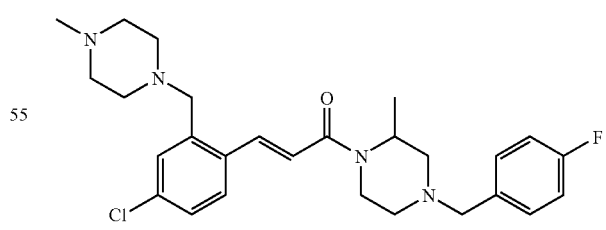

1H-NMR (400 MHz, DMSO-d6): 1.25 (d, 3H), 1.88-2.00 (m, 1H), 2.04-2.17 (m, 1H), 2.20-2.46 (m, 9H), 2.66 (d, 1H), 2.82 (d, 1H), 3.43 and 3.52 (AB-Sys., 2H), 3.52 (s, 2H), 4.10-4.28 (m, 1H), 4.45-4.65 (m, 1H), 7.08 (d, 1H), 7.16 (t, 2H), 7.33-7.40 (m, 4H), 7.29 (d, 1H), 7.30 (d, 1H).
MS (ESI+): 485 [M+H]+

Example 71

(E)-3-[2-(4-Acetyl-piperazin-1-ylmethyl)-4-chloro-phenyl]-1-[4-(4-fluoro-benzyl)-2-methyl-piperazin-1-yl]-propenone a) 1-[4-(2-Bromo-5chloro-benzyl)-piperazin-1-yl]thanone

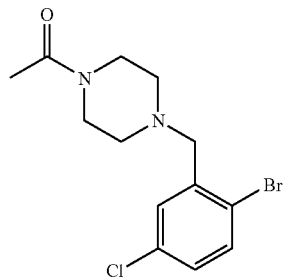

1H-NMR (400 MHz, DMSO-d6): 1.98 (s, 3H), 2.35-2.41 (m, 2H), 2.43-2.48 (m, 2H), 3.40-3.49 (m, 4H), 3.55 (s, 2H), 7.30 (d, 1H), 7.53 (s, 1H), 7.64 (d, 1H).
MS (ESI+): 331 [M+H]+ b) (E)-3-[2-(4-Acetyl-piperazin-1-ylmethyl)-4-chloro-phenyl]-1-[4-(4-fluoro-benzyl)-2-methyl-piperazin-1-yl]-propenone

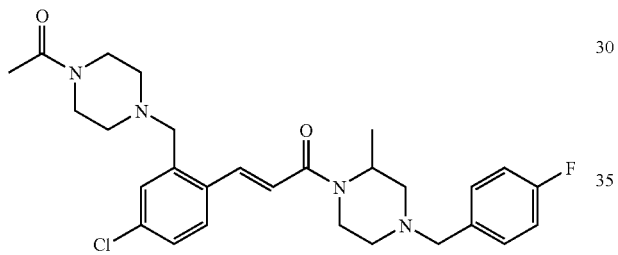

1H-NMR (400 MHz, DMSO-d6): 1.24 (d, 3H), 1.90-2.00 (m, 1H), 1.98 (s, 3H), 2.04-2.14 (m, 1H), 2.32 (t, 2H), 2.39 (t, 2H), 2.66 (d, 1H), 2.82 (d, 1H), 3.40 (br s, 4H), 3.43 and 3.52 (AB-Sys., 2H), 3.57 (s, 2H), 4.09-4.28 (m, 1H), 4.43-4.67 (m, 1H), 7.10 (d, 1H), 7.16 (t, 2H), 7.33-7.41 (m, 3H), 7.42 (s, 1H), 7.82 (d, 1H), 7.83 (d, 1H).
MS (ESI+): 513 [M+H]+

Example 72

(E)-3-[4-Chloro-2-(4-isopropyl-piperazin-1-ylmethyl)-phenyl]-1-[(R)-4-(4-fluoro-benzyl)-2-methyl-piperazin-1-yl]-propenone a) 1-(2-Bromo-5-chloro-benzyl)-4-isopropyl-piperazine

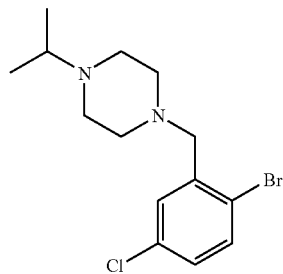

1H-NMR (400 MHZ, DMSO-d6): 0.97 (d, 6H), 2.38-2.50 (m, 8H), 2.62 (sept., 1H), 3.49 (s, 2H), 7.27 (dd, 1H), 7.47 (d, 1H), 7.60 (d, 1H).
MS (ESI+): 331 [M+H]+ b) (E)-3-[4-Chloro-2-(4-isopropyl-piperazin-1-ylmethyl)-phenyl]-1-[(R)-4-(4-fluoro-benzyl)-2-methyl-piperazin-1-yl]-propenone

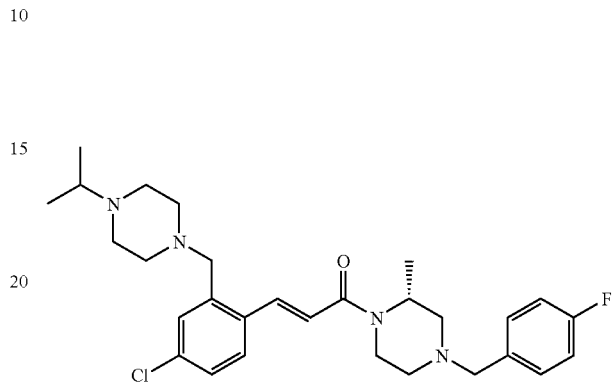

1H-NMR (400 MHZ, DMSO-d6): 0.94 (d, 6H), 1.24 (br s, 3H), 1.88-2.15 (m, 2H), 2.28-2.46 (m, 8H), 2.59 (sept., 1H), 2.66 (d, 1H), 2.78-2.86 (m, 1H), 3.35-3.55 (m, 3H), 3.49 (s, 2H), 4.06
MS (ESI+): 513 [M+H]+

Example 73

1-(5-Chloro-2-{(E)-3-[(R)-4-(4-fluoro-benzyl)-2-methyl-piperazin-1-yl]-3-oxo-propenyl}-benzyl)-3-oxa-1-aza-spiro[4.4]nonan-2-one a) 1-(2-Bromo-5-chloro-benzyl)-3-oxa-1-aza-spiro[4.4]nonan-2-one

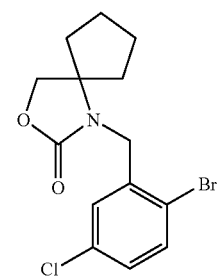

1H-NMR (400 MHZ, DMSO-d6): 1.48-1.76 (m, 8H), 3.68 (s, 2H), 5.18 (s, 2H), 7.37 (dd, 1H), 7.68 (d, 1H), 7.72 (d, 1H), 7.81 (s, 1H).
MS (EI) m/z: 263 [M-Br]+ b) 1-(5-Chloro-2-{(E)-3-[(R)-4-(4-fluoro-benzyl)-2-methyl-piperazin-1-yl]-3-oxo-propenyl}-benzyl)-3-oxa-1-aza-spiro[4.4]nonan-2-one

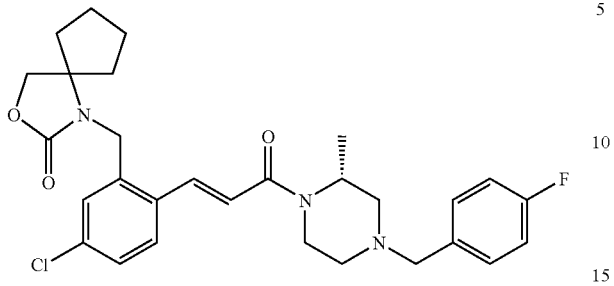

1H-NMR (400 MHZ, DMSO-d6): 1.18-1.33 (m, 5H), 1.43-1.79 (m, 6H), 1.84-2.18 (m, 2H), 2.66 (d, 1H), 2.78-3.05 (m, 2H), 3.42 and 3.51 (AB-Sys., 2H), 4.02-4.68 (m, 2H), 4.21 (s, 2H), 4.43 (s, 2H), 7.10 (d, 1H), 7.14 (t, 2H), 7.27 (d, 1H), 7.23-7.39 (m, 3H), 7.70 (d, 1H), 7.78 (d, 1H).

MS (ESI+) m/z: 526 [M+H]+

Example 74

3-(5-Chloro-2-{(E)-3-[(R)-4-(4-fluoro-benzyl)-2-methyl-piperazin-1-yl]-3-oxo-propenyl}-benzyl)-5,5-dimethyl-imidazolidine-2,4-dione a) 3-(2-Bromo-5-chloro-benzyl)-5,5-dimethyl-imidazolidine-2,4-dione

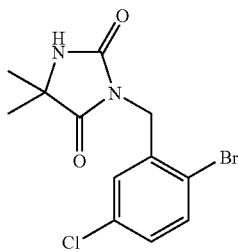

1H-NMR (400 MHZ, DMSO-d6): 1.88 (s, 3H), 2.01 (s, 3H), 4.73 (s, 2H), 7.28 (dd, 1H), 7.44 (d, 1H), 7.62 (d, 1H), 10.0 (br s, 1H).

MS (ESI+) m/z: 353 [M+Na]+ b) 3-(5-Chloro-2-{(E)-3-[(R)-4-(4-fluoro-benzyl)-2-methyl-piperazin-1-yl]-3-oxo-propenyl}-benzyl)-5,5-dimethyl-imidazolidine-2,4-dione

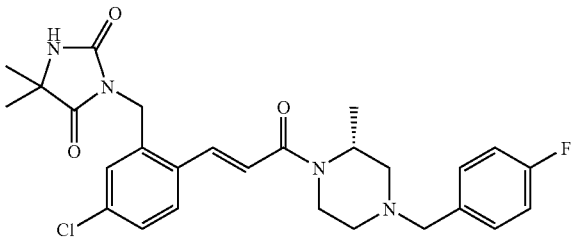

1H-NMR (400 MHZ, DMSO-d6): 1.24 (br s, 3H), 1.30 (s, 6H), 1.87-2.16 (m, 2H), 2.64 (d, 1H), 2.81 (d, 1H), 2.88-3.06 (m, 1H), 3.35-3.56 (m, 2H), 3.95-4.55 (m, 2H), 4.62 (s, 2H), 7.06-7.18 (m, 4H), 7.35 (d, 1H), 7.37 (dd, 2H), 7.70-7.82 (m, 2H), 8.41 (s, 1H).

MS (ESI+) m/z: 513 [M+H]+, 535 [M+Na]+

Example 75

3-(5-Chloro-2-{(E)-3-[(R)-4-(4-fluoro-benzyl)-2-methyl-piperazin-1-yl]-3-oxo-propenyl}-benzyl)-1-methyl-imidazolidine-2,4-dione a) 3-(2-Bromo-5-chloro-benzyl)-1-methyl-imidazolidine-2,4-dione

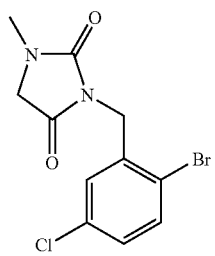

1H-NMR (400 MHZ, DMSO-d6): 2.90 (s, 3H), 4.08 (s, 2H), 4.54 (s, 2H), 7.26 (d, 1H), 7.33 (dd, 1H), 7.68 (d, 1H).

MS (ESI+) m/z: 337 [2M+Ca]2+ b) 3-(5-Chloro-2-{(E)-3-[(R)-4-(4-fluoro-benzyl)-2-methyl-piperazin-1-yl]-3-oxo-propenyl}-benzyl)-1-methyl-imidazolidine-2,4-dione

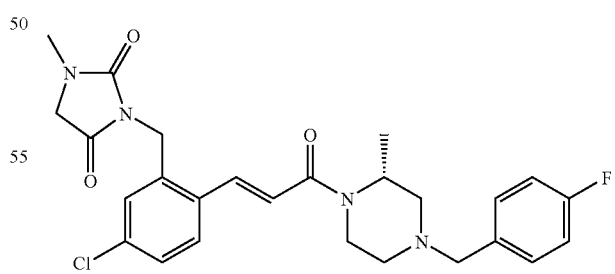

1H-NMR (400 MHZ, DMSO-d6):1.24 (br s, 3H), 1.87-2.18 (m, 2H), 2.65 (d, 1H), 2.82 (d, 1H), 2.88 (s, 3H), 2.90-3.04 (m, 1H), 3.42 and 3.52 (AB-Sys, 2H), 4.04 (s, 2H), 4.02-4.58 (m, 2H), 4.63 (s, 2H), 7.09 (d, 1H), 7.14 (t, 2H), 7.23 (s, 1H), 7.32-7.41 (m, 3H), 7.78 (d, 1H), 7.80 (d, 1H).

MS (ESI+) m/z: 499 [M+H]+, 521 [M+Na]+

Example 76

(E)-3-[4-Chloro-2-(5-methyl-tetrazol-1-ylmethyl)-phenyl]-1-[(R)-4-(4-fluoro-benzyl)-2-methyl-piperazin-1-yl]-propenone a) 1-(2-Bromo-5-chloro-benzyl)-5-methyl-1H-tetrazole

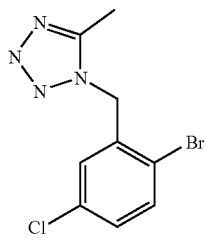

1H-NMR (400 MHZ, DMSO-d6): 2.59 (s, 3H), 5.61 (s, 2H), 7.39 (d, 1H), 7.43 (dd, 1H), 7.72 (d, 1H).
MS (ESI+) m/z: 287 [M+H]+ b) (E)-3-[4-Chloro-2-(5-methyl-tetrazol-1-ylmethyl)-phenyl]-1-[(R)-4-(4-fluoro-benzyl)-2-methyl-piperazin-1-yl]-propenone

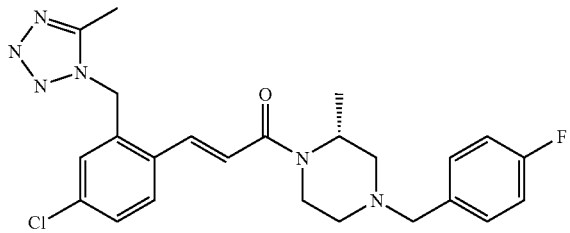

1H-NMR (400 MHZ, DMSO-d6): 1.22 (br s, 3H), 1.84-2.18 (m, 2H), 2.58 (s, 3H), 2.64 (d, 1H), 2.81 (d, 1H), 2.86-3.05 (m, 1H), 3.37-3.56 (m, 2H), 3.96-4.18 (m, 2H), 5.74 (s, 2H), 7.10 (d, 1H), 7.15 (t, 2H), 7.29 (d, 1H), 7.35 (dd, 2H), 7.49 (dd, 1H), 7.67 (d, 1H), 7.88 (d, 1H).
MS (ESI+) m/z: 469 [M+H]+

Example 77

5-Chloro-2-{(E)-3-[(R)-4-(4-fluoro-benzyl)-2-methyl-piperazin-1-yl]-3-oxo-propenyl}-N-methoxy-N-methyl-benzamide a)
2-Bromo-5-chloro-N-methoxy-N-methyl-benzamide

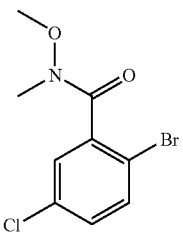

1H-NMR (400 MHZ, DMSO-d6): 3.28 (s, 3H), 3.46 (s, 3H), 7.42 (dd, 1H), 7.59 (d, 1H), 7.68 (d, 1H).
MS (EI) m/z: 277 [M]+ b) 5-Chloro-2-{(E)-3-[(R)-4-(4-fluoro-benzyl)-2-methyl-piperazin-1-yl]-3-oxo-propenyl}-N-methoxy-N-methyl-benzamide

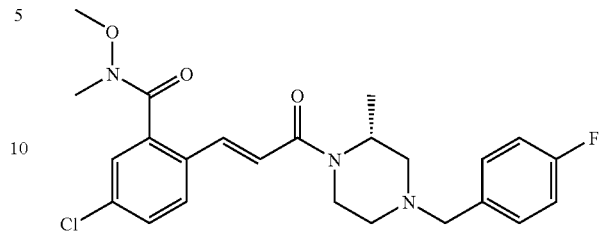

1H-NMR (400 MHZ, DMSO-d6): 1.24 (br s, 3H), 1.87-2.18 (m, 2H), 2.16 (d, 1H), 2.82 (d, 1H), 2.90-3.15 (m, 1H), 3.31 (s, 3H), 3.33 (s, 3H), 3.36-3.58 (m, 2H), 4.02-4.30 (m, 1H), 4.35-4.70 (m, 1H), 7.15 (t, 2H), 7.23 (d, 1H), 7.30-7.38 (m, 3H), 7.50 (s, 1H), 7.53 (d, 1H), 8.01 (d, 1H).
MS (ESI+) m/z: 460 [M+H]+, 482 [M+Na]+

Example 78

5-Chloro-2-{(E)-3-[4-(4-fluoro-benzyl)-2-methyl-piperazin-1-yl]-3-oxo-propenyl}-benzoic acid methyl ester

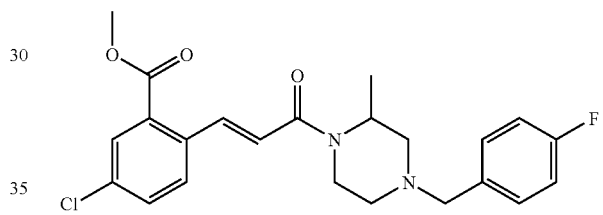

1H-NMR (400 MHz, DMSO-d6): 1.25 (br s, 3H), 1.86-2.19 (m, 2H), 2.66 (d, 1H), 2.83 (d, 1H), 2.87-3.08 (m, 1H), 3.43 and 3.52 (AB-Sys., 2H), 3.88 (s, 3H), 4.04-4.72 (m, 2H), 7.12-7.20 (m, 3H), 7.38 (t, 2H), 7.70 (d, 1H), 7.84 (s, 1H), 7.95-8.04 (m, 2H).
MS (ESI+): 431 [M+H]+

Example 79

(5-Chloro-2-{(E)-3-[4-(4-fluoro-benzyl)-2-methyl-piperazin-1-yl]-3-oxo-propenyl}-phenyl)-acetic acid methyl ester

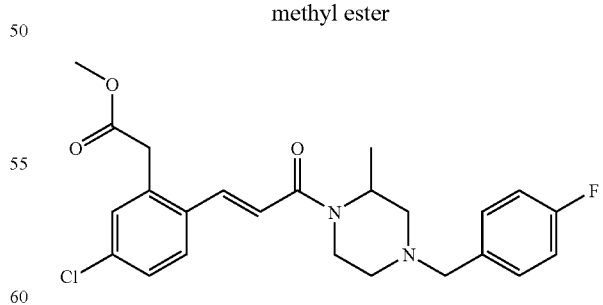

1H-NMR (400 MHz, DMSO-d6): 1.24 (br s, 3H), 1.88-2.17 (m, 2H), 2.65 (d, 1H), 2.82 (d, 1H), 2.87-3.13 (m, 1H), 3.43 and 3.52 (AB-Sys., 2H), 3.61 (s, 3H), 3.88 (s, 2H), 4.05-4.68 (m, 2H), 7.12 (d, 1H), 7.16 (t, 2H), 7.33-7.40 (m, 3H), 7.42 (d 1H), 7.54 (d, 1H), 7.86 (d, 1H).
MS (ESI+): 467 [M+Na]+

Example 80

5-Chloro-2-{(E)-3-[4-(4-fluoro-benzyl)-2-methyl-piperazin-1-y]-3-oxo-propenyl}-benzoic acid

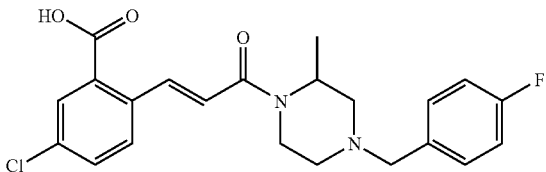

1.56 g (3.6 mmol) 5-Chloro-2-{(E)-3-[4-(4-fluoro-benzyl)-2-methyl-piperazin-1-yl]-3-oxo-propenyl}-benzoic acid methyl ester (Example 78) was suspended in a 1:1 mixture of methanol and water (20 ml). 0.5 ml 10 N NaOH was added and the mixture was stirred overnight. After acidification using 6.5 ml 1N HCl the product precipitated. Filtration and drying yielded 1.32 g (3.2 mmol, 87%) of the desired acid.

1H-NMR (400 MHz, DMSO-d6): 1.24 (bs, 3H), 1.88-2.17 (m, 2H), 2.65 (d, 1H), 2.82 (d, 1H), 2.86-3.06 (m, 1H), 3.43 and 3.52 (AB-Sys., 2H), 4.02-4.70 (m, 2H), 7.05 (d, 1H), 7.17 (t, 2H), 7.38 (dd, 2H), 7.42-7.53 (m, 1H), 7.64 (br s, 1H), 7.84 (d, 1H), 8.12 (d, 1H), COOH not observable.

MS (ESI+): 417 [M+H]+

Example 81

5-Chloro-2-{(E)-3-[(R)-4-(4-fluoro-benzyl)-2-methyl-piperazin-1-yl]-3-oxo-propenyl}-benzoic acid

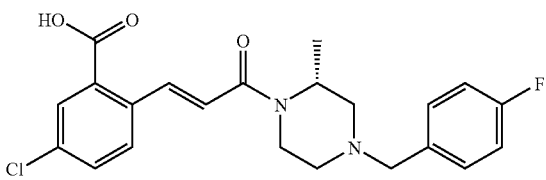

In an identical reaction sequence the corresponding 5-Chloro-2-{(E)-3-[(R)-4-(4-fluoro-benzyl)-2-methyl-piperazin-1-yl]-3-oxo-propenyl}-benzoic acid was synthesized starting from (R)-1-(4-Fluoro-benzyl)-3-methyl-piperazine. Spectroscopic data were identical to the ones obtained with the racemate.

Example 82

(E)-3-[4-Chloro-2-(4-methyl-piperazine-1-carbonyl)-phenyl]-1-[4-(4-fluoro-benzyl)-2-methyl-piperazin-1-yl]-propenone

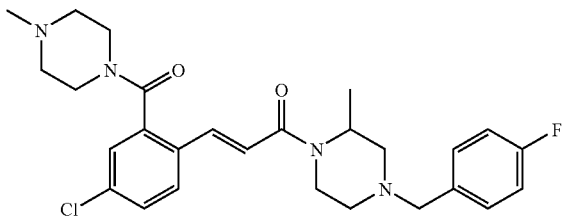

0.15 g (0.36 mmol) benzoic acid from Example 80, 43 mg N-methylpiperazine (0.43 mmol), 83 mg EDCI (0.43 mmol) and 58 mg HOBt (0.43 mmol) were dissolved in 5 ml DMF. The reaction mixture was stirred overnight then partitioned between ethylacetate and aq. sodiumbicarbonate solution. The organic phase was further washed with water and brine. Removal of the solvent gave a crude product which was further purified by crystallisation from acetonitrile. Thus 75 mg (0.15 mmol, 42%) of the desired amide was otained.

1H-NMR (400 MHz, DMSO-d6): 1.24 (br s, 3H), 1.87-2.14 (m, 4H), 2.21-2.35 (m, 2H), 2.65 (d, 1H), 2.82 (d, 1H), 2.91-3.18 (m, 3H), 3.37-3.56 (m, 3H), 3.77-3.88 (m, 1H), 4.00-4.68 (m, 2H), 7.17 (t, 2H), 7.24 (d, 1H), 7.35 (d, 1H), 7.36 (dd, 2H), 7.40 (d, 1H), 7.53 (dd, 1H), 8.02 (d, 1H).

MS (ESI+): 499 [M+H]+

In analoguous manner the following products were prepared:

Example 83

5-Chloro-2-{(E)-3-[4-(4-fluoro-benzyl)-2-methyl-piperazin-1-yl]-3-oxo-propenyl}-N-isopropyl-benzamide

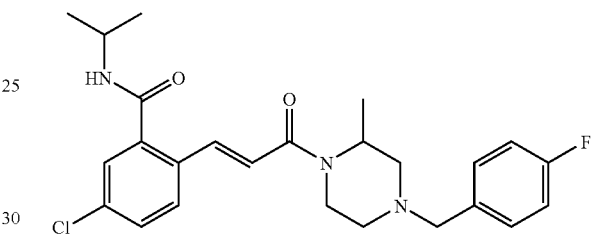

1H-NMR (400 MHz, DMSO-d6): 1.15 (d, 6H), 1.24 (br s, 3H), 1.87-2.15 (m, 2H), 2.65 (d, 1H), 2.82 (d, 1H), 2.88-3.08 (m, 1H), 3.42 and 3.52 (AB-Sys., 2H), 4.04 (sept., 1H), 4.08-4.68 (m, 2H), 7.17 (t, 2H), 7.19 (d, 1H), 7.37 (dd, 2H), 7.40 (d, 1H), 7.53 (dd, 1H), 7.62 (d, 1H), 7.97 (d, 1H), 8.40 (d, 1H).

MS (ESI+): 458 [M+H]+

Example 84

5Chloro-2-{(E)-3-[4-(4-fluoro-benzyl)-2-methyl-piperazin-1-yl]-3-oxo-propenyl}-N-(1-methyl-piperidin-4-yl)-benzamide

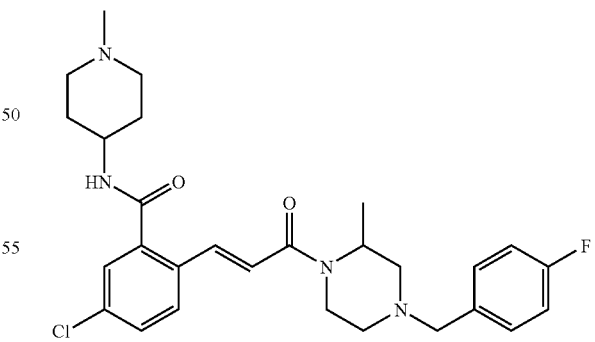

1H-NMR (400 MHz, DMSO-d6): 1.23 (bs, 3H), 1.45-1.57 (m, 2H), 1.74-1.83 (m, 2H), 1.87-2.15 (m, 5H), 2.17 (s, 3H), 2.60-2.86 (m, 4H), 3.42 and 3.57 (AB-Sys., 2H), 3.63-3.75 (m, 1H), 4.00-4.68 (m, 2H), 7.17 (t, 2H), 7.19 (d, 1H), 7.36 (dd, 2H), 7.41 (d, 1H), 7.54 (dd, 1H), 7.61 (d. 1H), 7.96 (d, 1H), 8.46 (d, 1H).

MS (ESI+): 513 [M+H]+

Example 85

N-(1-Benzyl-piperidin-4-yl)-5-chloro-2-{(E)-3-[4-(4-fluoro-benzyl)-2-methyl-piperazin-1-yl]-3-oxo-propenyl}-benzamide

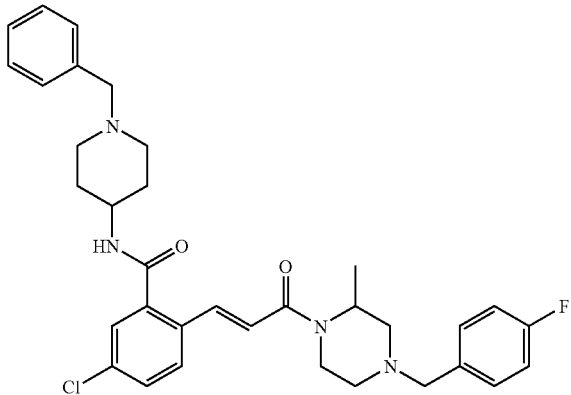

1H-NMR (400 MHz, DMSO-d6): 1.23 (bs, 3H), 1.44-1.57 (m, 2H), 1.76-1.84 (m, 2H), 1.87-2.15 (m, 4H), 2.64 (d, 1H), 2.73-2.85 (m, 3H), 3.42 and 3.51 (AB-Sys., 2H), 3.47 (s, 2H), 3.68-3.79 (m, 1H), 4.00-4.65 (m, 2H), 7.17 (t, 2H), 7.19 (d, 1H), 7.22-7.39 (m, 7H), 7.40 (d, 1H), 7.53 (dd, 1H), 7.60 (d, 1H), 7.97 (d, 1H), 8.46 (d, 1H).
MS (ESI+): 589 [M+H]+

Example 86

4-(5-Chloro-2-{(E)-3-[4-(4-fluoro-benzyl)-2-methyl-piperazin-1-yl]-3-oxo-propenyl}-benzoylamino)-piperidine-1-carboxylic acid ethyl ester

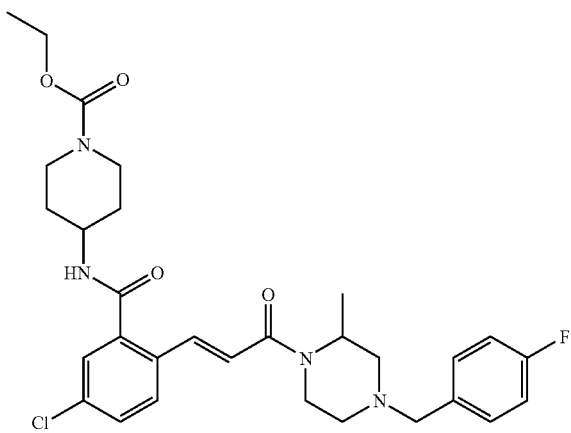

1H-NMR (400 MHz, DMSO-d6): 1.18 (t, 3H), 1.24 (bs, 3H), 1.30-1.44 (m, 2H), 1.79-2.03 (m, 4H), 2.66 (d, 1H), 2.82 (d, 1H), 2.88-3.06 (m, 2H), 3.42 and 3.52 (AB-Sys., 2H), 3.85-3.98 (m, 3H), 4.04 (q, 2H), 4.06-4.73 (m, 2H), 7.18 (t, 2H), 7.21 (d, 1H), 7.37 (dd, 2H), 7.44 (d, 1H), 7.54 (dd, 1H), 7.62 (d, 1H), 7.98 (d, 1H), 8.51 (d, 1H).
MS (ESI+): 571 [M+H]+, 593 [M+Na]+

Example 87

(2S,4R)-1-(5-Chloro-2-{(E)-3-[(R)-4-(4-fluoro-benzyl)-2-methyl-piperazin-1-yl]-3-oxo-propenyl}-benzoyl)-4-hydroxy-pyrrolidine-2-carboxylic acid methyl ester

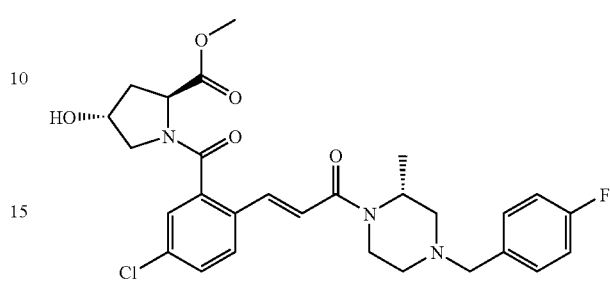

1H-NMR (400 MHz, DMSO-d6):1.18-1.32 (m, 3H), 1.88-2.28 (m, 4H), 2.62-2.69 (m, 1H), 2.82 (d, 1H), 3.02 (d, 1H), 3.30-3.56 (m, 4H), 3.72 (s, 3H), 3.98-4.66 (m, 3H), 5.16 (d, 1H), 7.15 (t, 2H), 7.22 (d, 1H), 7.31 (d, 1H), 7.35 (dd, 2H), 7.46 (d, 1H), 7.54 (dd, 1H), 8.02 (d, 1H).
MS (ESI+): 544 [M+H]+

Example 88

(E)-3-[4-Chloro-2-((R)-3-dimethylamino-pyrrolidine-1-carbonyl)-phenyl]-1-[(R)-4-(4-fluoro-benzyl)-2-methyl-piperazin-1-yl]-propenone

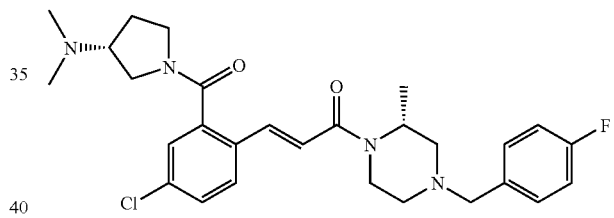

1H-NMR (400 MHz, DMSO-d6): 1.24 (br s, 3H), 1.60-1.80 (m, 1H), 1.84-2.13 (m, 3H), 2.04 (s, 3H), 2.16 (s, 3H), 2.62-2.93 (m, 4H), 3.05-3.22 (m, 2H), 3.35-3.56 (m, 3H), 3.62-3.80 (m, 1H), 3.98-4.67 (m, 2H), 7.15 (t, 2H), 7.20 (dd, 1H), 7.31 (d, 1H), 7.35 (dd, 2H), 7.43 (s, 1H), 7.50 (d, 1H), 7.97 (d, 1H).
MS (ESI+): 513 [M+H]+

Example 89

(E)-3-[4-Chloro-2-((S)-3-dimethylamino-pyrrolidine-1-carbonyl)-phenyl]-1-[(R)-4-(4-fluoro-benzyl)-2-methyl-piperazin-1-yl]-propenone

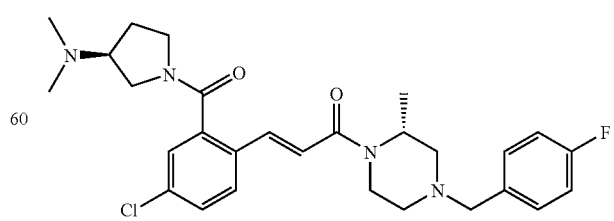

1H-NMR (400 MHz, DMSO-d6): 1.24 (br s, 3H), 1.62-1.78 (m, 1H), 1.84-2.13 (m, 3H), 2.04 (s, 3H), 2.17 (s, 3H), 2.62-2.91 (m, 4H), 3.05-3.22 (m, 2H), 3.38-3.55 (m, 3H), 3.62-3.80 (m, 1H), 3.98-4.67 (m, 2H), 7.15 (t, 2H), 7.20 (dd, 1H), 7.29-7.48 (m, 3H), 7.43 (s, 1H), 7.50 (d, 1H), 7.97 (d, 1H).

MS (ESI+): 513 [M+H]+

Example 90

(E)-3-[2-(4-Acetyl-piperazine-1-carbonyl)-4-chloro-phenyl]-1-[(R)-4-(4-fluoro-benzyl)-2-methyl-piper-azin-1-yl]-propenone

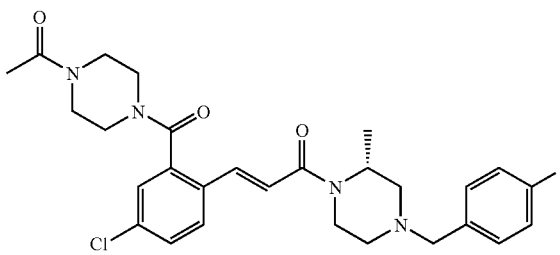

1H-NMR (400 MHz, DMSO-$d_6$, 120° C.); 1.27 (d, 3H), 2.00 (s, 3H), 2.03 (dd, 1H), 2.17 (dd, 1H), 2.68 (d, 1H), 2.74-2.85 (m, 1H), 3.10-3.22 (m, 1H), 3.30-3.64 (m, 8H), 4.04-4.11 (m, 2H), 4.42-4.51 (m, 1H), 7.04 (d, 1H), 7.08 (t, 2H), 7.30-7.38 (m, 4H), 7.46 (d, 1H), 7.83 (d, 1H).

MS (ESI+): 527 [M+H]+

Example 91

N-(5-Chloro-2-{(E)-3-[4-(4-chloro-benzyl)-2-methyl-piperazin-1-yl]-3-oxo-propenyl}-phenyl)-acetamide

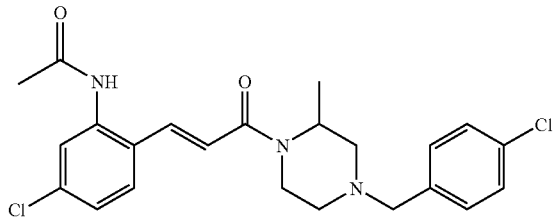

a) 1-(4-Chloro-benzyl)-3-methyl-piperazine 3.49 g (17.0 mmol) 4-Chlorobenzylbromide was added dropwise to a mixture of 2.04 g (20.4 mmol) 2-Methyl piperazine and 2.40 ml (17 mmol) triethylamine in 60 ml DMF at room temperature. The reaction mixture was stirred for 16 hours at room temperature, the poured onto aq. sodium bicarbonate solution and extracted with ethylacetate. Purification of the crude product by flash chromatography gave 2.26 g (10.1 mmol, 59%) of 1-(4-chloro-benzyl)-3-methyl-piperazine as colorless oil.

1H-NMR (400 MHz, DMSO-d6): 0.91 (d, 3H), 1.56 (t, 1H), 1.90 (td, 1H), 1.91-2.03 (m, 1H), 2.56-2.74, m, 4H), 2.79 (dt, 1H), 3.40 and 3.44 (AB-Sys., 2H), 7.33 (d, 2H), 7.40 (d, 2H).

MS (ESI+): 225 [M+H]+ b) N-(5-Chloro-2-{(E)-3-[4-(4-chloro-benzyl)-2-methyl-piperazin-1-yl]-3-oxo-propenyl}-phenyl)-acetamide 0.10 g (0.42 mmol) (E)-3-(2-Acetylamino-4-chloro-phenyl)-acrylic acid, 85 mg 1-(4-Chloro-benzyl)-3-methyl-piperazine (0.38 mmol), 87 mg EDCI (0.45 mmol) and 61 mg HOBt (0.45 mmol) were dissolved in 5 ml DMF. The reaction mixture was stirred overnight, then partitioned between ethylacetate and aq. sodiumbicarbonate solution. The organic phase was further washed with water and brine. Removal of the solvent gave a crude product which was further purified by prep. HPLC (Waters XT column, acetonitrile/water). 0.11 mg (0.24 mmol, 63%) of the title compound was obtained as an pale yellow solid.

1H-NMR (400 MHz, DMSO-d6): 1.25 (d, 3H), 1.83-2.15 (m, 2H), 2.66 (d, 1H), 2.82 (d, 1H), 2.88-3.08 (m, 1H), 3.43 and 3.54 (AB-Sys., 2H), 4.04-4.72 (m, 2H), 7.18 (d, 1H), 7.28 (dd, 1H), 7.33-7.43 (m, 4H), 7.58 (d, 1H), 7.63 (d, 1H), 7.89 (d, 1H), 9.88 (s, 1H).

MS (ESI+): 446 [M+H]+

Analogously the following compounds were prepared:

Example 92

N-(5-Chloro-2-{(E)-3-[4-(3-fluoro-benzyl)-2-methyl-piperazin-1-yl]-3-oxo-propenyl}-phenyl)-acetamide a) 1-(3-Fluoro-benzyl)-3-methyl-piperazine 1H-NMR (400 MHz, DMSO-d6): 0.92 (d, 3H), 1.60 (t, 1H), 1.93 (td, 1H), 2.55-2.76 (m, 5H), 2.81 (dt, 1H), 3.45 (s, 2H), 7.04-7.17 (m, 3H), 7.38 (q, 1H).

MS (ESI+): 209 [M+H]+ b) N-(5-Chloro-2-{(E)-3-[4-(3-fluoro-benzyl)-2-methyl-piperazin-1-yl]-3-oxo-propenyl}-phenyl)-acetamide 1H-NMR (400 MHz, DMSO-d6): 1.27 (br s, 3H), 1.88-2.22 (m, 2H), 2.08 (s, 3H), 2.67 (d, 1H), 2.84 (d, 1H), 2.90-3.12 (m, 1H), 3.46 and 3.57 (AB-Sys., 2H), 4.95-4.70 (m, 2H), 7.09 (td, 1H), 7.13-7.21 (, 3H), 7.28 (dd, 1H), 7.34-7.43 (m, 1H), 7.57 (d, 1H), 7.62 (d, 1H), 7.89 (d, 1H), 9.88 (s, 1H).

MS (ESI+): 430 [M+H]+

Example 93

N-(5-Chloro-2-{(E)-3-[4-(2,4difluoro-benzyl)-2-methyl-piperazin-1-y]-3-oxo-propenyl}-phenyl)-acetamide

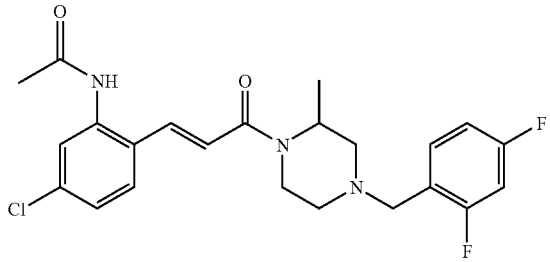

a) 1-(2,4-Difluoro-benzyl)-3-methyl-piperazine

1H-NMR (400 MHz, DMSO-d6): 0.91 (d, 3H), 1.59 (t, 1H), 1.82-1.97 (m, 2H), 2.56-2.70 (m, 4H), 2.78 (dt, 1H), 3.46 (s, 2H), 7.07 (td, 1H), 7.19 (td, 1H), 7.44 (q, 1H).
MS (ESI+): 227 [M+H]+ b) N-(5 Chloro-2-{(E)-3-[4-(2,4difluoro-benzyl)-2-methyl-piperazin-1-yl]-3-oxo-propenyl}-phenyl)-acetamide 1H-NMR (400 MHz, DMSO-d6): 1.23 (br s, 3H), 1.88-2.22 (m, 2H), 2.08 (s, 3H), 2.68 (d, 1H), 2.82 (d 1H), 2.88-3.40 (m, 1H), 3.53 (s, 2H), 4.04-4.70 (m, 2H), 7.08 (td, 1H), 7.17 (d, 1H), 7.22 (dd, 1H), 7.27 (d, 1H), 7.49 (q, 1H), 7.57 (s, 1H), 7.61 (d, 1H), 7.89 (d, 1H), 9.88 (s, 1H).
MS (ESI+): 448 [M+H]+

Example 94

N-(5Chloro-2-{(E)-3-[4-(4-cyano-benzyl)-2-methyl-piperazin-1-yl]-3-oxo-propenyl}-phenyl)-acetamide

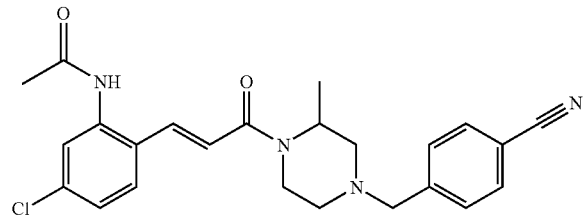

a) 4(3-Methyl-piperazin-1-ylmethyl)-benzonitrile

1H-NMR (400 MHz, DMSO-d6): 0.91 (d, 3H), 1.60 (t, 1H), 1.87-1.97 (m, 2H), 2.57-2.74 (m, 4H), 2.80 (dt, 1H), 3.54 (s, 2H), 7.52 (d, 2H), 7.80 (d, 2H).
MS (ESI+): 216 [M+H]+ b) N-(5-Chloro-2-{(E)-3-[4-(4-cyano-benzyl)-2-methyl-piperazin-1-yl]-3-oxo-propenyl}-phenyl)-acetamide 1H-NMR (400 MHz, DMSO-d6): 1.28 (br d, 3H), 1.89-2.24 (m, 2H), 2.08 (s, 3H), 2.65 (d, 1H), 2.83 (d, 1H), 2.92-3.43 (m, 1H), 3.54 and 3.64 (AB-Sys., 2H), 4.05-4.70 (m, 1H), 7.18 (d, 1H), 7.27 (dd, 1H), 7.53-7.59 (m, 3H), 7.3 (d, 1H), 7.83 (d, 2H), 7.89 (d, 1H), 9.88 (s, 1H).
MS (ESI+): 437 [M+H]+

Example 95

N-(5-Chloro-2-{(E)-3-[(R)-4-(4-fluoro-benzyl)-2-methyl-piperazin-1-yl]-3-oxo-prop-enyl}-4-methoxy-phenyl)-acetamide

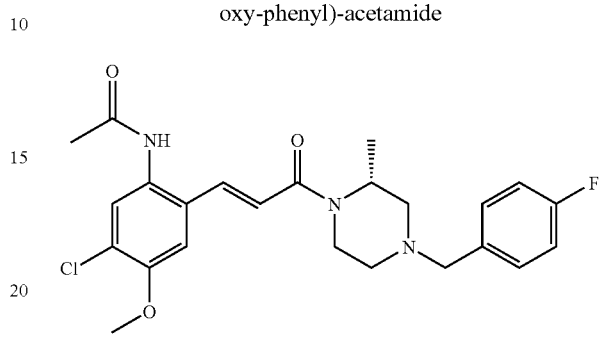

a) 2-Bromo-5-chloro-4-methoxy-aniline 5.0 g (32 mmol) 3-chloro-p-anisidine was dissolved in 50 ml THF. At r.t. 5.65 g (32 mmol) N-bromo succinimide was added. The mixture was stirred for 16 h at r.t., taken up in 400 ml ethyl acetate, washed with $Na_2S_2O_3$, $NaHCO_3$ and brine. After removal of the solvent 6.36 g (85%) of the desired brominated product were obtained.

1H-NMR (400 MHZ, DMSO-d6): 3.72 (s, 3H), 5.05 (s, 2H), 6.88 (s, 1H), 7.14 (s, 1H).
MS (EI) m/z: 235 [M]+ b) N-(2-Bromo-5-chloro-4-methoxy-phenyl)-acetamide 4.40 g (18.6 mmol) 2-Bromo-5-chloro-4-methoxy-aniline and 3.1 ml (22.0 mmol) triethylamine were dissolved in 50 ml THF. 1.42 ml (20.0 mmol) acetylchloride were added dropwise at room temperature. The reaction mixture was stirred at room temperature for additional 2 hours, saturated $NaHCO_3$ solution was added and the mixture was extracted with ethyl acetate. Removal of the solvent and crystallisation with ether gave 3.6 g (12.9 mmol, 69%) of the title compound.

1H-NMR (400 MHZ, DMSO-d6): 2.04 (s, 3H), 3.87 (s, 3H), 7.40 (s, 1H), 7.59 (s, 1H), 9.47 (br s, 1H).
MS (EI) m/z: 277 [M]+ c) N-(5-Chloro-2-{(E)-3-[(R)-4-(4-fluoro-benzyl)-2-methyl-piperazin-1-yl]-3-oxo-prop-enyl}-4-methoxy-phenyl)-acetamide Pd-catalysed coupling as described in example 67 gave 26 mg (0.057 mmol, 10%) of the title compound.

1H-NMR (400 MHZ, DMSO-d6): 1.24 (br s, 3H), 1.87-2.21 (m, 2H), 2.04 (s, 3H), 2.68 (d, 1H), 2.84 (d, 1H), 2.90-3.08 (m, 1H), 3.38-3.58 (m, 2H), 3.92 (s, 3H), 4.07-4.30 (m, 1H), 4.43-44.68 (m, 1H), 7.16 (t, 2H), 7.20 (d, 1H), 7.36 (dd, 2H), 7.43 (s, 1H), 7.47 (s, 1H), 7.55 (d, 1H), 9.69 (s, 1H).
MS (ESI+) m/z: 460 [M+H]+

In similar manner the following examples were prepared:

Example 96

N-(5-Chloro-4-fluoro-2-{(E)-3-[(R)-4-(4-fluoro-benzyl)-2-methyl-piperazin-1-yl]-3-oxo-propenyl}-phenyl)-acetamide

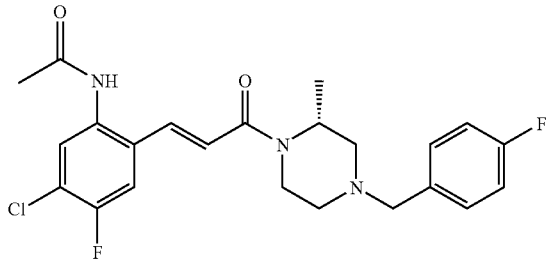

a) 2-Bromo-5-chloro-4-fluoro-aniline

1H-NMR (400 MHZ, DMSO-d6): 5.42 (s, 2H), 6.90 (d, 1H), 7.49 (d, 1H).
MS (EI) m/z: 223 [M]+ b) N-(2-Bromo-5-chloro-4-fluoro-phenyl)-acetamide

1H-NMR (400 MHZ, DMSO-d6): 2.07 (s, 3H), 7.80 (d, 1H), 7.88 (d, 1H), 9.60 (s, 1H).
MS (ESI−) m/z: 264 [M−H]− c) N-(5-Chloro-4-fluoro-2-{(E)-3-[(R)-4-(4-fluoro-benzyl)-2-methyl-piperazin-1-yl]-3-oxo-propenyl}-phenyl)-acetamide 1H-NMR (400 MHZ, DMSO-d6): 1.25 (d, 3H), 1.84-2.18 (m, 2H), 2.08 (s, 3H), 2.66 (d, 1H), 2.82 (d, 1H), 2.88-3.04 (m, 1H), 3.36-3.58 (m, 2H), 4.09-4.30 (m, 1H), 4.45-4.69 (m, 1H), 7.15 (t, 2H), 7.26 (d, 1H), 7.35 (dd, 2H), 7.54 (d, 1H), 7.62 (d, 1H), 8.00 (d, 1H), 9.86 (s, 1H).
MS (ESI+) m/z: 448 [M+H]+, 470 [M+Na]+

Example 97

(5-Chloro-2-{(E)-3-[(R)-4-(4-fluoro-benzyl)-2-methyl-piperazin-1-yl]-3-oxo-propenyl}-4-methoxy-phenyl)-urea

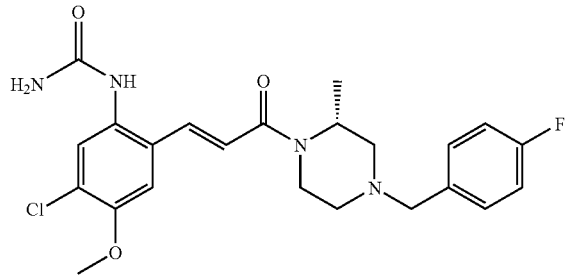

a) (2-Bromo-5-chloro-4-methoxy-phenyl)-urea

To a solution of 2.0 g (8.5 mmol) 2-bromo-5-chloro-4-methoxy aniline in 20 ml acetic acid and 20 ml water was added in small portions 1.37 g (17 mmol) potassium cyanate. The mixture was stirred at r.t. for 2 hours, neutralized with 2N NaOH and the product was extracted into ethyl acetate. Removal of the solvent and crystallization with ether gave 0.69 g (29%) of the desired urea.

1H-NMR (400 MHZ, DMSO-d6): 3.81 (s, 3H), 6.32 (s, 2H), 7.32 (s, 1H), 7.79 (s, 1H), 8.03 (s, 1H).
MS (EI) m/z: 278 [M]+ b) (5-Chloro-2-{(E)-3-[(R)-4-(4-fluoro-benzyl)-2-methyl-piperazin-1-yl]-3-oxo-propenyl}-4-methoxy-phenyl)-urea 1H-NMR (400 MHZ, DMSO-d6): 1.26 (d, 3H), 1.85-2.20 (m, 2H), 2.68 (d, 1H), 2.83 (d, 1H), 2.88-3.05 (m, 1H), 3.34-3.59 (m, 2H), 4.08-4.31 (m, 1H), 4.42-4.69 (m, 1H), 6.02 (s, 2H), 7.15 (t, 2H), 7.17 (d, 1H), 7.35 (dd, 2H), 7.37 (s, 1H), 7.61 (d, 1H), 7.70 (s, 1H), 8.14 (s, 1H).
MS (ESI+) m/z: 461 [M+H]+

Example 98

N-(5-Chloro-4-fluoro-2-{(E)-3-[(R)-4-(4-fluoro-benzyl)-2-methyl-piperazin-1-yl]-3-oxo-propenyl}-phenyl)-methanesulfonamide

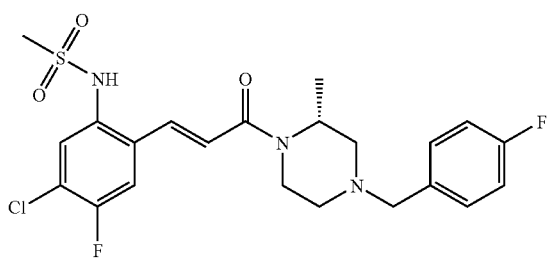

a) N-(2-Bromo-5-chloro-4-fluoro-phenyl)-methane-sulfonamide

1H-NMR (400 MHZ, DMSO-d6): 2.98 (s, 3H), 7.57 (d, 1H), 7.81 (d, 1H), 9.59 (s, 1H).
MS (EI) m/z: 301 [M]+ b) N-(5Chloro-4-fluoro-2-{(E)-3-[(R)-4-(4-fluoro-benzyl)-2-methyl-piperazin-1-yl]-3-oxo-propenyl}-phenyl)-methanesulfonamide 1H-NMR (400 MHZ, DMSO-d6): 1.25 (br s, 3H), 1.83-2.20 (m, 2H), 2.66 (d, 1H), 2.82 (d, 1H), 3.00 (s, 3H), 3.36-3.58 (m, 2H), 4.10-4.29 (m, 1H), 4.45-4.68 (m, 1H), 7.15 (t, 2H), 7.27 (d, 1H), 7.35 (dd, 2H), 7.51 (d, 1H), 7.74 (d, 1H), 8.08 (d, 1H), 9.66 (br s, 1H).
MS (ESI+) m/z: 484 [M+H]+

Example 99

(5-Chloro-4-fluoro-2-{(E)-3-[(R)(4-fluoro-benzyl)-2-methyl-piperazin-1-yl]-3-oxo-propenyl}-phenyl)-urea

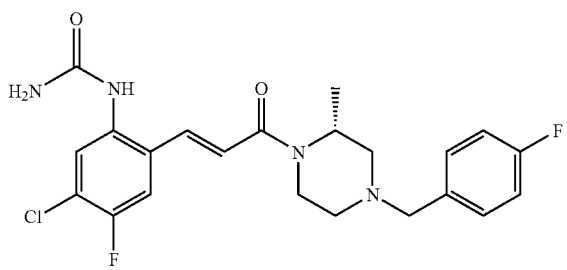

a) (2-Bromo-5-chloro-4-fluoro-phenyl)-urea

1H-NMR (400 MHZ, DMSO-d6): 6.49 (s, 2H), 7.77 (d, 1H), 7.96 (s, 1H), 8.23 (d, 1H).
MS (EI) m/z: 266 [M]+ b) (5-Chloro-4-fluoro-2-{(E)-3-[(R)-4-(4-fluoro-benzyl)-2-methyl-piperazin-1-yl]-3-oxo-propenyl}-phenyl)-urea 1H-NMR (400 MHZ, DMSO-d6): 1.26 (d, 3H), 1.85-2.18 (m, 2H), 2.66 (d, 1H), 2.72 (d, 1H), 2.89-3.03 (m, 1H), 3.33-3.60 (m, 2H), 4.07-4.32 (m, 1H), 4.44-4.68 (m, 1H), 6.17 (s, 2H), 7.15 (t, 2H), 7.21 (d, 1H), 7.34 (dd, 2H), 7.59 (d, 1H), 7.88 (d, 1H), 7.94 (d, 1H), 8.34 (s, 1H).
MS (ESI+) m/z: 449 [M+H]+

Example 100

N-(5-Chloro-4-cyano-2-{(E)-3-[(R)-4-(4-fluoro-benzyl)-2-methyl-piperazin-1-yl]-3-oxo-propenyl}-phenyl)-acetamide

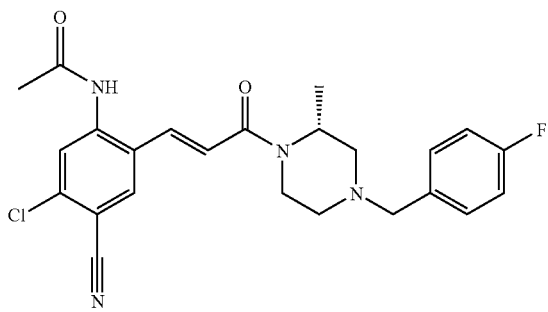

1H-NMR (400 MHZ, DMSO-d6): 1.26 (d, 3H), 1.85-2.08 (m, 2H), 2.14 (s, 3H), 2.60-2.72 (m, 1H), 2.84 (d, 1H), 2.89-3.04 (m, 1H), 3.32-3.60 (m, 2H), 4.10-4.32 (m, 1H), 4.45-4.69 (m, 1H), 7.15 (t, 2H), 7.32 (d, 1H), 7.35 (dd, 2H), 7.63 (d, 1H), 8.03 (s, 1H), 8.49 (s, 1H), 10.15 (s, 1H).
MS (ESI+) m/z: 455 [M+H]+

Example 101

N-(5-Chloro-2-{(E)-3-[(R)-4-(4-fluoro-benzyl)-2-methyl-piperazin-1-yl]-3-oxo-propenyl}-4-trifluoromethoxy-phenyl)-acetamide

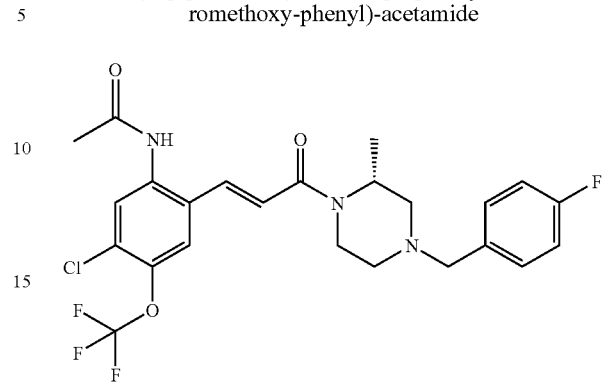

a) N-(2-Bromo-5-chloro-4-trifluoromethoxy-phenyl)-acetamide

1H-NMR (400 MHZ, DMSO-d6): 2.12 (s, 3H), 7.97 (s, 1H), 8.08 (s, 1H), 9.93 (s, 1H).
MS (ESI+) m/z: 332 [M+H]+ b) N-(5-Chloro-2-{(E)-3-[(R)-4-(4-fluoro-benzyl)-2-methyl-piperazin-1-yl]-3-oxo-propenyl}-4-trifluoromethoxy-phenyl)-acetamide 1H-NMR (400 MHZ, DMSO-d6): 1.25 (br d, 3H), 1.80-2.22 (m, 2H), 2.11 (s, 3H), 2.61-2.71 (m, 1H), 2.83 (br d, 1H), 2.88-3.60 (m, 3H), 4.05-4.32 (m, 1H), 4.42-4.68 (m, 1H), 7.14 (t, 2H), 7.28 (d, 1H), 7.34 (dd, 2H), 7.57 (d, 1H), 7.79 (s, 1H), 8.06 (s, 1H), 9.98 (s, 1H).
MS (ESI+) m/z: 514 [M+H]+

Example 102

(5-Chloro-2-{(E)-3[(R)-4-(4-fluoro-benzyl)-2-methyl-piperazin-1-yl]-3-oxo-propenyl}-4-trifluoromethoxy-phenyl)-urea

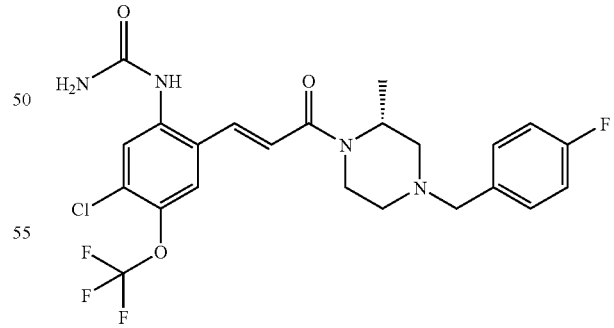

a) (2-Bromo-5-chloro-4-trifluoromethoxy-phenyl)-urea

1H-NMR (400 MHZ, DMSO-d6): 6.64 (s, 2H), 7.84 (s, 1H), 8.11 (s, 1H), 8.41 (s, 1H).
MS (EI) m/z: 332 [M]+ b) (5-Chloro-2-{(E)-3-[(R)-4-(4-fluoro-benzyl)-2-methyl-piperazin-1-yl]-3-oxo-propenyl}-4-trifluoromethoxy-phenyl)-urea 1H-NMR (400 MHZ, DMSO-d6): 1.26 (br d, 3H), 1.82-2.18 (m, 2H), 2.60-2.72 (m, 1H), 2.83 (d, 1H), 2.90-3.55 (m, 3H), 4.08-4.33 (m, 1H), 4.43-4.70 (m, 1H), 6.29 (s, 2H), 7.15 (t, 2H), 7.24 (d, 1H), 7.34 (dd, 2H), 7.59 (d, 1H), 7.92 (s, 1H), 8.15 (s, 1H), 8.48 (s, 1H).
MS (ESI+) m/z: 514 [M+H]+

Example 103

N-(5-Chloro-2-{(E)-3-[(R)-4-(4-fluoro-benzyl)-2-methyl-piperazin-1-yl]-3-oxo-propenyl}-4-isobutoxy-phenyl)-acetamide

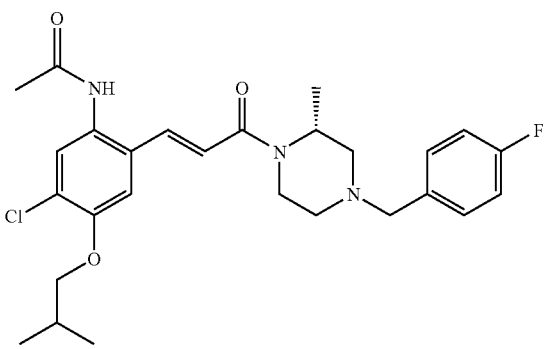

a) 2-Chloro-1-isobutoxy-4-nitro-benzene 5.00 g (28.5 mmol) 3-chloro-4-fluoro-nitrobenzene, 7.90 ml (75 mmol) isobutanol and 19.7 g (125 mmol) potassium carbonate in 200 ml DMF were heated at 70° C. for 48 hours. Addition of water, extraction with ethyl acetate and removal of solvent gave 5.9 g (25.7 mmol, 90%) of the crude isobutyl ether.
1H-NMR (400 MHZ, DMSO-d6): 1.01 (d, 6H), 2.04-2.15 (m, 1H), 3.99 (d, 2H), 7.33 (d, 1H), 8.18 (dd, 1H), 8.28 (d, 1H).
MS (EI) m/z: 229 [M]+ b) N-(2-Bromo-5-chloro-4-isobutoxy-phenyl)-acetamide 5.5 g (27.4 mmol) 2-Chloro-1-isobutoxy-4-nitro-benzene was dissolved in 150 ml THF and 30 ml water. After addition of 36.4 g (192 mmol) SnCl$_2$ the reaction mixture was refluxed for 15 minutes. NaHCO$_3$ solution was added, the mixture was extracted with ethyl acetate, dried and concentrated. The crude aniline (5.2 g, 95%) was used without further purification. 2.0 g (10.0 mmol) of the aniline were treated with 1.78 g (10.0 mmol) NBS in 60 ml THF for 20 hours at room temperature. Extraction with ethyl acetate, washings with Na$_2$S$_2$O$_3$ and Na$_2$CO$_3$, drying of the organic phase and removal of solvent yielded 2.75 g of the desired 2-Bromo-5-chloro-4-isobutoxy-aniline.
Treatment of 1.0 g (3.6 mmol) of the aniline with acetylchloride in THF using NEt$_3$ as base as described in example 95 gave 1.04 g (3.2 mmol, 90%) of the title compound.
1H-NMR (400 MHZ, DMSO-d6): 0.99 (d, 6H), 1.98-2.10 (m, 1H), 2.04 (s, 3H), 3.85 (d, 2H), 7.38 (s, 1H), 7.57 (s, 1H), 9.45 (s, 1H).
MS (ESI+) m/z: 320 [M+H]+ c) N-(5-Chloro-2-{(E)-3-[(R)-4-(4-fluoro-benzyl)-2-methyl-piperazin-1-yl]-3-oxo-propenyl}-4-isobutoxy-phenyl)-acetamide Pd-catalyzed Heck—Reaction as described in example 95 gave the title compound in 12% yield.
1H-NMR (400 MHZ, DMSO-d6): 1.04 (d, 6H), 1.25 (br s, 3H), 1.88-2.17 (m, 3H), 2.63-2.72 (m, 1H), 2.84 (br d, 1H), 3.18-3.60 (m, 3H), 3.92 (d, 2H), 4.03-4.28 (m, 1H), 4.38-4.70 (m, 1H), 7.10-7.20 (m, 3H), 7.36 (dd, 2H), 7.42 (s, 1H), 7.44 (s, 1H), 7.53 (d, 1H), 9.67 (s, 1H).
MS (ESI+) m/z: 502 [M+H]+

Example 104

N-(5-Chloro-2-{(E)-3-[(R)-4-(4-fluoro-benzyl)-2-methyl-piperazin-1-yl]-3-oxo-propenyl}-4-isopropoxy-phenyl)-acetamide

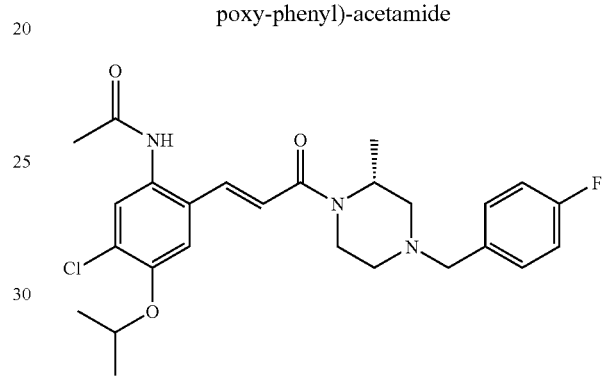

The title compound was prepared analogously to example 103.
1H-NMR (400 MHZ, DMSO-d6): 1.24 (br s, 3H), 1.28 (d, 3H), 1.29 (d, 3H), 1.85-2.18 (m, 2H), 2.03 (s, 3H), 2.67 (d, 1H), 2.83 (d, 1H), 2.88-3.25 (m, 1H), 3.43 and 3.53 (AB-Sys., 2H), 4.05-4.30 (m, 1H), 4.42-4.70 (m, 1H), 4.81 (sept., 1H), 7.15 (t, 2H), 7.17 (d, 1H), 7.36 (dd, 2H), 7.42 (s, 1H), 7.51 (s, 1H), 7.53 (d, 1H), 9.67 (s, 1H).
MS (ESI+) m/z: 488 [M+H]+

Example 105

3-(5Chloro-2-{(E)-3-[(R)-4-(4-fluoro-benzyl)-2-methyl-piperazin-1-yl]-3-oxo-propenyl}-4-methoxy-phenyl)-5,5-dimethyl-imidazolidine-2,4-dione

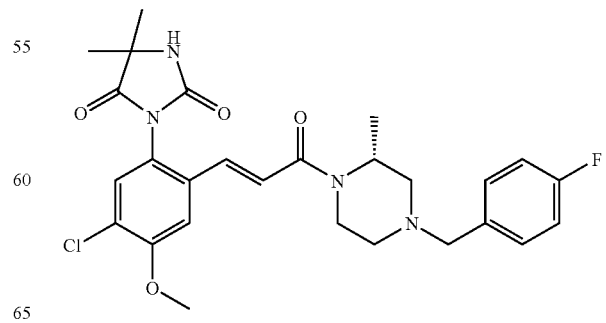

a) 3-(2-Bromo-5-chloro-4-methoxy-phenyl)-5,5-dimethyl-imidazolidine-2,4-dione To a solution of 0.60 g (2.54 mmol) 2-bromo-5-chloro-4-methoxy aniline and 0.88 ml (6.35 mmol) triethylamine in 20 ml chloroform was added 0.30 g (1.0 mmol) triphosgene at room temperature. The reaction mixture was stirred for 5 hours at r.t., then 0.47 g (3.0 mmol) 2-Amino-2-methyl-propionic acid methyl ester×HCl was added and the mixture was stirred at 60° C. overnight. The reaction was quenched with NaHCO$_3$ solution, extracted into ethyl acetate. The organic phase was dried, evaporated and the product was purified by RP-HPLC to give 0.41 g (47%) of the desired hydantoin.

1H-NMR (400 MHZ, DMSO-d6): 1.41 (s, 3H), 1.42 (s, 3H), 3.93 (s, 3H), 7.52 (s, 1H), 7.70 (s, 1H), 8.54 (s, 1H).

MS (ESI+) m/z: 347 [M+H]+, 369 [M+Na]+ b) 3-(5Chloro-2-{(E)-3-[(R)(4-fluoro-benzyl)-2-methyl-piperazin-1-yl]-3oxo-propenyl}-4-methoxy-phenyl)-5,5-dimethyl-imidazolidine-2,4-dione 1H-NMR (400 MHZ, DMSO-d6): 1.22 (br s, 3H), 1.41, s, 3H), 1.43 (s, 3H), 1.87-2.15 (m, 2H), 2.60-3.03 (m, 3H), 3.35-3.57 (m, 2H), 3.98 (s, 3H), 4.10-4.20 (m, 1H), 4.50-4.61 (m, 1H), 7.10-7.19 (m, 3H), 7.29 (d, 1H), 7.34 (dd, 2H), 7.55 (s, 1H), 7.61 (s, 1H), 8.58 (s, 1H).

MS (ESI+) m/z: 529 [M+H]+

Analogously the following compounds were synthesized:

Example 106

3-(5-Chloro-2-{(E)-3-[(R)-4-(4-fluoro-benzyl)-2-methyl-piperazin-1-yl]-3-oxo-propenyl}-4-methoxy-phenyl)-imidazolidine-2,4-dione

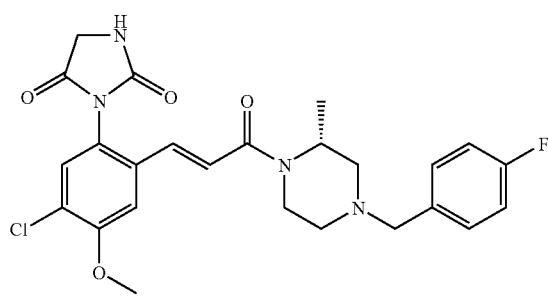

1H-NMR (400 MHZ, DMSO-d6, 100° C.): 1.27 (d, 3H), 2.02 (td, 1H), 2.17 (dd, 1H), 2.68 (d, 1H), 2.84 (br d, 1H), 3.18 (t, 1H), 3.46 and 3.53 (AB-Sys., 2H), 3.99 (s, 3H), 4.06-4.16 (m, 3H), 4.47-4.56 (m, 1H), 7.06-7.15 (m, 3H), 7.19 (d, 1H), 7.35 (dd, 2H), 7.40 (s, 1H), 7.54 (s, 1H), 8.00 (s, 1H).

MS (ESI+) m/z: 501 [M+H]+

Example 107

3-(5-Chloro-2-{(E)-3-[(R)-4-(4-fluoro-benzyl)-2-methyl-piperazin-1-yl]-3-oxo-propenyl}-4-methoxy-phenyl)-1,3-diaza-spiro[4.4]nonane-2,4-dione

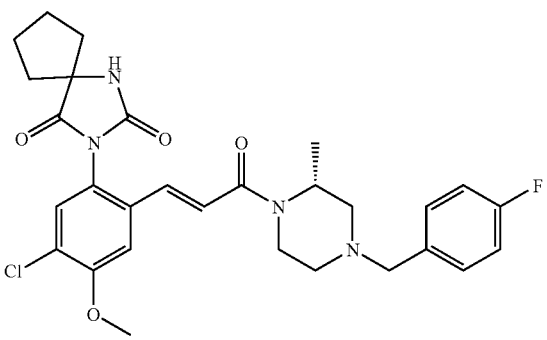

1H-NMR (400 MHZ, DMSO-d6): 1.24 (br s, 3H), 1.72-2.14 (m, 10H), 2.67 (d, 1H), 2.83 (d, 1H), 2.90-3.10 (m, 1H), 3.38-3.58 (m, 2H), 3.99 (s, 3H), 4.11-4.23 (m, 1H), 4.50-4.62 (m, 1H), 7.14 (d, 1H), 7.15 (t, 2H), 7.28 (d, 1H), 7.35 (dd, 2H), 7.53 (s, 1H), 7.61 (s, 1H), 8.76 (s, 1H).

MS (ESI+) m/z: 555 [M+H]+

Example 108

3-(5-Chloro-4-fluoro-2-{(E)-3-[(R)-4-(4-fluoro-benzyl)-2-methyl-piperazin-1-yl]-3-oxo-propenyl}-phenyl)-1,3-diaza-spiro[4.5]decane-2,4-dione

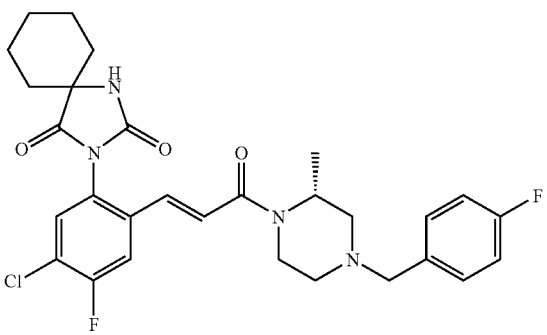

a) 3-(2-Bromo-5-chloro-4-fluoro-phenyl)-1,3-diaza-spiro[4.5]decane-2,4-dione MS (EI) m/z: 374 [M]+ b) 3-(5-Chloro-4-fluoro-2-{(E)-3-[(R)-4-(4-fluoro-benzyl)-2-methyl-piperazin-1-yl]-3-oxo-propenyl}-phenyl)-1,3-diaza-spiro[4.5]decane-2,4-dione 1H-NMR (400 MHZ, DMSO-d6): 1.15-1.38 (m, 5H), 1.52-1.85 (m, 10H), 2.60-2.70 (m, 1H), 2.82 (br d, 1H), 3.33-3.58 (m, 3H), 4.12-4.22 (m, 1H), 4.50-4.60 (m, 1H), 7.10 (br d, 1H), 7.15 (t, 2H), 7.31-7.40 (m, 3H), 7.78 (d, 1H), 8.21 (br d, 1H), 9.08 (s, 1H).

MS (ESI+) m/z: 557 [M+H]+

Example 109

3-(5-Chloro-4-fluoro-2-{(E)-3-[(R)-4-(4-fluoro-benzyl)-2-methyl-piperazin-1-yl]-3-oxo-propenyl}phenyl)-5,5-dimethyl-imidazolidine-2,4-dione

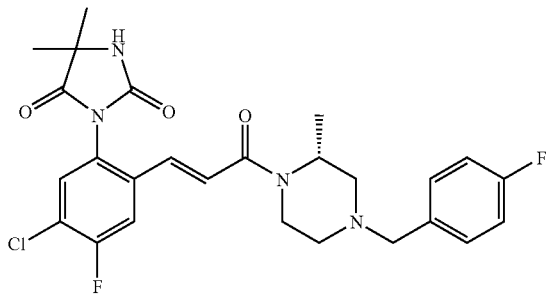

a) 3-(2-Bromo-5-chloro-4-fluoro-phenyl)-5,5-dimethyl-imidazolidine-2,4-dione

1H-NMR (400 MHZ, DMSO-d6): 1.41 (s, 3H), 1.43 (s, 3H), 7.96 (d, 1H), 8.03 (d, 1H), 8.62 (s, 1H).
MS (EI) m/z: 334 [M]+ b) 3-(5-Chloro-4-fluoro-2-{(E)-3-[(R)-4-(4-fluoro-benzyl)-2-methyl-piperazin-1-yl]-3-oxo-propenyl}-phenyl)-5,5-dimethyl-imidazolidine-2,4-dione 1H-NMR (400 MHZ, DMSO-d6): 1.16-1.32 (m, 3H), 1.43 (s, 3H), 1.44 (s, 3H), 1.82-2.18 (m, 2H), 2.57-2.70 (m, 1H), 2.81 (d, 1H), 2.86-3.57 (3H), 4.12-4.24 (m, 1H), 4.48-4.62 (m, 1H), 7.12 (br d, 1H), 7.15 (t, 2H), 7.31-7.41 (m, 3H), 7.79 (d, 1H), 8.22 (br d, 1H), 8.68 (s, 1H).
MS (ESI+) m/z: 517 [M+H]+

Example 110

Morpholine-4-carboxylic acid (5-chloro-2-{(E)-3-[(R)-4-(4-fluoro-benzyl)-2-methyl-piperazin-1-yl]-3-oxo-propenyl}-4-methoxy-phenyl)-amide

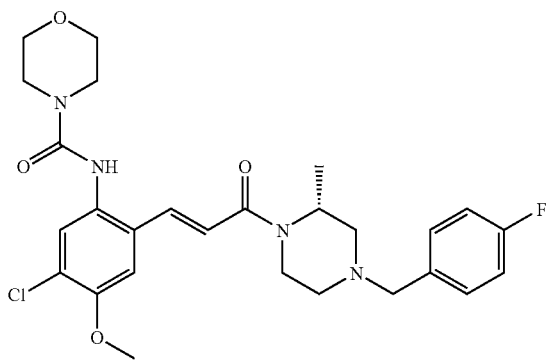

a) Morpholine-4-carboxylic acid (2-bromo-5-chloro-4-methoxy-phenyl)-amide

Prepared as described in example 105.
1H-NMR (400 MHZ, DMSO-d6): 3.40 (t, 4H), 3.60 (t, 4H), 7.38 (s, 1H), 7.47 (s, 1H), 8.19 (s, 1H)
MS (ESI+) m/z: 349 [M+H]+ .

b) Morpholine-4-carboxylic acid (5-chloro-2-{(E)-3-[(R)-4-(4-fluoro-benzyl)-2-methyl-piperazin-1-yl]-3-oxo-propenyl}4-methoxy-phenyl)-amide 1H-NMR (400 MHZ, DMSO-d6): 1.25 (br s, 3H), 1.88-2.17 (m, 2H), 2.67 (d, 1H), 2.84 (d, 1H), 3.32-3.56 (m, 7H), 3.61 (t, 4H), 3.92 (s, 3H), 4.08-4.25 (m, 1H), 4.50-4.65 (m, 1H), 7.08 (m, 3H), 7.26 (s, 1H), 7.35 (dd, 2H), 7.46 (s, 1H), 7.52 (d, 1H), 8.35 (s, 1H).
MS (ESI+) m/z: 531 [M+H]+

Example 111

Pyrrolidine-1-carboxylic acid (5-chloro-2-{(E)-3-[(R)-4-(4-fluoro-benzyl)-2-methyl-piperazin-1-yl]-3-oxo-propenyl}-4-methoxy-phenyl)-amide

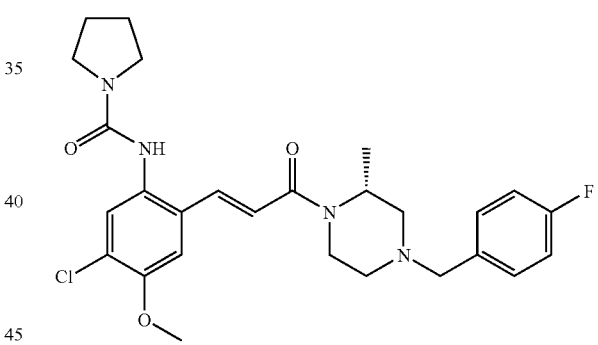

a) Pyrrolidine-1-carboxylic acid (2-bromo-5-chloro-4-methoxy-phenyl)-amide

1H-NMR (400 MHZ, DMSO-d6): 1.82-1.90 (m, 4H), 3.32-3.39 (m, 4H), 3.86 (s, 3H), 7.38 (s, 1H), 7.59 (s, 1H), 7.64 (s, 1H).
MS (ESI+) m/z: 333 [M+H]+ b) Pyrrolidine-1-carboxylic acid (5-chloro-2-{(E)-3-[(R)-4-(4-fluoro-benzyl)-2-methyl-piperazin-1-yl]-3-oxo-propenyl}-4-methoxy-phenyl)-amide 1H-NMR (400 MHZ, DMSO-d6): 1.25 (br s, 3H), 1.80-2.15 (m, 6H), 2.64-2.70 (m, 1H), 2.83 (d, 1H), 3.30-3.57 (m, 7H), 3.92 (s, 3H), 4.11-4.26 (m, 1H), 4.48-4.65 (m, 1H), 7.13 (d, 1H), 7.14 (t, 2H), 7.30 (s, 1H), 7.35 (dd, 2H), 7.44 (s, 1H), 7.57 (d, 1H), 7.96 (s, 1H).
MS (ESI+) m/z: 515 [M+H]+

Example 112

5-Chloro-2-{(E)-3-[(R)-4-(4-fluorobenzyl)-2-methyl-piperazin-1-yl]-3-oxo-propenyl}-4-methoxy-benzoic acid methyl ester

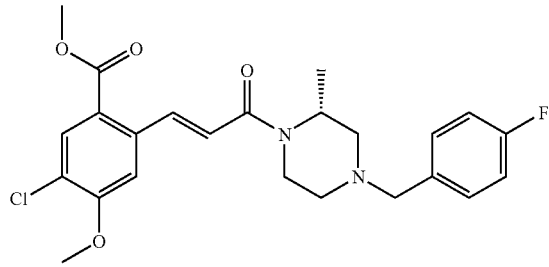

a) 5-Chloro-2-hydroxy-4-methoxy-benzoic acid methyl ester 5.00 g (27.4 mmol) 2-hydroxy-4-methoxybenzoic acid methyl ester and 4.03 g (30.2 mmol) N-chloro succinimde in 100 ml acetonitrile were refluxed for 16 hours. The reaction was quenched by addition of aq. NaHCO$_3$ solution and extracted with ethyl acetate. Evaporation of the solvent and crystallization with ether gave 4.68 g (78%) of the desired compound.

1H-NMR (400 MHZ, DMSO-d6): 3.86 (s, 3H), 3.89 (s, 3H), 6.72 (s, 1H), 7.71 (s, 1H), 10.68 (s, 1H).

MS (EI) m/z: 216 [M]+ b) 5-Chloro-2-{(E)-3-[(R)-4-(4-fluoro-benzyl)-2-methyl-piperazin-1-yl]-3-oxo-propenyl}-4-methoxy-benzoic acid methyl ester A mixture of 0.02 g (0.92 mmol) 5-Chloro-2-hydroxy-4-methoxy-benzoic acid methyl ester, 0.33 g (0.92 mmol) N-phenyl-bis-trifluoromethanesulfonamide and 0.38 g (2.7 mmol) K$^2$CO$_3$ in 30 ml THF were refluxed for 16 hours. Extraction with aq. NaHCO$_3$ solution and ethylacetate gave 0.26 g (80%) of the triflate which was used without further purification. Heck reaction using the triflate described above, 1-[(R)-4-(4-Fluoro-benzyl)-2-methyl-piperazin-1-yl]-propenone and as catalyst PdCl$_2$(PPh$_3$)$_2$ as desribed in example 67 yielded the desired product in 20% yield.

1H-NMR (400 MHZ, DMSO-d6): 1.25 (br s. 3H), 1.90-2.22 (m, 2H), 2.67 (d, 1H), 2.83 (d, 1H), 2.90-3.20 (m, 1H), 3.43 and 3.52 (AB-Sys., 2H), 3.81 (s, 3H), 4.02 (s, 3H), 4.05-4.68 (m, 2H), 7.14 (t, 2H), 7.15 (d, 1H), 7.36 (dd, 2H), 7.46 (s, 1H), 7.89 (s, 1H), 8.10 (d, 1H).

MS (ESI+) m/z: 461 [M+H]+

Example 113

(E)-3-[2-(4-Acetyl-piperazine-1-carbonyl)-4-chloro-5-methoxy-phenyl]-1-[(R)-4-(4-fluoro-benzyl)-2-methyl-piperazin-1-yl]-propenone

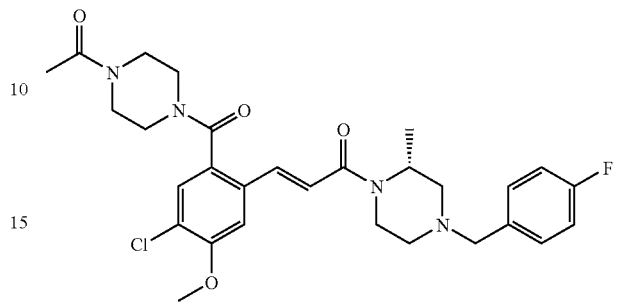

Prepared by saponification of the ester (example 112) and coupling with N-acetyl-piperazine under standard conditions (cf. example 80/82) in 82% yield.

1H-NMR (400 MHZ, DMSO-d6, 120° C.): 1.28 (d, 3H), 2.01 (s, 3H), 2.05 (dd, 1H), 2.19 (dd, 1H), 2.69 (dt, 1H), 2.74-2.93 (m, 8H), 3.19 (td, 1H), 3.35-3.57 (m, 3H), 3.99 (s, 3H), 4.10 (br d, 1H), 4.50 (brs, 1H), 7.08 (d, 1H), 7.10 (t, 2H), 7.30-7.38 (m, 4H), 7.48 (s, 1H).

MS (ESI+) m/z: 557 [M+H]+

Assays:

Preparation of membranes from CHO cells expressing hCCR1:

Membranes were prepared from CHO-K1 cells stably transfected with a plasmid coding for the full-length human CCR1.

Cells were grown in large cell culture dishes (30×30 cm) to a confluency of between 80 and 90% (~30×10$^7$ cells); in one experiment cells were grown to confluency without loss in receptor density of the membrane preparation.

All subsequent steps to prepare the membranes were performed at 4° C. or on ice. After discarding the medium, 30 ml ice-cold PBS containing 1 mM EDTA were added and the cells removed from the dishes using a scraper. After centrifugation at 10'000 rpm at 40° C. for 10 minutes in a SS34 rotor the supernatant was discarded and the cells resuspended in 10 mL buffer A (20 mM HEPES, 10 mM EDTA, pH 7.4) containing protease inhibitor cocktail (Roche, Complete). The cell suspension was homogenized using a Polytron homogenizer at 28,000 rpm at two intervals of 30 seconds each. In order to collect the membranes the homogenate was centrifuged at 18,000 rpm for 20 minutes at 4° C. using a SS34 rotor. The supernatant was discarded and the pellet resuspended by vortexing in 10 mL buffer B (20 mM HEPES, 0.1 mM EDTA, pH 7.4) containg protease inhibitors followed by a second round of homogenization (2×30 sec at 28,000 rpm, Polytron). After another centrifugation step (20 min at 4° C., 18,000 rpm) the pellet was resuspended in 5 mL buffer B by vortexing and subsequent homogenization (Polytron, 10 sec).

The protein concentration of the membrane preparation was determined using the BioRAD Protein Assay and human IgG as standard. The protein concentration of the membrane preparation was adjusted to 1-3 mg/mL and either aliquoted into Eppendorf tubes and quickfrozen in liquid nitrogen or, alternatively, the membrane preparation was added dropwise (by a peristaltic pump) into liquid nitrogen where it collects as frozen pellets (50-100 μL) at the bottom of the Dewar vessel.

PA-Binding Assay:

125 μg hCCR1 membranes were thawed and diluted into 340 μl ice-cold Buffer 2 (75 mM HEPES; pH 7.4, 300 mM NaCl, 6 mM CaCl$_2$, 15 mM MgCl$_2$, 1.5% BSA, Protease inhibitor cocktail (Complete Mini, Roche #61540601), 1 tablet in 10 mL). The final volume was adjusted to 1 mL with ice-cold Buffer 3 (20 mM HEPES, 0.1 mM EDTA, pH 7.4). The suspension was homogenized with three strokes and kept on ice.

The assay was performed in a final volume of 200 μl per well in OptiPlate-96 well plates. The components were added per well in the following order
- 50 μL—CCR1-membranes (2.5 μg/well) diluted as described above
- 50 μL—WGA-SPA beads (1 mg/well) in Buffer 1 (HBSS (1×) (Gibco#1 4025-050), 10 mM HEPES; pH 7.4, 0.1% BSA (Fluka #05480))
- inhibitor diluted in Buffer 1
- 50 μL—80 pM [125I]MIP-1α, diluted in Buffer 1 (to give a final concentration of 20 pM in the well)

After the addition of all components the plates were sealed with Top-Seal and incubated at RT for 120 minutes with constant shaking. Following incubation, the plates were centrifuged for 10 minutes at 3000 rpm and counted within 10 hours for 3 minutes per well with a TOP COUNT instrument (Packard).

Compounds of the invention demonstrated inhibition of binding of MIP1α to the human CCR1 receptor with IC50s ranging from 0.1 nM to 1000 nM.

Calcium Flux:

THP-1 cells are cultured in RPMI 1640 medium supplemented with 10% FCS. The cells are harvested, spun down and resuspended at about 2.106 cells per ml in HBSS 20 mM Hepes in absence of BSA. They are loaded in presence of 2 μM Fluo-4 for 30 min at 37° C. in a waterbath. After two washes with HBSS 20 mM Hepes, they are resuspended at 0.67×106 cells/ml in the same buffer supplemented with 0.1% BSA and 150 μl containing 105 cells are distributed per well in a black/clear bottom 96-well plate.

The test compounds are prepared from stock solutions at 20 mM in pure DMSO to reach final concentrations ranking 10-5M to 10-11M in HBSS 20 mM Hepes supplemented with 0.1% BSA The agonist rh-MIP-1α is prepared as an eight-fold concentrated solution in the same buffer. Usually a final concentration of 3 nM is used for the screening.

Twenty-five microliters of the compounds are mixed to the 150 μl cells and the plates are let standing for an additional half an hour at RT in the dark to allow cell sedimentation and interaction with the compounds. Then the plate are transferred to the Flexstation (Molecular Devices fluorometer) where the fluo-4 fluorescence of the cells is measured continuously for 2 min in total but after 16 sec. of the base line measurement, 25 μl of the MIP1α solution are injected to the cells at a rate of one (about 26 μl/sec) and a height of 160 μl with two mixing cycles using a volume of 25 μl at a height of 150 μl and a rate of one.

The calcium response expressed as the maximal fluorescence in relative fluorescence unit is plotted versus the compound concentration to determine IC$_{50}$ concentrations.

Compounds of the invention demonstrated inhibition of Ca$^{2+}$ mobilisation in response to MIP1α with IC$_{50}$s ranging from 0.1 nM to 1000 nM As indicated in the above assays Agents of the Invention potently block the effects of MIP1α, and CCR1. Accordingly, the Agents of the Invention have pharmaceutical utility as follows:

Agents of the Invention are useful for the prophylaxis and treatment of CCR1 or MIP1α mediated diseases or medical conditions. CCR1 and MIP1α play an important role in leukocyte trafficking, in particular in monocyte migration to inflammatory sites and thus the Agents of the Invention may be used to inhibit monocyte migration e.g. in the treatment of inflammatory conditions, allergies and allergic conditions, autoimmune diseases, graft rejection, cancers which involve leukocyte infiltration, stenosis or restenosis, atherosclerosis, rheumatoid arthritis and osteoarthritis.

Diseases or conditions which may be treated with the Agents of the Invention include: Inflammatory or allergic conditions, including respiratory allergic diseases such as asthma, allergic rhinitis, COPD, hypersensitivity lung diseases, hypersensitivity pneumonitis, interstitial lung disease (ILD), (e.g. idiopathic pulmonary fibrosis, or ILD associated with autoimmune diseases such as RA, SLE, etc.); anaphylaxis or hypersensitivity responses, drug allergies (e.g. to penicillins or cephalosporins), and insect sting allergies; inflammatory bowel diseases, such as Crohn's disease and ulcerative colitis; spondyloarthropathies, sclerodoma; psoriasis and inflammatory dermatoses such as dermatitis, eczema, atopic dermatitis, allergic contact dermatitis, uticaria; vasculitis;

Autoimmune diseases, in particular autoimmune diseases with an aetiology including an inflammatory component such as arthritis (for example rheumatoid arthritis, arthritis chronica progrediente, psoriatic arthritis and arthritis deformans) and rheumatic diseases, including inflammatory conditions and rheumatic diseases involving bone loss, inflammatory pain, hypersensitivity (including both airways hypersensitivity and dermal hypersensitivity) and allergies, Specific autoimmune diseases for which Agents of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), autoimmune thyroiditis, Behcet's disease, endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, and glomerulonephritis (with and without nephrotic syndrome, e.g. including idiopathic nephrotic syndrome or minimal change nephropathy);

graft rejection (e.g. in transplantation including heart, lung, combined heart-lung, liver, kidney, pancreatic, skin, or corneal transplants) including allograft rejection or xenograft rejection or graft-versus-host disease, and organ transplant associated arteriosclerosis; atherosclerosis;

cancer with leukocyte infiltration of the skin or organs;

stenosis or restenosis of the vasculature, particularly of the arteries, e.g. the coronary artery, including stenosis or restenosis which results from vascular intervention, as well as neointimal hyperplasia;

and other diseases or conditions involving inflammatory responses including reperfusion injury, hematologic malignancies, cytokine induced toxicity (e.g. septic shock or endotoxic shock), polymyositis, dermatomyositis, and granulomatous diseases including sarcoidosis.

The term "treatment" as used herein is to be understood as including both therapeutic and prophylactic modes of therapy e.g. in relation to the treatment of neoplasia, therapy to prevent the onset of clinically or preclinically evident neoplasia, or for the prevention of initiation of malignant cells or to arrest or reverse the progression of premalignant to malignant cells, as well as the prevention or inhibition of neoplasia growth or metastasis. In this context, the present invention is, in particular, to be understood as embracing the use of compounds of the present invention to inhibit or prevent development of skin cancer, e.g. squamus or basal cell carcinoma consequential to UV light exposure, e.g. resultant from chronic exposure to the sun.

Agents of the Invention are particularly useful for treating diseases of bone and cartilage metabolism including osteoarthritis, osteoporosis and other inflammatory arthritides, e.g. rheumatoid arthritis, and bone loss in general, including age—Related bone loss, and in particular periodontal disease.

The Agents of the Invention may also be used in ocular applications which include the treatment of ocular disorders, in particular of ocular inflammatory disorders, of ocular pain including pain associated with ocular surgery such as PRK or cataract surgery, of ocular allergy, of photophobia of various etiology, of elevated intraocular pressure (in glaucoma) by inhibiting the production of trabecular meshwork inducible glucocorticoid response (TIGR) protein, and of dry eye disease.

For the above indications, the appropriate dosage will, of course, vary depending upon, for example, the particular Agent of the Invention to be employed, the subject to be treated, the mode of administration and the nature and severity of the condition being treated. However, in prophylactic use, satisfactory results are generally indicated to be obtained at dosages from about 0.05 mg to about 10 mg per kilogram body weight. Agent of the Invention is conveniently administered orally, parenterally, intravenously, e.g. into the antecubital or other peripheral vein, intramuscularly, or subcutaneously. For example, treatment typically comprises administering the Agent of the Invention once daily up to 3 times a day.

Pharmaceutical compositions of the invention may be manufactured in conventional manner The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 1000 mg of Agent of the Invention per unit dosage.

In accordance with the foregoing the present invention also provides in a further series of embodiments:

A. A method of inhibiting Chemokine Receptor 1 (CCR-1) or of reducing inflammation in a subject (i.e., a mammal, especially a human) in need of such treatment which method comprises administering to said subject an effective amount of an Agent of the Invention, or a method of treating any of the above mentioned conditions, particularly a method of treating an inflammatory or autoimmune disease or condition, e.g. rheumatoid arthritis, or alleviating one or more symptoms of any of the above mentioned conditions.

B. An Agent of the Invention for use as a pharmaceutical, e.g. for use as an immunosuppressant or antiinflammatory agent or for use in the prevention, amelioration or treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

The invention claimed is:

1. A compound of formula I, or a pharmaceutically acceptable salt or ester thereof,

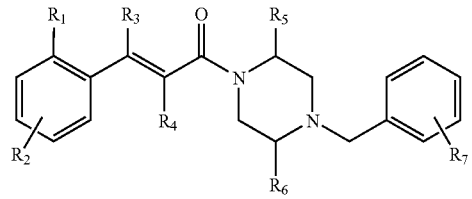

wherein $R_1$ is —X—$R_{10}$, —X—$(R_{10})_2$ or —$NR_{11}R_{12}$ wherein X is a linker having 1, 2, 3 or 4 atom or independently selected from N, C, or S, and wherein when said linker has 2 or more C atoms the linker may have 1 or more C=C or C≡C bonds;

wherein any of said atoms has up to 2 optional substituents selected from hydrogen, oxo, cyano, halo, nitro or optionally substituted oxy, lower alkyl, lower alkyenyl, lower alkynyl, carbonyl, sulfur amino; sulfinyl, sulfonyl;

$R_{10}$ is optionally substituted and is independently selected from the group consisting of hydrogen, cyano, halo, nitro or optionally substituted oxy, lower alkyl, lower alkyenyl, lower alkynyl, carbonyl, amino, cycloalkyl, heterocycloalkyl, aryl, heteroaryl;

$R_{11}$ and $R_{12}$ are optionally substituted and each represent a lower alkyl group connected together such that $R_1$ is an optionally substituted heterocycloalkyl or heteroaryl group;

$R_2$ and $R_7$ are optionally substituted and represent one or more substituents attached to the phenyl ring selected from the group consisting of hydrogen, cyano, halo, nitro or optionally substituted oxy, lower alkyl, lower alkyenyl, lower alkynyl, carbonyl, amino, sulfur, cycloalkyl, heterocycloalkyl, aryl, heteroaryl or a substituent forming a bicyclic ring system of which the phenyl ring to which it is attached forms part of the bicycle for example butadiene forming napthyl, or heterobutadiene forming quinolinyl, quinoxalinyl or isoquinolinyl;

$R_3$ and $R_4$ are optionally substituted and independently selected from the group consisting of hydrogen, cyano, halo, lower alkyl, lower alkyenyl, lower alkynyl, carbonyl, cycloalkyl, heterocycloalkyl, aryl;

$R_5$ and $R_6$ are optionally substituted and independently selected from the group consisting of hydrogen; cyano, lower alkyl, lower alkyenyl, lower alkynyl, carbonyl, cycloalkyl, heterocycloalkyl, aryl;

the optional substituents on X are one or more independently selected from the group consisting of hydrogen, oxo, cyano, halo, nitro or optionally substituted oxy, lower alkyl, lower alkyenyl, lower alkynyl, lower alkynyl, amino, carbonyl, sulfur, sulfinyl, sulfonyl;

wherein the optionally substituted substituents are optionally substituted once or more by a substituent independently selected from the group consisting of hydrogen, oxo, cyano, halo, nitro, oxy, lower alkyl, lower alkyenyl, lower alkynyl, amino, sulfur, cycloalkyl, heterocyloalkyl, aryl;

the optional substituents on $R_{10}$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl; wherein the optionally substituted substituents are optionally substituted once or more by a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

the optional substituents on $R_{11}$ and $R_{12}$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

the optional substituents on $R_2$ and $R_7$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

wherein the optionally substituted substituents are optionally substituted once or more by a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

the optional substituents on $R_3$ and $R_4$ are one or more substituents independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

wherein the optionally substituted substituents are optionally substituted once or more by a substituent independently selected from the group consisting of hydrogen, oxo, cyano, halo, nitro or optionally substituted oxy, lower alkyl, lower alkyenyl, lower alkynyl, carbonyl, amino, sulfur, cycloalkyl, heterocycloalkyl, aryl;

the optional substituents on $R_5$ and $R_6$ are one or more substituents independently selected from the group consisting of hydrogen, oxo, cyano, hydroxyl, optionally substituted oxy, lower alkyl, lower alkyenyl, lower alkynyl, carbonyl, cycloalkyl, heterocycloalkyl, aryl, imino, oxime;

wherein the optionally substituted substituents are optionally substituted once or more by a substituent independently selected from the group consisting of hydrogen, oxo, hydroxyl, cyano, halo, nitro or optionally substituted oxy, lower alkyl, lower alkyenyl, lower alkynyl, carbonyl, amino, sulfur, cycloalkyl, heterocycloalkyl, or aryl.

2. a compound of formula II, or a pharmaceutically acceptable salt or ester thereof,

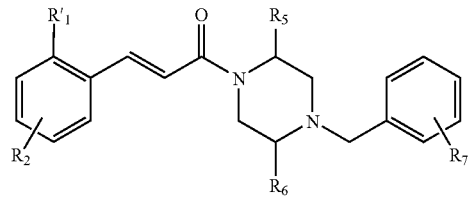

wherein
$R'_1$ is —X'—$R'_{10}$
wherein X' is a linker independently selected from optionally substituted —N—C—N—, —N—C—, —N—S—, —N—S—N—, —C—N—, —S—N—, —C≡C—, —C=C—, —N—C—S—, —C—, or
—S—N—S—$R'_{10}$ wherein $R_2$—$R_{10}$ are as herein before defined;
$R'_{10}$ is one or more substituents independently selected from the group consisting of hydrogen, halo, optionally substituted methyl, optionally substituted isopropyl, optionally substituted imidazolyl or thiazolyl 3-oxa-1-aza-spiro[4,4]nonan-2-one, hydroxy, optionally substituted pyrrolidinyl, morpholino, piperazinyl, formic acid methyl ester, [1,2,4]triazol, imidazolidinyl, tetrazolyl, —N(CH$_3$)—OCH$_3$ or methoxy, optionally substituted carbonyl, amino, heterocycloalkyl and aryl;
when $R'_1$ is —N—C—N—$R'_{10}$ the C atom is substituted by oxo, =N—C≡N or =C—NO$_2$;
when $R'_1$ is —N—C—N—$R'_{10}$, $R'_{10}$ is hydrogen;
when $R'_1$ is —N—C—N—$R'_{10}$, $R'_{10}$ is optionally substituted by hydrogen;
when $R'_1$ is —N—C—$R'_{10}$ or —C—N—$R'_{10}$ the C atom is substituted by oxo;
when $R'_1$ is —N—C—$R'_{10}$ or —C—N—$R'_{10}$, $R'_{10}$ is optionally substituted methyl, piperidinyl, imidazolidinyl, pyrrolidinyl, morpholino;
when $R'_1$ is —N—C—$R'_{10}$ or —C—N—$R'_{10}$, $R'_{10}$ is substituted by hydrogen, methyl, benzyl, acetyl, oxo, dimethylamino, isopropyl, hydroxy, formic acid ethyl ester;
when $R'_1$ is —N—S—$R'_{10}$ or
$R'_{10}$—S—N—S—$R'_{10}$ the S atom or atoms are substituted twice by oxo;
when $R'_1$ is —N—S—$R'_{10}$ or
$R'_{10}$—S—N—S—$R'_{10}$ $R'_{10}$ is optionally substituted methyl;
when $R'_1$ is —N—S—$R'_{10}$ or
$R'_{10}$—S—N—S—$R'_{10}$ $R'_{10}$ is optionally substituted by hydrogen;
when $R'_1$ is —N—S—N—$R'_{10}$ the S atom is substituted twice by oxo and the N atom is independently optionally substituted by methyl;
when $R'_1$ is —N—S—N—$R'_{10}$ $R'_{10}$ is hydrogen or optionally substituted methyl, imidazolyl, thiazolyl;

when R'₁ is —N—S—N—R'₁₀, R'₁₀ is optionally substituted by hydrogen, methyl, acetamidyl;
R'₁ is —NR"₁₁R"₁₂
wherein —NR"₁₁R"₁₂ collectively represents imidazolidinyl-2,4-dione, optionally substituted once or twice by a lower alkyl group.

3. A compound of formula IIa, or a pharmaceutically acceptable salt or ester thereof,

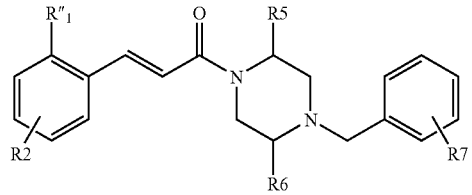

IIa wherein
N-(5-Chloro-2-[(E)-3-[(R)-4-(4-fluorobenzyl)-2-methylpiperazin-1-yl]-3-oxopropenyl]phenyl)-N,N-dimethylsulfamide,
N-(5-Chloro-2-[(E)-3-[(R)-4-(4-fluorobenzyl)-2-methylpiperazin-1yl]-3-oxopropenyl]phenyl)-methanesulfonamide,
1-Acetyl-piperidine-4-carboxylic acid (5-chloro-2-{(E)-3-[(R)4-(4-fluoro-benzyl)-2-methyl-piperazin-1-yl]-3-oxo-propenyl}-phenyl)-amide,
1-Methyl-1H-imidazole-4-sulfonic acid (5-Chloro-2-[(E)-3-[(R)-4-(4-fluoro-benzyl)-2-methyl-piperazin-1-yl]-3-oxo-propenyl]-phenyl)-amide,
N-(5-(5-Chloro-2-[(E)-3[(R)-4-(4-fluoro-benzyl)-2-methyl-piperazin-1-yl]-3-oxo-propenyl]-phenylsufamoyl)-thiazol-2yl]-acetamide,
2-Oxo-imidazolidine-1-carboxylic acid (5-Chloro-2[(E)-3-[(R)-4-(4-fluoro-benzyl)-7-methyl-piperazin-1-yl]-3oxo-propenyl]-phenyl)-amide,
N-(4-Chloro-2-[(E)-3-[4-(4-fluorobenzyl)-2-methylpiperazin-1-yl]-3-oxopropenyl]-phenyl)-methylthio-N'-cyano thiourea,
N-(4-Chloro-2[(E)-3-[4-(4-fluorobenzyl)-2-methylpiperazin-1-yl]-3-oxopropenyl]-phenyl)-sulfonylurea,
(5-Chloro-2-[(E)-3-[(2R,5S)-4-(4-fluorobenzyl)-2,5-dimethylpiperazin-1-yl]-3-oxopropenyl]-phenyl)-urea,
(5-Chloro-2-[(E)-3-[(2R,5S)-4-(4-fluorobenzyl)-2,5-dimethylpiperazin-1-yl]-3-oxopropenyl]-phenyl)-urea,
N-(5-Chloro-2-[(E)-3-[(2R,5S)-4-(4-fluorobenzyl)-2,5-dimethyl-piperazin-1-yl]-3-oxopropenyl]-phenyl)-acetamide,
N-(5-Chloro-2-[(E)-3-[(2S,5R)-4-(4-fluorobenzyl)-2,5-dimethyl-piperazin-1-yl]-3-oxopropenyl]-phenyl)-acetamide,
(5-Chloro-2-[(E)-3-[(2S,5R)-4-(4-fluorobenzyl)-2,5-dimethylpiperazin-1-yl]-3-oxopropenyl]-phenyl)-urea,
N-(5-Chloro-2-[(E)-3-[-4-(4-fluorobenzyl)-piperazin-1-yl]-3-oxopropenyl)-phenyl)-acetamide,
(5-Chloro-2-[(E)-3-[-4-(4-fluorobenzyl)-piperazin-1-yl]-3-oxopropenyl]-phenyl)-urea,
(E)-3-[4-Chloro-2-(4-hydroxy-1-methylpiperidin-4-yl-ethynyl)-phenyl]-1-[(R)-4-(4-fluorobenzyl)-2-methylpiperazin-1-yl]-propenone,
(E)-3-[4-Chloro-2-(4-hydroxy-1-methylpiperidin-4-yl-ethynyl)-phenyl]-1-[(S)-4-(4-fluorobenzyl)-2-methylpiperazin-1-yl]-propenone,
(E)-3-[4-Chloro-2-[(E)-2-(4-hydroxy-1-methylpiperidin-4-yl)-vinyl]-phenyl]-1-[(R)-4-(4-fluorobenzyl)-2methylpiperazin-1-yl]-propenone,
(E)-3-[4-Chloro-2-[(E)-2-(4hydroxy-1-methylpiperidin-4-yl)-vinyl]-phenyl]-1[(S)-4-(4-fluorobenzyl)-2-methylpiperazin-1-yl]-propenone,
4(5-Chloro-2-[(E)-3-[(R)-4-(4-fluorobenzyl)-2-methylpiperazin-1-yl]-3-oxopropenyl]-phenylethynyl)-4-hydroxypiperidine-1-carboxylic acid tert butyl ester,
(E)-3-[4-Chloro-2-(4-hydroxypiperidin-4-ylethynyl)-phenyl]-1-[(R)-4-(4-fluorobenzyl)-2-methylpiperazin-1yl]-propenone,
(E)-3-[2-(3-Amino-3-methylbut-1-ynyl-4-Chlorophenyl]-1-[(R)-4-(4fluorobenzyl)-2-methylpiperazin-1-yl]-propenone,
(E)-3-[4-Chloro-2-(3-dimethylaminoprop-1-ynyl)-phenyl]-1[4-(4-fluorobenzyl)-2-methylpiperazin-1-yl]-propenone,
(E)-3-[4-Chloro-2-(3-hydroxy-3-methylbut-1-ynyl)-phenyl]-1-[4-(4-fluorobenzyl)-2-methylpiperazin-1-yl]-propenone,
N-(3-[(E)-3[(R)-4-(4-Fluorobenzyl)-2-methylpiperazin-1-yl]-3-oxopropenyl]-naphthalen-2-yl)-acetamide,
(3-[(E)-3-[(R)-4-(4-fluorobenzyl)methylpiperazin-1yl]-3--oxopropenyl]-naphthalen-2-yl)-urea,
N-(3-[(E)-3-[(R)-4-(4-Fluorobenzyl)-2-methylpiperazin-1yl]-3-oxopropenyl]-naphthalen-2-yl)-N'-cyanoguanidine,
N-(4-Chloro-2-[(E)-3-[4-(4fluorobenzyl)-2-methylpiperazin-1yl]-3-oxopropenyl]phenyl)-N'-cyanoguanidine,
N-(4-Chloro-2-[(E)-3-[4-(4fluorobenzyl)-2-methylpiperazin-1yl]-3-oxopropenyl]-phenyl)-acetamide,
N-(6-[(E)-3-[(R)-4-(4-Fluorobenzyl)-2-methylpiperazin-1-yl]-3-oxopropenyl]-quinolin-7-yl)-acetamide,
(6-[(E)-3-[(R)-4-(4-Fluorobenzyl)-2-methylpiperazin-1-yl]-3-oxopropenyl]-quinolin-7-yl)-urea,
N-(7-[(E)-3-[(R)-4(4-Fluorobenzyl)-2-methylpiperazin-1-yl]-3-oxopropenyl)-quinolin-6-yl)-acetamide,
2-Dimethylamino-N-(7-[(E)-3-[(R)-4-(4-fluorobenzyl)-2-methylpiperazin-1-yl]-3-oxopropenyl]-quinolin-6-yl)-acetamide,
N-(7-[(E)-3-[(R)-4-(4-Fluorobenzyl)-2-methylpiperazin-1-yl]-3-oxopropenyl]-quinolin-6-yl)-methanesulfonamide,
N-(5-Chloro-2-[(E)-3-[(2R,5S)-4-(4-fluorobenzyl)-2,5-dimethylpiperazin-1-yl]-3-oxopropenyl]-phenyl)-cyanoguanidine,
N-(5-Chloro-2-[(E)-3-[(2R,5S)-4-(4 -fluorobenzyl)2,5-dimethylpiperazin-1-yl]-3-oxopropenyl ]-2-dimethylacetamide,
N-(5-Chloro-2-[(E)-3-[(2R,5S)-4-(4-fluorobenzyl)-2,5-dimethylpiperazin-1-yl]-3-oxopropenyl]-phenyl)-methanesulfonamide,
N-(5-Chloro-2-[(E)-3-[(2R,5S)-4-(4-fluorobenzyl)-2,5-dimethylpiperazin-1-yl]-3-oxopropenyl]-4-methoxyphenyl)-acetamide,
N-(5-Chloro-2-[(E)-3-[(3R,5S)-4-(4-fluorobenzyl)-2,5-dimethylpiperazin-1-yl]-3-oxopropenyl]-4-methoxyphenyl)-methanesulfonamide,
N-(5-Chloro-2-[(E)-3-(R)-4-(4-fluorobenzyl)-2-methylpiperazin-1-yl]-3-oxopropenyl)-4-(2-methoxyethoxy)-phenyl]-acetamide,
N-(5-Chloro-2-[(E)-3-(R)-4-(4-fluorobenzyl)-2-methylpiperazin-1-yl]-3-oxopropenyl]-4-morpholin-4-ylphenyl)-acetamide,
N-(5-Chloro-2-{(E)-3-[(R)-2-ethyl-4-(4-fluorobenzyl)-piperazin-1-yl]-3-oxo-propenyl}-phenyl)-acetamide,
(5-Chloro-2-{(E)-3-[(R)-2-ethyl-4-(4-fluoro-benzyl)-piperazin-1-yl]-3-oxo-propenyl}-phenyl)-urea, N-(5-Chloro-4-ethoxy-2-{(E)-3-[(R)-4-(4-fluorobenzyl)-2-methyl-piperazin-1-yl]-3-oxo-propenyl}-phenyl)-acetamide, (5-Chloro-4-ethoxy-2-{(E)-3-[(R)-4-(4-fluorobenzyl)-2-methyl-piperazin-1-yl]-3-oxo-propenyl}-phenyl)-urea, N-(5-Chloro-4-ethoxy-2-{(E)-3-[(R)-4-(4-fluorobenzyl)-2-methyl-piperazin-1-yl ]-3-oxo-propenyl}-phenyl)-methanesulfonamide, 5-Oxo-pyrrolidine-2-carboxylic acid (5-chloro-4-ethoxy-2-{(E)-3-[®-4-(4-fluorobenzyl)-2-methyl-piperazin-1-yl]-3-oxo-propenyl}-phenyl)-amide, N-(5-Chloro-2-{(E)-3-[(S)-4-(4-fluoro-benzyl)-2-hydroxymethyl-piperazin-1-yl]-3-oxo-propenyl}-4-methoxy-phenyl)-acetamide, N-(5-Chloro-2-{(E)-3-[(S)-4-(4-fluoro-benzyl)-2-hydroxymethyl-piperazin-1-yl]-3-oxo-propenyl}-4-methoxy-phenyl)-methanesulfonamide, (5-Chloro-2-{(E)-3-[(S)-4-(4fluoro-benzyl)-2-hydroxymethyl-piperazin-1-yl]-3-oxo-propenyl}-4-methoxy-phenyl)-urea, 5-Oxo-pyrrolidine-2-carboxylic acid (5-chloro-2-{(E)-3-[(S)-4-(4-fluoro-benzyl)-2-hydroxymethyl-piperazin-1-yl]-3-propenyl}-4-methoxy-phenyl)-amide, N-(5-chloro-2-{(E)-3-[(S)-4-(4-flouro-benzyl)-2-hydorxymethyl-piperazin-1-yl]-3-oxo-propenyl}-phenyl) acetamide, N-(2-{(E)-3-[(R)-2-Aminomethyl-4-(4-fluoro-benzyl)-piperazin-1-yl-3-oxo-propenyl}-5-chloro-phenyl)-acetamide, N-(5-Chloro-2-{(E)-3-[(S)-4-(4fluoro-benzyl)-2-((S)-1-hydroxy-ethyl)-piperazin-1-yl]-3-oxo-propenyl}-phenyl)-acetamide, N-(2-{(E)-3-[(S)-2-Acetyl-4-(4-fluoro-benzyl)-piperazin-1-yl]-3-oxo-propenyl}-5-chloro-phenyl)-acetanide, N-{5-Chloro-2-[(E)-3-((S)-4-(4-fluoro-benzyl)-2-{1-[hydroxyimino]-ethyl}-piperazin-1-yl)-3-oxo-propenyl}-acetamide, N-(2-{(E)-3-[(2S,5S)-2-Benzyloxymethyl-4-(4-fluoro-benzyl)-5-methyl-piperazin-1-yl]-3-oxo-propenyl}-5-chloro-phenyl)-acetamide, (S)-1-Acetyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide, (S)-1-Isopropyl-pyrrolidine-2-carboxylic acid (5-chloro-2-{(E)3-[(R)4-(4-fluoro-benzyl)-2-methyl-piperazin-1-yl]-3-oxo-propenyl}-4-methoxy-phenyl)-amide, (R)-1-isopropyl-pyrrolidine-2-carboxylic acid (5-chloro-2-{(E)-3-[(R)-4-(4-fluoro-benzyl)-2-methyl-piperazin-1-yl]-3-oxo-propenyl}-4-methoxy-phenyl)-amide, (2S, 4R)-1-Acetyl-4-hydroxy-pyrrolidine-2-carboxylic acid (5-chloro-2-{(E)-3[(R)-4-(4-fluoro-benzyl)-2-methyl-piperazin-1-yl]-3-oxo-propenyl}-4-methoxy-phenyl)-amide, (E)-3-(4-Chloro-2-morpholin-4-ylmethyl-phenyl)-1-[4-(4-fluoro-benzyl)-2-methyl-piperazin-1-yl]-propenone, 1-(5-Chloro-2-{(E)-3-[4-(4-fluoro-benzyl)-2-methyl-piperazin-1-yl]-3-oxo-propenyl}-benzyl)-pyrrolidin-2-one, (E)-3-(4-Chloro-2-[1,2,4]triazol-1-ylmethyl-phenyl)-1-[4-(4fuoro-benzyl)-2-methyl-piperazin-1-yl]propenone, (E)-3-[4-Chloro-2-(4-methyl-piperazin-1-ylmethyl)-phenyl]-1-[4-(4-fluoro-benzyl-2-methyl-piperzin-1-yl]-propenene, (E)-3-[2-(4-Acetyl-piperazin-1-ylmethyl)-4-chloro-phenyl]-1-[4-(4-fluoro-benzyl)-2-methyl-piperazin-1-yl]-propenone, (E)-3-[4-Chloro-2-(4-isopropyl-pioerazin-1-ylmethyl)-phenyl]-1-[(R)-4-(4fluoro-benzyl)-2-methyl-piperazin-1-yl]-propenone, 1-(5-Chloro-2-{(E)-3-[(R)-4-(4-fluoro-benzyl)-2-methyl-piperazin-1-yl]-3-oxo-propenyl}-benzyl)3-oxa-1-azaspiro[4,4]nonan-2one, 3-(5-Chloro-2-{(E)-3-[(R)-4-(4-fluoro-benzyl)-2-methyl-piperazin-1-yl]-3-oxo-propenyl}-benzyl)-5,5-dimethyl-imidazolidine-2,4dione, 3-(5-Chloro-2-{(E)-3-[(R)-4-(4-fluoro-benzyl)-2-methyl-piperazin-1-yl]-3oxo-propenyl}-benzyl)-1-methyl-imidazolidine-2,4-dione, (E)-3-[4-Chloro-2(5-methyl-tetrazol-1-ylmethyl)-phenyl]-1-[(R)-4-(4-fluoro-benzyl)-2-methyl-piperazin-1-yl]-propenone, 5-Chloro-2-{(E)-3-[(R)4-(4-fluoro-benzyl)-2-methyl-piperazin-1-yl]-3-oxo-propenyl}-N-methoxy-N-methyl-benzamide, 5-Chloro-2-{(E)-3-[4-(4fluoro-benzyl)-2-methyl-piperazin-1-yl]-3-oxo-propenyl}-benzoic acid methyl ester, (5-Chloro-2-{(E)-3-[4-(4-fluoro-benzyl)-2-methyl-piperazin-1-yl]-3-oxo-propenyl}-phenyl)-acetic acid methyl ester, (5-Chloro-2-{(E)-3-[4-(4-fluoro-benzyl)-2-methyl-piperazin-1-yl]-3-oxo-propenyl}-benzoic acid, (5-Chloro-2-{(E)-3-[(R)-4-(4-fluoro-benzyl)-2-methyl-piperazin-1-yl]-3-oxo-propenyl}-benzoic acid, (E)-3-[4-Chloro-2-(4-methyl-piperazin-1-carbonyl)-phenyl]-1-[4-(4-fluoro-benzyl)-2-methyl-piperazin-1-yl]-propenone, 5-Chloro-2-{(E)-3-[4-(4-fluoro-benzyl)-2-methyl-piperazin-1-yl]-3-oxo-propenyl}-N-isopropyl-benzamide, 5-Chloro-2-{(E)-3-[4-(4-fluoro-benzyl)-2-methyl-piperazin-1-yl]-3-oxo-propenyl}-N-(1-methyl-piperidin-4-yl)-benzamide, N-(1-Benzyl-piperidin-4-yl)-5-chloro-2-{(E)-3-[4-(4-fluoro-benzyl)-2-methyl-piperazin-1-yl]-3oxo-propenyl}-benzamide, 4-(5-Chloro-2-{(E)-3-[4-(4-fluoro-benzyl)-2-methyl-piperazin-1-yl]-3-oxo-propenyl}-benzoylamino)-piperidine-1-carboxylic acid ethyl ester, (2S,4R)-1-(5-Chloro-2-{(E)-3-[(R)-4-(4-fluoro-benzyl)-2-methyl-piperazin-1-yl]-3oxo-propenyl}-benzoyl)-4hydroxy-pyrrolidine-2-carboxylic acid methyl ester, (E)-3-[4-Chloro-2-((R)-3-dimethylamino-pyrrolidine-1-carbonyl)-phenyl]-1-[(R)-4-(4-fluoro-benzyl)-2methyl-piperazin-1-yl]-propenone, (E)-3-[4-Chloro-2-((S)-3-dimethylamino-pyrrolidine-1-carbonyl)-phenyl]-1-[(R)-4-(4-fluoro-benzyl)-2methyl-piperazin-1-yl]-propenone, (E)-3-[2-(4-Acetyl-piperazine-1-carbonyl)-4-Chloro-phenyl]-1-[(R)-4-(4-fluoro-benzyl)-2-methyl-piperazin-1-yl]-propenone, N-(5-Chloro-2-{(E)-3-[4-(4-chloro-benzyl)-2-methyl-piperazin-1-yl]-3-oxo-propenyl}-phenyl)-acetamide, N-(5-Chloro-2-{(E)-3-[4-(3-fluoro-benzyl)-2-methyl-piperazin-1-yl]-3-oxo-propenyl}-phenyl)-acetamide, N-(5-Chloro-2-{(E)-3-[4-(2,4-difluoro-benzyl)-2-methyl-piperazin-1-yl]-3-oxo-propenyl}-phenyl)-acetamide, N-(5-Chloro-2-{(E)-3-[4-(4-cyano-benzyl)-2-methyl-piperazin-1-yl]-3-oxo-propenyl}-phenyl)-acetamide, N-(5-Chloro-2-{(E)-3-[(R)-4-(4-fluoro-benzyl)-2-methyl-piperazin-1-yl]-3-oxo-prop-enyl}-4-methoxy-phenyl)-acetamide, N-(5-Chloro-4-fluoro-2-{(E)-3-[(R)-4-(4-fluoro-benzyl)-2-methyl-piperazin-1yl]-3-oxo-propenyl}-phenyl)-acetamide,
(5-Chloro-2-{(E)-3-[(R)-4-(4-fluoro-benzyl)-2-methyl-piperazin-1-yl]-3-oxo-propenyl}-4-methoxy-phenyl)-urea,
N-(5-Chloro-4-fluoro-2-{(E)-3-[(R)-4-(4-fluoro-benzyl)-2-methyl-piperazin-1-yl]-3-oxo-propenyl}-phenyl)-methanesulfonamide,
(5-Chloro-4-fluoro-2-{(E)-3-[(R)-4-(4-fluoro-benzyl)-2-methyl-piperazin-1-yl]-3-oxo-propenyl}-phenyl)-urea,
(5-Chloro-4-cyano-2-{(E)-3-[(R)-4-(4-fluoro-benzyl)-2-methyl-piperazin-1-yl]-3-oxo-propenyl}-phenyl)-acetamide,
(5-Chloro-2-{(E)-3-[(R)-4-(4-fluoro-benzyl)-2-methyl-piperazin-1-yl]-3-oxo-propenyl}-4-trifluoromethoxy-phenyl)-acetamide,
(5-Chloro-2-{(E)-3-[(R)-4-(4-fluoro-benzyl)-2-methyl-piperazin-1-yl]-3-oxo-propenyl}-4-trifluoromethoxy-phenyl)-urea,
N-(5-Chloro-2-{(E)-3-[(R)-4-(4-fluoro-benzyl)-2-methyl-piperazin-1-yl]-3-oxo-propenyl}-4-isobutoxy-phenyl)-acetamide,
N-(5-Chloro-2-{(E)-3-[(R)-4-(4-fluoro-benzyl)-2-methyl-piperazin-1-yl]-3-oxo-propenyl}-4-isobutoxy-phenyl)-acetamide,
3-(5-Chloro-2-{(E)-3-[(R)-4-(4-fluoro-benzyl)-2-methyl-piperazin-1-yl]-3-oxo-propenyl}-4-methoxy-phenyl)-5,5-dimethyl-imidazolidine-2,4-dione,
3-(5-Chloro-2-{(E)-3-[(R)-4-(4-fluoro-benzyl)-2-methyl-piperazin-1-yl]-3-oxo-propenyl}-4-methoxy-phenyl)-imidazolidine-2,4-dione,
3-(5-Chloro-2-{(E)-3-[(R)-4-(4-fluoro-benzyl)-2-methyl-piperazin-1-yl]-3-oxo-propenyl}-4-methoxy-phenyl)-1,3-diaza-spiro[4,4]nonane-2,4-dione,
3-(5-Chloro-4-fluoro-2-{(E)-3-[(R)-4-(4-fluoro-benzyl)-2-methyl-piperazin-1-yl]-3-oxo-propenyl}-phenyl)-1,3-diaza-spiro[4,5]decane-2,4-dione,
3-(5-Chloro-4-fluoro-2-{(E)-3-[(R)-4-(4-fluoro-benzyl)-2-methyl-piperazin-1-yl]-3-oxo-propenyl}-phenyl)-5,5-dimethyl-imidazolidine-2,4-dione,
Morpholine-4-carboxylic acid (5-Chloro-2-{(E)-3-[(R)-4-(4-fluoro-benzyl)-2-methyl-piperazin-1-yl]-3-oxo-propenyl}-4-methoxy-phenyl)-amide,
Pyrrolidine-1-carboxylic acid (5-chloro-2-{(E)-3-[(R)-4-(4-fluoro-benzyl)-2-methyl-piperazin-1-yl]-3-oxo-propenyl}-4-methoxy-phenyl)-amide,
5-Chloro-2-{(E)-3-[(R)-4-(4-fluoro-benzyl-2-methyl-piperazin-1-yl]-3-oxo-proneny}-4-methoxy-benzoic acid methyl ester, and
(E)-3-[-2-(4-Acetyl-piperazine-1-carbonyl)-4-chloro-5-methoxy-phenyl]-1-[(R)-4-(4-fluoro-benzyl)-2-methyl-piperazin-1-yl]-propenone,
or a pharmaceutically acceptable salt, or ester thereof.

4. A compound of formula III or a pharmaceutically acceptable salt or ester thereof,

III

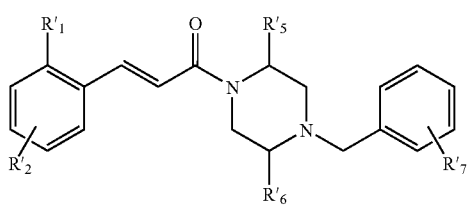

wherein $R'_1$ is as herein before defined;
$R'_2$ and $R'_7$ are hydrogen, cyano, halo, butadienyl, methoxy, ethoxy, 2-methoxyethoxy, morpholino, trifluoromethoxy, 2-methylpropoxy, 2-propoxy;
$R'_5$ and $R'_6$ are independently selected from the group consisting of hydrogen and lower alkyl, acetyl.

5. A pharmaceutical composition comprising a compound according to claim 1 in association with a pharmaceutically acceptable diluent or carrier.

6. A compound of claim 1 selected from the group consisting of:
N-(5-Chloro-2-[(E-)3-[(R)-4-(4-fluorobenzyl)-2-methylpiperazin-1-yl]-3-oxopropenyl]phenyl)-N'-cyanoguanidine,
N-(5-Chloro-2-[(E)-3-[(R)-4-(4-fluorobenzyl)2-methylpiperazin-1yl]-3-oxopropenyl]phenyl)-acetamide
N-(5-Chloro-2-[(E)-3-[(S)-4-(4-fluorobenzyl)-2-methylpiperazin-1-yl]-3-oxopropenyl]phenyl)-acetamide,
(5-Chloro-2-[(E)-3-[(R)-4-(4-fluorobenzyl)-2-methylpiperazin-1-yl]-3-oxopropenyl]-phenyl)-urea,
(5-Chloro-2-[(E)-3-[(S)-4-(4-fluorobenzyl)-2-methylpiperazin-1-yl]-3-oxopropenyl]-phenyl)-urea,
when $R'_1$ is —C≡C—$R'_{10}$, $R'_{10}$ is optionally substituted methyl, isopropyl or piperidinyl;
when $R'_1$ is —C≡C—$R'_{10}$, $R'_{10}$ is optionally substituted by hydrogen or amine;
when $R'_1$ is —C≡C—$R'_{10}$, $R'_{10}$ is optionally substituted piperidinyl,
when $R'_1$ is —C≡C—$R'_{10}$, $R'_{10}$ is optionally substituted by hydroxy, methyl;
when $R'_1$ is —N—C—S—$R'_{10}$ the C atom is substituted by =N—C≡N or

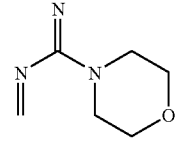

when $R'_1$—N—C—S—$R'_{10}$, $R'_{10}$ is optionally substituted methyl,
when $R'_1$ is —N—C—S—$R'_{10}$, $R'_{10}$ is optionally substituted by hydrogen;
when $R'_1$ is —C—$R'_{10}$ the C atom is optionally substituted by oxo,
when $R'_1$—C—$R'_{10}$, $R'_{10}$ is 3-oxa-1-aza-spiro[4,4]nonan-2-one, hydroxy, optionally substituted pyrrolidinyl, morpholino, piperazinyl, formic acid methyl ester, [1,2,4]triazol, imidazolidinyl, tetrazolyl, —N(CH$_3$)—OCH$_3$ or methoxy;
when $R'_1$ is —C—$R'_{10}$, $R'_{10}$ is optionally substituted by hydrogen, oxo, methyl, acetyl, isopropyl, methoxy, hydroxy, formic acid methyl ester, dimethylamino or ethanone;
the optional substituents on $R'_{10}$ are one or more substituents independently selected from the group consisting of hydrogen, or optionally substituted oxy, lower alkyl, carbonyl, amino;
wherein the optionally substituted substituents are optionally substituted once or more by a substituent independently selected from the group consisting of hydrogen, optionally substituted oxy; or optionally substituted lower alkyl.

* * * * *

UNITED STATES PATENT AND TRADEMARK OFFICE
CERTIFICATE OF CORRECTION

PATENT NO. : 7,645,760 B2  Page 1 of 1
APPLICATION NO. : 10/532331
DATED : January 12, 2010
INVENTOR(S) : Birgit Bollbuck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this

Ninth Day of November, 2010

David J. Kappos
*Director of the United States Patent and Trademark Office*